US012529699B2

(12) United States Patent
Russell et al.

(10) Patent No.: US 12,529,699 B2
(45) Date of Patent: Jan. 20, 2026

(54) DETECTION ASSAYS FOR CORONAVIRUS NEUTRALIZING ANTIBODIES

(71) Applicants: REGENERON PHARMACEUTICALS, INC., Tarrytown, NY (US); VYRIAD, INC., Rochester, MN (US)

(72) Inventors: Stephen J. Russell, Rochester, MN (US); Kah Whye Peng, Rochester, MN (US); Patrycja Lech, Rochester, MN (US); Rianna Vandergaast, Rochester, MN (US); Timothy Carey, Rochester, MN (US)

(73) Assignees: REGENERON PHARMACEUTICALS, INC, Tarrytown, NY (US); VYRIAD, INC., Rochester, MN (US)

( * ) Notice: Subject to any disclaimer, the term of this patent is extended or adjusted under 35 U.S.C. 154(b) by 489 days.

(21) Appl. No.: 17/919,133

(22) PCT Filed: Apr. 19, 2021

(86) PCT No.: PCT/US2021/027909
§ 371 (c)(1),
(2) Date: Jun. 7, 2023

(87) PCT Pub. No.: WO2021/212096
PCT Pub. Date: Oct. 21, 2021

(65) Prior Publication Data

US 2023/0184765 A1 Jun. 15, 2023

Related U.S. Application Data

(60) Provisional application No. 63/151,623, filed on Feb. 19, 2021, provisional application No. 63/078,214, filed on Sep. 14, 2020, provisional application No. 63/029,267, filed on May 22, 2020, provisional application No. 63/020,445, filed on May 5, 2020, provisional application No. 63/012,066, filed on Apr. 17, 2020, provisional application No. 63/012,074, filed on Apr. 17, 2020.

(51) Int. Cl.
*C12N 15/10* (2006.01)
*G01N 33/569* (2006.01)

(52) U.S. Cl.
CPC ... *G01N 33/56983* (2013.01); *C12N 15/1055* (2013.01); *G01N 2333/145* (2013.01); *G01N 2333/165* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 5,888,727 | A | 3/1999 | Lund et al. |
| 6,168,943 | B1 | 1/2001 | Rose |
| 6,653,103 | B2 | 11/2003 | Petersen et al. |
| 6,797,462 | B1 | 9/2004 | Kappes et al. |
| 7,081,243 | B1 | 7/2006 | Rose et al. |
| 7,153,510 | B1 | 12/2006 | Rose |
| 7,166,447 | B2 | 1/2007 | Umezawa et al. |
| 7,176,287 | B2 | 2/2007 | Hamilton et al. |
| 7,442,518 | B2 | 10/2008 | Piwnica-Worms et al. |
| 7,696,330 | B2 | 4/2010 | Meulen et al. |
| 7,731,974 | B2 | 6/2010 | Bell et al. |
| 7,955,821 | B2 | 6/2011 | Waldo et al. |
| 8,012,489 | B2 | 9/2011 | Jones et al. |
| 8,173,791 | B2 | 5/2012 | Gambhir et al. |
| 8,287,878 | B2 | 10/2012 | Clarke et al. |
| 8,470,974 | B2 | 6/2013 | Ozawa et al. |
| 8,685,667 | B2 | 4/2014 | Waldo et al. |
| 9,081,014 | B2 | 7/2015 | Waldo et al. |
| 9,248,178 | B2 | 2/2016 | Kang et al. |
| 9,540,678 | B2 | 1/2017 | Ozawa et al. |
| 9,630,996 | B2 | 4/2017 | Kang et al. |
| 9,732,122 | B2 | 8/2017 | Kang et al. |
| 9,737,597 | B2 | 8/2017 | Kang et al. |

(Continued)

FOREIGN PATENT DOCUMENTS

| | | | |
|---|---|---|---|
| CN | 101747438 | A | 6/2010 |
| JP | 4024525 | B2 | 10/2007 |

(Continued)

OTHER PUBLICATIONS

Van den Pol AN, Davis JN. Highly attenuated recombinant vesicular stomatitis virus VSV-12'GFP displays immunogenic and oncolytic activity. J Virol. 2013;87(2):1019-1034 (Year: 2005).*

(Continued)

*Primary Examiner* — Agnieszka Boesen

(74) *Attorney, Agent, or Firm* — Troutman Pepper Locke LLP

(57) ABSTRACT

The disclosure provides methods for determining the presence of coronavirus neutralizing antibodies in a sample as well as associated compositions and kits. The methods of the disclosure use recombinant vesicular stomatitis virus (VSV) particles, wherein the VSV glycoprotein (G) is replaced by a coronavirus spike(S) glycoprotein or a fragment or a derivative thereof. In a specific embodiment, the S glycoprotein is derived from Severe Acute Respiratory Syndrome coronavirus 2 (SARS-CoV-2) and the methods are used for determining the presence of SARS-CoV-2 neutralizing antibodies.

24 Claims, 22 Drawing Sheets

Specification includes a Sequence Listing.

(56) References Cited

U.S. PATENT DOCUMENTS

| | | | |
|---|---|---|---|
| 9,861,668 B2 | 1/2018 | Peng et al. | |
| 9,943,593 B2 | 4/2018 | Kang et al. | |
| 10,953,089 B1 * | 3/2021 | Smith | A61K 39/215 |
| 2007/0022484 A1 | 1/2007 | Umezawa et al. | |
| 2007/0136825 A1 | 6/2007 | Frommer et al. | |
| 2007/0254311 A1 | 11/2007 | Alagic et al. | |
| 2008/0233589 A1 | 9/2008 | Piwnica-Worms | |
| 2009/0220942 A1 | 9/2009 | Broude et al. | |
| 2012/0121650 A1 | 5/2012 | Johnston et al. | |
| 2014/0271564 A1 | 9/2014 | Russell et al. | |
| 2023/0346981 A1 * | 11/2023 | Davidson | C12N 15/86 |

FOREIGN PATENT DOCUMENTS

| | | |
|---|---|---|
| JP | 5258084 B2 | 5/2013 |
| WO | 2007051002 A2 | 5/2007 |
| WO | 2010066113 A1 | 6/2010 |
| WO | 2016116398 A1 | 7/2016 |
| WO | 2020010474 A1 | 1/2020 |
| WO | 2021168318 A1 | 8/2021 |
| WO | 2021211704 A1 | 10/2021 |

OTHER PUBLICATIONS

Wu et al., "A new coronavirus associated with human respiratory disease in China" (Nature. 2020;579(7798):265-269 (Year: 2020).*

Kim et al. (Virology, 2007, p. 41-53).*

Kraaijeveld, C., et al.; Enzyme-Linked Immunosorbent Assay for Detection of Antibody in Volunteers Experimentally Infected with Human Coronavirus Strain 229E; Journal of Clinical Microbiology; Oct. 1980; vol. 12; No. 4; 493-497.

Kreer, C., et al.; Longitudinal isolation of potent near-germline SARS-CoV-2-neutralizing antibodies from COVID-19 patients; 2020; bioRxiv preprint doi: https://doi.org/10.1101/2020.06.12.146290.

Kugelman, J., et al.; Emergence of Ebola Virus Escape Variants in Infected Nonhuman Primates Treated with the MB-003 Antibody Cocktail; 2015; Cell Reports 12, 2111-2120; http://dx.doi.org/10.1016/j.celrep.2015.08.038.

Lan, J., et al.; Structure of the SARS-CoV-2 spike receptor-binding domain bound to the ACE2 receptor; 2020; https://doi.org/10.1038/s41586-020-2180-5.

Larsen, M., et al.; Afucosylated immunoglobulin G responses are a hallmark of enveloped virus infections and show an exacerbated phenotype in COVID-19; 2020; bioRxiv preprint doi: https://doi.org/10.1101/2020.05.18.099507.

Lee, C., et al.; CD8+ T cell cross-reactivity against SARS-CoV-2 conferred by other coronavirus strains and influenza virus; 2020; bioRxiv preprint doi: https://doi.org/10.1101/2020.05.20.107292.

Li, T., et al.; Potent synthetic nanobodies against SARS-CoV-2 and molecular basis for neutralization; 2020; bioRxiv preprint doi: https://doi.org/10.1101/2020.06.09.143438.

Li, W., et al.; Potent neutralization of SARS-CoV-2 in vitro and in an animal model by a human monoclonal antibody; 2020; bioRxiv preprint doi: https://doi.org/10.1101/2020.05.13.093088.

Loening, A., et al.; Consensus guided mutagenesis of Renilla luciferase yields enhanced stability and light output; Protein Engineering, Design & Selection; vol. 19; No. 9; 391-400; 2006; doi: 10.1093/protein/gzl023.

Lokman, S., et al.; Exploring the genomic and proteomic variations of SARS-CoV-2 spike glycoprotein: A computational biology approach; Infection, Genetics and Evolution; 84; 2020; 104389.

Lou, Y., et al.; Cross-neutralization antibodies against SARS-CoV-2 and RBD mutations from convalescent patient antibody libraries; 2020; bioRxiv preprint doi: https://doi.org/10.1101/2020.06.06.137513.

Lui, I., et al.; Trimeric SARS-CoV-2 Spike interacts with dimeric ACE2 with limited intra-Spike avidity, 2020; bioRxiv preprint doi: https://doi.org/10.1101/2020.05.21.109157.

Lurie, N., et al.; Developing Covid-19 Vaccines at Pandemic Speed; The New England Journal Of Medicine; Perspective; 2020; DOI: 10.1056/NEJMp2005630.

Lv, Z., et al.; Structural basis for neutralization of SARS-CoV-2 and SARS-CoV by a potent therapeutic antibody; 2020; bioRxiv preprint doi: https://doi.org/10.1101/2020.06.02.129098.

Macnaughton, Malcolm R., Occurrence and Frequency of Coronavirus Infections in Humans as Determined by Enzyme-Linked Immunosorbent Assay, Infection and Immunity, Nov. 1982, vol. 38, 419-423, http://iai.asm.org.

Meirson, T., et al.; Structural basis of SARS-CoV-2 spike protein induced by ACE2; 2020; bioRxiv preprint doi: https://doi.org/10.1101/2020.05.24.113175.

Miersch, S., et al.; Synthetic Antibodies neutralize SARS-CoV-2 infection of mammalian cells; 2020; bioRxiv preprint doi: https://doi.org/10.1101/2020.06.05.137349.

Montefiori, D., et al.; Evaluating Neutralizing Antibodies Against HIV, SIV, and SHIV in Luciferase Reporter Gene Assays; 2004; Current Protocols in Immunology; 12.11.1-12.11.17.

Müller, M., et al.; Presence of Middle East respiratory syndrome coronavirus antibodies in Saudi Arabia: a nationwide, cross-sectional, serological study; Lancet Infectious Diseases; 2015; 15: 559-64; http://dx.doi.org/10.1016/S1473-3099(15)70090-3.

Nakane, S., et al.; Dual Split Protein (DSP) Assay to Monitor Cell-Cell Membrane Fusion; 2015; Cell Fusion: Overviews and Methods, Methods in Molecular Biology, vol. 1313, DOI 10.1007/978-1-4939-2703-6_17.

Nascimento, Jr., J., et al.; SARS, MERS and SARS-CoV-2 (COVID-19) treatment: a patent review; 2020; Expert Opinion on Therapeutic Patents, DOI: 10.1080/13543776.2020.1772231.

Ng, K., et al.; Pre-existing and de novo humoral immunity to SARS-CoV-2 in humans; 2020; bioRxiv preprint doi: https://doi.org/10.1101/2020.05.14.095414.

Ni, L., et al.; Detection of SARS-CoV-2-Specific Humoral and Cellular Immunity in COVID-19 Convalescent Individuals; https://doi.org/10.1016/j.immuni.2020.04.023.

Noy-Porat, T., et al.; Tiger team: a panel of human neutralizing mAbs targeting SARS-CoV-2 spike at multiple epitopes; 2020; bioRxiv preprint doi: https://doi.org/10.1101/2020.05.20.106609.

Okba, N., et al.; SARS CoV2 Antibody Responses in COVID Patients; 2020; vol. 26; No. 7; https://doi.org/10.1101/2020.03.18.20038059.

Park, T., et al.; Spike protein binding prediction with neutralizing antibodies of SARS-CoV-2; bioRxiv preprint doi: https://doi.org/10.1101/2020.02.22.951178; 2020.

Pinto, D., et al.; Cross-neutralization of SARS-CoV-2 by a human monoclonal SARS-CoV antibody; 2020; Nature; https://doi.org/10.1038/s41586-020-2349-y.

Poh, C., et al.; Two linear epitopes on the SARS-CoV-2 spike protein that elicit neutralising antibodies in COVID-19 patients; 2020; Nature Communications, 11:2806; https://doi.org/10.1038/s41467-020-16638-2.

Ravichandran, S., et al.; Antibody repertoire induced by SARS-CoV-2 spike protein immunogens; 2020; bioRxiv preprint doi: https://doi.org/10.1101/2020.05.12.091918.

Raybould, M., et al.; CoV-AbDab: the Coronavirus Antibody Database; 2020; bioRxiv preprint doi: https://doi.org/10.1101/2020.05.15.077313.

Robbiani, D., et al.; Convergent Antibody Responses to SARS-CoV-2 Infection in Convalescent Individuals; 2020; Nature 584, 437-442. https://doi.org/10.1038/s41586-020-2456-9.

Rogers, T., et al.; Isolation of potent SARS-CoV-2 neutralizing antibodies and protection from disease in a small animal model; 2020; Science 10.1126/science.abc7520.

Rogers, T., et al.; Rapid isolation of potent SARS-CoV-2 neutralizing antibodies and protection in a small animal model; 2020; bioRxiv preprint doi: https://doi.org/10.1101/2020.05.11.088674.

Saw, W., et al.; Using a split luciferase assay (SLA) to measure the kinetics of cell-cell fusion mediated by herpes simplex virus glycoproteins; 2015; Methods 90, 68-75.

Seydoux, E., et al.; Analysis of a SARS-CoV-2 infected individual reveals development of potent neutralizing antibodies to distinct

(56) References Cited

OTHER PUBLICATIONS epitopes with limited somatic mutation; 2020; Immunity; doi: https://doi.org/10.1016/j.immuni.2020.06.001.
Seydoux, E., et al.; Characterization of neutralizing antibodies from a SARS-CoV-2 infected individual; May 12, 2020; bioRxiv; https://doi.org/10.1101/2020.05.12.091298.
Shi, R., et al.; A human neutralizing antibody targets the receptor binding site of SARS-CoV-2; 2020; Nature; https://doi.org/10.1038/s41586-020-2381-y.
Spenlehauer, C., et al.; A Luciferase-Reporter Gene-Expressing T-Cell Line Facilitates Neutralization and Drug-Sensitivity Assays That Use Either R5 or X4 Strains of Human Immunodeficiency Virus Type 1; Virology; vol. 280; 292-300; 2001.
Sun, X., et al.; Internalization and fusion mechanism of vesicular stomatitis virus and related rhabdoviruses; Future Virol.; 2010; 5;1; 85-96; doi:10.2217/FVL.09.72.
Suthar, M., et al.; Rapid generation of neutralizing antibody responses in COVID-19 patients; 2020; Cell Reports Medicine; https://doi.org/10.1016/j.xcrm.2020.100040.
Tai, W., et al.; Identification of SARS-CoV RBD-targeting monoclonal antibodies with crossreactive or neutralizing activity against SARS-CoV-2; 2020; Elsevier; https://doi.org/10.1016/j.antiviral.2020.104820.
Teng, S., et al.; Systemic Effects of Missense Mutations on SARS-CoV-2 Spike Glycoprotein Stability and Receptor Binding Affinity; 2020; bioRxiv; https://doi.org/10.1101/2020.05.21.109835.
Ter Meulen, J., et al.; Human Monoclonal Antibody Combination against SARS Coronavirus: Synergy and Coverage of Escape Mutants; 2006; PLoS Med 3(7): e237. DOI: 10.1371/journal.pmed.0030237.
Valenzuela Nieto, G., et al.; Fast isolation of sub-nanomolar affinity alpaca nanobody against the Spike RBD of SARS-CoV-2 by combining bacterial display and a simple single-step density gradient selection; 2020; bioRxiv; https://doi.org/10.1101/2020.06.09.137935.
Vandergaast, R., et al.; Immuno-COVTM 1 v2.0: Development and Validation of a High-Throughput Clinical Assay for Measuring SARS-CoV-2-Neutralizing Antibody Titers; Feb. 19, 2021; medRxiv preprint doi: https://doi.org/10.1101/2021.02.16.21251653.
Walls, A., et al.; Structure, Function, and Antigenicity of the SARSCoV-2 Spike Glycoprotein; 2020, Cell 180, 281-292.
Wan, J., et al.; Human IgG cell neutralizing monoclonal antibodies block SARS-CoV-2 infection; 2020; bioRxiv; https://doi.org/10.1101/2020.05.19.104117.
Wan, Y., et al.; Receptor Recognition by the Novel Coronavirus from Wuhan: an Analysis Based on Decade-Long Structural Studies of SARS Coronavirus; Journal of Virology; Apr. 2020 vol. 94 Issue 7 e00127-20; 94:e00127-20. https://doi.org/10.1128/JVI.00127-20.
Wang, C., et al.; A human monoclonal antibody blocking SARS-CoV-2 infection; Nature Communications; 2020; 11:2251 | https://doi.org/10.1038/s41467-020-16256-y.
Wang, C., et al.; A human monoclonal antibody blocking SARS-CoV-2 infection; Nature Communications; 2020; 11:2251 | Supplemental Information.
Albertini, A., et al.; Molecular and Cellular Aspects of Rhabdovirus Entry; Viruses; 2012; vol. 4; 117-139; doi:10.3390/v4010117.
Anderson, K., et al.; The proximal origin of SARS-CoV-2; Nature Medicine; 2017; https://doi.org/10.1038/s41591-020-0820-9.
Andreano, E., et al.; Identification of neutralizing human monoclonal antibodies from Italian Covid-19 convalescentg patients; May 2020; bioRxiv preprint doi: https://doi.org/10.1101/2020.05.05.078154.
Barnes, C., et al.; Structures of human antibodies bound to SARS-CoV-2 spike reveal common epitopes and recurrent features of antibodies; Cell; 2020; doi: https://doi.org/10.1016/j.cell.2020.06.025.
Baum, A., et al.; Antibody cocktail to SARS-CoV-2 spike protein prevents rapid mutational escape seen with individual antibodies; Science; 2020; www.sciencemag.org, 10.1126/science.abd0831.
Baum, A., et al.; Supplementary Materials for Antibody cocktail to SARS-CoV-2 spike protein prevents rapid mutational escape seen with individual antibodies; Science; 2020; www.sciencemag.org, 10.1126/science.abd0831.
Belot, L., et al.; Structural and cellular biology of rhabdovirus entry; Advances in Virus Research; vol. 104; 147-183; 2019; https://doi.org/10.1016/bs.aivir.2019.05.003.
Bertoglio, F., et al.; SARS-CoV-2 neutralizing human recombinant antibodies selected from pre-pandemic healthy donors binding at RBD-ACE2 interface; Jun. 2020; bioRxiv preprint doi: https://doi.org/10.1101/2020.06.05.135921.
Black, B., et al.; The Role of Vesicular Stomatitis Virus Matrix Protein in Inhibition of Host-Directed Gene Expression is Genetically Separable from Its Function in Virus Assembly; Journal of Virology; Aug. 1993; vol. 67; No. 8; 4814-4821; http://jvi.asm.org.
Brouwer, P., et al.; Potent neutralizing antibodies from COVID-19 patients define multiple targets of vulnerability; 2020; bioRxiv preprint doi: https://doi.org/10.1101/2020.05.12.088716.
Cao, Y., et al.; Potent neutralizing antibodies against SARS-CoV-2 identified by high-throughput single-cell sequencing of convalescent patients' B cells; Cell; 2020; https://doi.org/10.1016/j.cell.2020.05.025.
Case, J., et al.; Neutralizing antibody and soluble ACE2 inhibition of a replication-competent VSV-2 SARS-CoV-2 and a clinical isolate of SARS-CoV-2; 2020; Neutralizing antibody and soluble ACE2 inhibition of a replication-competent VSV-2 SARS-CoV-2 and a clinical isolate of SARS-CoV-2.
Chen, X., et al.; Human monoclonal antibodies block the binding of SARS-CoV-2 spike protein to angiotensin converting enzyme 2 receptor; 2020; Cellular & Molecular Immunology; www.nature.com/cmi https://doi.org/10.1038/s41423-020-0426-7.
Cheng, M., et al.; An insertion unique to SARS-CoV-2 exhibits superantigenic character strengthened by recent mutations; 2020; bioRxiv preprint doi: https://doi.org/10.1101/2020.05.21.109272.
Chi, X., et al.; A neutralizing human antibody binds to the N-terminal domain of the Spike protein of SARS-CoV-2; 2020; Science; doi: 10.1126/science.abc6952.
Chi, X., et al.; A potent neutralizing human antibody reveals the N-terminal domain of the Spike protein of SARS-CoV-2 as a site of vulnerability; 2020; bioRxiv preprint doi: https://doi.org/10.1101/2020.05.08.083964.
Chi, X., et al.; Humanized Single Domain Antibodies Neutralize SARS-CoV-2 by Targeting Spike Receptor Binding Domain; bioRxiv preprint doi: https://doi.org/10.1101/2020.04.14.042010; 2020.
Choi, J., et al.; Characterization of a human monoclonal antibody generated from a B-cell specific for a prefusion-stabilized spike protein of Middle East respiratory syndrome coronavirus; 2020; PLoS ONE 15(5): e0232757. https://doi.org/10.1371/journal.pone.0232757.
Choudhury, A., et al.; In silico studies on the comparative characterization of the interactions of SARS-CoV-2 spike glycoprotein with ACE-2 receptor homologs and human TLRs; J Med Virol. Oct. 2020;92(10):2105-2113. doi: 10.1002/jmv.25987. Epub May 17, 2020. PMID: 32383269; PMCID: PMC7267663.
Crooke, S., et al.; Immunoinformatic identification of B cell and T cell epitopes in the SARS-CoV-2 proteome; 2020; bioRxiv preprint doi: https://doi.org/10.1101/2020.05.14.093757.
Cui, et al., Origin and evolution of pathogeniccoronaviruses, Nature Reviews, Microbiology, vol. 17, 181-191, Mar. 2019, https://doi.org/10.1038/s41579-018-0118-9.
Custódio, T., et al.; Selection, biophysical and structural analysis of synthetic nanobodies that effectively neutralize SARS-CoV-2; 2020; bioRxiv preprint doi: https://doi.org/10.1101/2020.06.23.165415.
Davidson, E., et al.; Mechanism of Binding to Ebola Virus Glycoprotein by the ZMapp, ZMAb, and MB-003 Cocktail Antibodies; 2015; J Virol, vol. 89, No. 21, pp. 10982-10992; doi:10.1128/JVI.01490-15.
Dieterle, M., et al.; A Replication-Competent Vesicular Stomatitis Virus for Studies of SARS-CoV-2 Spike-Mediated Cell Entry and Its Inhibition; 2020; Cell Host & Microbe 28, 486-496; https://doi.org/10.1016/j.chom.2020.06.020.
Dinnon III, K., et al.; A mouse-adapted SARS-CoV-2 model for the evaluation of COVID-19 medical countermeasures; 2020; bioRxiv preprint doi: https://doi.org/10.1101/2020.05.06.081497.

(56) References Cited

OTHER PUBLICATIONS

Dong, J., et al.; Development of multi-specific humanized llama antibodies blocking SARS-CoV-2/ACE2 interaction with high affinity and avidity; 2020; Emerging Microbes & Infections, 9:1, 1034-1036, DOI: 10.1080/22221751.2020.1768806.
Ejemel, M., et al.; IgA MAb blocks SARS-CoV-2 Spike-ACE2 interaction providing mucosal immunity; 2020; bioRxiv preprint doi: https://doi.org/10.1101/2020.05.15.096719.
Fukushi, S., et al.; Vesicular stomatitis virus pseudotyped with severe acute respiratory syndrome coronavirus spike protein; 2005; Journal of General Virology; 86, 2269-2274; DOI 10.1099/vir.0.80955-0.
Fung, T., et al.; Human Coronavirus: Host-Pathogen Interaction; 2019; Annu. Rev. Microbiol. 2019. 73:529-57; https://doi.org/10.1146/annurev-micro-020518-115759.
Galson, J., et al.; Deep sequencing of B cell receptor repertoires from COVID-19 patients reveals strong convergent immune signatures; 2020; bioRxiv preprint doi: https://doi.org/10.1101/2020.05.20.106294.
Giron, C., et al.; On the interactions of the receptor-binding domain of SARS-CoV-1 and SARS-CoV-2 spike proteins with monoclonal antibodies and the receptor ACE2; 2020; Virus Research 285; https://doi.org/10.1016/j.virusres.2020.198021.
Gonçalves, R., et al.; SARS-CoV-2 mutations and where to find them: An in silico perspective of structural changes and antigenicity of the Spike protein; 2020; bioRxiv preprint doi: https://doi.org/10.1101/2020.05.21.108563.
Graham, R., et al.; A decade after SARS: Strategies to control emerging coronaviruses; 2013; Nat Rev Microbiol; 11(12): 836-848, doi:10.1038/nrmicro3143.
Grifoni, A., et al.; Targets of T cell responses to SARS-CoV-2 coronavirus in humans with COVID-19 disease and unexposed individuals; Cell; https://doi.org/10.1016/j.cell.2020.05.015.
Hanke, L., et al.; An alpaca nanobody neutralizes SARS-CoV-2 by blocking receptor interaction; 2020; bioRxiv preprint doi: https://doi.org/10.1101/2020.06.02.130161.
Hansen, J., et al.; Studies in humanized mice and convalescent humans yield a SARS-CoV-2 antibody cocktail; 2020; Science; www.sciencemag.org doi: 10.1126/science.abd0827.
Hansen, J., et al.; Supplementary Materials for Studies in humanized mice and convalescent humans yield a SARS-CoV-2 antibody cocktail; 2020; Science; www.sciencemag.org doi: 10.1126/science.abd0827.
Hoffmann, M., et al.; SARS-CoV-2 Cell Entry Depends on ACE2 and TMPRSS2 and Is Blocked by a Clinically Proven Protease Inhibitor; 2020; Cell; https://doi.org/10.1016/j.cell.2020.02.052.
Hsieh, C., et al.; Structure-based Design of Prefusion-stabilized SARS-CoV-2 Spikes; 2020; bioRxiv preprint doi: https://doi.org/10.1101/2020.05.30.125484.
Huibin, L., et al.; Cross-reactive Antibody Response between SARSCoV-2 and SARS-CoV Infections; 2020, Cell Reports 31, 107725; https://doi.org/10.1016/j.celrep.2020.107725.
Huo J., et al.; Neutralization of SARS-CoV-2 by destruction of the prefusion Spike; bioRxiv preprint doi: https://doi.org/10.1101/2020.05.05.079202; 2020.
Hurlburt, N., et al.; Structural basis for potent neutralization of SARS-CoV-2 and role of antibody affinity maturation; 2020; bioRxiv preprint doi: https://doi.org/10.1101/2020.06.12.148692.
Igonet, S., et al.; SnapShot: Viral and Eukaryotic Protein Fusogens; Cell; vol. 151, 1634; Dec. 21, 2012; DOI: http://dx.doi.org/10.1016/j.cell.2012.11.041.
Ishikawa, H., et al., Generation of a dual-functional split-reporter protein for monitoring membrane fusion using self-associating split GFP, Protein Engineering, Design & Selection, vol. 25, No. 12, 813-820, 2012.
Ju, B., et al.; Human neutralizing antibodies elicited by SARS-CoV-2 infection; 2020; Nature; https://doi.org/10.1038/s41586-020-2380-z.
Kapadia, S., et al.; Long-term protection from SARS coronavirus infection conferred by a single immunization with an attenuated VSV-based vaccine; Virology; 340; 2005; 174-182; doi:10.1016/j.virol.2005.06.016.
Kapadia, S., et al.; SARS vaccine based on a replication-defective recombinant vesicular stomatitis virus is more potent than one based on a replication-competent vector; Virology; 376; 2008; 165-172; doi:10.1016/j.virol.2008.03.002.
Keeffe, J., et al.; A Combination of Two Human Monoclonal Antibodies Prevents Zika Virus Escape Mutations in Non-human Primates; 2018; Cell Reports; https://doi.org/10.1016/j.celrep.2018.10.031.
Kondo, N., et al.; Conformational Changes of the HIV-1 Envelope Protein during Membrane Fusion Are Inhibited by the Replacement of Its Membrane-spanning Domain; The Journal of Biological Chemistry; vol. 85; No. 19; 14681-14688; May 7, 2010; DOI 10.1074/jbc.M109.067090.
Wang, P., et al.; SARS-CoV-2 Neutralizing Antibody Responses Are More Robust in Patients with Severe Disease; 2020; bioRxiv; https://doi.org/10.1101/2020.06.13.150250.
Wang, Q., et al.; Structural and Functional Basis of SARS-CoV-2 Entry by Using Human ACE2; 2020; Cell 181,894-904; https://doi.org/10.1016/j.cell.2020.03.045.
Watanabe, Y., et al.; Site-specific glycan analysis of the SARS-CoV-2 spike; 2020; Science; http://science.sciencemag.org.
Watanabe, Y., et al.; Vulnerabilities in coronavirus glycan shields despite extensive glycosylation; 2020; Nature Communications; https://doi.org/10.1038/s41467-020-16567-0.
Wec, A., et al.; Broad neutralization of SARS-related viruses by human monoclonal antibodies; 2020; Science 10.1126/science.abc7424.
Wec, A., et al.; Broad neutralization of SARS-related viruses by human monoclonal antibodies—Supplemental Materials; 2020; science.sciencemag.org/cgi/content/full/science.abc7424/DC1.
Wec, A., et al.; Broad sarbecovirus neutralizing antibodies define a key site of vulnerability on the SARS-CoV-2 spike protein; 2020; bio.
Wei, X., et al.; Antibody neutralization and escape by HIV-1; 2003; Nature; vol. 422; www.nature.com/nature, doi:10.1038/nature01470.
Wölfel, R., et al.; Virological assessment of hospitalized patients with COVID-2019; Nature; 2020; https://doi.org/10.1038/s41586-020-2196-x.
Wrapp, D., et al.; Structural Basis for Potent Neutralization of Betacoronaviruses by Single-Domain Camelid Antibodies; 2020, Cell 181, 1-12; https://doi.org/10.1016/j.cell.2020.04.031.
Wu, Y., et al.; A noncompeting pair of human neutralizing antibodies block COVID-19 virus binding to its receptor ACE2; 2020; Science 10.1126/science.abc2241.
Wu, Y., et al.; Fully human single-domain antibodies against SARS-CoV-2; bioRxiv preprint doi: https://doi.org/10.1101/2020.03.30.015990; 2020.
Wu, Y., et al.; Identification of Human Single-Domain Antibodies against SARS-CoV-2; 2020; Cell Host & Microbe 27, 1-8; https://doi.org/10.1016/j.chom.2020.04.023.
Yi, C., et al.; Key residues of the receptor binding motif in the spike protein of SARS-CoV-2 that interact with ACE2 and neutralizing antibodies; 2020; Cellular & Molecular Immunology; https://doi.org/10.1038/s41423-020-0458-z.
Yu, J., et al.; DNA vaccine protection against SARS-CoV-2 in rhesus macaques; 2020; Science; 10.1126/science.abc6284.
Yuan, A., et al.; Isolation of and Characterization of Neutralizing Antibodies to Covid-19 from a Large Human Naïve scFv Phage Display Library; 2020; bioRxiv; https://doi.org/10.1101/2020.05.19.104281.
Yuan, M., et al.; A highly conserved cryptic epitope in the receptor binding domains of SARS-CoV-2 and SARS-CoV; 2020; Science 368, 630-633; http://science.sciencemag.org.
Zang, J., et al.; Immunization with the receptor-binding domain of SARS-CoV-2 elicits antibodies cross-neutralizing SARS-CoV-2 and SARS-CoV without antibody-dependent enhancement; 2020; bioRxiv; https://doi.org/10.1101/2020.05.21.107565.

(56) References Cited

OTHER PUBLICATIONS

Zeng, X., et al.; Isolation of a human monoclonal antibody specific for the receptor binding domain of SARS-CoV-2 using a competitive phage biopanning strategy; 2020; Antibody Therapeutics; vol. 3, No. 2 95-100; doi:10.1093/abt/tbaa008.

Zheng, M., et al.; Novel antibody epitopes dominate the antigenicity of spike glycoprotein in SARS-CoV-2 compared to SARS-CoV; 2020; ellular & Molecular Immunology; 17:536-538; https://doi.org/10.1038/s41423-020-0385-z.

Zost, S., et al.; Potently neutralizing human antibodies that block SARS-CoV-2 receptor binding and protect animals; 2020; BioRxiv; https://doi.org/10.1101/2020.05.22.111005.

Zost, S., et al.; Rapid isolation and profiling of a diverse panel of human monoclonal antibodies targeting the SARS-CoV-2 spike protein; 2020; bioRxiv; https://doi.org/10.1101/2020.05.12.091462.

International Search Report and Written Opinion mailed Sep. 1, 2021 for International Patent Application No. PCT/US2021/027909 which was filed Apr. 21, 2021 (Applicant: Regeneron Pharmaceuticals, Inc. // Inventor: Russell, et al. (25 pages).

Nie, Jianhui et al: “Establishment and validation of a pseudovirus neutralization assay for SARS-CoV-2”, Emerging Microbes & Infections, vol. 9, No. 1, Mar. 24, 2020 (Mar. 24, 2020), pp. 680-686, XP55818011, DOI: 10.1080/22221751.2020.1743767 Retrieved from the Internet: URL:https://www.tandfonline.com/doi/pdf/10.1080/22221751.2020.1743767? needAccess=true.

Xiong, Hua-Long et al: “Robust neutralization assay based on SARS-CoV-2 S-bearing vesicular stomatitis virus (VSV) pseudovirus and ACE2-overexpressed BHK21 cells”, bioRxiv, Apr. 9, 2020 (Apr. 9, 2020), XP55818007, DOI: 10.1101/2020.04.08.026948 Retrieved from the Internet: URL:https://www.biorxiv.org/content/10.1101/2020.04.08.026948v1.full.pdf [retrieved on Jun. 25, 2021].

Lester, Sandra et al: “Middle East respiratory coronavirus (MERS-CoV) spike (S) protein vesicular stomatitis virus pseudoparticle neutralization assays offer a reliable alternative to the conventional neutralization assay in human seroepidemiological studies”, Access Microbiology, vol. 1, No. 9, Nov. 1, 2019 (Nov. 1, 2019), XP55818130, DOI: 10.1099/acmi.0.000057; Retrieved from the Internet: URL:https://www.microbiologyresearch.org/docserver/fulltext/acmi/1/9/acmi000057.pdf? expires=1624618030&id=id&accname-guest&checksum=990E4F090A9ECB.

Fukushi, Shuetsu et al: “Evaluation of a novel vesicular stomatitis virus pseudotype-based assay for detection of neutralizing antibody responses to SARS-CoV”, Journal of Medical Virology, vol. 78, No. 12, Dec. 1, 2006 (Dec. 1, 2006), pp. 1509-1512, XP55818133, US; ISSN: 0146-6615, DOI: 10.1002/jmv.20732; Retrieved from the Internet: URL:https://www.ncbi.nlm.nih.gov/pmc/articles/PMC7166816/pdf/JMV-78-1509.pdf.

Yamamoto, Mizuki et al: “Identification of Nafamostat as a Potent Inhibitor of Middle East Respiratory Syndrome Coronavirus S Protein-Mediated Membrane Fusion Using the Split-Protein-Based Cell-Cell Fusion Assay”, Antimicrobial Agents and Chemotherapy, vol. 60, No. 11, Nov. 1, 2016 (Nov. 1, 2016), pp. 6532-6539, XP055536983, US ISSN: 0066-4804, DOI: 10.1128/AAC.01043-16.

Avilov S. V. et al: “Replication-Competent Influenza A Virus That Encodes a Split-Green Fluorescent Protein-Tagged PB2 Polymerase Subunit Allows Live-Cell Imaging of the Virus Life Cycle”, Journal of Virology, vol. 86, No. 3, Nov. 23, 2011 (Nov. 23, 2011), pp. 1433-1448, XP55818035, US ISSN: 0022-538X, DOI: 10.1128/JVI.05820-11.

Vandergaast Rianna et al: “Development and validation of Immuno-COVTM: a highthroughput clinical assay for detecting antibodies that neutralize SARS-CoV-2”, bioRxiv, May 27, 2020 (May 27, 2020), XP55818020, DOI: 10.1101/2020.05.26.117549 Retrieved from the Internet: URL:https://www.biorxiv.org/content/10.1101/2020.05.26.117549v1.full.pdf [retrieved on Jun. 25, 2021].

Lui, R., et al.; A recombinant VSV-vectored MERS-CoV vaccine induces neutralizing antibody and T Cell responses in rhesus monkeys after single dose immunization; Antiviral Research; vol. 150, Dec. 12, 2017 (Dec. 12, 2017), pp. 30-38, XP055681795, NL ISSN: 0166-3542, DOI: 10.1016/j.antiviral.2017.12.007.

Andersen, K.G., Rambaut, A., Lipkin, W.I. et al. The proximal origin of SARS-CoV-2. Nat Med 26, 450-452 (2020). https://doi.org/10.1038/s41591-020-0820-9.

Li, H., et al., Establishment of replication-competent vesicular stomatitis virus-based recombinant viruses suitable for SARS-CoV-2 entry and neutralization assays; Emerging Microbes & Infections; 2020, vol. 9 https://doi.org/10.1080/22221751.2020.1830715.

* cited by examiner

C

D

| VNU | ARDS | Pneumonia | Fever | Feverish | Chills | Myalgia | Rhinorrhea | Sore Throat | Cough | Dyspnea | Nausea/ | Headache | Abdominal pain | Diarrhea |
|---|---|---|---|---|---|---|---|---|---|---|---|---|---|---|
| 30-100 | 0% | 0% | 38% | 25% | 50% | 50% | 13% | 13% | 50% | 25% | 13% | 50% | 0% | 38% |
| 100-250 | 25% | 0% | 75% | 38% | 63% | 63% | 50% | 38% | 88% | 63% | 13% | 75% | 38% | 25% |
| 250-500 | 14% | 14% | 71% | 14% | 57% | 86% | 29% | 43% | 100% | 86% | 43% | 71% | 43% | 43% |
| 500+ | 25% | 13% | 75% | 38% | 88% | 88% | 38% | 38% | 75% | 63% | 50% | 88% | 25% | 50% |

Assay

1. Thaw and add virus to wells (2,000-10,000 TCID50 units/well)
2. Add dilutions of serum (1:100, 1:1000, etc.) – Incubate 30 min at RT
3. Add split DSP Vero luciferase Cells (4 x $10^4$ cells/well) - Incubate 24-30 hours at 37°C

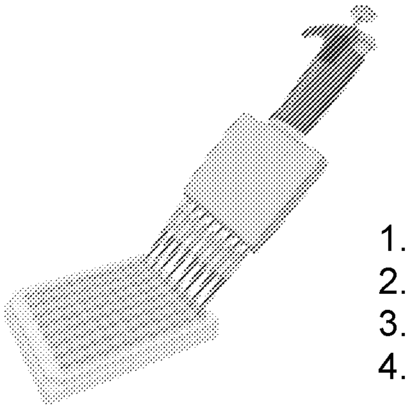

1. Add luciferase substrate (EnduRen™)
2. Quantify luciferase signal
3. Calculate antibody titer
4. Report

Critical Reagents

1. Qualified viruses (VSV-SARS-CoV2-S-Δ19CT or VSV-SARS-CoV2-S)
2. Qualified cells (Vero DSP luciferase)
3. Control

FIG. 10

Assay: IMMUNO-COV DBS

Plate: ____ of ____

U-well plate

| | 1 | 2 | 3 | 4 | 5 | 6 | 7 | 8 | 9 | 10 | 11 | 12 |
|---|---|---|---|---|---|---|---|---|---|---|---|---|
| A | S1 1:4 | S1 1:8 | S1 1:16 | S1 1:32 | S1 1:64 | S1 1:128 | S4 1:4 | S4 1:8 | S4 1:16 | S4 1:32 | S4 1:64 | S4 1:128 |
| B | S2 1:4 | S2 1:8 | S2 1:16 | S2 1:32 | S2 1:64 | S2 1:128 | S5 1:4 | S5 1:8 | S5 1:16 | S5 1:32 | S5 1:64 | S5 1:128 |
| C | S3 1:4 | S3 1:8 | S3 1:16 | S3 1:32 | S3 1:64 | S3 1:128 | S6 1:4 | S6 1:8 | S6 1:16 | S6 1:32 | S6 1:64 | S6 1:128 |
| D | ST1 | ST2 | ST3 | ST4 | ST5 | ST6 | NC | PC | Media | | | |
| E | | | | | | | | | | | | |
| F | | | | | | | | | | | | |
| G | | | | | | | | | | | | |
| H | | | | | | | | | | | | |

| | |
|---|---|
| Tech: | |
| Date: | |
| Time virus added: | |
| Virus lot: | |

FIG. 23

Assay Plate

| | 1 | 2 | 3 | 4 | 5 | 6 | 7 | 8 | 9 | 10 | 11 | 12 |
|---|---|---|---|---|---|---|---|---|---|---|---|---|
| A | S1 1:4 | S1 1:8 | S1 1:16 | S1 1:32 | S1 1:64 | S1 1:128 | S4 1:4 | S4 1:8 | S4 1:16 | S4 1:32 | S4 1:64 | S4 1:128 |
| B | S1 1:4 | S1 1:8 | S1 1:16 | S1 1:32 | S1 1:64 | S1 1:128 | S4 1:4 | S4 1:8 | S4 1:16 | S4 1:32 | S4 1:64 | S4 1:128 |
| C | S2 1:4 | S2 1:8 | S2 1:16 | S2 1:32 | S2 1:64 | S2 1:128 | S5 1:4 | S5 1:8 | S5 1:16 | S5 1:32 | S5 1:64 | S5 1:128 |
| D | S2 1:4 | S2 1:8 | S2 1:16 | S2 1:32 | S2 1:64 | S2 1:128 | S5 1:4 | S5 1:8 | S5 1:16 | S5 1:32 | S5 1:64 | S5 1:128 |
| E | S3 1:4 | S3 1:8 | S3 1:16 | S3 1:32 | S3 1:64 | S3 1:128 | S6 1:4 | S6 1:8 | S6 1:16 | S6 1:32 | S6 1:64 | S6 1:128 |
| F | S3 1:4 | S3 1:8 | S3 1:16 | S3 1:32 | S3 1:64 | S3 1:128 | S6 1:4 | S6 1:8 | S6 1:16 | S6 1:32 | S6 1:64 | S6 1:128 |
| G | ST1 | ST2 | ST3 | ST4 | ST5 | ST6 | NC | PC | Media | | | |
| H | ST1 | ST2 | ST3 | ST4 | ST5 | ST6 | NC | PC | Media | | | |

| | |
|---|---|
| Tech: | |
| Date: | |
| Time start (T=0h): | |
| Plate label: | |
| Read by: | |
| Date read: | |
| Time read: | |
| Read program: | |
| File name: | |

FIG. 24

DETECTION ASSAYS FOR CORONAVIRUS NEUTRALIZING ANTIBODIES

CROSS REFERENCE TO RELATED APPLICATIONS

This patent application is a U.S. National Phase of International Patent Application No. PCT/US2021/027909 filed on Apr. 19, 2021, which claims priority to U.S. Provisional Application No. 63/151,623, filed Feb. 19, 2021, U.S. Provisional Application No. 63/078,214, filed Sep. 14, 2020, U.S. Provisional Application No. 63/029,267, filed May 22, 2020, U.S. Provisional Application No. 63/020,445, filed May 5, 2020, U.S. Provisional Application No. 63/012,066, filed Apr. 17, 2020, and U.S. Provisional Application No. 63/012,074, filed Apr. 17, 2020, the disclosure of each of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Apr. 15, 2021, is named 250298_000213_SL.txt and is 147,568 bytes in size.

TECHNICAL FIELD

Described herein are methods for determining the presence of coronavirus neutralizing antibodies in a sample as well as associated compositions and kits. The methods of the disclosure use recombinant vesicular stomatitis virus (VSV) particles, wherein the VSV glycoprotein (G) is replaced by a coronavirus spike(S) glycoprotein or a fragment or a derivative thereof. In a specific embodiment, the S glycoprotein is derived from Severe Acute Respiratory Syndrome coronavirus 2 (SARS-CoV-2) and the methods are used for determining the presence of SARS-CoV-2 neutralizing antibodies.

BACKGROUND

Three coronaviruses are known to cause severe pneumonia in humans: Severe Acute Respiratory Syndrome coronavirus (SARS-CoV or SARS-CoV-1), Middle East Respiratory Syndrome coronavirus (MERS-CoV), and Severe Acute Respiratory Syndrome coronavirus 2 (SARS-CoV-2). SARS-CoV-1 emerged in China in 2002 and spread to five continents infecting over 8,000 people and causing 774 deaths. MERS-CoV emerged in 2012 in the Arabian Peninsula infecting almost 2,500 people and causing 858 deaths in 27 countries. In December 2019, a new coronavirus emerged in Wuhan, China and caused an acute respiratory disease now known as coronavirus disease 2019 (COVID-19) (Zhou et al., Nature, published online Feb. 3, 2020; available at doi.org/10.1038/s41586-020-2012-7; Zhu et al., New Engl J Med, 2020, 382:727-733). COVID-19 symptoms include fever, cough, shortness of breath, pneumonia, acute respiratory distress syndrome (ARDS), acute lung syndrome, loss of sense of smell, loss of sense of taste, sore throat, nasal discharge, gastro-intestinal symptoms (e.g., diarrhea), organ failure (e.g., kidney failure and renal dysfunction), septic shock and death in severe cases. The virus causing COVID-19 was identified to be related to SARS-CoV-1 and thus was named SARS-CoV-2 (also sometimes referenced as nCov-2019, Wuhan coronavirus, or SARS nCoV19). While some individuals are asymptomatic or experience only mild illness, many experience severe symptoms and require hospitalization. SARS-CoV-2 spread quickly around the globe and was declared a global pandemic on Mar. 11, 2020 by the World Health Organization. As of May 20, 2020, the virus has infected almost 5 million people worldwide causing more than 328,000 deaths. Many of the patients who develop COVID-19 have mild upper respiratory symptoms, but some (especially older people and people with underlying medical conditions such as chronic lung disease, asthma, heart conditions, diabetes, immunocompromised patients, etc.) develop atypical pneumonia and its associated complications (Wölfel et al., Nature, published online on Apr. 1, 2020, available at doi.org/10.1038/s41586-020-2196-x). SARS-CoV-2 is highly contagious and can be spread by asymptomatic carriers.

PCR assays that detect active SARS-CoV-2 infection are playing an important role in tracking disease spread, while serological tests that detect antibodies against SARS-CoV-2 are being used to detect and measure previous infections, identify individuals who are likely immune to SARS-CoV-2 and evaluate the efficacy of vaccines and therapies. How well the available serological tests accurately reflect antibody-mediated immunity is still poorly understood.

Generation of virus-neutralizing antibodies is essential for blocking subsequent viral infections, and the presence of neutralizing antibodies correlates with protective immunity following vaccination (Koff 2013). Yet typically, only a small subset of virus-specific antibodies are neutralizing. It is not currently understood how total antibody levels relate to neutralizing antibody levels for SARS-CoV-2, and improved testing of SARS-CoV-2 neutralizing antibody responses is urgently needed. Early data from convalescent plasma therapy trials have shown promising results (Casadevall 2020), but screening of plasma donors is inadequate if acceptance criteria are based on total anti-SARS2-CoV-2 antibody levels and not specifically on neutralizing antibody levels. Likewise, efficacy studies of new SARS-CoV-2 vaccines must consider not only total antibody responses, but neutralizing antibody responses.

Thus, there is a great need in the art for a potent and efficient seropositivity assay for SARS-CoV-2 and other coronaviruses, especially for assays assessing virus neutralizing antibodies.

SUMMARY

As specified in the Background section, above, there is a great need for development of effective seropositivity assays for SARS-CoV-2 and other coronaviruses, especially for assays assessing virus neutralizing antibodies. The present disclosure addresses these and other needs. The present disclosure provides assays for determining the presence of coronavirus neutralizing antibodies in a sample as well as associated compositions and kits. The seropositivity assays of the disclosure use recombinant vesicular stomatitis virus (VSV) particles, wherein the VSV glycoprotein (G) is replaced by a coronavirus spike(S) glycoprotein or a fragment or a derivative thereof. In a specific embodiment, the S glycoprotein is derived from Severe Acute Respiratory Syndrome coronavirus 2 (SARS-CoV-2) and the methods are used for determining the presence of SARS-CoV-2 neutralizing antibodies.

In one aspect, provided herein is a method for determining the presence of a coronavirus neutralizing antibody in a sample, the method comprising:

a) contacting the sample with a recombinant rhabdovirus particle, wherein the rhabdovirus glycoprotein (G) is replaced by a coronavirus spike(S) glycoprotein or a fragment or a derivative thereof, wherein said S glycoprotein, fragment or derivative is capable of mediating infection of a first target cell and a second target cell;

b) after step (a), contacting the recombinant rhabdovirus particle with the first target cell expressing a first portion of a reporter protein and the second target cell expressing a second portion of the reporter protein to form a syncytium comprising both the first and the second portion of the reporter protein and producing a detectable reporter signal, and wherein the first target cell and the second target cell are capable of fusing with one another when contacted with the recombinant rhabdovirus particle;

c) measuring the reporter signal in the cells after step (b), and d) comparing the reporter signal measured in step (c) with a control.

In one embodiment, both the first target cell and/or the second target cell comprise angiotensin-converting enzyme 2 (ACE2).

In one embodiment, the first target cell is Vero-DSP1 (Vero-DSP-1-Puro; CLR-73) and the second target cell is Vero-DSP2 (Vero-DSP-2-Puro; CLR-74).

In one embodiment, the first portion of the reporter protein comprises amino acids 1-229 of *Renilla* luciferase or a mutant thereof and the second portion of the reporter protein comprises amino acids 230-311 of *Renilla* luciferase or a mutant thereof. In another embodiment, the first portion of the reporter protein comprises amino acids 1-155 of *Renilla* luciferase or a mutant thereof and the second portion of the reporter protein comprises amino acids 156-311 of *Renilla* luciferase or a mutant thereof. In one specific embodiment, the first portion of the reporter protein comprises amino acids 1-155 of *Renilla* luciferase mutant RLuc8 and the second portion of the reporter protein comprises amino acids 156-311 of *Renilla* luciferase mutant RLuc8.

In one embodiment, the first portion of the reporter protein comprises amino acids 1-156 of green fluorescent protein (GFP) or a mutant thereof, and the second portion of the reporter protein comprises amino acids 157-231 of GFP or a mutant thereof. In another embodiment, the first portion of the reporter protein comprises amino acids 1-213 of superfolder GFP, and the second portion of the reporter protein comprises amino acids 214-230 of superfolder GFP. In yet another embodiment, the first portion of the reporter protein comprises amino acids 1-154 of superfolder yellow fluorescent protein (YFP), and the second portion of the reporter protein comprises amino acids 155-262 of superfolder YFP.

In another aspect, provided herein a method for determining the presence of a coronavirus neutralizing antibody in a sample, the method comprising:

a) contacting the sample with a recombinant rhabdovirus particle wherein (i) the rhabdovirus glycoprotein (G) is replaced by a coronavirus spike(S) glycoprotein or a fragment or a derivative thereof, wherein said S glycoprotein, fragment or derivative is capable of mediating infection of a target cell and wherein (ii) the rhabdovirus particle comprises a reporter protein and/or a nucleic acid molecule encoding said reporter protein;

b) after step (a), contacting the recombinant rhabdovirus particle with the target cell;

c) measuring the reporter signal in the cell after step (b), and d) comparing the reporter signal measured in step (c) with a control.

In one embodiment, the recombinant rhabdovirus particle comprises a nucleic acid molecule encoding said reporter protein. In one specific embodiment, the nucleic acid sequence encoding the reporter protein is inserted between the nucleic acid sequence encoding the coronavirus S glycoprotein or the fragment or derivative thereof and the nucleic acid sequence encoding the rhabdovirus large (L) protein. In one embodiment, the target cell is a Vero cell (including Vero-αHis cell), Vero-Ace-2 cell, Vero-TRMPSS2 cell, or Vero-E6 cell. In one embodiment, the target cell comprises angiotensin-converting enzyme 2 (ACE2). In one embodiment, the genome of the recombinant rhabdovirus particle lacks a functional rhabdovirus G gene and encodes the coronavirus S glycoprotein, fragment or derivative thereof. In one embodiment, the genome of the recombinant rhabdovirus particle lacks the rhabdovirus G gene and encodes the coronavirus S glycoprotein, fragment or derivative thereof.

In one embodiment of any of the above methods, the recombinant rhabdovirus particle is a recombinant vesiculovirus particle. In one embodiment of any of the above methods, the recombinant vesiculovirus particle is a recombinant vesicular stomatitis virus (VSV) particle.

In one embodiment of any of the above methods, the reporter protein comprises a luciferase. Non-limiting examples of useful luciferase include, e.g., *Renilla* luciferase, RLuc8 mutant *Renilla* luciferase, (dCpG) Luciferase, NanoLuc reporter, firefly luciferase, *Gaussia* luciferase (gLuc), MetLuc, *Vibrio fischeri* lumazine protein, *Vibrio harveyi* luminaze protein, inoflagellate luciferase, firefly luciferase YY5 mutant, firefly luciferase LGR mutant, firefly luciferase mutant E, and fragments or derivatives thereof.

In one embodiment of any of the above methods, the reporter protein comprises a fluorescent protein. Non-limiting examples of useful fluorescent proteins include, e.g., green fluorescent protein (GFP), GFP-like fluorescent proteins, (GFP-like), enhanced green fluorescent protein (EGFP), yellow fluorescent protein (YFP), enhanced yellow fluorescent protein (EYFP), blue fluorescent protein (BFP), enhanced blue fluorescent protein (EBFP), cyan fluorescent protein (CFP), enhanced cyan fluorescent protein (ECFP); red fluorescent protein, superfolder GFP, superfolder YFP, orange fluorescent protein, red fluorescent protein, small ultrared fluorescent protein, FMN-binding fluorescent protein, dsRed, qFP611, Dronpa, TagRFP, KFP, EosFP, IrisFP, Dendra, Kaede, KikGr1, emerald fluorescent protein, Azami Green, mWasabi, TagGFP, TurboGFP, AcGFP, ZsGreen, T-Sapphire, and fragments or derivatives thereof.

In one embodiment of any of the above methods, the method comprises adding a reporter protein substrate for obtaining the reporter signal. Non-limiting examples of useful reporter protein substrates for luciferases include, e.g., Luciferin (e.g., d-luciferin), EnduRen, and coelenterazine luciferase substrates.

In one embodiment of any of the above methods, the recombinant rhabdovirus particle is a replication competent rhabdovirus particle.

In one embodiment of any of the above methods, the coronavirus S glycoprotein, fragment or derivative thereof is derived from Severe Acute Respiratory Syndrome coronavirus 2 (SARS-CoV-2). In one embodiment, the coronavirus S glycoprotein is a full-length SARS-CoV-2 S glycoprotein. In one specific embodiment, the SARS-CoV-2 S glycoprotein comprises the amino acid sequence of SEQ ID NO: 1. In one specific embodiment, the SARS-CoV-2 S glycoprotein consists of the amino acid sequence of SEQ ID NO: 1. In another embodiment, the coronavirus S glycoprotein fragment is a SARS-CoV-2 S glycoprotein fragment lacking 19 C-terminal amino acids. In one specific embodiment, the SARS-CoV-2 S glycoprotein fragment comprises the amino acid sequence of SEQ ID NO: 3. In one specific embodiment, the SARS-CoV-2 S glycoprotein fragment consists of the amino acid sequence of SEQ ID NO: 3. In one embodiment, the coronavirus S glycoprotein fragment or derivative has at least 77% amino acid sequence identity to the amino acid sequence of SEQ ID NO: 1. In one embodiment, the coronavirus S glycoprotein fragment or derivative has at least 64% amino acid sequence identity to S1 subunit of the amino acid sequence of SEQ ID NO: 1. In one embodiment, the coronavirus S glycoprotein fragment or derivative has at least 64% amino acid sequence identity to amino acids 14-684 of the amino acid sequence of SEQ ID NO: 1. In one embodiment, the coronavirus S glycoprotein fragment or derivative has at least 74% amino acid sequence identity to RBD domain of the amino acid sequence of SEQ ID NO: 1. In one embodiment, the coronavirus S glycoprotein fragment or derivative has at least 74% amino acid sequence identity to amino acids 319-541 of the amino acid sequence of SEQ ID NO: 1. In one embodiment, the coronavirus S glycoprotein fragment or derivative results in a more fusogenic recombinant rhabdovirus particle as compared to a comparable recombinant rhabdovirus comprising the rhabdovirus genome expressing a full-length wild-type SARS-CoV-2 S glycoprotein inserted in the same location of the rhabdovirus genome. In certain embodiments, the SARS-CoV-2 S glycoprotein derivative, or fragment thereof, may comprise or consist of an insertion, deletion, and/or substitution of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 residues of the SARS-CoV-2 S glycoprotein. Non-limiting examples of amino acids for potential deletion include, e.g., a tyrosine at position (145), an asparagine at position (679), a serine at position (680), proline at position (681), an arginine at position (682), an arginine at position (683), an alanine at position (684), and/or an arginine at position (685), positions as denoted in SEQ ID NO: 1, or the equivalent amino acid residue in a mutant SARS-CoV-2 S glycoprotein sequence. Non-limiting examples of amino acids for potential substitution include, e.g., a leucine changed to a phenylalanine at position (5) a tyrosine changed to an asparagine at position (28), a threonine changed to an isoleucine at position (29), a histidine changed to a tyrosine at position (49), a leucine changed to a phenylalanine at position (54), an asparagine changed to a lysine at position (74), a glutamic acid changed to an aspartic acid at position (96), an aspartic acid changed to an asparagine at position (111), a phenylalanine changed to a leucine at position (157), a glycine changed to a valine at position (181), a serine changed to a tryptophan at position (221), a serine changed to an arginine at position (247), an alanine changed to a threonine at position (348), an arginine changed to an isoleucine at position (408), a glycine changed to a serine at position (476), a valine changed to an alanine at position (483), a histidine changed to a glutamine at position (519), an alanine changed to a serine at position (520), an aspartic acid changed to an asparagine at position (614), an aspartic acid changed to a glycine at position (614), an asparagine changed to an isoleucine at position (679), a serine change to a leucine at position (680), an arginine changed to a glycine at position (682), an arginine changed to a serine at position (683), an arginine changed to a glutamine at position (685), an arginine changed to a serine at position (685), a phenylalanine changed to a cysteine at position (797), an alanine changed to a valine at position (930), an aspartic acid changed to a tyrosine at position (936), an alanine changed to a valine at position (1078), an aspartic acid changed to a histidine at position (1168), and/or an aspartic acid changed to a histidine at position (1259), positions as denoted in SEQ ID NO: 1, or the equivalent amino acid residue in a mutant SARS-CoV-2 S glycoprotein sequence. See Becerra-Flores and Cardozo, "SARS-CoV-2 viral spike G614 mutation exhibits higher case fatality rate," *The International Journal of Clinical Practice*, published online May 6, 2020; Eaaswarkhanth et al., "Could the D614G substitution in the SARS-CoV-2 spike(S) protein be associated with higher COVID-19 mortality?" *International Journal of Infectious Diseases,* 96: July 2020, Pages 459-460; Tang et al., "The SARS-CoV-2 Spike Protein D614G Mutation Shows Increasing Dominance and May Confer a Structural Advantage to the Furin Cleavage Domain," *Preprints* 2020, 2020050407 (doi: 10.20944/preprints 202005.0407.v1); Hansen et. al., "Studies in humanized mice and convalescent humans yield a SARS-CoV-2 antibody cocktail" Science, published online Jun. 15, 2020; Lokman et al., "Exploring the genomic and proteomic variations of SARS-CoV-2 spike glycoprotein: A computational biology approach", *Infection, Genetics and Evolution: Journal of Molecular Epidemiology and Evolutionary Genetics in Infectious Diseases,* 2020 June; 84:104389. DOI: 10.1016/j.meegid.2020.104389, each of which incorporated herein by reference in their entirety for all intended purposes. Additional non-limiting examples of amino acid residue positions for insertion, deletion, and/or substitution include those as listed in Tables 8 and 9 (amino acid residue positions are denoted using SEQ ID NO: 1 as a reference sequence, which can be used as a reference for identifying the equivalent amino acid residue in any SARS-CoV-2 S glycoprotein sequence (same as above); references in Table 8 are incorporated herein by reference in their entirety for all intended purposes). Each residue modification listed in Table 8 can separately be used alone or in combination with others to generate variants of a recombinant vesicular stomatitis virus (VSV) particle. In certain embodiments, the SARS-CoV-2 S glycoprotein derivative, or fragments thereof, differs in amino acid sequence from the reference peptide or polypeptide (e.g., wild-type SARS-CoV-2 spike protein) by changing a serine to an arginine at position (247), an aspartic acid to an asparagine at position (614), and/or an arginine to a glutamine at position (685), positions as denoted in SEQ ID NO: 1, or the equivalent amino acid residue in a mutant SARS-CoV-2 S glycoprotein sequence. In certain embodiments, the SARS-CoV-2 S glycoprotein derivative, or fragments thereof, differs in amino acid sequence from the reference peptide or polypeptide by changing a serine to an arginine at position (247). In certain embodiments, the SARS-CoV-2 S glycoprotein derivative, or fragments thereof, differs in amino acid sequence from the reference peptide or polypeptide by changing an aspartic acid to an asparagine at position (614). In certain embodiments, the SARS-CoV-2 S glycoprotein derivative, or fragments thereof, differs in amino acid sequence from the reference peptide or polypeptide by changing an arginine to a glutamine at position (685). In certain embodiments, the SARS-CoV-2 S glycoprotein derivative, or fragments thereof, differs in amino acid sequence from the reference peptide or polypeptide by changing a serine to an arginine at position (247) and an aspartic acid to an asparagine at position (614). In certain embodiments, the SARS-CoV-2 S glycoprotein derivative, or fragments thereof, differs in amino acid sequence from the reference peptide or polypeptide by changing a serine to an arginine at position (247) and an arginine to a glutamine at position (685). In certain embodiments, the SARS-CoV-2 S glycoprotein derivative, or fragments thereof, differs in amino acid sequence from the reference peptide or polypeptide by changing an aspartic acid to an asparagine at position (614) and an arginine to a glutamine at position (685). In certain embodiments, the SARS-CoV-2 S glycoprotein derivative, or fragments thereof, differs in amino acid sequence from the reference peptide or polypeptide by changing a serine to an arginine at position (247), an aspartic acid to an asparagine at position (614), and an arginine to a glutamine at position (685). In certain embodiments, the SARS-CoV-2 S glycoprotein derivative, or fragments thereof, result in a more lytic phenotype. In certain embodiments, the SARS-CoV-2 S glycoprotein fragment or derivative may comprise the amino acid sequence of SEQ ID NO: 42, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to the amino acid sequence of SEQ ID NO: 42. In certain embodiments, the SARS-CoV-2 S glycoprotein fragment or derivative may be encoded by a codon optimized nucleotide sequence. In various embodiments, SARS-CoV-2 S glycoprotein fragment or derivative may be encoded by the polynucleotide sequence of SEQ ID NO: 43 or a sequence that has at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% polynucleotide sequence identity to SEQ ID NO: 43. In certain embodiments, the SARS-CoV-2 S glycoprotein fragment or derivative may comprise the amino acid sequence of SEQ ID NO: 44, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to the amino acid sequence of SEQ ID NO: 44. In certain embodiments, the SARS-CoV-2 S glycoprotein derivative, or fragments thereof, differs in amino acid sequence from the reference peptide or polypeptide (e.g., wild-type SARS-CoV-2 spike protein) by changing an asparagine to a tyrosine at position (501), and/or a glutamic acid to a lysine at position (484), and/or an aspartic acid to a glycine at position (614), and/or deletion of residues 69-70, positions as denoted in SEQ ID NO: 1, or the equivalent amino acid residue in a mutant SARS-CoV-2 S glycoprotein sequence. In certain embodiments, the SARS-CoV-2 S glycoprotein derivative, or fragments thereof, differs in amino acid sequence from the reference peptide or polypeptide by changing an asparagine to a tyrosine at position (501). In certain embodiments, the SARS-CoV-2 S glycoprotein derivative, or fragments thereof, differs in amino acid sequence from the reference peptide or polypeptide by changing a glutamic acid to a lysine at position (484). In certain embodiments, the SARS-CoV-2 S glycoprotein derivative, or fragments thereof, differs in amino acid sequence from the reference peptide or polypeptide by changing an aspartic acid to a glycine at position (614). In certain embodiments, the SARS-CoV-2 S glycoprotein derivative, or fragments thereof, differs in amino acid sequence from the reference peptide or polypeptide by deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501) and a glutamic acid to a lysine at position (484). In certain embodiments, the SARS-CoV-2 S glycoprotein derivative, or fragments thereof, differs in amino acid sequence from the reference peptide or polypeptide by changing an asparagine to a tyrosine at position (501) and an aspartic acid to a glycine at position (614). In certain embodiments, the SARS-CoV-2 S glycoprotein derivative, or fragments thereof, differs in amino acid sequence from the reference peptide or polypeptide by changing an asparagine to a tyrosine at position (501) and deletion of residues 69-70. In certain embodiments, the SARS-CoV-2 S glycoprotein derivative, or fragments thereof, differs in amino acid sequence from the reference peptide or polypeptide by changing a glutamic acid to a lysine at position (484) and an aspartic acid to a glycine at position (614). In certain embodiments, the SARS-CoV-2 S glycoprotein derivative, or fragments thereof, differs in amino acid sequence from the reference peptide or polypeptide by changing a glutamic acid to a lysine at position (484) and deletion of residues 69-70. In certain embodiments, the SARS-CoV-2 S glycoprotein derivative, or fragments thereof, differs in amino acid sequence from the reference peptide or polypeptide by changing an aspartic acid to a glycine at position (614) and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), a glutamic acid to a lysine at position (484), and an aspartic acid to a glycine at position (614). In certain embodiments, the SARS-CoV-2 S glycoprotein derivative, or fragments thereof, differs in amino acid sequence from the reference peptide or polypeptide by changing an asparagine to a tyrosine at position (501), changing a glutamic acid to a lysine at position (484), and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), changing an aspartic acid to a glycine at position (614), and deletion of residues 69-70. In certain embodiments, the SARS-CoV-2 S glycoprotein derivative, or fragments thereof, differs in amino acid sequence from the reference peptide or polypeptide by changing a glutamic acid to a lysine at position (484), changing an aspartic acid to a glycine at position (614), and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), changing a glutamic acid to a lysine at position (484), changing an aspartic acid to a glycine at position (614) and deletion of residues 69-70. In certain embodiments, the SARS-CoV-2 S glycoprotein derivative, or fragments thereof, differs in amino acid sequence from the reference peptide or polypeptide (e.g., wild-type SARS-CoV-2 spike protein) by inactivating the furin cleavage site within the spike protein. In certain embodiments, the SARS-CoV-2 S glycoprotein derivative, or fragments thereof, differs in amino acid sequence from the reference peptide or polypeptide (e.g., wild-type SARS-CoV-2 spike protein) by changing Q677TNSPRRARSV687 (SEQ ID NO: 65), as denoted in SEQ ID NO: 1, or the equivalent amino acid residue in a mutant SARS-CoV-2 S glycoprotein sequence, to QTILRSV (SEQ ID NO: 66) or to QTNSPGSASSV (SEQ ID NO: 67). In certain embodiments, the SARS-CoV-2 S glycoprotein derivative, or fragments thereof, result in a monobasic furin cleavage site in the S1/S2 interface (QTILRSV (SEQ ID NO: 66)) or deletion of the furin cleavage site (QTNSPGSASSV (SEQ ID NO: 67)) phenotype. In certain embodiments, the alteration to the furin cleavage site can lead to a spike stabilized pseudoparticles. See Hansen et. al., "Studies in humanized mice and convalescent humans yield a SARS-CoV-2 antibody cocktail" Science, published online Jun. 15, 2020, incorporated herein by reference in its entirety for all intended purposes.

In certain embodiments of any of the above methods, step (a) comprises contacting the sample (e.g., simultaneously or sequentially) with two or more different recombinant rhabdovirus particles, wherein said two or more different recombinant rhabdovirus particles comprise different coronavirus spike(S) glycoproteins, fragments or derivatives thereof. In certain embodiments, at least one of the two or more different coronavirus spike(S) glycoproteins, fragments or derivatives thereof comprises the amino acid sequence selected from SEQ ID NO: 1, SEQ ID NO: 3 and SEQ ID NO: 44, or comprises one or more amino acid insertions, deletions, and/or substitutions listed in Tables 8 and 9, wherein the positions of said insertions, deletions, and/or substitutions are specified in relation to SEQ ID NO: 1. In certain embodiments of the methods, wherein the rhabdovirus particles comprise reporter proteins and/or nucleic acid molecules encoding said reporter proteins, the two or more different recombinant rhabdovirus particles comprise different reporter proteins and/or different nucleic acid molecules encoding said different reporter proteins. In certain embodiments of the methods, wherein the rhabdovirus particles comprise reporter proteins and/or nucleic acid molecules encoding said reporter proteins, the two or more different recombinant rhabdovirus particles comprise the same reporter proteins and/or the same nucleic acid molecules encoding said reporter proteins.

In one embodiment, provided herein a method for determining the presence of a Severe Acute Respiratory Syndrome coronavirus 2 (SARS-CoV-2) neutralizing antibody in a sample, the method comprising:

a) contacting the sample with a replication competent recombinant vesicular stomatitis virus (VSV) particle, wherein the genome of the recombinant VSV particle lacks a functional VSV glycoprotein (G) gene and encodes the full-length SARS-CoV-2 spike(S) glycoprotein or a fragment thereof lacking 19 C-terminal amino acids;
b) after step (a), contacting the recombinant VSV particle with a mixture of Vero-DSP1 cells and Vero-DSP2 cells;
c) measuring the luciferase signal and/or GFP signal in the cells after step (b), and
d) comparing the signal measured in step (c) with a control.

In another embodiment, provided herein is a method for determining the presence of a Severe Acute Respiratory Syndrome coronavirus 2 (SARS-CoV-2) neutralizing antibody in a sample, the method comprising:

a) contacting the sample with a replication competent recombinant vesicular stomatitis virus (VSV) particle wherein (i) the genome of the recombinant VSV particle lacks a functional VSV glycoprotein (G) gene and encodes the full-length SARS-CoV-2 spike(S) glycoprotein or a fragment thereof lacking 19 C-terminal amino acids and wherein (ii) the genome of the recombinant VSV particle further encodes a luciferase protein;
b) after step (a), contacting the recombinant VSV particle with a cell selected from Vero cell, Vero-Ace-2 cell and Vero-E6 cell;
c) measuring the luciferase signal in the cell after step (b), and
d) comparing the signal measured in step (c) with a control.

In one embodiment of the above two methods, the full-length SARS-CoV-2 S glycoprotein consists of the amino acid sequence of SEQ ID NO: 1. In one embodiment of the above two methods, the SARS-CoV-2 S glycoprotein fragment lacking 19 C-terminal amino acids consists of the amino acid sequence of SEQ ID NO: 3.

In certain embodiments of the above two methods, step (a) comprises contacting the sample (e.g., simultaneously or sequentially) with two or more different recombinant VSV particles, wherein said two or more different recombinant VSV particles comprise different full-length SARS-CoV-2 S glycoproteins or fragments thereof lacking 19 C-terminal amino acids. In certain embodiments, at least one of the two or more different full-length SARS-CoV-2 S glycoproteins or fragments thereof lacking 19 C-terminal amino acids comprises the amino acid sequence selected from SEQ ID NO: 1, SEQ ID NO: 3 and SEQ ID NO: 44, or comprises one or more amino acid insertions, deletions, and/or substitutions listed in Tables 8 and 9, wherein the positions of said insertions, deletions, and/or substitutions are specified in relation to SEQ ID NO: 1. In certain embodiments of the methods, wherein the VSV particles comprise reporter proteins and/or nucleic acid molecules encoding said reporter proteins, the two or more different recombinant VSV particles comprise different reporter proteins and/or different nucleic acid molecules encoding said different reporter proteins. In certain embodiments of the methods, wherein the VSV particles comprise reporter proteins and/or nucleic acid molecules encoding said reporter proteins, the two or more different recombinant VSV particles comprise the same reporter proteins and/or the same nucleic acid molecules encoding said reporter proteins.

In one embodiment of any of the above methods, after step (b) and before step (c) cells are exposed to trypsin.

In one embodiment of any of the above methods, the recombinant rhabdovirus particle comprises a mutant rhabdovirus matrix (M) protein. In one embodiment, the genome of the recombinant rhabdovirus particle encodes a mutant rhabdovirus M protein. In one embodiment, the recombinant rhabdovirus particle is a recombinant VSV particle comprising the mutant VSV M protein which comprises a mutation at methionine 51. In one specific embodiment, the mutation at methionine 51 is from methionine (M) to arginine (R). In one specific embodiment, the mutant VSV M protein comprises the amino acid sequence of SEQ ID NO: 7. In one specific embodiment, the mutant VSV M protein consists of the amino acid sequence of SEQ ID NO: 7.

In one embodiment of any of the above methods, the recombinant rhabdovirus particle comprises a wild-type rhabdovirus matrix (M) protein. In one embodiment, the genome of the recombinant rhabdovirus particle encodes a wild-type rhabdovirus M protein. In one embodiment, the recombinant rhabdovirus particle is a recombinant VSV particle comprising the wild-type VSV M protein which comprises the amino acid sequence of SEQ ID NO: 9. In one specific embodiment, the wild-type VSV M protein consists of the amino acid sequence of SEQ ID NO: 9.

In one embodiment of any of the above methods, the sample is serum or plasma. In one embodiment of any of the above methods, the sample is saliva. In one embodiment of any of the above methods, the sample is a dried bloodspot. In one embodiment, the method further comprises diluting the sample by a factor of about 1:10 to about 1:320. For example, the sample may be diluted by a factor of about 1:10, about 1:16, about 1:20, about 1:32, about 1:64, about 1:80, about 1:100, about 1:128, or about 1:160. In one embodiment the method further comprises diluting the sample by a factor of about 1:100. In one embodiment the method further comprises diluting the sample by a factor of about 1:20. In some embodiments, the method further comprises diluting the recombinant rhabdovirus particle to about 200-800 pfu/well. For example, the recombinant rhabdovirus particle may be diluted to about 200, about 300, about 400, about 500, about 600, about 700, about 720, or about 800 pfu/well. In one embodiment, the sample is heat-inactivated. In another embodiment, the sample is not heat-inactivated. In one embodiment, the method further comprises treating the sample with an antibiotic and/or filtering the sample to prevent bacterial contamination.

In one embodiment of any of the above methods, the control is the reporter signal obtained with a control sample not comprising the coronavirus neutralizing antibodies, and the method comprises concluding that the tested sample comprises the coronavirus neutralizing antibodies when the reporter signal obtained in step (c) is reduced as compared to the control. In one embodiment, the method comprises concluding that the tested sample comprises the coronavirus neutralizing antibodies when the reporter signal obtained in step (c) is reduced by more than 50% as compared to the control. In one embodiment, the method further comprises comparing the reporter signal obtained in step (c) with the reporter signal obtained with a control sample comprising a coronavirus neutralizing antibody, or a molecule that blocks interaction of the coronavirus S glycoprotein with a protein with which it interacts on the target cell, or a molecule that blocks target cell fusion, or any combination thereof. In one embodiment, the method comprises determining the concentration of coronavirus neutralizing antibodies in the tested sample by comparing the reporter signal to a calibration curve determined from a serial dilution of the control sample comprising a coronavirus neutralizing antibody, or a molecule that blocks interaction of the coronavirus S glycoprotein with a protein with which it interacts on the target cell, or any combination thereof. In one specific embodiment, the control sample comprises mAb10914. In one specific embodiment, the serial dilution of the control sample comprises about 0.01 μg/mL to about 3 μg/mL mAb10914. In one specific embodiment, the control sample comprises mAb10922. In one specific embodiment, the serial dilution of the control sample comprises about 0.01 μg/mL to about 3 μg/mL mAb10922.

In one embodiment of any of the above methods, the report signal has been corrected to remove background signal measured from a control sample not contacted with the recombinant rhabdovirus particle.

In one embodiment of any of the above methods, the reporter signal is measured between about 18 to 30 hours after step (b). In one embodiment of any of the above methods, the reporter signal is measured between about 24 to 30 hours after step (b).

In one embodiment of any of the above methods, in step (a) the sample is contacted with the recombinant rhabdovirus particle for about 30 minutes at room temperature.

In one embodiment of any of the above methods, the method is conducted in a high throughput format. In one specific embodiment, the method is conducted in a 96-well plate. In one specific embodiment, when the method is conducted in a 96-well plate, density of the first target cell and the second target cell is about $6\times10^4$ cells/well.

In another aspect, provided herein is a recombinant rhabdovirus particle, wherein the rhabdovirus glycoprotein (G) is replaced by a coronavirus spike(S) glycoprotein or a fragment or a derivative thereof, wherein said S glycoprotein, fragment or derivative is capable of mediating infection of a target cell.

In one embodiment, the rhabdovirus particle further comprises a reporter protein and/or a nucleic acid molecule encoding said reporter protein. In one embodiment, the rhabdovirus particle comprises a nucleic acid molecule encoding said reporter protein. In one specific embodiment, the nucleic acid sequence encoding the reporter protein is inserted between the nucleic acid sequence encoding the coronavirus S glycoprotein or the fragment or derivative thereof and the nucleic acid sequence encoding rhabdovirus large (L) protein.

In one embodiment, the recombinant rhabdovirus particle is a replication competent rhabdovirus particle.

In one embodiment, the recombinant rhabdovirus particle is a recombinant vesiculovirus particle. In one embodiment, the recombinant vesiculovirus particle is a recombinant vesicular stomatitis virus (VSV) particle.

In one embodiment, the coronavirus S glycoprotein, fragment or derivative thereof is derived from Severe Acute Respiratory Syndrome coronavirus 2 (SARS-CoV-2). In one embodiment, the coronavirus S glycoprotein is a full-length SARS-CoV-2 S glycoprotein. In one specific embodiment, the SARS-CoV-2 S glycoprotein comprises the amino acid sequence of SEQ ID NO: 1. In one specific embodiment, the SARS-CoV-2 S glycoprotein consists of the amino acid sequence of SEQ ID NO: 1. In one embodiment, the coronavirus S glycoprotein fragment is a SARS-CoV-2 S glycoprotein fragment lacking 19 C-terminal amino acids. In one specific embodiment, the SARS-CoV-2 S glycoprotein fragment comprises the amino acid sequence of SEQ ID NO: 3. In one specific embodiment, the SARS-CoV-2 S glycoprotein fragment consists of the amino acid sequence of SEQ ID NO: 3. In one embodiment, the coronavirus S glycoprotein fragment or derivative has at least 77% amino acid sequence identity to the amino acid sequence of SEQ ID NO: 1. In one embodiment, the coronavirus S glycoprotein fragment or derivative has at least 64% amino acid sequence identity to S1 subunit of the amino acid sequence of SEQ ID NO: 1. In one embodiment, the coronavirus S glycoprotein fragment or derivative has at least 64% amino acid sequence identity to amino acids 14-684 of the amino acid sequence of SEQ ID NO: 1. In one embodiment, the coronavirus S glycoprotein fragment or derivative has at least 74% amino acid sequence identity to RBD domain of the amino acid sequence of SEQ ID NO: 1. In one embodiment, the coronavirus S glycoprotein fragment or derivative has at least 74% amino acid sequence identity to amino acids 319-541 of the amino acid sequence of SEQ ID NO: 1. In one embodiment, the coronavirus S glycoprotein fragment or derivative results in a more fusogenic recombinant rhabdovirus particle as compared to a comparable recombinant rhabdovirus comprising the rhabdovirus genome expressing a full-length wild-type SARS-CoV-2 S glycoprotein inserted in the same location of the rhabdovirus genome. In certain embodiments, the SARS-CoV-2 S glycoprotein derivative, or fragment thereof, may comprise or consist of an insertion, deletion, and/or substitution of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 residues of the SARS-CoV-2 S glycoprotein. Non-limiting examples of amino acids for potential deletion include, e.g., a tyrosine at position (145), an asparagine at position (679), a serine at position (680), proline at position (681), an arginine at position (682), an arginine at position (683), an alanine at position (684), and/or an arginine at position (685), positions as denoted in SEQ ID NO: 1, or the equivalent amino acid residue in a mutant SARS-CoV-2 S glycoprotein sequence. Non-limiting examples of amino acids for potential substitution include, e.g., a leucine changed to a phenylalanine at position (5) a tyrosine changed to an asparagine at position (28), a threonine changed to an isoleucine at position (29), a histidine changed to a tyrosine at position (49), a leucine changed to a phenylalanine at position (54), an asparagine changed to a lysine at position (74), a glutamic acid changed to an aspartic acid at position (96), an aspartic acid changed to an asparagine at position (111), a phenylalanine changed to a leucine at position (157), a glycine changed to a valine at position (181), a serine changed to a tryptophan at position (221), a serine changed to an arginine at position (247), an alanine changed to a threonine at position (348), an arginine changed to an isoleucine at position (408), a glycine changed to a serine at position (476), a valine changed to an alanine at position (483), a histidine changed to a glutamine at position (519), an alanine changed to a serine at position (520), an aspartic acid changed to an asparagine at position (614), an aspartic acid changed to a glycine at position (614), an asparagine changed to an isoleucine at position (679), a serine change to a leucine at position (680), an arginine changed to a glycine at position (682), an arginine changed to a serine at position (683), an arginine changed to a glutamine at position (685), an arginine changed to a serine at position (685), a phenylalanine changed to a cysteine at position (797), an alanine changed to a valine at position (930), an aspartic acid changed to a tyrosine at position (936), an alanine changed to a valine at position (1078), an aspartic acid changed to a histidine at position (1168), and/or an aspartic acid changed to a histidine at position (1259), positions as denoted in SEQ ID NO: 1, or the equivalent amino acid residue in a mutant SARS-CoV-2 S glycoprotein sequence. See Becerra-Flores and Cardozo, "SARS-CoV-2 viral spike G614 mutation exhibits higher case fatality rate," *The International Journal of Clinical Practice*, published online May 6, 2020; Eaaswarkhanth et al., "Could the D614G substitution in the SARS-CoV-2 spike(S) protein be associated with higher COVID-19 mortality?" *International Journal of Infectious Diseases,* 96: July 2020, Pages 459-460; Tang et al., "The SARS-CoV-2 Spike Protein D614G Mutation Shows Increasing Dominance and May Confer a Structural Advantage to the Furin Cleavage Domain," *Preprints* 2020, 2020050407 (doi: 10.20944/preprints202005.0407.v1); Hansen et. al., "Studies in humanized mice and convalescent humans yield a SARS-CoV-2 antibody cocktail" *Science*, published online Jun. 15, 2020; Lokman et al., "Exploring the genomic and proteomic variations of SARS-CoV-2 spike glycoprotein: A computational biology approach", *Infection, Genetics and Evolution: Journal of Molecular Epidemiology and Evolutionary Genetics in Infectious Diseases,* 2020 June; 84:104389. DOI: 10.1016/j.meegid.2020.104389, each of which incorporated herein by reference in their entirety for all intended purposes. Additional non-limiting examples of amino acid residue positions for insertion, deletion, and/or substitution include those as listed in Tables 8 and 9 (amino acid residue positions are denoted using SEQ ID NO: 1 as a reference sequence, which can be used as a reference for identifying the equivalent amino acid residue in any SARS-CoV-2 S glycoprotein sequence (same as above); references in Table 8 are incorporated herein by reference in their entirety for all intended purposes). Each residue modification listed in Table 8 can separately be used alone or in combination with others to generate variants of a recombinant vesicular stomatitis virus (VSV) particle. In certain embodiments, the SARS-CoV-2 S glycoprotein derivative, or fragments thereof, differs in amino acid sequence from the reference peptide or polypeptide (e.g., wild-type SARS-CoV-2 spike protein) by changing a serine to an arginine at position (247), an aspartic acid to an asparagine at position (614), and/or an arginine to a glutamine at position (685), positions as denoted in SEQ ID NO: 1, or the equivalent amino acid residue in a mutant SARS-CoV-2 S glycoprotein sequence. In certain embodiments, the SARS-CoV-2 S glycoprotein derivative, or fragments thereof, differs in amino acid sequence from the reference peptide or polypeptide by changing a serine to an arginine at position (247). In certain embodiments, the SARS-CoV-2 S glycoprotein derivative, or fragments thereof, differs in amino acid sequence from the reference peptide or polypeptide by changing an aspartic acid to an asparagine at position (614). In certain embodiments, the SARS-CoV-2 S glycoprotein derivative, or fragments thereof, differs in amino acid sequence from the reference peptide or polypeptide by changing an arginine to a glutamine at position (685). In certain embodiments, the SARS-CoV-2 S glycoprotein derivative, or fragments thereof, differs in amino acid sequence from the reference peptide or polypeptide by changing a serine to an arginine at position (247) and an aspartic acid to an asparagine at position (614). In certain embodiments, the SARS-CoV-2 S glycoprotein derivative, or fragments thereof, differs in amino acid sequence from the reference peptide or polypeptide by changing a serine to an arginine at position (247) and an arginine to a glutamine at position (685). In certain embodiments, the SARS-CoV-2 S glycoprotein derivative, or fragments thereof, differs in amino acid sequence from the reference peptide or polypeptide by changing an aspartic acid to an asparagine at position (614) and an arginine to a glutamine at position (685). In certain embodiments, the SARS-CoV-2 S glycoprotein derivative, or fragments thereof, differs in amino acid sequence from the reference peptide or polypeptide by changing a serine to an arginine at position (247), an aspartic acid to an asparagine at position (614), and an arginine to a glutamine at position (685). In certain embodiments, the SARS-CoV-2 S glycoprotein derivative, or fragments thereof, result in a more lytic phenotype. In certain embodiments, the SARS-CoV-2 S glycoprotein fragment or derivative may comprise the amino acid sequence of SEQ ID NO: 42, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to the amino acid sequence of SEQ ID NO: 42. In certain embodiments, the SARS-CoV-2 S glycoprotein fragment or derivative may be encoded by a codon optimized nucleotide sequence. In various embodiments, SARS-CoV-2 S glycoprotein fragment or derivative may be encoded by the polynucleotide sequence of SEQ ID NO: 43 or a sequence that has at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% polynucleotide sequence identity to SEQ ID NO: 43. In certain embodiments, the SARS-CoV-2 S glycoprotein fragment or derivative may comprise the amino acid sequence of SEQ ID NO: 44, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to the amino acid sequence of SEQ ID NO: 44. In certain embodiments, the SARS-CoV-2 S glycoprotein derivative, or fragments thereof, differs in amino acid sequence from the reference peptide or polypeptide (e.g., wild-type SARS-CoV-2 spike protein) by changing an asparagine to a tyrosine at position (501), and/or a glutamic acid to a lysine at position (484), and/or an aspartic acid to a glycine at position (614), and/or deletion of residues 69-70, positions as denoted in SEQ ID NO: 1, or the equivalent amino acid residue in a mutant SARS-CoV-2 S glycoprotein sequence. In certain embodiments, the SARS-CoV-2 S glycoprotein derivative, or fragments thereof, differs in amino acid sequence from the reference peptide or polypeptide by changing an asparagine to a tyrosine at position (501). In certain embodiments, the SARS-CoV-2 S glycoprotein derivative, or fragments thereof, differs in amino acid sequence from the reference peptide or polypeptide by changing a glutamic acid to a lysine at position (484). In certain embodiments, the SARS-CoV-2 S glycoprotein derivative, or fragments thereof, differs in amino acid sequence from the reference peptide or polypeptide by changing an aspartic acid to a glycine at position (614). In certain embodiments, the SARS-CoV-2 S glycoprotein derivative, or fragments thereof, differs in amino acid sequence from the reference peptide or polypeptide by deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501) and a glutamic acid to a lysine at position (484). In certain embodiments, the SARS-CoV-2 S glycoprotein derivative, or fragments thereof, differs in amino acid sequence from the reference peptide or polypeptide by changing an asparagine to a tyrosine at position (501) and an aspartic acid to a glycine at position (614). In certain embodiments, the SARS-CoV-2 S glycoprotein derivative, or fragments thereof, differs in amino acid sequence from the reference peptide or polypeptide by changing an asparagine to a tyrosine at position (501) and deletion of residues 69-70. In certain embodiments, the SARS-CoV-2 S glycoprotein derivative, or fragments thereof, differs in amino acid sequence from the reference peptide or polypeptide by changing a glutamic acid to a lysine at position (484) and an aspartic acid to a glycine at position (614). In certain embodiments, the SARS-CoV-2 S glycoprotein derivative, or fragments thereof, differs in amino acid sequence from the reference peptide or polypeptide by changing a glutamic acid to a lysine at position (484) and deletion of residues 69-70. In certain embodiments, the SARS-CoV-2 S glycoprotein derivative, or fragments thereof, differs in amino acid sequence from the reference peptide or polypeptide by changing an aspartic acid to a glycine at position (614) and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), a glutamic acid to a lysine at position (484), and an aspartic acid to a glycine at position (614). In certain embodiments, the SARS-CoV-2 S glycoprotein derivative, or fragments thereof, differs in amino acid sequence from the reference peptide or polypeptide by changing an asparagine to a tyrosine at position (501), changing a glutamic acid to a lysine at position (484), and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), changing an aspartic acid to a glycine at position (614), and deletion of residues 69-70. In certain embodiments, the SARS-CoV-2 S glycoprotein derivative, or fragments thereof, differs in amino acid sequence from the reference peptide or polypeptide by changing a glutamic acid to a lysine at position (484), changing an aspartic acid to a glycine at position (614), and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), changing a glutamic acid to a lysine at position (484), changing an aspartic acid to a glycine at position (614) and deletion of residues 69-70. In certain embodiments, the SARS-CoV-2 S glycoprotein derivative, or fragments thereof, differs in amino acid sequence from the reference peptide or polypeptide (e.g., wild-type SARS-CoV-2 spike protein) by inactivating the furin cleavage site within the spike protein. In certain embodiments, the SARS-CoV-2 S glycoprotein derivative, or fragments thereof, differs in amino acid sequence from the reference peptide or polypeptide (e.g., wild-type SARS-CoV-2 spike protein) by changing Q677TNSPRRARSV687 (SEQ ID NO: 65), as denoted in SEQ ID NO: 1, or the equivalent amino acid residue in a mutant SARS-CoV-2 S glycoprotein sequence, to QTILRSV (SEQ ID NO: 66) or to QTNSPGSASSV (SEQ ID NO: 67). In certain embodiments, the SARS-CoV-2 S glycoprotein derivative, or fragments thereof, result in a monobasic furin cleavage site in the S1/S2 interface (QTILRSV (SEQ ID NO: 66)) or deletion of the furin cleavage site (QTNSPGSASSV (SEQ ID NO: 67)) phenotype. In certain embodiments, the alteration to the furin cleavage site can lead to a spike stabilized pseudoparticles. See Hansen et. al., "Studies in humanized mice and convalescent humans yield a SARS-CoV-2 antibody cocktail" Science, published online Jun. 15, 2020, incorporated herein by reference in its entirety for all intended purposes.

In one embodiment, the recombinant rhabdovirus particle comprises a mutant rhabdovirus matrix (M) protein. In one embodiment, the genome of the recombinant rhabdovirus particle encodes a mutant VSV M protein. In one specific embodiment, the recombinant rhabdovirus particle is a recombinant VSV particle comprising the mutant VSV M protein which comprises a mutation at methionine 51. In one specific embodiment, the mutation at methionine 51 is from methionine (M) to arginine (R). In one specific embodiment, the mutant VSV M protein comprises the amino acid sequence of SEQ ID NO: 7. In one specific embodiment, the mutant VSV M protein consists of the amino acid sequence of SEQ ID NO: 7.

In one embodiment, the recombinant rhabdovirus particle comprises a wild-type rhabdovirus matrix (M) protein. In one embodiment, the genome of the recombinant rhabdovirus particle encodes a wild-type rhabdovirus M protein. In one specific embodiment, the recombinant rhabdovirus particle is a recombinant VSV particle comprising the wild-type VSV M protein which comprises the amino acid sequence of SEQ ID NO: 9. In one specific embodiment, the wild-type VSV M protein consists of the amino acid sequence of SEQ ID NO: 9.

In another aspect, provided herein is a polynucleotide encoding a rhabdovirus nucleoprotein (N), a rhabdovirus phosphoprotein (P), and a rhabdovirus large protein (L), or functional fragments or derivatives thereof, and further encoding a Severe Acute Respiratory Syndrome coronavirus 2 (SARS-CoV-2) spike(S) glycoprotein or fragment or derivative thereof, for expression on the viral envelope of a recombinant rhabdovirus particle.

In one embodiment, the polynucleotide further encodes a reporter protein. In one specific embodiment, the nucleic acid sequence encoding the reporter protein is inserted between the nucleic acid sequence encoding the coronavirus S glycoprotein or the fragment or derivative thereof and the nucleic acid sequence encoding rhabdovirus large (L) protein.

In one embodiment, the recombinant rhabdovirus particle is a replication competent rhabdovirus particle. In one embodiment, the coronavirus S glycoprotein, fragment or derivative thereof is derived from Severe Acute Respiratory Syndrome coronavirus 2 (SARS-CoV-2). In one embodiment, the coronavirus S glycoprotein is a full-length SARS-CoV-2 S glycoprotein. In one specific embodiment, the SARS-CoV-2 S glycoprotein comprises the amino acid sequence of SEQ ID NO: 1. In one specific embodiment, the SARS-CoV-2 S glycoprotein consists of the amino acid sequence of SEQ ID NO: 1. In one embodiment, the nucleotide sequence encoding SARS-CoV-2 S glycoprotein comprises the nucleotide sequence of SEQ ID NO: 2. In one embodiment, the coronavirus S glycoprotein fragment is a SARS-CoV-2 S glycoprotein fragment lacking 19 C-terminal amino acids. In one specific embodiment, the SARS-CoV-2 S glycoprotein fragment comprises the amino acid sequence of SEQ ID NO: 3. In one specific embodiment, the SARS-CoV-2 S glycoprotein fragment consists of the amino acid sequence of SEQ ID NO: 3. In one embodiment, the nucleotide sequence encoding SARS-CoV-2 S glycoprotein comprises the nucleotide sequence of SEQ ID NO: 4. In one embodiment, the coronavirus S glycoprotein fragment or derivative has at least 77% amino acid sequence identity to the amino acid sequence of SEQ ID NO: 1. In one embodiment, the coronavirus S glycoprotein fragment or derivative has at least 64% amino acid sequence identity to S1 subunit of the amino acid sequence of SEQ ID NO: 1. In one embodiment, the coronavirus S glycoprotein fragment or derivative has at least 64% amino acid sequence identity to amino acids 14-684 of the amino acid sequence of SEQ ID NO: 1. In one embodiment, the coronavirus S glycoprotein fragment or derivative has at least 74% amino acid sequence identity to RBD domain of the amino acid sequence of SEQ ID NO: 1. In one embodiment, the coronavirus S glycoprotein fragment or derivative has at least 74% amino acid sequence identity to amino acids 319-541 of the amino acid sequence of SEQ ID NO: 1. In one embodiment, the coronavirus S glycoprotein fragment or derivative results in a more fusogenic recombinant rhabdovirus particle as compared to a comparable recombinant rhabdovirus comprising the rhabdovirus genome expressing a full-length wild-type SARS-CoV-2 S glycoprotein inserted in the same location of the rhabdovirus genome. In one embodiment, the coronavirus S glycoprotein fragment or derivative results in a more fusogenic recombinant rhabdovirus particle as compared to a comparable recombinant rhabdovirus particle comprising the rhabdovirus genome expressing a full-length wild-type SARS-CoV-2 S glycoprotein inserted in the same location of the rhabdovirus genome. In one embodiment, the coronavirus S glycoprotein, fragment or derivative comprises one or more amino acid insertions, deletions, and/or substitutions listed in Tables 8 and 9, wherein the positions of said insertions, deletions, and/or substitutions are specified in relation to SEQ ID NO: 1. In one embodiment, the SARS-CoV-2 S glycoprotein comprises the amino acid sequence of SEQ ID NO: 44. In one embodiment of any of the above methods, step (a) comprises contacting the sample with two or more different recombinant rhabdovirus particles, wherein said two or more different recombinant rhabdovirus particles comprise different coronavirus spike(S) glycoproteins, fragments or derivatives thereof.at least one of the two or more different coronavirus spike(S) glycoproteins, fragments or derivatives thereof comprises the amino acid sequence selected from SEQ ID NO: 1, SEQ ID NO: 3 and SEQ ID NO: 44, or comprises one or more amino acid insertions, deletions, and/or substitutions listed in Tables 8 and 9, wherein the positions of said insertions, deletions, and/or substitutions are specified in relation to SEQ ID NO: 1. In certain embodiments, the SARS-CoV-2 S glycoprotein derivative, or fragment thereof, may comprise or consist of an insertion, deletion, and/or substitution of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 residues of the SARS-CoV-2 S glycoprotein. Non-limiting examples of amino acids for potential deletion include, e.g., a tyrosine at position (145), an asparagine at position (679), a serine at position (680), proline at position (681), an arginine at position (682), an arginine at position (683), an alanine at position (684), and/or an arginine at position (685), positions as denoted in SEQ ID NO: 1, or the equivalent amino acid residue in a mutant SARS-CoV-2 S glycoprotein sequence. Non-limiting examples of amino acids for potential substitution include, e.g., a leucine changed to a phenylalanine at position (5) a tyrosine changed to an asparagine at position (28), a threonine changed to an isoleucine at position (29), a histidine changed to a tyrosine at position (49), a leucine changed to a phenylalanine at position (54), an asparagine changed to a lysine at position (74), a glutamic acid changed to an aspartic acid at position (96), an aspartic acid changed to an asparagine at position (111), a phenylalanine changed to a leucine at position (157), a glycine changed to a valine at position (181), a serine changed to a tryptophan at position (221), a serine changed to an arginine at position (247), an alanine changed to a threonine at position (348), an arginine changed to an isoleucine at position (408), a glycine changed to a serine at position (476), a valine changed to an alanine at position (483), a histidine changed to a glutamine at position (519), an alanine changed to a serine at position (520), an aspartic acid changed to an asparagine at position (614), an aspartic acid changed to a glycine at position (614), an asparagine changed to an isoleucine at position (679), a serine change to a leucine at position (680), an arginine changed to a glycine at position (682), an arginine changed to a serine at position (683), an arginine changed to a glutamine at position (685), an arginine changed to a serine at position (685), a phenylalanine changed to a cysteine at position (797), an alanine changed to a valine at position (930), an aspartic acid changed to a tyrosine at position (936), an alanine changed to a valine at position (1078), an aspartic acid changed to a histidine at position (1168), and/or an aspartic acid changed to a histidine at position (1259), positions as denoted in SEQ ID NO: 1, or the equivalent amino acid residue in a mutant SARS-CoV-2 S glycoprotein sequence. See Becerra-Flores and Cardozo, "SARS-CoV-2 viral spike G614 mutation exhibits higher case fatality rate," *The International Journal of Clinical Practice*, published online May 6, 2020; Eaaswarkhanth et al., "Could the D614G substitution in the SARS-CoV-2 spike(S) protein be associated with higher COVID-19 mortality?" *International Journal of Infectious Diseases,* 96: July 2020, Pages 459-460; Tang et al., "The SARS-CoV-2 Spike Protein D614G Mutation Shows Increasing Dominance and May Confer a Structural Advantage to the Furin Cleavage Domain," *Preprints* 2020, 2020050407 (doi: 10.20944/preprints202005.0407.v1); Hansen et. al., "Studies in humanized mice and convalescent humans yield a SARS-CoV-2 antibody cocktail" *Science*, published online Jun. 15, 2020; Lokman et al., "Exploring the genomic and proteomic variations of SARS-CoV-2 spike glycoprotein: A computational biology approach", *Infection, Genetics and Evolution: Journal of Molecular Epidemiology and Evolutionary Genetics in Infectious Diseases,* 2020 June; 84:104389. DOI: 10.1016/j.meegid.2020.104389, each of which incorporated herein by reference in their entirety for all intended purposes. Additional non-limiting examples of amino acid residue positions for insertion, deletion, and/or substitution include those as listed in Tables 8 and 9 (amino acid residue positions are denoted using SEQ ID NO: 1 as a reference sequence, which can be used as a reference for identifying the equivalent amino acid residue in any SARS-CoV-2 S glycoprotein sequence (same as above); references in Table 8 are incorporated herein by reference in their entirety for all intended purposes). Each residue modification listed in Table 8 can separately be used alone or in combination with others to generate variants of a recombinant vesicular stomatitis virus (VSV) particle. In certain embodiments, the SARS-CoV-2 S glycoprotein derivative, or fragments thereof, differs in amino acid sequence from the reference peptide or polypeptide (e.g., wild-type SARS-CoV-2 spike protein) by changing a serine to an arginine at position (247), an aspartic acid to an asparagine at position (614), and/or an arginine to a glutamine at position (685), positions as denoted in SEQ ID NO: 1, or the equivalent amino acid residue in a mutant SARS-CoV-2 S glycoprotein sequence. In certain embodiments, the SARS-CoV-2 S glycoprotein derivative, or fragments thereof, differs in amino acid sequence from the reference peptide or polypeptide by changing a serine to an arginine at position (247). In certain embodiments, the SARS-CoV-2 S glycoprotein derivative, or fragments thereof, differs in amino acid sequence from the reference peptide or polypeptide by changing an aspartic acid to an asparagine at position (614). In certain embodiments, the SARS-CoV-2 S glycoprotein derivative, or fragments thereof, differs in amino acid sequence from the reference peptide or polypeptide by changing an arginine to a glutamine at position (685). In certain embodiments, the SARS-CoV-2 S glycoprotein derivative, or fragments thereof, differs in amino acid sequence from the reference peptide or polypeptide by changing a serine to an arginine at position (247) and an aspartic acid to an asparagine at position (614). In certain embodiments, the SARS-CoV-2 S glycoprotein derivative, or fragments thereof, differs in amino acid sequence from the reference peptide or polypeptide by changing a serine to an arginine at position (247) and an arginine to a glutamine at position (685). In certain embodiments, the SARS-CoV-2 S glycoprotein derivative, or fragments thereof, differs in amino acid sequence from the reference peptide or polypeptide by changing an aspartic acid to an asparagine at position (614) and an arginine to a glutamine at position (685). In certain embodiments, the SARS-CoV-2 S glycoprotein derivative, or fragments thereof, differs in amino acid sequence from the reference peptide or polypeptide by changing a serine to an arginine at position (247), an aspartic acid to an asparagine at position (614), and an arginine to a glutamine at position (685). In certain embodiments, the SARS-CoV-2 S glycoprotein derivative, or fragments thereof, result in a more lytic phenotype. In certain embodiments, the SARS-CoV-2 S glycoprotein fragment or derivative may comprise the amino acid sequence of SEQ ID NO: 42, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to the amino acid sequence of SEQ ID NO: 42. In certain embodiments, the SARS-CoV-2 S glycoprotein fragment or derivative may be encoded by a codon optimized nucleotide sequence. In various embodiments, SARS-CoV-2 S glycoprotein fragment or derivative may be encoded by the polynucleotide sequence of SEQ ID NO: 43 or a sequence that has at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% polynucleotide sequence identity to SEQ ID NO: 43. In certain embodiments, the SARS-CoV-2 S glycoprotein fragment or derivative may comprise the amino acid sequence of SEQ ID NO: 44, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to the amino acid sequence of SEQ ID NO: 44. In certain embodiments, the SARS-CoV-2 S glycoprotein derivative, or fragments thereof, differs in amino acid sequence from the reference peptide or polypeptide (e.g., wild-type SARS-CoV-2 spike protein) by changing an asparagine to a tyrosine at position (501), and/or a glutamic acid to a lysine at position (484), and/or an aspartic acid to a glycine at position (614), and/or deletion of residues 69-70, positions as denoted in SEQ ID NO: 1, or the equivalent amino acid residue in a mutant SARS-CoV-2 S glycoprotein sequence. In certain embodiments, the SARS-CoV-2 S glycoprotein derivative, or fragments thereof, differs in amino acid sequence from the reference peptide or polypeptide by changing an asparagine to a tyrosine at position (501). In certain embodiments, the SARS-CoV-2 S glycoprotein derivative, or fragments thereof, differs in amino acid sequence from the reference peptide or polypeptide by changing a glutamic acid to a lysine at position (484). In certain embodiments, the SARS-CoV-2 S glycoprotein derivative, or fragments thereof, differs in amino acid sequence from the reference peptide or polypeptide by changing an aspartic acid to a glycine at position (614). In certain embodiments, the SARS-CoV-2 S glycoprotein derivative, or fragments thereof, differs in amino acid sequence from the reference peptide or polypeptide by deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501) and a glutamic acid to a lysine at position (484). In certain embodiments, the SARS-CoV-2 S glycoprotein derivative, or fragments thereof, differs in amino acid sequence from the reference peptide or polypeptide by changing an asparagine to a tyrosine at position (501) and an aspartic acid to a glycine at position (614). In certain embodiments, the SARS-CoV-2 S glycoprotein derivative, or fragments thereof, differs in amino acid sequence from the reference peptide or polypeptide by changing an asparagine to a tyrosine at position (501) and deletion of residues 69-70. In certain embodiments, the SARS-CoV-2 S glycoprotein derivative, or fragments thereof, differs in amino acid sequence from the reference peptide or polypeptide by changing a glutamic acid to a lysine at position (484) and an aspartic acid to a glycine at position (614). In certain embodiments, the SARS-CoV-2 S glycoprotein derivative, or fragments thereof, differs in amino acid sequence from the reference peptide or polypeptide by changing a glutamic acid to a lysine at position (484) and deletion of residues 69-70. In certain embodiments, the SARS-CoV-2 S glycoprotein derivative, or fragments thereof, differs in amino acid sequence from the reference peptide or polypeptide by changing an aspartic acid to a glycine at position (614) and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), a glutamic acid to a lysine at position (484), and an aspartic acid to a glycine at position (614). In certain embodiments, the SARS-CoV-2 S glycoprotein derivative, or fragments thereof, differs in amino acid sequence from the reference peptide or polypeptide by changing an asparagine to a tyrosine at position (501), changing a glutamic acid to a lysine at position (484), and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), changing an aspartic acid to a glycine at position (614), and deletion of residues 69-70. In certain embodiments, the SARS-CoV-2 S glycoprotein derivative, or fragments thereof, differs in amino acid sequence from the reference peptide or polypeptide by changing a glutamic acid to a lysine at position (484), changing an aspartic acid to a glycine at position (614), and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), changing a glutamic acid to a lysine at position (484), changing an aspartic acid to a glycine at position (614) and deletion of residues 69-70. In certain embodiments, the SARS-CoV-2 S glycoprotein derivative, or fragments thereof, differs in amino acid sequence from the reference peptide or polypeptide (e.g., wild-type SARS-CoV-2 spike protein) by inactivating the furin cleavage site within the spike protein. In certain embodiments, the SARS-CoV-2 S glycoprotein derivative, or fragments thereof, differs in amino acid sequence from the reference peptide or polypeptide (e.g., wild-type SARS-CoV-2 spike protein) by changing Q677TNSPRRARSV687 (SEQ ID NO: 65), as denoted in SEQ ID NO: 1, or the equivalent amino acid residue in a mutant SARS-CoV-2 S glycoprotein sequence, to QTILRSV (SEQ ID NO: 66) or to QTNSPGSASSV (SEQ ID NO: 67). In certain embodiments, the SARS-CoV-2 S glycoprotein derivative, or fragments thereof, result in a monobasic furin cleavage site in the S1/S2 interface (QTILRSV (SEQ ID NO: 66)) or deletion of the furin cleavage site (QTNSPGSASSV (SEQ ID NO: 67)) phenotype. In certain embodiments, the alteration to the furin cleavage site can lead to a spike stabilized pseudoparticles. See Hansen et. al., "Studies in humanized mice and convalescent humans yield a SARS-CoV-2 antibody cocktail" Science, published online Jun. 15, 2020, incorporated herein by reference in its entirety for all intended purposes.

In one embodiment, the polynucleotide further comprises a Kozak sequence 3' to the sequence encoding SARS-CoV-2 S glycoprotein or a fragment or derivative thereof. In one embodiment, the Kozak sequence is a wild-type Kozak sequence. In one specific embodiment, the wild-type Kozak sequence comprises SEQ ID NO: 11 or a derivative thereof. In one embodiment, the Kozak sequence is an optimized Kozak sequence. In one specific embodiment, the optimized Kozak sequence comprises SEQ ID NO: 12 or a derivative thereof.

In one embodiment, the recombinant rhabdovirus particle is a recombinant vesiculovirus particle. In one embodiment, the recombinant vesiculovirus particle is a recombinant vesicular stomatitis virus (VSV) particle.

In a further aspect, provided herein is a kit for determining the presence of a coronavirus neutralizing antibody in a sample comprising:

a) a recombinant rhabdovirus particle, wherein the rhabdovirus glycoprotein (G) is replaced by a coronavirus spike(S) glycoprotein or a fragment or a derivative thereof, wherein said S glycoprotein, fragment or derivative is capable of mediating infection of a first target cell and a second target cell;
b) (i) the first target cell expressing a first portion of a reporter protein and (ii) the second cell expressing a second portion of the reporter protein, wherein the first target cell and the second target cell are capable of fusing with one another when contacted with the recombinant rhabdovirus particle, said fusion resulting in the generation of a detectable reporter signal; c) optionally, a control sample not comprising the coronavirus neutralizing antibodies;
d) optionally, a control sample comprising a coronavirus neutralizing antibody, or a molecule that blocks interaction of the coronavirus S glycoprotein with a protein with which it interacts on the target cell, or a molecule that blocks target cell fusion, or any combination thereof;
e) optionally, a substrate for the reporter protein, and
f) optionally, instructions for use.

In yet another aspect, provided herein is a kit for determining the presence of a coronavirus neutralizing antibody in a sample comprising:

a) a polynucleotide encoding a rhabdovirus nucleoprotein (N), a rhabdovirus phosphoprotein (P), and a rhabdovirus large protein (L), or functional fragments or derivatives thereof, and further encoding a Severe Acute Respiratory Syndrome coronavirus 2 (SARS-CoV-2) spike(S) glycoprotein or fragment or derivative thereof, for expression on the viral envelope of a recombinant rhabdovirus particle, wherein said S glycoprotein, fragment or derivative is capable of mediating infection of a first target cell and a second target cell;
b) (i) the first target cell expressing a first portion of a reporter protein and (ii) the second cell expressing a second portion of the reporter protein, wherein the first target cell and the second target cell are capable of fusing with one another if contacted with the recombinant rhabdovirus particle, said fusion resulting in the generation of a detectable reporter signal;
c) optionally, a control sample not comprising the coronavirus neutralizing antibodies;
d) optionally, a control sample comprising a coronavirus neutralizing antibody, or a molecule that blocks interaction of the coronavirus S glycoprotein with a protein with which it interacts on the target cell, or a molecule that blocks target cell fusion, or any combination thereof;
e) optionally, a substrate for the reporter protein, and
f) optionally, instructions for use.

In one embodiment, both the first target cell and/or the second target cell comprise angiotensin-converting enzyme 2 (ACE2). In one embodiment, the first target cell is Vero-DSP1 (Vero-DSP-1-Puro; CLR-73) and the second target cell is Vero-DSP2 (Vero-DSP-2-Puro; CLR-74).

In one embodiment, the first portion of the reporter protein comprises amino acids 1-229 of *Renilla* luciferase or a mutant thereof and the second portion of the reporter protein comprises amino acids 230-311 of *Renilla* luciferase or a mutant thereof. In another embodiment, the first portion of the reporter protein comprises amino acids 1-155 of

*Renilla* luciferase or a mutant thereof and the second portion of the reporter protein comprises amino acids 156-311 of *Renilla* luciferase or a mutant thereof. In one specific embodiment, the first portion of the reporter protein comprises amino acids 1-155 of *Renilla* luciferase mutant RLuc8 and the second portion of the reporter protein comprises amino acids 156-311 of *Renilla* luciferase mutant RLuc8.

In one embodiment, the first portion of the reporter protein comprises amino acids 1-156 of green fluorescent protein (GFP) or a mutant thereof, and the second portion of the reporter protein comprises amino acids 157-231 of GFP or a mutant thereof. In another embodiment, the first portion of the reporter protein comprises amino acids 1-213 of superfolder GFP, and the second portion of the reporter protein comprises amino acids 214-230 of superfolder GFP. In yet another embodiment, the first portion of the reporter protein comprises amino acids 1-154 of superfolder yellow fluorescent protein (YFP), and the second portion of the reporter protein comprises amino acids 155-262 of superfolder YFP.

In another aspect, provided herein is a kit for determining the presence of a coronavirus neutralizing antibody in a sample comprising:

a) a recombinant rhabdovirus particle wherein (i) the rhabdovirus glycoprotein (G) is replaced by a coronavirus spike(S) glycoprotein or a fragment or a derivative thereof, wherein said S glycoprotein, fragment or derivative is capable of mediating infection of a target cell and wherein (ii) the recombinant rhabdovirus particle comprises a reporter protein and/or a nucleic acid molecule encoding said reporter protein;
b) the target cell;
c) optionally, a control sample not comprising the coronavirus neutralizing antibodies;
d) optionally, a control sample comprising a coronavirus neutralizing antibody, or a molecule that blocks interaction of the coronavirus S glycoprotein with a protein with which it interacts on the target cell, or any combination thereof;
e) optionally, a substrate for the reporter protein, and
f) optionally, instructions for use.

In one embodiment, the recombinant rhabdovirus particle comprises a nucleic acid molecule encoding said reporter protein.

In a further aspect, provided herein is a kit for determining the presence of a coronavirus neutralizing antibody in a sample comprising:

a) a polynucleotide encoding a rhabdovirus nucleoprotein (N), a rhabdovirus phosphoprotein (P), and a rhabdovirus large protein (L), or functional fragments or derivatives thereof, and further encoding a reporter protein and a Severe Acute Respiratory Syndrome coronavirus 2 (SARS-CoV-2) spike(S) glycoprotein or fragment or derivative thereof, for expression on the viral envelope of a recombinant rhabdovirus particle, wherein said S glycoprotein, fragment or derivative is capable of mediating infection of a target cell;
b) the target cell;
c) optionally, a control sample not comprising the coronavirus neutralizing antibodies;
d) optionally, a control sample comprising a coronavirus neutralizing antibody, or a molecule that blocks interaction of the coronavirus S glycoprotein with a protein with which it interacts on the target cell, or any combination thereof;
e) optionally, a substrate for the reporter protein, and
f) optionally, instructions for use.

In one embodiment, the nucleic acid sequence encoding the reporter protein is inserted between the nucleic acid sequence encoding the coronavirus S glycoprotein or the fragment or derivative thereof and the nucleic acid sequence encoding rhabdovirus large (L) protein.

In one embodiment, the target cell is a Vero cell (including Vero-αHis cell), Vero-Ace-2 cell, Vero-TRMPSS2 cell, or Vero-E6 cell. In one embodiment, the target cell comprises angiotensin-converting enzyme 2 (ACE2).

In one embodiment of any of the above kits including a recombinant rhabdovirus particle, the recombinant rhabdovirus particle is a replication competent rhabdovirus particle.

In one embodiment of any of the above kits, the coronavirus S glycoprotein, fragment or derivative thereof is derived from Severe Acute Respiratory Syndrome coronavirus 2 (SARS-CoV-2). In one embodiment, the coronavirus S glycoprotein is a full-length SARS-CoV-2 S glycoprotein. In one specific embodiment, the SARS-CoV-2 S glycoprotein comprises the amino acid sequence of SEQ ID NO: 1. In one specific embodiment, the SARS-CoV-2 S glycoprotein consists of the amino acid sequence of SEQ ID NO: 1. In one embodiment, the nucleotide sequence encoding SARS-CoV-2 S glycoprotein comprises the nucleotide sequence of SEQ ID NO: 2. In one embodiment, the coronavirus S glycoprotein fragment is a SARS-CoV-2 S glycoprotein fragment lacking 19 C-terminal amino acids. In one specific embodiment, the SARS-CoV-2 S glycoprotein fragment comprises the amino acid sequence of SEQ ID NO: 3. In one specific embodiment, the SARS-CoV-2 S glycoprotein fragment consists of the amino acid sequence of SEQ ID NO: 3. In one embodiment, the nucleotide sequence encoding SARS-CoV-2 S glycoprotein comprises the nucleotide sequence of SEQ ID NO: 4. In one embodiment, the coronavirus S glycoprotein fragment or derivative has at least 77% amino acid sequence identity to the amino acid sequence of SEQ ID NO: 1. In one embodiment, the coronavirus S glycoprotein fragment or derivative has at least 64% amino acid sequence identity to S1 subunit of the amino acid sequence of SEQ ID NO: 1. In one embodiment, the coronavirus S glycoprotein fragment or derivative has at least 64% amino acid sequence identity to amino acids 14-684 of the amino acid sequence of SEQ ID NO: 1. In one embodiment, the coronavirus S glycoprotein fragment or derivative has at least 74% amino acid sequence identity to RBD domain of the amino acid sequence of SEQ ID NO: 1. In one embodiment, the coronavirus S glycoprotein fragment or derivative has at least 74% amino acid sequence identity to amino acids 319-541 of the amino acid sequence of SEQ ID NO: 1. In one embodiment, the coronavirus S glycoprotein fragment or derivative results in a more fusogenic recombinant rhabdovirus particle as compared to a comparable recombinant rhabdovirus comprising the rhabdovirus genome expressing a full-length wild-type SARS-CoV-2 S glycoprotein inserted in the same location of the rhabdovirus genome. In one embodiment, the coronavirus S glycoprotein fragment or derivative results in a more fusogenic recombinant rhabdovirus particle as compared to a comparable recombinant rhabdovirus particle comprising the rhabdovirus genome expressing a full-length wild-type SARS-CoV-2 S glycoprotein inserted in the same location of the rhabdovirus genome. In certain embodiments, the SARS-CoV-2 S glycoprotein derivative, or fragment thereof, may comprise or consist of an insertion, deletion, and/or substitution of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 residues of the SARS-CoV-2 S glycoprotein. Non-limiting examples of amino acids for potential deletion include, e.g., a tyrosine at position (145), an asparagine at position (679), a serine at position (680), proline at position (681), an arginine at position (682), an arginine at position (683), an alanine at position (684), and/or an arginine at position (685), positions as denoted in SEQ ID NO: 1, or the equivalent amino acid residue in a mutant SARS-CoV-2 S glycoprotein sequence. Non-limiting examples of amino acids for potential substitution include, e.g., a leucine changed to a phenylalanine at position (5) a tyrosine changed to an asparagine at position (28), a threonine changed to an isoleucine at position (29), a histidine changed to a tyrosine at position (49), a leucine changed to a phenylalanine at position (54), an asparagine changed to a lysine at position (74), a glutamic acid changed to an aspartic acid at position (96), an aspartic acid changed to an asparagine at position (111), a phenylalanine changed to a leucine at position (157), a glycine changed to a valine at position (181), a serine changed to a tryptophan at position (221), a serine changed to an arginine at position (247), an alanine changed to a threonine at position (348), an arginine changed to an isoleucine at position (408), a glycine changed to a serine at position (476), a valine changed to an alanine at position (483), a histidine changed to a glutamine at position (519), an alanine changed to a serine at position (520), an aspartic acid changed to an asparagine at position (614), an aspartic acid changed to a glycine at position (614), an asparagine changed to an isoleucine at position (679), a serine change to a leucine at position (680), an arginine changed to a glycine at position (682), an arginine changed to a serine at position (683), an arginine changed to a glutamine at position (685), an arginine changed to a serine at position (685), a phenylalanine changed to a cysteine at position (797), an alanine changed to a valine at position (930), an aspartic acid changed to a tyrosine at position (936), an alanine changed to a valine at position (1078), an aspartic acid changed to a histidine at position (1168), and/or an aspartic acid changed to a histidine at position (1259), positions as denoted in SEQ ID NO: 1, or the equivalent amino acid residue in a mutant SARS-CoV-2 S glycoprotein sequence. See Becerra-Flores and Cardozo, "SARS-CoV-2 viral spike G614 mutation exhibits higher case fatality rate," *The International Journal of Clinical Practice*, published online May 6, 2020; Eaaswarkhanth et al., "Could the D614G substitution in the SARS-CoV-2 spike(S) protein be associated with higher COVID-19 mortality?" *International Journal of Infectious Diseases,* 96: July 2020, Pages 459-460; Tang et al., "The SARS-CoV-2 Spike Protein D614G Mutation Shows Increasing Dominance and May Confer a Structural Advantage to the Furin Cleavage Domain," *Preprints* 2020, 2020050407 (doi: 10.20944/preprints202005.0407.v1); Hansen et. al., "Studies in humanized mice and convalescent humans yield a SARS-CoV-2 antibody cocktail" *Science*, published online Jun. 15, 2020; Lokman et al., "Exploring the genomic and proteomic variations of SARS-CoV-2 spike glycoprotein: A computational biology approach", *Infection, Genetics and Evolution: Journal of Molecular Epidemiology and Evolutionary Genetics in Infectious Diseases,* 2020 June; 84:104389. DOI: 10.1016/j.meegid.2020.104389, each of which incorporated herein by reference in their entirety for all intended purposes. Additional non-limiting examples of amino acid residue positions for insertion, deletion, and/or substitution include those as listed in Tables 8 and 9 (amino acid residue positions are denoted using SEQ ID NO: 1 as a reference sequence, which can be used as a reference for identifying the equivalent amino acid residue in any SARS-CoV-2 S glycoprotein sequence (same as above); references in Table 8 are incorporated herein by reference in their entirety for all intended purposes). Each residue modification listed in Table 8 can separately be used alone or in combination with others to generate variants of a recombinant vesicular stomatitis virus (VSV) particle. In certain embodiments, the SARS-CoV-2 S glycoprotein derivative, or fragments thereof, differs in amino acid sequence from the reference peptide or polypeptide (e.g., wild-type SARS-CoV-2 spike protein) by changing a serine to an arginine at position (247), an aspartic acid to an asparagine at position (614), and/or an arginine to a glutamine at position (685), positions as denoted in SEQ ID NO: 1, or the equivalent amino acid residue in a mutant SARS-CoV-2 S glycoprotein sequence. In certain embodiments, the SARS-CoV-2 S glycoprotein derivative, or fragments thereof, differs in amino acid sequence from the reference peptide or polypeptide by changing a serine to an arginine at position (247). In certain embodiments, the SARS-CoV-2 S glycoprotein derivative, or fragments thereof, differs in amino acid sequence from the reference peptide or polypeptide by changing an aspartic acid to an asparagine at position (614). In certain embodiments, the SARS-CoV-2 S glycoprotein derivative, or fragments thereof, differs in amino acid sequence from the reference peptide or polypeptide by changing an arginine to a glutamine at position (685). In certain embodiments, the SARS-CoV-2 S glycoprotein derivative, or fragments thereof, differs in amino acid sequence from the reference peptide or polypeptide by changing a serine to an arginine at position (247) and an aspartic acid to an asparagine at position (614). In certain embodiments, the SARS-CoV-2 S glycoprotein derivative, or fragments thereof, differs in amino acid sequence from the reference peptide or polypeptide by changing a serine to an arginine at position (247) and an arginine to a glutamine at position (685). In certain embodiments, the SARS-CoV-2 S glycoprotein derivative, or fragments thereof, differs in amino acid sequence from the reference peptide or polypeptide by changing an aspartic acid to an asparagine at position (614) and an arginine to a glutamine at position (685). In certain embodiments, the SARS-CoV-2 S glycoprotein derivative, or fragments thereof, differs in amino acid sequence from the reference peptide or polypeptide by changing a serine to an arginine at position (247), an aspartic acid to an asparagine at position (614), and an arginine to a glutamine at position (685). In certain embodiments, the SARS-CoV-2 S glycoprotein derivative, or fragments thereof, result in a more lytic phenotype. In certain embodiments, the SARS-CoV-2 S glycoprotein fragment or derivative may comprise the amino acid sequence of SEQ ID NO: 42, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to the amino acid sequence of SEQ ID NO: 42. In certain embodiments, the SARS-CoV-2 S glycoprotein fragment or derivative may be encoded by a codon optimized nucleotide sequence. In various embodiments, SARS-CoV-2 S glycoprotein fragment or derivative may be encoded by the polynucleotide sequence of SEQ ID NO: 43 or a sequence that has at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% polynucleotide sequence identity to SEQ ID NO: 43. In certain embodiments, the SARS-CoV-2 S glycoprotein fragment or derivative may comprise the amino acid sequence of SEQ ID NO: 44, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to the amino acid sequence of SEQ ID NO: 44. In certain embodiments, the SARS-CoV-2 S glycoprotein derivative, or fragments thereof, differs in amino acid sequence from the reference peptide or polypeptide (e.g., wild-type SARS-CoV-2 spike protein) by changing an asparagine to a tyrosine at position (501), and/or a glutamic acid to a lysine at position (484), and/or an aspartic acid to a glycine at position (614), and/or deletion of residues 69-70, positions as denoted in SEQ ID NO: 1, or the equivalent amino acid residue in a mutant SARS-CoV-2 S glycoprotein sequence. In certain embodiments, the SARS-CoV-2 S glycoprotein derivative, or fragments thereof, differs in amino acid sequence from the reference peptide or polypeptide by changing an asparagine to a tyrosine at position (501). In certain embodiments, the SARS-CoV-2 S glycoprotein derivative, or fragments thereof, differs in amino acid sequence from the reference peptide or polypeptide by changing a glutamic acid to a lysine at position (484). In certain embodiments, the SARS-CoV-2 S glycoprotein derivative, or fragments thereof, differs in amino acid sequence from the reference peptide or polypeptide by changing an aspartic acid to a glycine at position (614). In certain embodiments, the SARS-CoV-2 S glycoprotein derivative, or fragments thereof, differs in amino acid sequence from the reference peptide or polypeptide by deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501) and a glutamic acid to a lysine at position (484). In certain embodiments, the SARS-CoV-2 S glycoprotein derivative, or fragments thereof, differs in amino acid sequence from the reference peptide or polypeptide by changing an asparagine to a tyrosine at position (501) and an aspartic acid to a glycine at position (614). In certain embodiments, the SARS-CoV-2 S glycoprotein derivative, or fragments thereof, differs in amino acid sequence from the reference peptide or polypeptide by changing an asparagine to a tyrosine at position (501) and deletion of residues 69-70. In certain embodiments, the SARS-CoV-2 S glycoprotein derivative, or fragments thereof, differs in amino acid sequence from the reference peptide or polypeptide by changing a glutamic acid to a lysine at position (484) and an aspartic acid to a glycine at position (614). In certain embodiments, the SARS-CoV-2 S glycoprotein derivative, or fragments thereof, differs in amino acid sequence from the reference peptide or polypeptide by changing a glutamic acid to a lysine at position (484) and deletion of residues 69-70. In certain embodiments, the SARS-CoV-2 S glycoprotein derivative, or fragments thereof, differs in amino acid sequence from the reference peptide or polypeptide by changing an aspartic acid to a glycine at position (614) and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), a glutamic acid to a lysine at position (484), and an aspartic acid to a glycine at position (614). In certain embodiments, the SARS-CoV-2 S glycoprotein derivative, or fragments thereof, differs in amino acid sequence from the reference peptide or polypeptide by changing an asparagine to a tyrosine at position (501), changing a glutamic acid to a lysine at position (484), and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), changing an aspartic acid to a glycine at position (614), and deletion of residues 69-70. In certain embodiments, the SARS-CoV-2 S glycoprotein derivative, or fragments thereof, differs in amino acid sequence from the reference peptide or polypeptide by changing a glutamic acid to a lysine at position (484), changing an aspartic acid to a glycine at position (614), and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), changing a glutamic acid to a lysine at position (484), changing an aspartic acid to a glycine at position (614) and deletion of residues 69-70. In certain embodiments, the SARS-CoV-2 S glycoprotein derivative, or fragments thereof, differs in amino acid sequence from the reference peptide or polypeptide (e.g., wild-type SARS-CoV-2 spike protein) by inactivating the furin cleavage site within the spike protein. In certain embodiments, the SARS-CoV-2 S glycoprotein derivative, or fragments thereof, differs in amino acid sequence from the reference peptide or polypeptide (e.g., wild-type SARS-CoV-2 spike protein) by changing Q677TNSPRRARSV687 (SEQ ID NO: 65), as denoted in SEQ ID NO: 1, or the equivalent amino acid residue in a mutant SARS-CoV-2 S glycoprotein sequence, to QTILRSV (SEQ ID NO: 66) or to QTNSPGSASSV (SEQ ID NO: 67). In certain embodiments, the SARS-CoV-2 S glycoprotein derivative, or fragments thereof, result in a monobasic furin cleavage site in the S1/S2 interface (QTILRSV (SEQ ID NO: 66)) or deletion of the furin cleavage site (QTNSPGSASSV (SEQ ID NO: 67)) phenotype. In certain embodiments, the alteration to the furin cleavage site can lead to a spike stabilized pseudoparticles. See Hansen et. al., "Studies in humanized mice and convalescent humans yield a SARS-CoV-2 antibody cocktail" Science, published online Jun. 15, 2020, incorporated herein by reference in its entirety for all intended purposes.

In one embodiment of any of the above kits, the recombinant rhabdovirus particle is a recombinant vesiculovirus particle. In one embodiment, the recombinant vesiculovirus particle is a recombinant vesicular stomatitis virus (VSV) particle.

In one embodiment of any of the above kits including a recombinant rhabdovirus particle, the recombinant rhabdovirus particle comprises a mutant VSV matrix (M) protein. In one embodiment, the genome of the recombinant rhabdovirus particle encodes a mutant VSV M protein. In one specific embodiment, the recombinant rhabdovirus particle is a recombinant VSV particle comprising the mutant VSV M protein which comprises a mutation at methionine 51. In one specific embodiment, the mutation at methionine 51 is from methionine (M) to arginine (R). In one specific embodiment, the mutant VSV M protein comprises the amino acid sequence of SEQ ID NO: 7. In one specific embodiment, the mutant VSV M protein consists of the amino acid sequence of SEQ ID NO: 7.

In one embodiment of any of the above kits including a recombinant rhabdovirus particle, the recombinant rhabdovirus particle comprises a wild-type rhabdovirus matrix (M) protein. In one embodiment, the genome of the recombinant rhabdovirus particle encodes a wild-type rhabdovirus M protein. In one specific embodiment, the recombinant rhabdovirus particle is a recombinant VSV particle comprising the wild-type VSV M protein which comprises the amino acid sequence of SEQ ID NO: 9. In one specific embodiment, the wild-type VSV M protein consists of the amino acid sequence of SEQ ID NO: 9.

In one embodiment of any of the above kits, the reporter protein comprises a luciferase. Non-limiting examples of useful luciferases include, e.g., *Renilla* luciferase, RLuc8 mutant *Renilla* luciferase, (dCpG) Luciferase, NanoLuc reporter, firefly luciferase, *Gaussia* luciferase (gLuc), Met-Luc, *Vibrio fischeri* lumazine protein, *Vibrio harveyi* luminaze protein, inoflagellate luciferase, firefly luciferase YY5 mutant, firefly luciferase LGR mutant, firefly luciferase mutant E, and derivatives thereof.

In one embodiment of any of the above kits, the reporter protein comprises a fluorescent protein. Non-limiting examples of useful fluorescent proteins include, e.g., green fluorescent protein (GFP), GFP-like fluorescent proteins, (GFP-like), enhanced green fluorescent protein (EGFP), yellow fluorescent protein (YFP), enhanced yellow fluorescent protein (EYFP), blue fluorescent protein (BFP), enhanced blue fluorescent protein (EBFP), cyan fluorescent protein (CFP), enhanced cyan fluorescent protein (ECFP); red fluorescent protein, superfolder GFP, superfolder YFP, orange fluorescent protein, red fluorescent protein, small ultrared fluorescent protein, FMN-binding fluorescent protein, dsRed, qFP611, Dronpa, TagRFP, KFP, EosFP, IrisFP, Dendra, Kaede, KikGr1, emerald fluorescent protein, Azami Green, mWasabi, TagGFP, TurboGFP, AcGFP, ZsGreen, T-Sapphire, and derivatives thereof.

In one specific embodiment of any of the above kits, the reporter protein comprises a luciferase and the substrate for the reporter protein comprises Luciferin (e.g., d-luciferin), coelenterazine, or EnduRen luciferase substrate.

In one specific embodiment of any of the above kits, the control sample comprising a coronavirus neutralizing antibody is a control sample comprising mAb10914. In one specific embodiment of any of the above kits, the control sample comprising a coronavirus neutralizing antibody is a control sample comprising mAb10922.

These and other aspects described herein will be apparent to those of ordinary skill in the art in the following description, claims and drawings.

BRIEF DESCRIPTION OF THE DRAWINGS

FIG. 10 is a schematic representation of DSP Vero luciferase assay workflow.

FIG. 15A shows luciferase activity upon incubation of VSV-SARS-CoV-2-S-Δ19CT-Fluc or media alone (no virus control) with pooled SARS-CoV-2 seronegative sera (at a dilution of 1:80) mixed with 2 or 0.2 μg/mL of mAb10914. After a 30-minute room temperature incubation, the virus/sera mixes were overlaid onto monolayers of cells (Vero-αHis, Vero-E6 or Vero-Ace-2). After an additional 26 hours, d-luciferin substrate was added to the wells and luciferase activity (RLUs) was measured using a luminometer. FIG. 15B shows luciferase activity upon incubation of pooled SARS-CoV-2 seronegative sera (at 1:80 dilution) with VSV-SARS-CoV-2-S-Δ19CT-gLuc (4800 TCID50/well) alone or spiked with 0.2 μg/mL mAb10914. After 30 minutes at room temperature, the virus/sera mixes were overlaid onto Vero-αHis, Vero-Ace-2, or Vero-Ace-2/TMPRSS2 cell monolayers seeded the day before in black, clear-bottomed 96-well plates at 1e4 cells/well. After an additional 24 hours, luciferase activity in the wells was measured after the addition of d-luciferin.

FIG. 23 depicts an exemplar layout map for a 96-well U-well (or U-bottom) Plate.

FIG. 24 depicts an exemplar layout map for a 96-well Assay Plate.

DETAILED DESCRIPTION

Definitions

Figure 1:
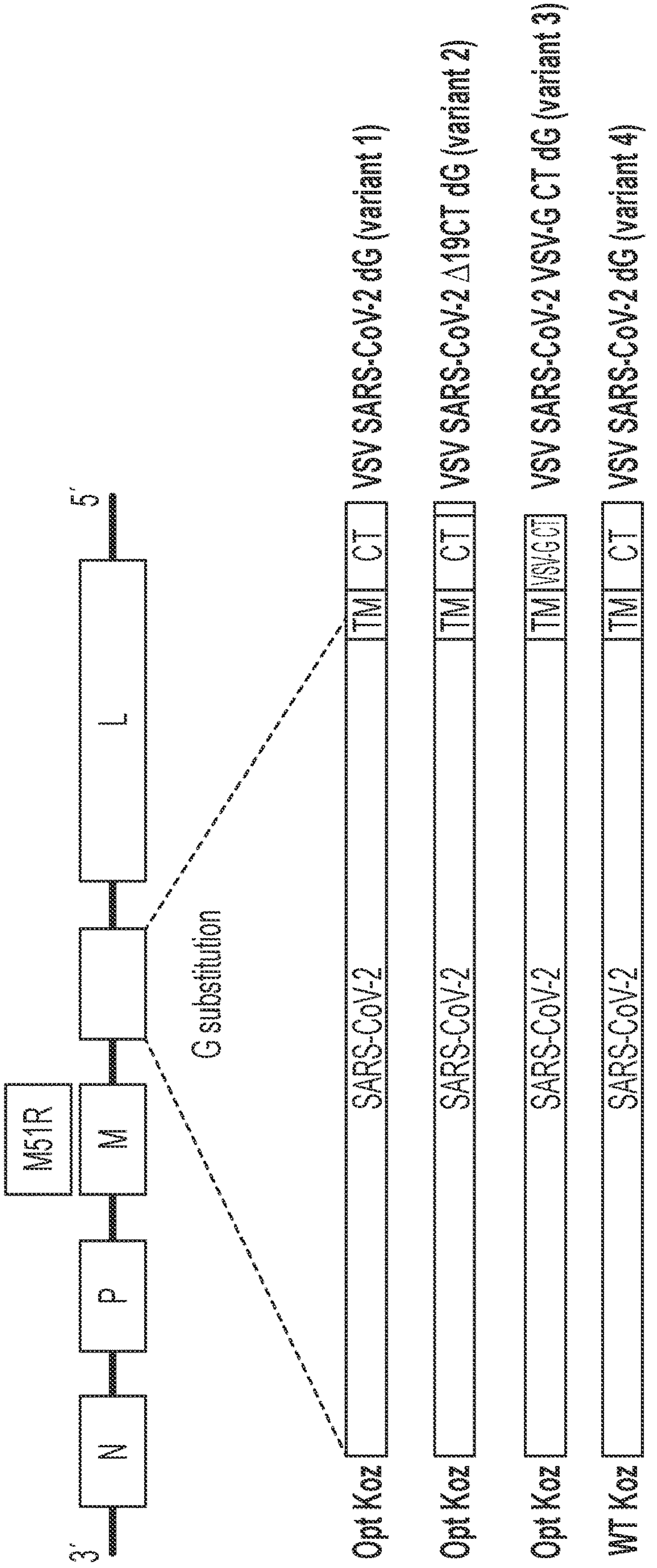
FIG. 1 depicts the VSV SARS-CoV-2 constructs tested in the Examples (variants 1-4). In these constructs, the VSV G glycoprotein was substituted by: (1) the full length SARS-CoV-2 spike(S) glycoprotein sequence (variant 1; VSV SARS-CoV-2 dG=VSV-SARS-CoV-2-S; amino acid sequence SEQ ID NO: 1; codon-optimized nucleotide sequence SEQ ID NO: 2), (2) SARS-CoV-2 S glycoprotein sequence with a deletion of 19 amino acids KFDEDDSEPVLKGVKLHYT (SEQ ID NO: 20) in the cytoplasmic tail (variant 2; VSV SARS-CoV-2 A19CT dG=VSV-SARS-CoV-2-S-A19CT; amino acid sequence SEQ ID NO: 3; codon-optimized nucleotide sequence SEQ ID NO: 4), (3) SARS-CoV-2 S glycoprotein sequence with a replacement of the S cytoplasmic tail with VSV G glycoprotein cytoplasmic tail sequence KLKHTKKRQIYTDIEMNRLGK (SEQ ID NO: 21) (variant 3; VSV SARS-CoV-2 VSV-G CT dG; amino acid sequence SEQ ID NO: 5; codon-optimized nucleotide sequence SEQ ID NO: 6), or (4) the full length SARS-CoV-2 S glycoprotein sequence but using the wild-type VSV Kozak sequence (cActATG; SEQ ID NO: 11) in place of the optimized Kozak sequence (caccATG; SEQ ID NO: 12) used in the other three constructs (variant 4; VSV-SARS-CoV-2-S; amino acid sequence SEQ ID NO: 1; codon-optimized nucleotide sequence SEQ ID NO: 2). One set of variant 1-4 constructs was prepared that encoded wild-type M protein (amino acid sequence SEQ ID NO: 9; nucleotide sequence SEQ ID NO: 10). A second set of variant 1-4 constructs was prepared that encoded M protein with the substitution M51R (amino acid sequence SEQ ID NO: 7; nucleotide sequence SEQ ID NO: 8) resulting in virus attenuation.

Unless defined otherwise, all technical and scientific terms used herein have the same meaning as commonly understood by one of ordinary skill in the art to which this disclosure belongs.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The terms "comprise(s)," "include(s)," "having," "has," and "contain(s)," are intended to be open-ended transitional phrases, terms, or words that do not preclude the possibility of additional acts or structures.

The terms "assay" or "test" as used herein may be used interchangeably with the term "method".

"Antibody" as used herein encompasses polyclonal and monoclonal antibodies and refers to immunoglobulin molecules of classes IgA (e.g., IgA1 or IgA2), IgD, IgE, IgG (e.g., IgG1, IgG2, IgG3 and IgG4) or IgM, or fragments, or derivatives thereof, including without limitation Fab, F(ab')2, Fd, single chain antibodies, diabodies, bispecific antibodies, bifunctional antibodies, humanized antibodies, and various derivatives thereof.

In the context of the present disclosure, the term "neutralizing antibody" refers to an antibody that binds to a pathogen (e.g., a virus) and interferes with its ability to infect a cell. Non-limiting examples of neutralizing antibodies include antibodies that bind to a viral particle and inhibit successful transduction, e.g., one or more steps selected from binding, entry, trafficking to the nucleus, and transcription of the viral genome. Some neutralizing antibodies may block a virus at the post-entry step.

The term "immune response" refers to a response of a cell of the immune system (e.g., a B-cell, T-cell, macrophage or polymorphonucleocyte) to a stimulus such as an antigen (e.g., a viral antigen). Active immune responses can involve differentiation and proliferation of immunocompetent cells, which leads to synthesis of antibodies or the development of cell-mediated reactivity, or both. An active immune response can be mounted by the host after exposure to an antigen (e.g., by infection or by vaccination). Active immune response can be contrasted with passive immunity, which can be acquired through the transfer of substances such as, e.g., an antibody, transfer factor, thymic graft, and/or cytokines from an actively immunized host to a non-immune host.

As used herein in connection with a viral infection and vaccination, the terms "protective immune response" or "protective immunity" refer to an immune response that that confers some benefit to the subject in that it prevents or reduces the infection or prevents or reduces the development of a disease associated with the infection. Without wishing to be bound by theory, the presence of SARS-CoV-2 neutralizing antibodies in a subject can indicate the presence of a protective immune response in the subject.

The terms "immunogenic composition", "vaccine composition", or "vaccine", which are used interchangeably, refer to a composition comprising at least one immunogenic and/or antigenic component that induces an immune response in a subject (e.g., humoral and/or cellular response). In certain embodiments, the immune response is a protective immune response. A vaccine may be administered for the prevention or treatment of a disease, such as an infectious disease. A vaccine composition may include, for example, live or killed infectious agents, recombinant infectious agents (e.g., recombinant viral particles, virus-like particles, nanoparticles, liposomes, or cells expressing immunogenic and/or antigenic components), antigenic proteins or peptides, nucleic acids, etc. Vaccines may be administered with an adjuvant to boost the immune response.

The term "operably linked" includes a linkage of nucleic acid elements in a functional relationship. A nucleic acid sequence is "operably linked" when it is placed into a functional relationship with another nucleic acid sequence. For instance, a promoter or enhancer, or a 5' regulatory region containing a promoter or enhancer, is operably linked to a coding sequence if it effects the transcription of the coding sequence.

As used herein, the term "promoter" means a genetic sequence generally in cis and located upstream of a gene, and which facilitates the transcription of the gene. Promoters can be regulated (developmental, tissue specific, or inducible (chemical, temperature)) or constitutively active. In certain embodiments, the promoter is a constitutive mammalian promoter, such as the ubiquitin C promoter (see Schorpp et al., Nucl. Acids Res. 24 (9): 1787-1788, 1996); Byun et al., Biochem. Biophys. Res. Comm 332 (2): 518-523, 2005) or the CMV-IE promoter (see Addison et al., J. Gen. Virol. 78 (7): 1653-1661, 1997; Hunninghake et al., J. Virol. 63 (7): 3026-3033, 1989), or the hCMV-IE promoter (human cytomegalovirus immediate early gene promoter) (see Stinski & Roehr, J. Virol. 55 (2): 431-441, 1985; Hunninghake et al., J. Virol. 63 (7): 3026-3033, 1989). A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative non-limiting examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can direct localization of a polypeptide. A signal peptide may be capable of directing the polypeptide into a cell's secretory pathway. Signal peptides are often located at the N-terminus of the polypeptides and are often cleaved from the remainder of the polypeptide (often referred to as the "mature protein"), upon secretion from the cell.

The terms "derivative" and "variant" are used herein interchangeably to refer to an entity that has significant structural identity with a reference entity but differs structurally from the reference entity in the presence or level of one or more chemical moieties as compared with the reference entity. In many embodiments, a derivative also differs functionally from its reference entity. In general, whether a particular entity is properly considered to be a "derivative" of a reference entity is based on its degree of structural identity with the reference entity. As will be appreciated by those skilled in the art, any biological or chemical reference entity has certain characteristic structural elements. A derivative, by definition, is a distinct entity that shares one or more such characteristic structural elements. To give but a few examples, a small molecule may have a characteristic core structural element (e.g., a macrocycle core) and/or one or more characteristic pendent moieties so that a derivative of the small molecule is one that shares the core structural element and the characteristic pendent moieties but differs in other pendent moieties and/or in types of bonds present (single vs double, E vs Z, etc.) within the core. Derivatives which are nucleic acids and polypeptides/proteins encompass mutants. A derivative nucleic acid may have a characteristic sequence element comprised of a plurality of nucleotide residues having designated positions relative to one another in linear or three-dimensional space. In some embodiments, the nucleic acid sequence of a derivative may be 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, 99.5% or more identical over the full length of the reference sequence or a fragment thereof. A derivative peptide or polypeptide may have a characteristic sequence element comprised of a plurality of amino acids having designated positions relative to one another in linear or three-dimensional space and/or contributing to a particular biological function. Derivative peptides and polypeptides include peptides and polypeptides that differ in amino acid sequence from the reference peptide or polypeptide by the insertion, deletion, and/or substitution of one or more amino acids, but retain at least one biological activity of such reference peptide or polypeptide (e.g., the ability to mediate cell infection by a virus, the ability to mediate membrane fusion, the ability to be bound by a specific antibody or to promote an immune response, etc.). In some non-limiting embodiments, a derivative peptide or polypeptide shows the sequence identity over the full length with the reference peptide or polypeptide (or a fragment thereof) that is at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, 99.5% or more. Alternatively or in addition, a derivative peptide or polypeptide may differ from a reference peptide or polypeptide as a result of one or more and/or one or more differences in chemical moieties attached to the polypeptide backbone (e.g., in glycosylation, phosphorylation, acetylation, myristoylation, palmitoylation, oxidation, formylation, amidation, polyglutamylation, ADP-ribosylation, pegylation, biotinylation, etc.). In some embodiments, a derivative peptide or polypeptide lacks one or more of the biological activities of the reference polypeptide or has a reduced or increased level of one or more biological activities as compared with the reference polypeptide. Derivatives of a particular peptide or polypeptide may be found in nature or may be synthetically or recombinantly produced. As used herein, the term "derivative" or "variant" also encompassed various chimeric, fusion proteins and conjugates, including fusions or conjugates with detection tags (e.g., HA tag, histidine tag, biotin, fusions with fluorescent or luminescent domains, etc.), dimerization/multimerization sequences, Fc, signaling sequences, etc.

The term "coronavirus" as used herein refers to the subfamily Coronavirinae within the family Coronaviridae, within the order Nidovirales. Based on the phylogenetic relationships and genomic structures, this subfamily consists of four genera: Alphacoronavirus, Betacoronavirus, Gammacoronavirus and Deltacoronavirus. The alphacoronaviruses and betacoronaviruses infect only mammals. The gammacoronaviruses and deltacoronaviruses infect birds, but some of them can also infect mammals. Alphacoronaviruses and betacoronaviruses usually cause respiratory illness in humans and gastroenteritis in animals. The three highly pathogenic viruses, SARS-CoV-2, SARS-CoV-1 and MERS-CoV cause severe respiratory syndrome in humans. The other four human coronaviruses, HCoV-NL63, HCoV- 229E, HCoV-OC43 and HKU1, induce only mild upper respiratory diseases in immunocompetent hosts, although some of them can cause severe infections in infants, young children and elderly individuals. Additional non-limiting examples of commercially important coronaviruses include transmissible gastroenteritis coronavirus (TGEV), porcine respiratory coronavirus, canine coronavirus, feline enteric coronavirus, feline infectious peritonitis virus, rabbit coronavirus, murine hepatitis virus, sialodacryoadenitis virus, porcine hemagglutinating encephalomyelitis virus, bovine coronavirus, avian infectious bronchitis virus, and turkey coronavirus. Reviewed in Cui et al., Nature Reviews Microbiology, 2019, 17:181-192; Fung et al., Annu. Rev. Microbiol., 2019, 73:529-557.

Coronaviruses form enveloped and spherical particles of 80-160 nm in diameter. They contain a positive-sense, non-segmented, single-stranded RNA (ssRNA) genome of 27-32 kb in size. The 5'-terminal two-thirds of the genome encodes polyproteins, pp1a and pp1ab. The 3' terminus encodes structural proteins, including envelope glycoproteins spike(S), envelope (E), membrane (M) and nucleocapsid (N). The genomic RNA is 5'-capped and 3'-polyadenylated and contains multiple open reading frames (ORFs). The invariant gene order is 5'-replicase-S-E-M-N-3', with numerous small ORFs (encoding accessory proteins) scattered among the structural genes. The coronavirus replicase is encoded by two large overlapping ORFs (ORF1a and ORF1b) occupying about two-thirds of the genome and is directly translated from the genomic RNA (gRNA). The structural and accessory genes, however, are translated from subgenomic RNAs (sgRNAs) generated during genome transcription/replication. Infection starts with the attachment of the coronavirus to the cognate cellular receptor, which induces endocytosis. Membrane fusion typically occurs in the endosomes, releasing the viral nucleocapsid to the cytoplasm. The genomic RNA (gRNA) serves as the template for translation of polyproteins pp1a and pp1ab, which are cleaved to form nonstructural proteins (nsps). Nsps induce the rearrangement of cellular membrane to form double-membrane vesicles (DMVs), where the viral replication transcription complexes (RTCs) are anchored. Full-length gRNA is replicated via a negative-sense intermediate, and a nested set of subgenomic RNA (sgRNA) species are synthesized by discontinuous transcription. These sgRNAs encode viral structural and accessory proteins. Particle assembly occurs in the ER-Golgi intermediate complex (ERGIC), and mature virions are released in smooth-walled vesicles via the secretory pathway.

Coronavirus entry into host cells is mediated by the transmembrane spike(S) glycoprotein (interchangeably referred to as "spike glycoprotein", "S glycoprotein", "S protein" or "spike protein") which is the main target of anti-viral neutralizing antibodies and is the focus of therapeutic and vaccine design. S glycoprotein forms homotrimers protruding from the viral surface. S glycoprotein comprises two functional subunits responsible for binding to the host cell receptor (S1 subunit) and fusion of the viral and cellular membranes (S2 subunit). For many coronaviruses, including SARS-CoV-1 and SARS-CoV-2, S glycoprotein is cleaved at the boundary between the S1 and S2 subunits, which remain non-covalently bound in the prefusion conformation. The distal S1 subunit comprises the receptor-binding domain(s) (RBD) and contributes to stabilization of the prefusion state of the membrane-anchored S2 subunit that contains the fusion machinery. S is further cleaved by host proteases at the S2' site located immediately upstream of the fusion peptide. This cleavage has been proposed to activate the protein for membrane fusion via conformational changes. Walls et al., Cell, published online Mar. 9, 2020; available at doi.org/10.1016/j.cell.2020.02.058.

SARS-CoV-1 and SARS-CoV-2 interact directly with angiotensin-converting enzyme 2 (ACE2) to enter target cells and may employ the cellular serine protease, transmembrane protease, serine 2 (TMPRSS2) for S protein priming (Hoffmann et al., Cell, 2020, 181:1-10; available at doi.org/10.1016/j.cell.2020.02.052). SARS—CoV—S and SARS-CoV-2-S share 76% amino acid identity. The receptor binding domain (RBD) in the S glycoprotein is involved in binding to the ACE2 receptor. Six RBD amino acids have been shown to be critical for binding to the ACE2 receptor and for determining the host range of SARS-CoV-like viruses. They are Y442, L472, N479, D480, T487 and Y4911 in SARS-CoV, which correspond to L455, F486, Q493, S494, N501 and Y505 in SARS-CoV-2 (Andersen et al., Nature Medicine, 2020; available at doi.org/10.1038/s41591-020-0820-9).

The term "rhabdovirus" as used herein refers to Rhabdoviridae family of viruses in the order Mononegavirales encompassing more than 150 viruses of vertebrates, invertebrates and plants. Examples of rhabdoviruses include rabies virus (RABV) from the Lyssavirus genus, vesiculoviruses from Vesiculovirus genus, the viral hemorrhagic septicemia virus (VHSV) and infectious hematopoietic necrosis virus, both from the Novirhabdovirus genus. Rhabdoviruses are bullet-shaped enveloped viruses with negative-sense single-stranded RNA genome 11-15 kb in length. The genome of rhabdoviruses comprises up to ten genes among which only five are common to all members of the family. These genes encode the nucleoprotein (N), the phosphoprotein (P), the matrix protein (M), the glycoprotein (G) and the large protein (L). The genome is associated with N, L and P to form the nucleocapsid, which is condensed by the M protein into a tightly coiled helical structure. The condensed nucleocapsid is surrounded by a lipid bilayer containing the viral glycoprotein G that constitutes the spikes that protrude from the viral surface. Rhabdoviruses enter the cell via the endocytic pathway and subsequently fuse with the cellular membrane within the acidic environment of the endosome. Both receptor recognition and membrane fusion are mediated by a single transmembrane viral glycoprotein (G). Fusion between the viral envelope and the endosomal membrane is triggered via a low-pH induced (in the endosome) structural rearrangement of the G resulting in the release the viral genome and associated proteins into the cytoplasm of target cells.

As used herein, the term "vesiculovirus" refers to any virus in the Vesiculovirus genus. Non-limiting examples of vesiculoviruses include, e.g., Vesicular Stomatitis Virus (VSV) (e.g., VSV-New Jersey, VSV-Indiana), Alagoas vesiculovirus, Cocal vesiculovirus, Jurona vesiculovirus, Carajas vesiculovirus, Maraba vesiculovirus, Piry vesiculovirus, Calchaqui vesiculovirus, Yug Bogdanovac vesiculovirus, Isfahan vesiculovirus, Chandipura vesiculovirus, Perinct vesiculovirus, Porton-S vesiculovirus. Vesicular Stomatitis Virus (VSV), in the Vesiculovirus genus, is a prototypic rhabdovirus. While VSV is used as an example in the present disclosure, this disclosure can also be used for other vesiculoviruses and other rhabdoviruses. There are two major serotypes of VSV, New Jersey and Indiana, both of which can infect insects and mammals, causing economically important diseases in cattle, equines and swine. The VSV genome is composed of single-stranded, negative-sense RNA of 11-12 kb, which encodes five viral proteins: the nucleoprotein (N), the phosphoprotein (P), the matrix protein (M), the glycoprotein (G) and the large protein (L). G monomers associate to form trimeric spikes anchored in the viral membrane. Reviewed in, e.g., Sun et al., Future Virol., 2010, 5 (1): 85-96 and Aurélie et al., Viruses 2012, 4:117-139.

As used herein, the phrase "non-essential portion(s) of the recombinant VSV genome" refers to a region of the VSV genome that can be modified without affecting the development and/or growth of the virus in vitro and/or in vivo and without affecting the virus's functions required to act as an immunogenic composition or vaccine.

As used herein in connection with various recombinant enveloped viral particles, the term "pseudotyped" refers to viral particles comprising in their lipid envelope molecules, e.g., proteins, glycoproteins, etc, which are mutated and/or heterologous compared to molecules typically found on the surface of a virus from which the particles are derived (i.e., a "reference virus"), and which may affect, contribute to, direct, redirect and/or completely change the tropism of the viral particle in comparison to the reference virus. In some embodiments, a viral particle is pseudotyped such that it recognizes, binds and/or infects a target (ligand or cell) that is different to that of the reference virus. In some embodiments, a viral particle is pseudotyped such that it does not recognize, bind, and/or infect a target (ligand or cell) of the reference virus.

The term "fusogen" or "fusogenic molecule" is used herein to refer to any molecule that can trigger membrane fusion when present on the surface of a virus particle. A fusogen can be, for example, a protein (e.g., a viral glycoprotein) or a fragment or derivative thereof.

The term "replication-competent" is used herein to refer to viruses (including wild-type and recombinant viral particles) that are capable of infecting and propagating within a susceptible cell.

The term "encoding" as used herein can refer to encoding from either the (+) or (−) sense strand of the polynucleotide for expression in the virus particle.

The terms "specifically binds", "specifically adheres", "specifically targets", "selectively binds" or "binding specificity" refer to the ability of spike(S) glycoproteins, recombinant viral particles, vaccines, neutralizing antibodies, or other molecules described herein to bind to their target. In certain embodiments, specific binding refers to binding to a target with an affinity that is at least 10, 50, 100, 250, 500, or 1000 times greater than the affinity for a non-target. In certain embodiments, this affinity is determined by an affinity ELISA assay. In certain embodiments, affinity is determined by a BIAcore assay. In certain embodiments, affinity is determined by a kinetic method. In certain embodiments, affinity is determined by an equilibrium/solution method.

As used herein, the term "reporter protein" refers to any protein which produces a detectable quantifiable signal when present in a cell. Non-limiting examples of reporter proteins useful in the assays of the present disclosure include, e.g., luciferases (including but not limited to, *Renilla* luciferase, mutant *Renilla* luciferase RLuc 8, (dCpG) Luciferase, NanoLuc reporter, firefly luciferase, *Gaussia* luciferase (gLuc), MetLuc, *Vibrio fischeri* lumazine protein, *Vibrio harveyi* luminaze protein, inoflagellate luciferase, firefly luciferase YY5 mutant, firefly luciferase LGR mutant, firefly luciferase mutant E, and derivatives thereof) and fluorescent proteins (including but not limited to, green fluorescent protein (GFP) [e.g., *Aequoria victoria* GFP, *Renilla muelleri* GFP, *Renilla reniformis* GFP, *Renilla ptilosarcus* GFP], GFP-like fluorescent proteins, (GFP-like), enhanced green fluorescent protein (EGFP), yellow fluorescent protein (YFP) [e.g., Topaz, Venus, mCitrine, YPet, TagYFP, PhiYFP, ZsYellow1, mBanana], enhanced yellow fluorescent protein (EYFP), blue fluorescent protein (BFP) [e.g., EBFP2, Azurite, GFP2, GFP10, and mTagBFP], enhanced blue fluorescent protein (EBFP), cyan fluorescent protein (CFP) [e.g., mECFP, Cerulean, CyPet, AmCyan1, Midori-Ishi Cyan, TagCFP, mCFPmm, mTFP1 (Teal)], enhanced cyan fluorescent protein (ECFP), superfolder GFP, superfolder YFP, orange fluorescent protein [e.g., Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine], red fluorescent protein [e.g., mRuby, mApple, mStrawberry, AsRed2, mRFP1, JRed, mCherry, HcRed1, mRaspberry, dKeima-Tandem, HcRed-Tandem, mPlum, tdTomato, AQ143], small ultrared fluorescent protein, FMN-binding fluorescent protein, dsRed, qFP611, Dronpa, TagRFP, KFP, EosFP, IrisFP, Dendra, Kaede, KikGr1, emerald fluorescent protein, Azami Green, mWasabi, TagGFP, TurboGFP, AcGFP, ZsGreen, T-Sapphire, and derivatives thereof), β-galactosidase, β-glucuronidase, β-geo, etc.

The term "effective" applied to dose or amount refers to that quantity of a compound (e.g., a recombinant virus) or composition (e.g., pharmaceutical, vaccine or immunogenic composition) that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

In the context of the present disclosure insofar as it relates to any of the disease conditions recited herein, the terms "treat", "treatment", and the like mean to relieve or alleviate at least one symptom associated with such condition, or to slow or reverse the progression of such condition. Within the meaning of the present disclosure, the term "treat" also denotes to arrest, delay the onset (i.e., the period prior to clinical manifestation of a disease) and/or reduce the risk of developing or worsening a disease. The terms "treat", "treatment", and the like regarding a state, disorder or condition may also include (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. Non-limiting examples of the symptoms of the COVID-19 disease, include, without limitation, fever, cough, shortness of breath, pneumonia, acute respiratory distress syndrome (ARDS), acute lung syndrome, loss of sense of smell, loss of sense of taste, sore throat, nasal discharge, gastro-intestinal symptoms (e.g., diarrhea), organ failure (e.g., kidney failure and renal dysfunction), septic shock, and death. When used in connection with a disease caused by a viral infection (e.g., SARS-CoV-2 infection), the terms "prevent", "preventing" or "prevention" refer to prevention of spread of infection in a subject exposed to the virus, e.g., prevention of the virus from entering the subject's cells.

The terms "individual" or "subject" or "patient" or "animal" refers to humans, veterinary animals (e.g., cats, dogs, cows, horses, sheep, pigs, etc.), veterinary avian species, and experimental animal models of diseases (e.g., mice, rats, ferrets, monkeys, etc.). In a preferred embodiment, the subject is a human.

The terms "nucleic acid", "polynucleotide" and "nucleotide" are used interchangeably and encompass both DNA and RNA, including positive- and negative-stranded, single- and double-stranded, unless specified otherwise.

The phrase "pharmaceutically acceptable", as used in connection with compositions described herein, refers to molecular entities and other ingredients of such compositions that are physiologically tolerable and do not typically produce untoward reactions when administered to a subject (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The practice of the present disclosure employs, unless otherwise indicated, conventional techniques of statistical analysis, molecular biology (including recombinant techniques), virology, microbiology, cell biology, chemistry and biochemistry, which are within the skill of the art. Such tools and techniques are described in detail in e.g., Sambrook, Fritsch & Maniatis, Molecular Cloning: A Laboratory Manual, Second Edition. Cold Spring Harbor, NY: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82:488-492 (1985), U.S. Pat. No. 5,071,743, Fukuoka et al., Biochem. Biophys. Res. Commun. 263:357-360 (1999); Kim and Maas, BioTech. 28:196-198 (2000); Parikh and Guengerich, BioTech. 24:4 28-431 (1998); Ray and Nickoloff, BioTech. 13:342-346 (1992); Wang et al., BioTech. 19:556-559 (1995); Wang and Malcolm, BioTech. 26:680-682 (1999); Xu and Gong, BioTech. 26:639-641 (1999), U.S. Patents Nos. 5,789, 166 and 5,932, 419, Hogrefe, Strategies 14. 3:74-75 (2001), U.S. Pat. Nos. 5,702,931, 5,780,270, and 6,242,222, Angag and Schutz, Biotech. 30:486-488 (2001), Wang and Wilkinson, Biotech. 29:976-978 (2000), Kang et al., Biotech. 20:44-46 (1996), Ogel and McPherson, Protein Engineer. 5:467-468 (1992), Kirsch and Joly, Nucl. Acids. Res. 26:1848-1850 (1998), Rhem and Hancock, J. Bacteriol. 178:3346-3349 (1996), Boles and Miogsa, Curr. Genet. 28:197-198 (1995), Barrenttino et al., Nuc. Acids. Res. 22:541-542 (1993), Tessier and Thomas, Meths. Molec. Biol. 57:229-237, and Pons et al., Meth. Molec. Biol. 67:209-218.

Viral Particles

One aspect of the disclosure provides recombinant vesicular stomatitis virus (VSV) particles. VSV is an attractive virus for production of recombinant viral particles, because it can be produced in high titers and does not cause serious pathology in humans. In certain embodiments, in the recombinant VSV particles of the disclosure, the VSV glycoprotein (G) is replaced by a coronavirus spike(S) glycoprotein or a fragment or a derivative thereof Recombinant VSV particles of the disclosure can be produced using methods known in the art, e.g., by providing in an appropriate host cell: (a) DNA that can be transcribed to encode VSV antigenomic (+) RNA (complementary to the VSV genome), (b) a recombinant source of VSV nucleoprotein (N) protein, (c) a recombinant source of VSV phosphoprotein (P) protein, (d) a recombinant source of VSV large protein (L), and (e) foreign DNA; under conditions such that the DNA is transcribed to produce the antigenomic RNA, and a VSV is produced that contains genomic RNA complementary to the antigenomic RNA produced and foreign RNA, which is not naturally a part of the VSV genome, from the DNA. Methods and compositions useful for generating recombinant VSV particles may be found, for example, in U.S. Pat. Nos. 7,153,510; 9,861,668; 8,012,489; 9,630,996; 8,287,878; 9,248,178 U.S. Patent Publication Nos. 2014/0271564; 2012/0121650; Fukishi et al., J. Gen. Virol., 2005, 86:2269-2274, all of which are incorporated by reference herein in their entirety.

In certain embodiments, the foreign RNA contained within the genome of the recombinant VSV particles, upon expression in an appropriate host cell, produces one or more foreign proteins. In certain embodiments, one foreign protein is a coronavirus spike(S) glycoprotein (e.g., S glycoprotein from SARS-CoV-2) or a fragment or derivative thereof as described in greater detail below.

In certain embodiments, in addition to encoding a coronavirus spike(S) glycoprotein (e.g., S glycoprotein from SARS-CoV-2) or a fragment or derivative thereof, the genome of the recombinant VSV encodes a reporter protein. Non-limiting examples of reporter proteins include, e.g., luciferases (including but not limited to, *Renilla* luciferase, RLuc8 mutant *Renilla* luciferase, (dCpG) Luciferase, NanoLuc reporter, firefly luciferase, *Gaussia* luciferase (gLuc), MetLuc, *Vibrio fischeri* lumazine protein, *Vibrio harveyi* luminaze protein, inoflagellate luciferase, firefly luciferase YY5 mutant, firefly luciferase LGR mutant, firefly luciferase mutant E, and derivatives thereof) and fluorescent proteins (including but not limited to, green fluorescent protein (GFP) [e.g., *Aequoria victoria* GFP, *Renilla muelleri* GFP, *Renilla reniformis* GFP, *Renilla* ptilosarcus GFP], GFP-like fluorescent proteins, (GFP-like), enhanced green fluorescent protein (EGFP), yellow fluorescent protein (YFP) [e.g., Topaz, Venus, mCitrine, YPet, TagYFP, PhiYFP, ZsYellow1, mBanana], enhanced yellow fluorescent protein (EYFP), blue fluorescent protein (BFP) [e.g., EBFP2, Azurite, GFP2, GFP10, and mTagBFP], enhanced blue fluorescent protein (EBFP), cyan fluorescent protein (CFP) [e.g., mECFP, Cerulean, CyPet, AmCyan1, Midori-Ishi Cyan, TagCFP, mCFPmm, mTFP1 (Teal)], enhanced cyan fluorescent protein (ECFP), superfolder GFP, superfolder YFP, orange fluorescent protein [e.g., Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine], red fluorescent protein [e.g., mRuby, mApple, mStrawberry, AsRed2, mRFP1, JRed, mCherry, HcRed1, mRaspberry, dKeima-Tandem, HcRed-Tandem, mPlum, tdTomato, AQ143], small ultrared fluorescent protein, FMN-binding fluorescent protein, dsRed, qFP611, Dronpa, TagRFP, KFP, EosFP, IrisFP, Dendra, Kaede, KikGr1, emerald fluorescent protein, Azami Green, mWasabi, TagGFP, TurboGFP, AcGFP, ZsGreen, T-Sapphire, and derivatives thereof), β-galactosidase, β-glucuronidase, β-geo, etc.

In certain alternative embodiments, the one or more foreign proteins (e.g., a coronavirus S glycoprotein and/or a reporter protein) are not encoded by the genome of the recombinant VSV particle but are incorporated into said VSV particle as proteins upon production of the recombinant viral particles.

In certain embodiments, the recombinant VSV particle is a replication competent viral particle. In certain embodiments, the recombinant VSV particle is a replication-defective viral particle.

In certain embodiments, the recombinant VSV particles of the disclosure are used for seropositivity assays for determining the presence of a coronavirus neutralizing antibody (e.g., a SARS-CoV-2 neutralizing antibody) in a sample from a subject. Such seropositivity assays can be used, for example, for determining whether or not the subject was previously infected by said coronavirus and has produced neutralizing antibodies protecting such subject from the infection (and thus allowing such subject to return to work, etc.). Seropositivity assays of the disclosure can be also used, for example, for determining effectiveness of vaccination, for development of therapeutic antibodies, for selecting best donors for convalescent plasma therapy, for patient contact tracing, for identifying the viral reservoir hosts, for determining the burden of disease, for determining the rate of asymptomatic infections, for identifying the extent of virus spread in households, communities, and specific settings, etc.

In certain embodiments, the seropositivity assays of the disclosure use more than one type of recombinant VSV particles. In certain embodiments, such assays use a mixture of two or more recombinant VSV particles encoding different coronaviral S glycoproteins (e.g., SARS-CoV-2 S glycoproteins originating from different viral strains, variants or mutants).

In certain aspects, the current disclosure provides cells for production of the recombinant VSV particles of the disclosure. Exemplary cells include, but are not limited to, any cell in which VSV grows, e.g., mammalian cells and some insect (e.g., *Drosophila*) cells. A vast number of primary cells and cell lines commonly known in the art can be used as host cells. By way of example, useful cell lines include but are not limited to BHK (baby hamster kidney) cells, CHO (Chinese hamster ovary) cells, HeLA (human) cells, mouse L cells, Vero (monkey) cells (including Vero-αHis cells), Vero-Ace-2 cells, Vero-TRMPSS2 cells, Vero-E6 cells, ESK-4, PK-15, EMSK cells, MDCK (Madin-Darby canine kidney) cells, MDBK (Madin-Darby bovine kidney) cells, 293 (human) cells, Hep-2 cells, primary chick embryo fibroblasts, primary chick embryo fibroblasts, quasi-primary continuous cell lines (e.g. AGMK-African green monkey kidney cells), human diploid primary cell lines (e.g. WI-38 and MRC5 cells), and Monkey Diploid Cell Line (e.g. FRhL-Fetal Rhesus Lung cells).

VSV DNA for Transcription to Produce VSV Antigenomic (+) RNA

Vesicular Stomatitis Virus (VSV) is a rhabdovirus that comprises a single (non-segmented) negative-stranded genomic RNA that is generally transcribed by a virion polymerase into five mRNAs encoding five structural proteins. The five structural proteins include glycoprotein (G), large protein (L), phosphoprotein (P), matrix protein (M), and nucleoprotein (N). The nucleocapsid protein encapsidates the RNA genome. Two proteins that form a polymerase complex are bound to the nucleocapsid. A matrix (M) protein is associated with the nucleocapsid and the membrane. A single (transmembrane) envelope spike glycoprotein (G) extends from the viral envelope. The G protein functions to bind virus to a cellular receptor and to catalyze fusion of the viral membrane with cellular membranes to initiate the infectious cycle. The size of the VSV genome is about 11 kilobases.

VSV can be transmitted to a variety of mammalian hosts, generally cattle, horses, swine and rodents. VSV infection of humans is uncommon, and in general is either asymptomatic or characterized by mild flu-like symptoms that resolve in three to eight days without complications. VSV is not considered a human pathogen and pre-existing immunity to VSV is rare in the human population making VSV an attractive viral vector for vaccine and therapeutic applications. Other beneficial characteristics of VSV include, but are not limited to, (i) ability to replicate robustly in cell culture, (ii) inability to either integrate into host cell DNA or undergo genetic recombination, (iii) multiple serotypes can allow for prime-boost immunization strategies, and (iv) foreign genes of interest can be inserted into the VSV genome and expressed abundantly by the viral transcriptase.

Fusion of rhabdoviruses (e.g., VSV) to cells, and their subsequent uptake, is described in Belot, L. et al., "Structural and cellular biology of rhabdovirus entry", Adv. Virus Res., 2019, 104:147-183, which is incorporated by reference herein in its entirety, and Albertini, A. A. V. et al., "Molecular and Cellular Aspects of Rhabdovirus Entry" Viruses, 2012, 4:117-139, which is incorporated by reference herein in its entirety. Further description of endocytosis of VSV is found in Sun, X. et al., "Internalization and fusion mechanism of vesicular stomatitis virus and related rhabdoviruses" Future Virol., 2010, 5 (1): 85-96, which is incorporated by reference herein in its entirety. For general information on virus-cell fusion, see Igonet, S. et al., "SnapShot: Viral and Eukaryotic Protein Fusogens" Cell, 2012, 151: 1634el, which is incorporated by reference herein in its entirety.

Cell-cell fusion mediated by other viruses, such as HIV virus, has been described in Kondo, N. et al., "Conformational changes of the HIV-1 envelope protein during membrane fusion are inhibited by the replacement of its membrane-spanning domain" Journ. Biol. Chem., 2010, 285 (19): 14681-88, which is incorporated by reference herein in its entirety.

Many vesiculoviruses are known in the art and can be made recombinant according to the methods disclosed herein. Non-limiting examples of such vesiculoviruses are listed below:

| Virus | Source of virus in nature |
|---|---|
| VSV-New Jersey | Mammals, mosquitoes, midges, blackflies, houseflies |
| VSV-Indiana | Mammals, mosquitoes, sandflies |
| Alagoas | Mammals, sandflies |
| Cocal | Mammals, mosquitoes, mites |
| Jurona | Mosquitoes |
| Carajas | Sandflies |
| Maraba | Sandflies |
| Piry | Mammals |
| Calchaqui | Mosquitoes |
| Yug Bogdanovac | Sandflies |
| Isfahan | Sandflies, ticks |
| Chandipura | Mammals, sandflies |
| Perinct | Mosquitoes, sandflies |
| Porton-S | Mosquitoes |

In certain embodiments, VSVs are the vesiculoviruses used to make the recombinant viruses of the disclosure. In certain embodiments, the recombinant VSV is a recombinant VSV-New Jersey or VSV-Indiana. In certain embodiments, the recombinant VSV is a recombinant VSV-New Jersey. VSV is used as an example in the disclosure below, and this disclosure can also be used for other vesiculoviruses.

Any DNA that can be transcribed to produce VSV antigenomic (+) RNA (complementary to the VSV genome) can be used for the construction of a recombinant DNA containing foreign DNA encoding a heterologous (foreign) protein or peptide, for use in producing the recombinant VSV particles of the disclosure. In certain embodiments, the DNA that can be transcribed to encode VSV antigenomic (+) RNA comprises at least genes for the VSV nucleoprotein (N), the VSV phosphoprotein (P), and the VSV large protein (L).

The VSV vector can be genetically modified to include one or more mutations or "mutation classes" in the genome. "Mutation class", "mutation classes" or "classes of mutation" are used interchangeably, and refer to mutations known in the art, when used singly, to attenuate VSV. Exemplary mutation classes include, but are not limited to, a VSV temperature-sensitive N gene mutation (hereinafter, "N(ts)"), a temperature-sensitive L gene mutation (hereinafter, "L(ts)"), a point mutation, a G-stem mutation (hereinafter, "G(stem)"), a non-cytopathic M gene mutation (hereinafter, "M(ncp)"), a gene shuffling or rearrangement mutation, a truncated G gene mutation (hereinafter, "G(ct)"), an ambisense RNA mutation, a G gene insertion mutation, a gene deletion mutation and the like. Mutations can be insertions, deletions, substitutions, gene rearrangement or shuffling modifications.

In certain embodiments of the methods disclosed herein, the recombinant VSV particle is replication-competent. In certain other embodiments, the recombinant VSV particle is replication-deficient.

In certain embodiments of the methods and compositions disclosed herein, in the recombinant VSV particle, the VSV G glycoprotein is replaced by a coronavirus spike(S) glycoprotein, or a fragment or derivative thereof, wherein said S glycoprotein, fragment or derivative is capable of mediating infection of a target cell. In certain embodiments, the genome of the recombinant VSV particle lacks a functional VSV G gene and encodes a coronavirus spike(S) glycoprotein, or a fragment or derivative thereof. Also provided is a VSV particle wherein (i) the VSV glycoprotein (G) is replaced by a coronavirus spike(S) glycoprotein or a fragment or a derivative thereof, wherein said S glycoprotein, fragment or derivative is capable of mediating infection of a target cell and wherein (ii) the VSV particle comprises a reporter protein and/or a nucleic acid molecule encoding said reporter protein. The nucleic acid sequence encoding the reporter protein may be inserted between the nucleic acid sequence encoding the S glycoprotein and the nucleic acid sequence encoding VSV large (L) protein.

The mutations can attenuate the infectivity, virulence or pathogenic effects of VSV. The attenuation can be additive or synergistic. With synergistic attenuation, the level of VSV attenuation is greater than additive. Synergistic attenuation of VSV can arise from combining at least two classes of mutation in the same VSV genome, thereby resulting in a reduction of VSV pathogenicity much greater than an additive attenuation level observed for each VSV mutation class alone. A synergistic attenuation of VSV can provide for an LD50 at least greater than the additive attenuation level observed for each mutation class alone (i.e., the sum of the two mutation classes), where attenuation levels (i.e., the LD50) are determined in a small animal neurovirulence model.

The VSV M gene encodes the virus matrix (M) protein, and two smaller in-frame polypeptides (M2 and M3). The M2 and M3 polypeptides can be translated from the same open reading frame (ORF) as the M protein and lack the first 33 and 51 amino acids, respectively. A recombinant VSV vector comprising non-cytopathic M gene mutations (i.e., VSV vectors that also do not express M2 and M3 proteins) can be generated and can further comprise one or more additional mutation(s) thereby resulting in a VSV vector that was highly attenuated in cell culture and in animals.

In certain embodiments, the recombinant VSV particles of the disclosure comprise a non-cytopathic mutation in the M gene. The VSV (Indiana serotype) M gene encodes a 229 amino acid M (matrix) protein in which the first thirty amino acids of the NH2-terminus comprise a proline-rich PPPY (PY) motif (SEQ ID NO: 68). The PY motif of VSV M protein is located at amino acid positions 24-27 in both VSV Indiana (Genbank Accession Number X04452) and New Jersey (Genbank Accession Number M14553) serotypes. The VSV may comprise mutations in the PY motif (e.g., APPY (SEQ ID NO: 69), AAPY (SEQ ID NO: 70), PPAY (SEQ ID NO: 71), APPA (SEQ ID NO: 72), AAPA (SEQ ID NO: 73) and PPPA (SEQ ID NO: 74)). The VSV can comprise any of various amino acid mutations (e.g., deletions, substitutions, insertions, etc.) into the M protein PSAP (PS) motif (SEQ ID NO: 75). These and other mutations in the PY motif may be effective to reduce virus yield by blocking a late stage in virus budding.

The recombinant VSV particles of the disclosure may comprise one or more M gene mutations. Non-limiting examples of M protein mutations include, e.g., a glycine changed to a glutamic acid at position (21), a leucine changed to a phenylalanine at position (111), a methionine changed to an arginine at position (51), a glycine changed to a glutamic acid at position (22), a methionine changed to an arginine at position (48), a leucine changed to a phenylalanine at position (110), a methionine changed to an alanine at position (51), and a methionine changed to an alanine at position (33). See, e.g., U.S. Pat. No. 9,630,996. In various embodiments of the methods described herein, the genome of the recombinant VSV encodes a mutant VSV matrix M protein comprising the M51R mutation. Mutation M51R eliminates M protein's ability to block cellular nucleocytoplasmic transport and thus substantially attenuates VSV infectivity.

In certain embodiments, the DNA that can be transcribed to encode VSV antigenomic (+) RNA comprises a gene that encodes a VSV M protein. In certain embodiments, the VSV M protein used in the methods and compositions described herein may comprise the amino acid sequence of SEQ ID NO: 9, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, 99.5% or more identical to the amino acid sequence of SEQ ID NO: 9. In certain embodiments, the VSV M protein used in the vaccines or methods described herein may consist of the amino acid sequence of SEQ ID NO: 9, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, 99.5% or more identical to the amino acid sequence of SEQ ID NO: 9. In certain embodiments, the mutated VSV M protein used in the vaccines or methods described herein may comprise the amino acid sequence of SEQ ID NO: 7, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, 99.5% or more identical to the amino acid sequence of SEQ ID NO: 7. In certain embodiments, the mutant VSV M protein used in the vaccines or methods described herein may consist of the amino acid sequence of SEQ ID NO: 7, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, 99.5% or more identical to the amino acid sequence of SEQ ID NO: 7.

DNA that can be transcribed to produce VSV (for example) antigenomic (+) RNA (such DNA being referred to herein as "VSV (–) DNA") is available in the art and/or can be obtained by standard methods. VSV (–) DNA for any serotype or strain known in the art, e.g., the New Jersey or Indiana serotypes of VSV, can be used. The complete nucleotide and deduced protein sequence of the VSV genome is known, and is available as Genbank VSVCG, Accession No. J02428; NCBI Seq ID 335873; and is published in Rose and Schubert, 1987, in The Viruses: The Rhabdoviruses, Plenum Press, NY, pp. 129-166. An example of the complete sequence of the VSV (–) DNA that is contained in plasmid pVSVFL (+) is shown, e.g., in U.S. Pat. No. 7,153,510, which is incorporated herein in its entirety for all intended purposes. Sequences of other vesiculovirus genomes have been published and are available in the art.

VSV (–) DNA, if not already available, can be prepared by standard methods, as follows: VSV genomic RNA can be purified from virus preparations, and reverse transcription with long distance polymerase chain reaction used to generate the v (–) DNA. Alternatively, after purification of genomic RNA, VSV mRNA can be synthesized in vitro, and cDNA prepared by standard methods, followed by insertion into cloning vectors (see, e.g., Rose and Gallione, 1981, J. Virol. 39 (2): 519-528). Individual cDNA clones of VSV RNA can be joined by use of small DNA fragments covering the gene junctions, generated by use of reverse transcription and polymerase chain reaction (RT-PCR) (Mullis and Faloona, 1987, Meth. Enzymol. 155:335-350) from VSV genomic RNA (see Section 6, infra). VSV and other vesiculoviruses are available in the art.

In certain embodiments, one or more, usually unique, restriction sites (e.g., in a polylinker) are introduced into the VSV (–) DNA, in intergenic regions, or 5' of the sequence complementary to the 3' end of the VSV genome, or 3' of the sequence complementary to the 5' end of the VSV genome, to facilitate insertion of the foreign DNA.

In certain embodiments, the VSV (–) DNA is constructed so as to have a promoter operatively linked thereto. The promoter should be capable of initiating transcription of the (–) DNA in an animal or insect cell in which it is desired to produce the recombinant VSV. Promoters which may be used include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); heat shock promoters (e.g., hsp70 for use in *Drosophila* S2 cells); the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318: 533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); and myosin light chain-2 gene control region which is active in skeletal muscle (Sani, 1985, Nature 314:283-286). Preferably, the promoter is an RNA polymerase promoter, preferably a bacteriophage or viral or insect RNA polymerase promoter, including but not limited to the promoters for T7 RNA polymerase, SP6 RNA polymerase, and T3 RNA polymerase. If an RNA polymerase promoter is used in which the RNA polymerase is not endogenously produced by the host cell in which it is desired to produce the recombinant VSV, a recombinant source of the RNA polymerase must also be provided in the host cell.

The VSV (–) DNA can be operably linked to a promoter before or after insertion of foreign DNA. In certain embodiments, a transcriptional terminator is situated downstream of the VSV (–) DNA.

In another embodiment, a DNA sequence that can be transcribed to produce a ribozyme sequence is situated at the immediate 3' end of the VSV (–) DNA, prior to the transcriptional termination signal, so that upon transcription a self-cleaving ribozyme sequence is produced at the 3' end of the antigenomic RNA, which ribozyme sequence will autolytically cleave (after a U) this fusion transcript to release the exact 3' end of the VSV antigenomic (+) RNA. Any ribozyme sequence known in the art may be used, as long as the correct sequence is recognized and cleaved. In a preferred aspect, hepatitis delta virus (HDV) ribozyme is used (Perrotta and Been, 1991, Nature 350:434-436; Pattnaik et al., 1992, Cell 69:1011-1020).

An example of a VSV (–) DNA for use, for insertion of foreign DNA, can thus comprises (in 5' to 3' order) the following operably linked components: the T7 RNA polymerase promoter, VSV (–) DNA, a DNA sequence that is transcribed to produce an HDV ribozyme sequence (immediately downstream of the VSV (–) DNA), and a T7 RNA polymerase transcription termination site.

Examples of plasmids that can be used are, pVSVFL (+) or pVSVSS1.

In certain embodiments, a coronavirus spike(S) protein can replace the endogenous VSV G protein in the recombinant VSV particle, or can be expressed as a fusion with the endogenous VSV G protein, or can be expressed in addition to the endogenous VSV G protein either as a fusion or nonfusion protein. For example, the G gene of VSV in the VSV (–) DNA of plasmid pVSVFL (+) can be excised and replaced, by cleavage at the NheI and MluI sites flanking the G gene and insertion of the desired sequence. In other embodiments, a coronavirus spike(S) protein is expressed as a fusion protein comprising the cytoplasmic domain (and, optionally, also the transmembrane region) of the VSV G protein. In certain embodiments, a coronavirus spike(S) protein forms a part of the VSV envelope and thus is surface-displayed in the VSV particle.

In certain embodiments, foreign DNA is inserted into an intergenic region, or a portion of the VSV (−) DNA that is transcribed to form the noncoding region of a viral mRNA. In certain embodiments, the foreign DNA is inserted into a coding region of the VSV genome that is non-essential to the virus's development, growth and/or functions required to act as a vaccine. In certain embodiments, the VSV G gene is disrupted. In certain embodiments, the foreign DNA insertion does not disrupt the G gene or G protein function.

Coronavirus Spike(S) Glycoprotein

Coronavirus entry into host cells is mediated by the transmembrane spike(S) glycoprotein (interchangeably referred to as "spike glycoprotein", "S glycoprotein", "S protein" or "spike protein") which is the main target of anti-viral neutralizing antibodies and is the focus of therapeutic and vaccine design. S glycoprotein forms homotrimers protruding from the viral surface. S glycoprotein comprises two functional subunits responsible for binding to the host cell receptor (S1 subunit) and fusion of the viral and cellular membranes (S2 subunit). For many coronaviruses, including SARS-CoV-1 and SARS-CoV-2, S glycoprotein is cleaved at the boundary between the S1 and S2 subunits, which remain non-covalently bound in the prefusion conformation. The distal S1 subunit comprises the receptor-binding domain(s) (RBD) and contributes to stabilization of the prefusion state of the membrane-anchored S2 subunit that contains the fusion machinery. S is further cleaved by host proteases at the S2' site located immediately upstream of the fusion peptide. This cleavage has been proposed to activate the protein for membrane fusion via conformational changes. Walls et al., Cell, published online Mar. 9, 2020; available at doi.org/10.1016/j.cell.2020.02.058.

SARS-CoV-1 and SARS-CoV-2 can interact directly with angiotensin-converting enzyme 2 (ACE2) to enter target cells and may also employ the cellular serine protease, transmembrane protease, serine 2 (TMPRSS2) for S protein priming (Hoffmann et al., Cell, 2020, 181:1-10; available at doi.org/10.1016/j.cell.2020.02.052). SARS—CoV-S und SARS-CoV-2-S share about 76% amino acid identity. The receptor binding domain (RBD) in the S glycoprotein is the most variable part of the coronavirus genome. Six RBD amino acids have been shown to be critical for binding to ACE2 receptors and for determining the host range of SARS-CoV-like viruses. They are Y442, L472, N479, D480, T487 and Y4911 in SARS-CoV, which correspond to L455, F486, Q493, S494, N501 and Y505 in SARS-CoV-2 (Andersen et al., Nature Medicine, 2020; available at doi.org/10.1038/s41591-020-0820-9).

In certain embodiments of the disclosure, the VSV particles comprise the SARS-CoV-2 S glycoprotein or a fragment or derivative thereof, wherein said S glycoprotein, fragment or derivative is capable of mediating infection of a target cell. In various embodiments, the S glycoprotein may be a full-length SARS-CoV-2 S glycoprotein (comprising or consisting of SEQ ID NO: 1) or a fragment or derivative thereof that has at least 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or more amino acid sequence identity to SEQ ID NO: 1.

The wild-type coronavirus S glycoprotein comprises an S1 subunit that facilitates binding of the coronavirus to cell surface proteins. Without wishing to be bound by theory, the S1 subunit of the wildtype S glycoprotein controls which cells are infected by the coronavirus. The wild-type S glycoprotein also comprises a S2 subunit, which is a transmembrane subunit that facilitates viral and cellular membrane fusion. In the various aspects and embodiments described herein, a fragment or derivative of SARS-CoV-2 S glycoprotein can comprise the S1 subunit of the SARS-CoV-2 S glycoprotein or a fragment or derivative that has at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or more amino acid sequence identity to the S1 subunit of the SARS-CoV-2 S glycoprotein. In some embodiments described herein, a fragment or derivative of SARS-CoV-2 S glycoprotein can comprise a sequence that has at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or more amino acid sequence identity to amino acids 14-684 of SEQ ID NO: 1. In the various aspects and embodiments described herein, a fragment or derivative of SARS-CoV-2 S glycoprotein can comprise the S2 subunit of the SARS-CoV-2 S glycoprotein or a fragment or derivative that has at least 91%, 92%, 93%, 94%, 95%, 96%, 97%, 98%, 99%, 99.5% or more amino acid sequence identity to the S2 subunit of the SARS-CoV-2 S glycoprotein.

The wild-type coronavirus S glycoprotein comprises a receptor binding domain (RBD) that facilitates binding of the coronavirus to its receptor on the host cell. The RBD of the SARS-CoV-2 spike(S) glycoprotein is described, e.g., in Anderson et al., Nature Medicine, 2020 (available at doi.org/10.1038/s41591-020-0820-9). In the various aspects and embodiments described herein, a fragment or derivative of SARS-CoV-2 S glycoprotein can comprise the RBD of the SARS-CoV-2 S glycoprotein, or a fragment or derivative that has at least 74%, 75%, 76%, 77%, 78%, 80%, 81%, 82%, 83%, 84%, 85%, 86%, 87%, 88%, 89%, 90%, 91%, 92%, 93%, 94%, 95%, 96%, 97%, 98%, 99%, 99.5% or more amino acid sequence identity to the RBD of the SARS-CoV-2 S glycoprotein. In some embodiments described herein, a fragment or derivative of SARS-CoV-2 S glycoprotein can comprise a sequence that has at least 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or more amino acid sequence identity to amino acids 319-541 of SEQ ID NO: 1.

In certain embodiments, the SARS-CoV-2 S glycoprotein derivative, or fragment thereof, may comprise or consist of an insertion, deletion, and/or substitution of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 residues of the SARS-CoV-2 S glycoprotein. Non-limiting examples of amino acids for potential deletion include, e.g., a tyrosine at position (145), an asparagine at position (679), a serine at position (680), proline at position (681), an arginine at position (682), an arginine at position (683), an alanine at position (684), and/or an arginine at position (685), positions as denoted in SEQ ID NO: 1, or the equivalent amino acid residue in a mutant SARS-CoV-2 S glycoprotein sequence. Non-limiting examples of amino acids for potential substitution include, e.g., a leucine changed to a phenylalanine at position (5) a tyrosine changed to an asparagine at position (28), a threonine changed to an isoleucine at position (29), a histidine changed to a tyrosine at position (49), a leucine changed to a phenylalanine at position (54), an asparagine changed to a lysine at position (74), a glutamic acid changed to an aspartic acid at position (96), an aspartic acid changed to an asparagine at position (111), a phenylalanine changed to a leucine at position (157), a glycine changed to a valine at position (181), a serine changed to a tryptophan at position (221), a serine changed to an arginine at position (247), an alanine changed to a threonine at position (348), an arginine changed to an isoleucine at position (408), a glycine changed to a serine at position (476), a valine changed to an alanine at position (483), a histidine changed to a glutamine at position (519), an alanine changed to a serine at position (520), an aspartic acid changed to an asparagine at position (614), an aspartic acid changed to a glycine at position (614), an asparagine changed to an isoleucine at position (679), a serine change to a leucine at position (680), an arginine changed to a glycine at position (682), an arginine changed to a serine at position (683), an arginine changed to a glutamine at position (685), an arginine changed to a serine at position (685), a phenylalanine changed to a cysteine at position (797), an alanine changed to a valine at position (930), an aspartic acid changed to a tyrosine at position (936), an alanine changed to a valine at position (1078), an aspartic acid changed to a histidine at position (1168), and/or an aspartic acid changed to a histidine at position (1259), positions as denoted in SEQ ID NO: 1, or the equivalent amino acid residue in a mutant SARS-CoV-2 S glycoprotein sequence. See Becerra-Flores and Cardozo, "SARS-CoV-2 viral spike G614 mutation exhibits higher case fatality rate," *The International Journal of Clinical Practice*, published online May 6, 2020; Eaaswarkhanth et al., "Could the D614G substitution in the SARS-CoV-2 spike(S) protein be associated with higher COVID-19 mortality?" *International Journal of Infectious Diseases,* 96: July 2020, Pages 459-460; Tang et al., "The SARS-CoV-2 Spike Protein D614G Mutation Shows Increasing Dominance and May Confer a Structural Advantage to the Furin Cleavage Domain," Preprints 2020, 2020050407 (doi: 10.20944/preprints202005.0407.v1); Hansen et. al., "Studies in humanized mice and convalescent humans yield a SARS-CoV-2 antibody cocktail" *Science*, published online Jun. 15, 2020; Lokman et al., "Exploring the genomic and proteomic variations of SARS-CoV-2 spike glycoprotein: A computational biology approach", *Infection, Genetics and Evolution: Journal of Molecular Epidemiology and Evolutionary Genetics in Infectious Diseases,* 2020 June; 84:104389. DOI: 10.1016/j.meegid.2020.104389, each of which incorporated herein by reference in their entirety for all intended purposes. Additional non-limiting examples of amino acid residue positions for insertion, deletion, and/or substitution include those as listed in Tables 8 and 9 (amino acid residue positions are denoted using SEQ ID NO: 1 as a reference sequence, which can be used as a reference for identifying the equivalent amino acid residue in any SARS-CoV-2 S glycoprotein sequence (same as above); references in Table 8 are incorporated herein by reference in their entirety for all intended purposes). Each residue modification listed in Table 8 can separately be used alone or in combination with others to generate variants of a recombinant vesicular stomatitis virus (VSV) particle. In certain embodiments, the SARS-CoV-2 S glycoprotein derivative, or fragments thereof, differs in amino acid sequence from the reference peptide or polypeptide (e.g., wild-type SARS-CoV-2 spike protein) by changing a serine to an arginine at position (247), an aspartic acid to an asparagine at position (614), and/or an arginine to a glutamine at position (685), positions as denoted in SEQ ID NO: 1, or the equivalent amino acid residue in a mutant SARS-CoV-2 S glycoprotein sequence. In certain embodiments, the SARS-CoV-2 S glycoprotein derivative, or fragments thereof, differs in amino acid sequence from the reference peptide or polypeptide by changing a serine to an arginine at position (247). In certain embodiments, the SARS-CoV-2 S glycoprotein derivative, or fragments thereof, differs in amino acid sequence from the reference peptide or polypeptide by changing an aspartic acid to an asparagine at position (614). In certain embodiments, the SARS-CoV-2 S glycoprotein derivative, or fragments thereof, differs in amino acid sequence from the reference peptide or polypeptide by changing an arginine to a glutamine at position (685). In certain embodiments, the SARS-CoV-2 S glycoprotein derivative, or fragments thereof, differs in amino acid sequence from the reference peptide or polypeptide by changing a serine to an arginine at position (247) and an aspartic acid to an asparagine at position (614). In certain embodiments, the SARS-CoV-2 S glycoprotein derivative, or fragments thereof, differs in amino acid sequence from the reference peptide or polypeptide by changing a serine to an arginine at position (247) and an arginine to a glutamine at position (685). In certain embodiments, the SARS-CoV-2 S glycoprotein derivative, or fragments thereof, differs in amino acid sequence from the reference peptide or polypeptide by changing an aspartic acid to an asparagine at position (614) and an arginine to a glutamine at position (685). In certain embodiments, the SARS-CoV-2 S glycoprotein derivative, or fragments thereof, differs in amino acid sequence from the reference peptide or polypeptide by changing a serine to an arginine at position (247), an aspartic acid to an asparagine at position (614), and an arginine to a glutamine at position (685). In certain embodiments, the SARS-CoV-2 S glycoprotein derivative, or fragments thereof, result in a more lytic phenotype. In certain embodiments, the SARS-CoV-2 S glycoprotein fragment or derivative may comprise the amino acid sequence of SEQ ID NO: 42, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to the amino acid sequence of SEQ ID NO: 42. In certain embodiments, the SARS-CoV-2 S glycoprotein fragment or derivative may be encoded by a codon optimized nucleotide sequence. In various embodiments, SARS-CoV-2 S glycoprotein fragment or derivative may be encoded by the polynucleotide sequence of SEQ ID NO: 43 or a sequence that has at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% polynucleotide sequence identity to SEQ ID NO: 43. In certain embodiments, the SARS-CoV-2 S glycoprotein fragment or derivative may comprise the amino acid sequence of SEQ ID NO: 44, or a sequence at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to the amino acid sequence of SEQ ID NO: 44. In certain embodiments, the SARS-CoV-2 S glycoprotein derivative, or fragments thereof, differs in amino acid sequence from the reference peptide or polypeptide (e.g., wild-type SARS-CoV-2 spike protein) by changing an asparagine to a tyrosine at position (501), and/or a glutamic acid to a lysine at position (484), and/or an aspartic acid to a glycine at position (614), and/or deletion of residues 69-70, positions as denoted in SEQ ID NO: 1, or the equivalent amino acid residue in a mutant SARS-CoV-2 S glycoprotein sequence. In certain embodiments, the SARS-CoV-2 S glycoprotein derivative, or fragments thereof, differs in amino acid sequence from the reference peptide or polypeptide by changing an asparagine to a tyrosine at position (501). In certain embodiments, the SARS-CoV-2 S glycoprotein derivative, or fragments thereof, differs in amino acid sequence from the reference peptide or polypeptide by changing a glutamic acid to a lysine at position (484). In certain embodiments, the SARS-CoV-2 S glycoprotein derivative, or fragments thereof, differs in amino acid sequence from the reference peptide or polypeptide by changing an aspartic acid to a glycine at position (614). In certain embodiments, the SARS-CoV-2 S glycoprotein derivative, or fragments thereof, differs in amino acid sequence from the reference peptide or polypeptide by deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501) and a glutamic acid to a lysine at position (484). In certain embodiments, the SARS-CoV-2 S glycoprotein derivative, or fragments thereof, differs in amino acid sequence from the reference peptide or polypeptide by changing an asparagine to a tyrosine at position (501) and an aspartic acid to a glycine at position (614). In certain embodiments, the SARS-CoV-2 S glycoprotein derivative, or fragments thereof, differs in amino acid sequence from the reference peptide or polypeptide by changing an asparagine to a tyrosine at position (501) and deletion of residues 69-70. In certain embodiments, the SARS-CoV-2 S glycoprotein derivative, or fragments thereof, differs in amino acid sequence from the reference peptide or polypeptide by changing a glutamic acid to a lysine at position (484) and an aspartic acid to a glycine at position (614). In certain embodiments, the SARS-CoV-2 S glycoprotein derivative, or fragments thereof, differs in amino acid sequence from the reference peptide or polypeptide by changing a glutamic acid to a lysine at position (484) and deletion of residues 69-70. In certain embodiments, the SARS-CoV-2 S glycoprotein derivative, or fragments thereof, differs in amino acid sequence from the reference peptide or polypeptide by changing an aspartic acid to a glycine at position (614) and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), a glutamic acid to a lysine at position (484), and an aspartic acid to a glycine at position (614). In certain embodiments, the SARS-CoV-2 S glycoprotein derivative, or fragments thereof, differs in amino acid sequence from the reference peptide or polypeptide by changing an asparagine to a tyrosine at position (501), changing a glutamic acid to a lysine at position (484), and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), changing an aspartic acid to a glycine at position (614), and deletion of residues 69-70. In certain embodiments, the SARS-CoV-2 S glycoprotein derivative, or fragments thereof, differs in amino acid sequence from the reference peptide or polypeptide by changing a glutamic acid to a lysine at position (484), changing an aspartic acid to a glycine at position (614), and deletion of residues 69-70. In certain embodiments, the SARS-CoV-2 S glycoprotein derivative, or fragments thereof, differs in amino acid sequence from the reference peptide or polypeptide by changing an asparagine to a tyrosine at position (501), changing a glutamic acid to a lysine at position (484), changing an aspartic acid to a glycine at position (614) and deletion of residues 69-70. In certain embodiments, the SARS-CoV-2 S glycoprotein derivative, or fragments thereof, differs in amino acid sequence from the reference peptide or polypeptide (e.g., wild-type SARS-CoV-2 spike protein) by inactivating the furin cleavage site within the spike protein. In certain embodiments, the SARS-CoV-2 S glycoprotein derivative, or fragments thereof, differs in amino acid sequence from the reference peptide or polypeptide (e.g., wild-type SARS-CoV-2 spike protein) by changing Q677TNSPRRARSV687 (SEQ ID NO: 65), as denoted in SEQ ID NO: 1, or the equivalent amino acid residue in a mutant SARS-CoV-2 S glycoprotein sequence, to QTILRSV (SEQ ID NO: 66) or to QTNSPGSASSV (SEQ ID NO: 67). In certain embodiments, the SARS-CoV-2 S glycoprotein derivative, or fragments thereof, result in a monobasic furin cleavage site in the S1/S2 interface (QTILRSV (SEQ ID NO: 66)) or deletion of the furin cleavage site (QTNSPGSASSV (SEQ ID NO: 67)) phenotype. In certain embodiments, the alteration to the furin cleavage site can lead to a spike stabilized pseudoparticles. See Hansen et. al., "Studies in humanized mice and convalescent humans yield a SARS-CoV-2 antibody cocktail" Science, published online Jun. 15, 2020, incorporated herein by reference in its entirety for all intended purposes.

In certain embodiments, the SARS-CoV-2 S glycoprotein fragment or derivative lacks one or more C-terminal residues of the full-length SARS-CoV-2 S glycoprotein. For example, the SARS-CoV-2 S glycoprotein fragment may lack 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 of the C-terminal residues of the SARS-CoV-2 S glycoprotein. In certain embodiments, the SARS-CoV-2 S glycoprotein fragment or derivative lacks the 19 C-terminal residues of the SARS-CoV-2 S glycoprotein. The SARS-CoV-2 S glycoprotein fragment or derivative may consist of the amino acid sequence of SEQ ID NO: 3, or a sequence at least 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or more identical to the amino acid sequence of SEQ ID NO: 3.

In certain embodiments, the SARS-CoV-2 S glycoprotein derivative is a chimeric or fusion molecule which comprises fusogen sequences from viruses other than SARS-CoV-2. In certain embodiments, such chimeras comprise S1 or RBD sequences of SARS-CoV-2 S glycoprotein. In certain embodiments, the fusion protein is a fusion between the extracellular and transmembrane sequence of SARS-CoV-2 S glycoprotein, or a fragment or derivative thereof and a cytoplasmic domain of a non-SARS-CoV-2 fusogen or a fragment or derivative thereof. In certain embodiments, the fusion protein is a fusion between the extracellular sequence of SARS-CoV-2 S glycoprotein, or a fragment or derivative thereof and transmembrane and cytoplasmic domains of a non-SARS-CoV-2 fusogen or a fragment or derivative thereof. Non-limiting examples of non-SARS-CoV-2 fusogens which can be used in the above chimeric and fusion molecules include, for example, coronavirus fusogens (e.g., from SARS-CoV-1 or MERS-CoV), fusogens from VSV or other vesiculoviruses or other viruses from the Rhabdoviridae family, viruses from the Retroviridae family (e.g., human immunodeficiency virus (HIV), murine leukemia virus (MLV), Avian sarcoma leukosis virus (ASLV), Jaagsiekte sheep retrovirus (JSRV)), viruses from the Paramyxoviridae family (e.g., parainfluenza virus 5 (PIV5)), viruses from the Herpesviridae family (e.g., herpes simplex virus (HSV)), viruses from the Togaviridae family (e.g., Semliki Forest virus (SFV), Rubella virus), viruses from the Flaviviridae family (e.g., tick-borne encephalitis virus (TBE), Dengue virus), viruses from the Orthomyxoviridae family (e.g., influenza virus), viruses from the Arenaviridae family (e.g., lymphocytic choriomenengitis virus (LCMV), Lassa fever virus (LASV)), viruses from the Bunyaviridae family (e.g., Uukuniemi Virus (UUKV)), viruses from the Filoviridae family (e.g., Ebola virus (EBOV)), viruses from the Poxviridae family (e.g., Vaccinia virus (VV)), viruses from the Asfaviridae family (e.g., African swine fever virus (ASFV)), viruses from the Arteriviridae family (e.g., porcine reproductive and respiratory syndrome virus (PRRSV)), viruses from the Bornaviridae family (e.g., Borna disease virus (BDV)), viruses from the Hepadnaviridae family (e.g., Hepatitis B virus (HBV)), and viruses from Hantaviridae family (e.g., Andes virus).

In certain embodiments, the fusion protein is a fusion between a SARS-CoV-2 S glycoprotein, or a fragment or derivative thereof and a VSV glycoprotein G protein or a fragment or derivative thereof. In certain embodiments, the fusion protein is a fusion between a SARS-CoV-2 S glycoprotein, or a fragment or derivative thereof and a cytoplasmic portion of the VSV G glycoprotein or a fragment or derivative thereof. In one specific embodiment, the fusion protein comprises the amino acid sequence SEQ ID NO: 5.

In certain embodiments of the assays of the disclosure, to ensure detection of a broader spectrum of the SARS-CoV-2 neutralizing antibodies, the SARS-CoV-2 S glycoprotein or a fragment or derivative thereof can comprise a consensus sequence derived from two or more different strains, mutants or variants of SARS-CoV-2. In other embodiments, to ensure detection of a broader spectrum of the SARS-CoV-2 neutralizing antibodies, the methods of the disclosure use a mixture of SARS-CoV-2 S glycoproteins (or fragments or derivatives thereof) from two or more different strains, mutants or variants of SARS-CoV-2.

Polynucleotide molecules encoding SARS-CoV-2 S glycoprotein or a fragment or derivative thereof can comprise a consensus sequence and/or modification(s) for improved expression of the SARS-CoV-2 S glycoprotein or the fragment or derivative thereof. Modification can include codon optimization, the addition of a Kozak sequence or modified (e.g., optimized) Kozak sequence for increased translation initiation, and/or the addition of a signal peptide/leader sequence (e.g., an immunoglobulin signal peptide such as, e.g., IgE or IgG signal peptide). In certain embodiments, the Kozak sequence or modified (e.g., optimized) Kozak sequence is 3' to the foreign gene. In certain embodiments, the Kozak sequence or modified (e.g., optimized) Kozak sequence is immediately 3' to the foreign gene. In certain embodiments, the Kozak sequence or modified (e.g., optimized) Kozak sequence is 5' to the foreign gene. In certain embodiments, the Kozak sequence or modified (e.g., optimized) Kozak sequence is immediately 5' to the foreign gene.

In some embodiments, the SARS-CoV-2 S glycoprotein or a fragment or derivative thereof comprises a fusions or conjugate with a detection tag (e.g., HA tag, histidine tag, biotin), a reporter protein or a fragment thereof, dimerization/multimerization sequences, Fc, signaling sequences, etc. In some embodiments, the recombinant VSV particles of the disclosure comprise, in addition to the SARS-CoV-2 S glycoprotein or a fragment or derivative thereof, a reporter protein or a fragment thereof, wherein said reporter protein or a fragment thereof is either encoded by the VSV particle genome or is included in it as a protein. Non-limiting examples of reporter proteins include, e.g., luciferases (including but not limited to, *Renilla* luciferase, RLuc8 mutant *Renilla* luciferase, (dCpG) Luciferase, NanoLuc reporter, firefly luciferase, *Gaussia* luciferase (gLuc), MetLuc, *Vibrio fischeri* lumazine protein, *Vibrio harveyi* luminaze protein, inoflagellate luciferase, firefly luciferase YY5 mutant, firefly luciferase LGR mutant, firefly luciferase mutant E, and derivatives thereof) and fluorescent proteins (including but not limited to, green fluorescent protein (GFP) [e.g., *Aequoria victoria* GFP, *Renilla muelleri* GFP, *Renilla reniformis* GFP, *Renilla* ptilosarcus GFP], GFP-like fluorescent proteins, (GFP-like), enhanced green fluorescent protein (EGFP), yellow fluorescent protein (YFP) [e.g., Topaz, Venus, mCitrine, YPet, Tag YFP, PhiYFP, ZsYellow1, mBanana], enhanced yellow fluorescent protein (EYFP), blue fluorescent protein (BFP) [e.g., EBFP2, Azurite, GFP2, GFP10, and mTagBFP], enhanced blue fluorescent protein (EBFP), cyan fluorescent protein (CFP) [e.g., mECFP, Cerulean, CyPet, AmCyan1, Midori-Ishi Cyan, TagCFP, mCFPmm, mTFP1 (Teal)], enhanced cyan fluorescent protein (ECFP), superfolder GFP, superfolder YFP, orange fluorescent protein [e.g., Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine], red fluorescent protein [e.g., mRuby, mApple, mStrawberry, AsRed2, mRFP1, JRed, mCherry, HcRed1, mRaspberry, dKeima-Tandem, HcRed-Tandem, mPlum, tdTomato, AQ143], small ultrared fluorescent protein, FMN-binding fluorescent protein, dsRed, qFP611, Dronpa, TagRFP, KFP, EosFP, IrisFP, Dendra, Kaede, KikGr1, emerald fluorescent protein, Azami Green, mWasabi, TagGFP, TurboGFP, AcGFP, ZsGreen, T-Sapphire, and derivatives thereof), β-galactosidase, β-glucuronidase, β-geo, and fragments thereof.

Production of Recombinant VSV Particles

Recombinant VSV particles are used as an example in the disclosure below, but this disclosure can also be used for other vesiculoviruses.

The recombinant VSV particles of the disclosure are produced by providing in an appropriate host cell: VSV (−) DNA, in which regions non-essential for replication have been inserted into or replaced by a foreign DNA comprising a sequence encoding a coronavirus S glycoprotein or a fragment or derivative thereof and optionally other sequences discussed above, and recombinant sources of VSV N protein, P protein, L protein and any additional desired VSV protein (e.g., M protein and/or G glycoprotein). In certain embodiments, the production is preferably in vitro (e.g., in cell culture).

The host cell used for recombinant VSV production can be any cell in which VSVs grows. Non-limiting sources of host cells include, prokaryotic cells or a eukaryotic cells, vertebrate cells, mammalian cells, some insect (e.g., *Drosophila*) cells, primary cells (e.g., primary chick embryo fibroblasts), or cell lines (e.g., BHK (baby hamster kidney) cells, CHO (Chinese hamster ovary) cells, HeLA (human) cells, mouse L cells, Vero (monkey) cells (including Vero-αHis cells), Vero-Ace-2 cells, Vero-TRMPSS2 cells, Vero-E6 cells, ESK-4, PK-15, EMSK cells, MDCK (Madin-Darby canine kidney) cells, MDBK (Madin-Darby bovine kidney) cells, 293 (human) cells, Hep-2 cells, Human Diploid Primary Cell Lines (e.g. WI-38 and MRC5 cells), Monkey Diploid Cell Line (e.g. FRhL-Fetal Rhesus Lung cells), and Quasi-Primary Continues Cell Line (e.g. AGMK-African green monkey kidney cells), etc.).

The sources of N, P, and L proteins and any additional desired VSV protein (e.g., M protein and/or G glycoprotein) can be the same or can be different recombinant nucleic acid(s), encoding and capable of expressing these proteins in the host cell in which it is desired to produce recombinant VSVs. The nucleic acids encoding the N, P and L proteins and any additional desired VSV protein (e.g., M protein and/or G glycoprotein) can be obtained by any means available in the art. The VSV N, P, L, M and G-encoding nucleic acid sequences have been disclosed and can be used. For example, see Genbank accession no. J02428; Rose and Schubert, 1987, in The Viruses: The Rhabdoviruses, Plenum Press, NY, pp. 129-166. The sequences encoding the N, P and L genes can also be obtained, for example, from plasmid pVSVFL (+), deposited with the ATCC and assigned accession no. 97134, e.g., by PCR amplification of the desired gene (see also U.S. Pat. Nos. 4,683,202, 4,683,195 and 4,889,818; Gyllenstein et al., 1988, Proc. Natl. Acad. Sci. USA 85:7652-7656; Ochman et al., 1988, Genetics 120:621-623; Loh et al., 1989, Science 243:217-220). If a nucleic acid clone of any of the N, P, L, M or G genes is not already available, the clone can be obtained by use of standard recombinant DNA methodology. For example, the DNA may be obtained by standard procedures known in the art such as, e.g., by purification of RNA from VSV virions followed by reverse transcription and PCR (Mullis and Faloona, 1987, Methods in Enzymology 155:335-350). Alternatives include, but are not limited to, chemically synthesizing the gene sequence itself. Other methods are possible and within the scope of the disclosure.

Nucleic acids that encode fragments and derivatives of VSV N, P, L, M, and/or G genes, as well as fragments and derivatives of the VSV (−) DNA can also be used in the present disclosure, as long as such fragments and derivatives retain the requisite function (e.g., the ability to produce replication competent or non-replication competent VSV particles which can be used in one or more methods of the disclosure). In particular, derivatives can be made by altering sequences by substitutions, additions, or deletions. Furthermore, due to the inherent degeneracy of the genetic code, other DNA sequences which encode substantially the same or a functionally equivalent amino acid sequence may be used in the practice of the methods of the disclosure. Amino acid substitutions may be made on the basis of similarity in polarity, charge, solubility, hydrophobicity, hydrophilicity and/or the amphipathic nature of the residues involved.

The desired N/P/L/M/G-encoding nucleic acid can be inserted into an appropriate expression vector, i.e., a vector which contains the necessary elements for the transcription and translation of the inserted protein-coding sequence in the host cell in which it is desired to produce recombinant VSV particles, to create a vector that functions to direct the synthesis of the VSV proteins that will subsequently assemble with the VSV genomic RNA (e.g., produced in the host cell from antigenomic VSV (+) RNA produced, e.g., by transcription of the VSV (−) DNA).

A variety of vector systems may be utilized to express the N, P and L VSV proteins and any additional desired VSV protein (e.g., M and/or G), as well as to transcribe the VSV (−) DNA (e.g., comprising a foreign DNA), as long as the vector is functional in the host cell and compatible with any other vector present. The expression elements of vectors vary in their strengths and specificities. Any one of a number of suitable transcription and translation elements may be used, as long as they are functional in the host cell.

Standard recombinant DNA methods may be used to construct expression vectors containing DNA encoding the VSV proteins, and the VSV (−) DNA containing the foreign DNA, comprising appropriate transcriptional/translational control signals (see, e.g., Sambrook et al., 1989, supra, and methods described hereinabove). Expression may be controlled by any promoter/enhancer element known in the art. Promoters which may be used to control expression can be constitutive or inducible. In a specific embodiment, the promoter is an RNA polymerase promoter.

Transcription termination signals (downstream of the gene), and selectable markers are preferably also included in the expression vector. In addition to promoter sequences, expression vectors for the N, P, L, and any additionally desired VSV proteins, as well as any coronavirus proteins, may contain specific initiation signals for efficient translation of the inserted sequences, e.g., a ribosome binding site.

Specific initiation signals maybe required for efficient translation of the protein coding sequences. These signals include the ATG initiation codon and adjacent sequences. In cases where the entire N, P, L, or other (e.g., M and/or G) VSV gene, including its own initiation codon and adjacent sequences, are inserted into the appropriate vectors, no additional translational control signals may be needed. However, in cases where only a portion of the gene sequence is inserted, exogenous translational control signals, including the ATG initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

In a specific embodiment, a recombinant expression vector provided herein, encoding an N, P, L, and/or other (e.g., M and/or G) protein or functional derivative thereof, comprises the following operatively linked components: a promoter which controls the expression of proteins (e.g., the N, P, L, and/or other VSV protein (for example, M and/or G), a coronavirus protein (e.g., a spike glycoprotein such as the SARS-CoV-2 spike glycoprotein), or a fragment or derivative thereof, a translation initiation signal, a DNA sequence encoding the VSV protein or functional fragment or derivative thereof, and a transcription termination signal. In certain embodiments, the above components are present in 5' to 3' order as listed above. In certain embodiments, genes encoding the M protein, G proteins, and/or coronavirus S glycoprotein or a fragment or derivative thereof are interspersed between the N, P, and/or L proteins. In certain embodiments, genes for the M protein, G protein, and/or coronavirus S glycoprotein or a fragment or derivative thereof are between the genes for P and L proteins (see FIG. 1). In certain embodiments, the N, P, and L proteins or functional fragment or derivative thereof are not present in the 5' to 3' order as listed above. In certain embodiments, the order is altered (e.g., to attenuate the recombinant VSV).

In certain embodiments, the genes encoding the N, P, L, and other (e.g., M and/or G) VSV proteins are inserted downstream of the T7 RNA polymerase promoter from phage T7 gene 10, situated with an A in the −3 position. A T7 RNA polymerase terminator and a replicon can be also included in the expression vector. T7 RNA polymerase can be provided to transcribe the VSV protein sequence. The T7 RNA polymerase can be produced from a chromosomally integrated sequence or an episomal vector. In certain embodiments, T7 RNA polymerase can be provided by intracellular expression from a recombinant vaccinia virus vector encoding the T7 RNA polymerase. In certain embodiments, the N, P, L, and/or other (e.g., M and/or G) VSV proteins are each encoded by a DNA sequence operably linked to a promoter in an expression plasmid, containing the necessary regulatory signals for transcription and translation of the encoded proteins. Such an expression plasmid preferably includes a promoter, the coding sequence, and a transcription termination/polyadenylation signal, and optionally, a selectable marker (e.g., β-galactosidase).

In certain embodiments, the N, P, L, and/or other (e.g., M and/or G) proteins can be encoded by the same or different plasmids, or a combination thereof. In other embodiments, one or more of the N, P, L, and other (e.g., M and/or G) VSV proteins can be expressed intrachromosomally.

The cloned sequences comprising the VSV (−) DNA containing the foreign DNA, and the cloned sequences comprising sequences encoding the VSV and foreign proteins can be introduced into the desired host cell by any method known in the art, e.g., transfection, electroporation, infection (when the sequences are contained in, e.g., a viral vector), microinjection, etc. In certain embodiments, a transfection facilitating reagent is added to increase DNA uptake by cells. Many of these reagents are known in the art (e.g., calcium phosphate; Lipofectace (Life Technologies, Gaithersburg, Md.), and Effectene (Qiagen, Valencia, Calif.) are non-limiting examples).

In certain embodiments, DNA comprising VSV (−) DNA containing foreign DNA encoding a coronavirus S glycoprotein or a fragment or derivative thereof, operably linked to an RNA polymerase promoter (e.g., a bacteriophage RNA polymerase promoter); DNA encoding N, operably linked to the same RNA polymerase promoter; DNA encoding P, operably linked to the same polymerase promoter; and DNA encoding L, operably linked to the same polymerase promoter; are all introduced (e.g., by transfection) into the same host cell, in which host cell the RNA polymerase has been cytoplasmically provided. In certain embodiments, the RNA polymerase is cytoplasmically provided by expression from a recombinant virus vector that replicates in the cytoplasm and expresses the RNA polymerase, most preferably a vaccinia virus vector, that has been introduced (e.g., by infection) into the same host cell. Cytoplasmic provision of RNA polymerase can be used, as this will result in cytoplasmic transcription and processing, of the VSV (−) DNA comprising the foreign DNA and of the N, P, L, and other (e.g., M and/or G protein) VSV proteins, avoiding splicing machinery in the cell nucleus, and, thereby, maximizing proper processing and production of N, P, L, and other (e.g., M and/or G protein) VSV proteins, and resulting assembly of the recombinant VSVs. Vaccinia virus vectors also cytoplasmically provide enzymes for processing (capping and polyadenylation) of mRNA, facilitating proper translation. In a most preferred aspect, T7 RNA polymerase promoters are employed, and a cytoplasmic source of T7 RNA polymerase is provided by also introducing into the host cell a recombinant vaccinia virus vector encoding T7 RNA polymerase into the host cell. Such vaccinia virus vector can be obtained by well-known methods. In certain embodiments, a recombinant vaccinia virus vector such as vTF7-3 (Fuerst et al., 1986, Proc. Natl. Acad. Sci. U.S.A. 83:8122-8126) can be used.

In other embodiments, the RNA polymerase (e.g., T7 RNA polymerase) can be provided by use of a host cell that expresses T7 RNA polymerase from a chromosomally integrated sequence (e.g., originally inserted into the chromosome by homologous recombination), optionally constitutively, or that expresses T7 RNA polymerase episomally, from a plasmid.

In other embodiments, the VSV (−) DNA encoding a coronavirus S glycoprotein or a fragment or derivative thereof, operably linked to a promoter, can be transfected into a host cell that stably recombinantly expresses the N, P, L, and any other (e.g., M and/or G protein) VSV proteins from chromosomally integrated sequences.

The cells are cultured and recombinant VSV particles can be recovered, e.g., using standard methods. By way of example, and not limitation, after approximately 24 hours, cells and medium can be collected, freeze-thawed, and the lysates clarified to yield virus preparations. Alternatively, the cells and medium can be collected and simply cleared of cells and debris by low-speed centrifugation.

Confirmation that the appropriate foreign sequence is present in the genome of the recombinant VSV and directs the production of the desired protein(s) in an infected cell, can be performed. Standard procedures known in the art can be used for this purpose. By way of example, and not limitation, genomic RNA can be obtained from the VSV by SDS phenol extraction from virus preparations, and can be subjected to reverse transcription (and/or PCR), followed by e.g., sequencing, Southern hybridization using a probe specific to the foreign DNA, or restriction enzyme mapping, etc. The virus can be used to infect host cells, which can then be assayed for expression of the desired protein by standard immunoassay techniques using an antibody to the protein (e.g., Western blotting), or by assays based on functional activity of the protein. Other techniques are known in the art and can be used.

Large Scale Growth and Purification of the Recombinant Viruses

VSVs are used as an example in the disclosure below, and this disclosure can also be used for other vesiculoviruses.

A non-limiting example of a large-scale production of a recombinant VSV virus following plaque-purification is presented below. Virus from a single plaque (~$10^5$ pfu) is recovered and used to infect ~$10^7$cells (e.g., BHK cells), to yield, generally, 10 ml at a titer of 109-1010 pfu/ml for a total of approximately 1011 pfu. Infection of ~$10^{12}$ cells can then be carried out (with a multiplicity of infection of e.g., 0.1), and the cells can be grown in suspension culture, large dishes, or roller bottles by standard methods known to those in the art.

Virus for vaccine preparations can then be collected from culture supernatants, and the supernatants clarified to remove cellular debris. If desired, one method of isolating and concentrating the virus that can be employed is by passage of the supernatant through a tangential flow membrane concentration. The harvest can be further reduced in volume by pelleting through a glycerol cushion and by concentration on a sucrose step gradient. An alternate method of concentration is affinity column purification (Daniel et al., 1988, Int. J. Cancer 41:601-608). However, other methods can also be used for purification (see, e.g., Arthur et al., 1986, J. Cell. Biochem. Suppl. 10A: 226), and any possible modifications of the above procedure will be readily recognized by one skilled in the art. Purification should be as gentle as possible, so as to maintain the integrity of the virus particle.

Assays

In one aspect, the disclosure provides a method for determining the presence of a coronavirus neutralizing antibody in a sample. In one embodiment, the sample is contacted with, or incubated with a recombinant vesicular stomatitis virus (VSV) particle, where the VSV glycoprotein (G) is replaced by a coronavirus spike(S) glycoprotein or a fragment or derivative thereof, wherein said S glycoprotein, fragment or derivative is capable of mediating infection of susceptible target cells. Either simultaneously or afterwards, the recombinant VSV particle is contacted with a first target cell expressing a first portion of a reporter protein and a second target cell expressing a second portion of the reporter protein to form a syncytium comprising both the first and the second portion of the reporter protein and producing a detectable reporter signal. The first target cell and the second target cell should be capable of fusing with one another if contacted with the recombinant VSV particle. The reporter signal is measured in the syncytium and compared with a control.

In certain embodiments, the first cell is Vero-DSP1 (Vero-DSP-1-Puro; CLR-73) and the second cell is (Vero-DSP-2-Puro; CLR-74). Vero-DSP1 and Vero-DSP2 are generated by lentivirus transduction of Vero cells. Vero-DSP1 cells express Rluc8 155-156DSP1-7 luciferase-GFP fusion protein (SEQ ID NO: 14) comprising mutant *Renilla* luciferase RLuc8 fragment amino acids 1-155 and engineered GFP fragment amino acids 1-156. Vero-DSP2 cells express Rluc8 155-156DSP8-11 luciferase-GFP fusion protein (SEQ ID NO: 16) comprising mutant *Renilla* luciferase RLuc8 fragment amino acids 156-311 and engineered GFP fragment amino acids 157-231. RLuc8 mutant *Renilla* luciferase contains the mutations A55T, C124A, S130A, K136R, A143M, M185V, M253L, and S287L (see SEQ ID NO: 19). The sequence of engineered GFP is provided in SEQ ID NO: 18.

The first portion of the reporter protein used in any of the above methods of the disclosure may comprise amino acids 1-229 of *Renilla* luciferase or a mutant thereof and the second portion of the reporter protein may comprise amino acids 230-311 of *Renilla* luciferase or a mutant thereof. Alternatively, the first portion of the reporter protein may comprise amino acids 1-155 of *Renilla* luciferase or a mutant thereof and the second portion of the reporter protein may comprise amino acids 156-311 of *Renilla* luciferase or a mutant thereof. Alternatively, or in addition, the first portion of the reporter protein may comprise amino acids 1-156 of green fluorescent protein (GFP) or a mutant thereof, and the second portion of the reporter protein may comprise amino acids 157-231 of GFP or a mutant thereof. Alternatively, the first portion of the reporter protein may comprise amino acids 1-213 of superfolder GFP, and the second portion of the reporter protein may comprise amino acids 214-230 of superfolder GFP. Alternatively, the first portion of the reporter protein may comprise amino acids 1-154 of superfolder yellow fluorescent protein (YFP), and the second portion of the reporter protein may comprise amino acids 155-262 of superfolder YFP.

In another aspect, the disclosure provides a method for determining the presence of a coronavirus neutralizing antibody in a sample, wherein the sample is contacted with a recombinant vesicular stomatitis virus (VSV) particle where the VSV glycoprotein (G) is replaced by a coronavirus spike(S) glycoprotein or a fragment or a derivative thereof, wherein said S glycoprotein, fragment or derivative is capable of mediating infection of a target cell and wherein the VSV particle comprises a reporter protein or a nucleic acid molecule encoding the reporter protein. The recombinant VSV particle is then contacted with the target cell. The reporter signal is then measured and compared with a control. In certain embodiments, the reporter protein is encoded by the genome of the recombinant VSV particle. In certain embodiments, the reporter protein is incorporated into the recombinant VSV particle without being encoded by the genome of the viral particle. The nucleic acid sequence encoding the reporter protein may be inserted between the nucleic acid sequence encoding the S glycoprotein and the nucleic acid sequence encoding VSV L protein. The target cell may be a Vero cell (including Vero-αHis cell), Vero-Ace-2 cell, Vero-TRMPSS2 cell, Vero-E6 cell, or any other cell comprising an angiotensin-converting enzyme 2 (ACE2).

In the above methods of the disclosure, the recombinant VSV particle may encode the coronaviral S glycoprotein in the VSV viral genome. Alternatively, the VSV particle may be pseudotyped with the coronaviral S glycoprotein without it being encoded in the genome (e.g., by using a separate plasmid in a packaging cell).

The sample used in the above methods of the disclosure may be, e.g., serum or plasma (e.g., heat-inactivated serum or plasma).

The first step in which the sample is contacted with the recombinant VSV particle may be conducted for about 1 hour at about 37° C. The second step in which the recombinant VSV particle with the target cell may be conducted for 1-12, 1-3, 2-4, 3-5, 4-6, 5-7, 6-8, 7-9, or 8-10 hours at about 37° C.

In various embodiments of the above methods of the disclosure, the methods comprise adding the reporter protein substrate for obtaining the reporter signal. The reporter protein may be a luciferase and the reporter protein substrate may be Luciferin (e.g., d-luciferin), coelenterazine, or EnduRen luciferase substrate.

In some embodiments, the coronavirus S protein, fragment or derivative thereof is derived from SARS-CoV-2. In certain embodiments, the coronavirus S protein is a full-length SARS-CoV-2 S protein (e.g., a protein comprising or consisting of the amino acid sequence of SEQ ID NO: 1). In certain embodiments, the coronavirus S protein is a SARS-CoV-2 S protein lacking 19 C-terminal amino acids (e.g., a protein comprising or consisting of the amino acid sequence of SEQ ID NO: 3). In certain embodiments, the coronavirus S protein, fragment or derivative has at least 77% amino acid sequence identity to the amino acid sequence of SEQ ID NO: 1. In certain embodiments, the coronavirus S protein, fragment or derivative has at least 64% amino acid sequence identity to the S1 subunit of the amino acid sequence of SEQ ID NO: 1. In certain embodiments, the coronavirus S protein, fragment or derivative has at least 64% amino acid sequence identity to amino acids 14-684 of the amino acid sequence of SEQ ID NO: 1. In certain embodiments, the coronavirus S protein, fragment or derivative has at least 74% amino acid sequence identity to the RBD domain of the amino acid sequence of SEQ ID NO: 1. In certain embodiments, the coronavirus S protein, fragment or derivative has at least 74% amino acid sequence identity to amino acids 319-541 of the amino acid sequence of SEQ ID NO: 1. In certain embodiments, the recombinant VSV particle comprises a mutant VSV matrix (M) protein. In certain embodiments, the genome of the recombinant VSV encodes a mutant VSV matrix M protein. In certain embodiments, the mutant matrix M protein comprises a mutation at methionine (M) 51 (e.g., a change from methionine (M) to arginine (R)). In certain embodiments, the mutant VSV matrix M protein comprises or consists of the amino acid sequence of SEQ ID NO: 7.

In certain embodiments of the above methods of the disclosure, the control is the reporter signal obtained with a control sample not comprising coronavirus neutralizing antibodies and the method comprises concluding that the tested sample comprises coronavirus neutralizing antibodies when the reporter signal obtained in the sample is reduced as compared to the control. In certain embodiments, the control sample comprises a VSV particle without the coronavirus S glycoprotein or a VSV particle with a mutant S glycoprotein which does not mediate infection of target cells. In certain embodiments of the above methods of the disclosure, the method further comprises comparing the reporter signal obtained in the sample with the reporter signal obtained with a control sample comprising coronavirus neutralizing antibodies or a molecule that blocks interaction of the coronavirus S glycoprotein with a protein with which it interacts on the target cell.

In certain embodiments of the above methods of the disclosure, the method is conducted in a high throughput format.

In one specific embodiment, provided herein is a method for determining the presence of a Severe Acute Respiratory Syndrome coronavirus 2 (SARS-CoV-2) neutralizing antibody in a sample. The method comprises:

a) contacting the sample with a recombinant vesicular stomatitis virus (VSV) particle, wherein the VSV glycoprotein (G) is replaced by the full-length SARS-CoV-2 spike(S) glycoprotein or a fragment thereof lacking 19 C-terminal amino acids;
b) after step (a), contacting the recombinant VSV particle with a mixture of Vero-DSP1 (Vero-DSP-1-Puro; CLR-73) cells and Vero-DSP2 (Vero-DSP-2-Puro; CLR-74) cells;
c) measuring the luciferase signal and/or GFP signal in the cells after step (b), and
d) comparing the signal measured in step (c) with a control.

In another specific embodiment, provided herein is a method for determining the presence of a Severe Acute Respiratory Syndrome coronavirus 2 (SARS-CoV-2) neutralizing antibody in a sample, the method comprising:

a) contacting the sample with a recombinant vesicular stomatitis virus (VSV) particle wherein (i) the VSV glycoprotein (G) is replaced by the full-length SARS-CoV-2 spike(S) glycoprotein or a fragment thereof lacking 19 C-terminal amino acids and wherein (ii) the VSV particle further comprises a luciferase protein and/or a nucleic acid molecule encoding said luciferase protein;
b) after step (a), contacting the recombinant VSV particle with a cell selected from Vero cell, Vero-Ace-2 cell and Vero-E6 cell;
c) measuring the luciferase signal in the cell after step (b), and
d) comparing the signal measured in step (c) with a control.

The cells used in any of the methods disclosed herein may comprise angiotensin-converting enzyme 2 (ACE2). ACE2 is a functional receptor for coronaviruses, in particular SARS-CoV-1 and SARS-CoV-2. The cells used in any of the methods disclosed herein may further comprise transmembrane protease, serine 2 (TMPRSS2). The non-limiting examples of susceptible target cells which can be used in the methods of the disclosure include, e.g., Vero green monkey kidney epithelial cells (including Vero-αHis cells), Vero-Ace-2 cells, Vero-TRMPSS2 cells, Vero-E6 cells, avian erythrocytes, and Madin-Darby canine kidney epithelial cells.

In some embodiments, addition of trypsin to a virus and cell mixture may be used to increase virus-mediated cell fusion. Trypsin may be added before the reporter signal is measured in the cells. Trypsin may be added after a virus and cell mixture are incubated with one another, e.g., 2-6 hours after incubation starts, 3-5 hours after incubation starts, about 4 hours after incubation starts, or 4 hours after incubation starts. Trypsin does not need to be removed from the virus and cell mixture after addition. As shown in the data below, addition of trypsin can promote cell fusion. The concentration of trypsin used can range from 0.1 to 4.0 μL trypsin/mL media (e.g., OptiMEM), or from 0.1 to 0.6 μL trypsin/mL media, 0.2 to 0.7 μL trypsin/mL media, 0.3 to 1.2 μL trypsin/mL media, 0.5 to 2.0 μL trypsin/mL media, 1.0 to 2.5 μL trypsin/mL media, 1.5 to 3.0 μL trypsin/mL media, or from 2.0 to 4.0 μL trypsin/mL media. Trypsin addition to the media during the fusion assay may make the assay more sensitive. Additional trypsin may allow for cell fusion to occur in less time. Additional trypsin may allow for the assay readout (e.g., luciferase activity) to occur more quickly than with less or no trypsin.

In some embodiments, trypsin is not used in the assay. If trypsin is excluded, an additional wash step may not be required even if the serum/virus mixes, or plasma/virus mixes, are removed and replaced with fresh serum media, or media suitable for plasma.

Reporter Proteins

Various split reporter proteins can be used in any of the aspects and embodiments described herein. For example, enzymes that catalyze the conversion of a substrate to a detectable product. Several such systems for split-polypeptide reassemblies include, but are not limited to reassembly of, β-galactosidase (Rossi et al., PNAS, 1997, 94:8405-8410), dihydrofolate reductase (DHFR) (Pelletier et al, PNAS, 1998, 95:12141-12146), TEM-1 B-lactamase (LAC) (Galarneau at al., Nat. Biotech. 2002; 20:619-622) and firefly luciferase (Ray et al., PNAS, 2002, 99:3105-3110 and Paulmurugan et al, 2002; PNAS, 99:15608-15613). For example, split β-lactamase has been used for the detection of double stranded DNA (see Ooi et al., Biochemistry, 2006, 45:3620-3525). Split polypeptide fragments can be used for real-time signal detection, wherein the fragments are in a fully folded mature conformation enabling rapid signal detection upon complementation.

The split polypeptide fragments can be any polypeptides which associate when brought into close proximity to one another to generate a protein, which can be detected by any means which allows recognition of the assembled polypeptide fragments but not the individual polypeptides fragments. In one embodiment of the current disclosure, the methods encompass the design of split-polypeptide fragments so that they are active immediately upon their reconstitution.

The split polypeptide fragments can be any polypeptide which associate when brought into close proximity to generate an active protein, which can be detected by any means which allows detection of the assembled active protein but not the individual fragments. For example, the two polypeptides may re-associate to generate a protein with enzymatic activity, to generate a protein with luciferase, chromogenic or fluorogenic activity, or which create a protein recognized by an antibody. Furthermore, they are designed so that they are in the active state and primed (i.e. in a ready-state) for reconstitution of the active protein in order to minimize any lag time that is traditionally seen with protein complementation in vitro and in vivo.

The split polypeptide fragments can be fluorescent proteins or polypeptides. In such an embodiment, one of the activated split fluorescent protein fragments contains a mature preformed chromophore that is primed and in the ready-state for immediate fluorescence upon complementation with its cognate activated split-fluorescent fragment(s).

For example, using inclusion bodies containing such a split fluorescent fragment comprises about half of a fully folded fluorescent protein with a correctly folded a mature chromophore that does not fluoresce alone, but is primed to fluoresce upon association with its cognate pair.

In the methods described herein, the reporter protein may be a luciferase. Various luciferase enzymes known to those of ordinary skill in the art may be used, with exemplary luciferases including but not limited to, *Renilla* luciferase, RLuc8 mutant *Renilla* luciferase, (dCpG) Luciferase, NanoLuc reporter, firefly luciferase, *Gaussia* luciferase (gLuc), MetLuc, *Vibrio fischeri* lumazine protein, *Vibrio harveyi* luminaze protein, inoflagellate luciferase, firefly luciferase mutant YY5 mutant, firefly luciferase LGR mutant, firefly luciferase mutant E, and derivatives thereof.

In the methods described herein where the recombinant VSV particle is contacted with a first cell expressing a first portion of a reporter protein and a second cell expressing a second portion of the reporter protein to form a syncytium, the reporter protein may be luciferase. The first portion and the second portion of the luciferase may be split-polypeptide luciferase fragments. When both of the split-polypeptide luciferase fragments are introduced in the assay system, the first protein and the second protein bind to each other, and as a consequence, will reconstitute the luciferase to recover luciferase activity so that the luciferase is capable of emitting light under adequate luminescent conditions. The luciferase activity may be measured, when the assay system is a cell, by adding luciferin to the cell culture, and preparing a cell extract to measure the luciferase activity. In this case, the activity is readily measurable by using a commercially available Emerald Luc Luciferase Assay Reagent/Lysis Solution (TOYOBO) or the like.

A fusion protein comprising a luciferase fragment can be detected. For example, when a first fusion protein that has been made by fusing a target protein to be detected with luciferase fragment exists in the assay system, a second fusion protein that has been made by fusing a binding protein that binds to the target protein with luciferase fragment is prepared as a probe and is introduced in the assay system. Then, the binding protein in the second fusion protein should bind to the target protein in the first fusion protein; thereby the luciferase fragments interact and gain luciferase activity. By detecting the luciferase activity, the target fusion protein having luciferase fragments can be detected. Specifically, an expression vector expressing the first fusion protein can be prepared and introduced in a cell. Next, an expression vector expressing the second fusion protein can be prepared and introduced in the cell expressing the first fusion protein. Then the fusion protein having a luciferase fragment can be detected by measuring the luciferase activity as described above.

Split luciferase assays are described further in, e.g., Saw, W. T. et al., "Using a split luciferase assay (SLA) to measure the kinetics of cell-cell fusion mediated by herpes simplex virus glycoproteins" Methods, 2015, 90:68-75, which is incorporated by reference herein in its entirety. The methods described therein can be conducted where both a luciferase and a fluorescent protein are fused together as the reporter protein.

The split polypeptide fragments can comprise fragments of an active enzyme, which can be detected using an enzyme activity assay. In such an embodiment, the enzyme activity is detected by a chromogenic or fluorogenic reaction. In one embodiment, the enzyme is dihydrofolate reductase or β-lactamase.

The enzyme can be dihydrofolate reductase (DHFR). For example, Michnick et al. have developed a "protein complementation assay" consisting of N- and C-terminal fragments of DHFR, which lack any enzymatic activity alone, but form a functional enzyme when brought into close proximity. See, e.g., U.S. Pat. Nos. 6,428,951, 6,294,330, and 6,270,964, which are hereby incorporated by reference. Methods to detect DHFR activity, including chromogenic and fluorogenic methods, are well known in the art.

Various fluorescent proteins may be used in any of the methods and compositions described herein. In the methods disclosed herein, the reporter protein may comprise a fluorescent protein.

The fluorescent protein may be green fluorescent protein (GFP), GFP-like fluorescent proteins (GFP-like), enhanced green fluorescent protein (EGFP). In alternative embodiments, the fluorescent protein is yellow fluorescent protein (YFP), an enhanced yellow fluorescent protein (EYFP), a blue fluorescent protein (BFP), an enhanced blue fluorescent protein (EBFP), a cyan fluorescent protein (CFP), an enhanced cyan fluorescent protein (ECFP), a red fluorescent protein (dsRED) superfolder GFP, superfolder YFP, orange fluorescent protein, red fluorescent protein, small ultrared fluorescent protein, FMN-binding fluorescent protein, dsRed, qFP611, Dronpa, TagRFP, KFP, EosFP, IrisFP, Dendra, Kaede, KikGr1, and derivatives thereof, or any other natural or genetically engineered fluorescent protein of those listed above. In yet further embodiments, the reconstituted fluorescent proteins may comprise of a mixture of fragments from the same or a combination any of the above listed fluorescent proteins.

Green Fluorescent Protein (GFP) is a 238 amino acid long protein derived from the jellyfish *Aequorea Victoria*. The engineered GFP used in the split constructs of the present disclosure is 231 amino acids long and consists of SEQ ID NO: 18. Fluorescent proteins have also been isolated from other members of the *Coelenterata*, such as the red fluorescent protein from *Discosoma* sp. (Matz, M. V. et al. 1999, Nature Biotechnology 17:969-973), GFP from *Renilla reniformis*, GFP from *Renilla Muelleri* or fluorescent proteins from other animals, fungi or plants. There are various modified forms of GFP. The blue fluorescent variant of GFP (BFP) is described by Heim et al., Proc. Natl. Acad. Sci. 91:26, 1994, pp 12501-12504), and is a Y66H variant of wild type GFP. The yellow fluorescent variant of GFP (YFP) comprises the S65G, S72A, and T203Y mutations, and is disclosed in International Patent Publication No. WO98/06737. The cyan fluorescent variant of GFP (CFP) comprises the Y66W color mutation and optionally the F64L, S65T, N1461, M153T, V163A folding/solubility mutations. CFP is described in Heim, R., Tsien, R. Y., Curr. Biol. 6, 1996, 178-182). The EGFP variant comprises the F64L and S65T mutations of GFP and insertion of one valine residue after the first methionine. EGFP is described in WO 97/11094 and WO96/23810. The F64L mutation is the amino acid in position 1 upstream from the chromophore. A GFP or GFP variant containing this folding mutation provides an increase in fluorescence intensity when the GFP or GFP variant is expressed in cells at a temperature above about 30° C. (WO 97/11094).

Non-limiting examples of GFPs include: *Aequoria victoria* GFP, *Renilla muelleri* GFP, *Renilla reniformis* GFP, *Renilla* ptilosarcus GFP, Emerald, Superfolder GFP, Azami Green, mWasabi, TagGFP, TurboGFP, AcGFP, ZsGreen, T-Sapphire.

Non-limiting examples of BFPs include: EBFP2, Azurite, GFP2, GFP10, and mTagBFP.

Non-limiting examples of CFPs include: mECFP, Cerulean, CyPet, AmCyan1, Midori-Ishi Cyan, TagCFP, mCFPmm, and mTFP1 (Teal).

Non-limiting examples of YFPs include: Topaz, Venus, mCitrine, YPet, TagYFP, PhiYFP, ZsYellow1, and mBanana.

Non-limiting examples of orange fluorescent proteins include: Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, and mTangerine Non-limiting examples of red fluorescent proteins include: mRuby, mApple, mStrawberry, AsRed2, mRFP1, JRed, mCherry, HcRed1, mRaspberry, dKeima-Tandem, HcRed-Tandem, mPlum, tdTomato, and AQ143.

Also encompassed are fragments and derivatives of the above reporter proteins.

The fluorescent protein may be split into two or more polypeptide or protein fragments, which may be activated. One or more of the activated split fluorescent protein fragments may comprise a mature preformed chromophore that is primed and in the ready-state for immediate fluorescence upon complementation with its cognate activated split-fluorescent fragment(s). For example, using inclusion bodies containing such a split fluorescent fragment comprises about half of a fully folded fluorescent protein with a correctly folded a mature chromophore that does not fluoresce alone, but is primed to fluoresce upon association with its cognate pair.

One or more of the activated split fluorescent protein fragments may comprise a mature preformed chromophore that is active but in a non-fluorescent state. The isolation of the chromophore in its mature, yet inactive, state can allow for the ability to immediately detect fluorescence upon complementation with its corresponding fragment.

The first portion of the reporter protein may comprise amino acids 1-157 of green fluorescent protein (GFP), and the second portion of the reporter protein may comprise amino acids 158-231 of GFP. If the GFP is truncated, the amino acid numbering must be adjusted accordingly. A C-terminal cysteine may be added to the first portion to aid in the conjugation of various nucleic acid binding motifs post expression. An N-terminal cysteine may be added to the second portion to aid in the conjugation of various nucleic acid binding motifs post expression. The first portion comprises an alpha fragment that contains a mature chromophore, which does not fluoresce alone, but is primed to fluoresce when paired with the second portion that comprises a beta fragment. Without wishing to be bound by theory, because the chromophore is preformed, it can immediately fluoresce. The alpha and beta fragments may not reassociate or fluoresce in the absence facilitated association.

The first portion of the reporter protein may comprise amino acids 1-213 of superfolder GFP, and the second portion of the reporter protein may comprise amino acids 214-230 of superfolder GFP. If the superfolder GFP is truncated, the amino acid numbering must be adjusted accordingly. A C-terminal cysteine may be added to the first portion to aid in the conjugation of various nucleic acid binding motifs post expression. An N-terminal cysteine may be added to the second portion to aid in the conjugation of various nucleic acid binding motifs post expression. The first portion comprises an alpha fragment that contains a mature chromophore, which does not fluoresce alone, but is primed to fluoresce when paired with the second portion that comprises a beta fragment.

The first portion of the reporter protein may comprise amino acids 1-154 of superfolder yellow fluorescent protein (YFP), and the second portion of the reporter protein may comprise amino acids 155-262 of superfolder YFP. If the superfolder YFP is truncated, the amino acid numbering must be adjusted accordingly. A C-terminal cysteine may be added to the first portion to aid in the conjugation of various nucleic acid binding motifs post expression. An N-terminal cysteine may be added to the second portion to aid in the conjugation of various nucleic acid binding motifs post expression. The first portion comprises an alpha fragment that contains a mature chromophore, which does not fluoresce alone, but is primed to fluoresce when paired with the second portion that comprises a beta fragment.

The fluorescent protein may detectable by one or more of: flow cytometry, fluorescence plate reader, fluorometer, microscopy, fluorescence resonance energy transfer (FRET), by the naked eye or by other methods known to persons skilled in the art. When using flow cytometry, fluorescence may be detected using a florescence activated cell sorter (FACS) or time lapse microscopy.

In another embodiment of the disclosure, association of activated split-polypeptide fragments can form an assembled protein which contains a discontinuous epitope, which may be detected by use of an antibody which specifically recognizes the discontinuous epitope on the assembled protein but not the partial epitope present on either individual polypeptide. These and other such derivatives can readily be made by the person of ordinary skill in the art based upon well-known techniques and screened for antibodies that recognize the assembled protein by neither protein fragment on its own.

The split polypeptide can be a split fluorescent molecule. The molecule can comprise at least two activated split fluorescent fragments selected from the group consisting of GFP, GFP-like fluorescent proteins, fluorescent proteins, and variants thereof. One of the split-fluorescent fragments can comprise a mature preformed chromophore which is active by in a non-fluorescent state in the dissociated fragment. The activated fluorescent fragments, when associated with each other can contain the full complement of beta-strands necessary for fluorescence but are not fluorescent by themselves. Each of the activated split-fluorescent fragments of the molecule further comprise nucleic acid binding motif. The binding of the nucleic acid binding motifs to a target nucleic acid can facilitate the association of at least two active split-fluorescent fragments and reconstitution of the active fluorescent protein and fluorescent phenotype in real time.

Split fluorescent protein assays are also described in International Patent Publication No. WO 2010/066113, published Jun. 17, 2010, which is incorporated by reference herein in its entirety, and U.S. Patent Publication No. 2009/0220942, which is incorporated by reference herein in its entirety.

A combination split luciferase and split fluorescent protein assay is described further in Nakane, S. et al., "Dual Split Protein (DSP) Assay to Monitor Cell-Cell Membrane Fusion", Methods Mol. Biol., 2015, 1313:229-36, which is incorporated by reference herein in its entirety.

In various embodiments, fluorescence may be measured through the use of a flow cytometer or a bead array reader. For example, a BioPlex-100, a BioPlex-200, a Luminex-100, or a Luminex-200 bead array reader may be used.

In some embodiments, before adding the VSV particle to the cells, plating media is removed and replaced with serum media (e.g., 50 μL/well OptiMEM). In other embodiments, before adding the virus/serum mixes to the cells, plating media is not changed.

The VSV particle may be present in the serum as a virus/serum mixture. In other embodiments, before adding the virus/serum mixes to the cells, plating media is not changed. The VSV particle may be present in the plasma as a virus/plasma mixture. In other embodiments, before adding the virus/plasma mixes to the cells, plating media is not changed.

The reporter signal in the cells is measured, and then compared with a control.

The period of time for incubating the recombinant VSV particle with the virus/serum mixture, or virus/plasma mixture, may be set as a time period appropriate for such an incubation, such as from about 30 minutes to 3 days, or from about 30 minutes to 75 minutes, from 45 minutes to 90 minutes, from 60 minutes to 2 hours, or from 90 minutes to 3 hours. An exemplary period of time may be about 1 hour.

In some embodiments, after the recombinant VSV particle (e.g., in a mixture with serum or plasma) is added to target cells, the cells with virus are further incubated for 2-6 hours, for about 4 hours, or for 4 hours. If serum or plasma is present after the incubation, the serum or plasma may be removed so as to enhance cell fusion or luciferase activity.

The sample (e.g., serum or plasma) can be obtained from a subject, for example from humans exposed to SARS-CoV-2 infection or vaccinated with SARS-CoV-2 vaccine or another immunogenic composition. The sample may or may not contain some level of SARS-CoV-2 neutralizing antibodies. Antibody responses in COVID-19 patients are described, e.g., in Okba, N. M. A. et al., "SARS-CoV-2 specific antibody responses in COVID-19 patients" Emerg. Infect. Dis., 2020, 26 (7) (available at doi.org/10.3201/eid2607.200841). It is desirable to quickly determine the level of neutralizing antibody response in a patient sample, and the methods described herein permit rapid evaluation of the presence and/or level of SARS-CoV-2 neutralizing antibodies.

The methods described in Montefiori, D. C., "Evaluating neutralizing antibodies against HIV, SIV, and SHIV in luciferase reporter gene assays." Curr. Protoc. Immunol., 2005, Chapter 12, Unit 12.11, which is incorporated by reference herein in its entirety, may also be used as part of the methods described herein.

Kits

The disclosure also provides kits in conjunction with various methods disclosed herein. In certain embodiments, the kit comprises in one or more containers (e.g., separate containers): (a) a first recombinant DNA that can be transcribed in a suitable host cell to produce a VSV antigenomic (+) RNA in which a foreign RNA sequence has been inserted; (b) a second recombinant DNA comprising a sequence encoding a VSV N protein or functional fragment or derivative thereof; (c) a third recombinant DNA comprising a sequence encoding a VSV L protein or functional fragment or derivative thereof; and (d) a fourth recombinant DNA comprising a sequence encoding a VSV P protein or functional fragment or derivative thereof; and optionally (e) a fifth recombinant DNA comprising a sequence encoding a VSV M protein or functional fragment or derivative thereof; and optionally (f) a sixth recombinant DNA comprising a sequence encoding a VSV G protein or functional fragment or derivative thereof. The second, third, fourth, and optionally fifth and/or sixth recombinant DNAs can be part of the same or different DNA molecules. In a preferred embodiment, the sequences encoding the N, L, P, and other proteins are each operably linked to a promoter that controls expression of the N, L, P, and other proteins, respectively, in the suitable host cell. In various embodiments, the kit can contain the various nucleic acids, e.g., plasmid expression vectors, described hereinabove for use in production of recombinant VSV particles.

In another embodiment, a kit of the disclosure comprises (a) a first recombinant DNA that can be transcribed in a suitable host cell to produce a VSV antigenomic DNA in which a portion of the RNA has been inserted into or replaced by a foreign RNA sequence; and (b) a host cell that recombinantly expresses VSV N, P and L proteins and optionally M and/or G proteins. In certain embodiments, the foreign RNA sequence is inserted into a non-essential portion of the recombinant VSV genome. In certain embodiments, the foreign RNA sequence replaces the VSV's G protein.

In certain embodiments, a kit of the disclosure comprises in separate containers:

(a) a first plasmid comprising the following operatively linked components: (i) a bacteriophage RNA polymerase promoter, (ii) a DNA comprising a sequence capable of being transcribed in a suitable host cell to produce an RNA molecule comprising a VSV antigenomic RNA in which a portion of the RNA of the VSV has been inserted into or replaced by a foreign RNA sequence, and in which the 3' end of the antigenomic RNA is immediately adjacent to a ribozyme sequence that cleaves at the 3' end of the antigenomic RNA, and (iii) a transcriptional termination signal for the bacteriophage RNA polymerase; and (b) a second plasmid comprising the following operatively linked components: (i) the bacteriophage RNA polymerase promoter, (ii) a DNA comprising a sequence encoding the VSV N protein or functional fragment or derivative thereof, and (ii) a transcriptional termination signal for the bacteriophage RNA polymerase; and (c) a third plasmid comprising the following operatively linked components: (i) the bacteriophage RNA polymerase promoter, (ii) a DNA comprising a sequence encoding the VSV P protein or functional fragment or derivative thereof, and (ii) a transcriptional termination signal for the bacteriophage RNA polymerase;

(d) a fourth plasmid comprising the following operatively linked components: (i) the bacteriophage RNA polymerase promoter, (ii) a DNA comprising a sequence encoding the VSV L protein or functional fragment or derivative thereof, and (ii) a transcriptional termination signal for the bacteriophage RNA polymerase;

optionally (e) a fifth plasmid comprising the following operatively linked components: (i) the bacteriophage RNA polymerase promoter, (ii) a DNA comprising a sequence encoding the VSV M protein or functional fragment or derivative thereof, and (ii) a transcriptional termination signal for the bacteriophage RNA polymerase; and optionally (f) a sixth plasmid comprising the following operatively linked components: (i) the bacteriophage RNA polymerase promoter, (ii) a DNA comprising a sequence encoding the VSV G protein or functional fragment or derivative thereof, and (ii) a transcriptional termination signal for the bacteriophage RNA polymerase. In certain embodiments, the foreign RNA sequence is inserted into a non-essential portion of the recombinant VSV genome. In certain embodiments, the foreign RNA sequence replaces the VSV's G protein.

In another embodiment, a kit of the disclosure further comprises in a separate container a recombinant vaccinia virus encoding and capable of expressing the bacteriophage RNA polymerase.

In certain embodiments, the components in the containers are in purified form.

The disclosure further provides a kit for detecting coronavirus neutralizing antibodies in a sample (e.g., neutralizing antibodies that target the SARS-CoV-2 S glycoprotein). The kit may comprise:

a) a recombinant vesicular stomatitis virus (VSV) particle, where the VSV glycoprotein (G) is replaced by a coronavirus spike(S) glycoprotein or a fragment or a derivative thereof, where the S glycoprotein, fragment or derivative is capable of mediating infection of target cells;

b) a first cell expressing a first portion of a reporter protein and a second cell expressing a second portion of the reporter protein, where the first cell and the second cells are capable of fusing with one another if contacted with the recombinant VSV particle, the fusion resulting in the generation of a detectable reporter signal;

c) optionally, a positive control and/or a negative control;

d) optionally, a substrate for the reporter protein, and e) optionally, instructions for use.

The reporter protein may be any of the enzymes (e.g., luciferase) or fluorescent proteins (e.g., GFP) described herein. In various embodiments, the reporter protein may be incorporated into the VSV particle without being encoded by the genome in the VSV particle. In various embodiments, the reporter protein is encoded by the genome of the VSV particle.

In some embodiments, the positive control may comprise a neutralizing antibody (e.g., an antibody against the SARS-CoV-2 spike(S) glycoprotein). A non-limiting example of a neutralizing antibody against the SARS-CoV-2 S glycoprotein is mAb10914 or mAb10922 (the amino acid and nucleotide sequences of mAb10914 and mAb10922 are provided in the Sequences section, below). Known amounts of a neutralizing antibody can be added to serum or plasma that does not comprise the neutralizing antibody so as to generate a positive control. In some embodiments, the positive control may comprise a molecule that blocks the interaction between the SARS-CoV-2 spike(S) glycoprotein and a protein with which it interacts on the cell surface, e.g., ACE2 or TMPRSS2. Non-limiting examples of such molecules include, e.g., anti-ACE2 antibodies (e.g., CL4013, AC18F, 881CT16.4.4, MA5-31395, and OTI1D2 antibodies), soluble ACE2 proteins (e.g., as disclosed in Fukuski et al., Journal of General Virology, 2005, 86:2269-74, incorporated by reference herein in its entirety), and anti-TMPRSS2 antibodies (e.g., H1H7017N antibody as described in International Patent Pub. No. WO2019/147831, incorporated by reference herein in its entirety). In some embodiments, the positive control may comprise a molecule (e.g., an antibody) that blocks cell-cell fusion. Non-limiting examples of such molecules include, e.g., MC5 and DL11 antibodies described in Saw, W. T. et al., Methods, 2015, 90:68-75, incorporated by reference herein in its entirety.

The negative control can comprise serum or plasma that does not comprise the neutralizing antibody. The negative control can comprise serum or plasma that does not comprise the neutralizing antibody but comprises other antibodies, such as, an antibody that specifically targets a VSV glycoprotein (G), an antibody that specifically targets a VSV matrix protein (M), an antibody that specifically targets another coronavirus spike(S) glycoprotein different from that being tested in the method (e.g., an antibody that specifically targets the SARS-CoV-1 spike(S) glycoprotein but does not bind to the SARS-CoV-2 spike(S) glycoprotein), or monoclonal antibodies specific for HIV antigens (e.g., IgG1b12, 2G12, X5, 2F5, 4E10 as described in Montefiori, D. C., Current Protocols in Immunology, 2004, Chapter 12: Unit 12.11.1, incorporated by reference herein), or any isotype-control antibodies.

In yet another embodiment, the kit may comprise:

a) a recombinant vesicular stomatitis virus (VSV) particle where (i) the VSV glycoprotein (G) is replaced by a coronavirus spike(S) glycoprotein or a fragment or a derivative thereof, where said S glycoprotein, fragment or derivative is capable of mediating infection of a target cell and where (ii) the VSV particle comprises a reporter protein and/or a nucleic acid molecule encoding said reporter protein;

b) cells susceptible to infection mediated by the coronavirus S glycoprotein;

c) optionally, a positive control and/or a negative control;

d) optionally, a substrate for the reporter protein, and e) optionally, instructions for use.

A cell growth media and/or fixative may optionally be included in any of the kits.

Examples

The present disclosure is also described and demonstrated by way of the following examples. However, the use of this and other examples anywhere in the specification is illustrative only and in no way limits the scope and meaning of the disclosure or of any exemplified term. Likewise, the disclosure is not limited to any particular preferred embodiments described here. Indeed, many modifications and variations of the disclosure may be apparent to those skilled in the art upon reading this specification, and such variations can be made without departing from the disclosure in spirit or in scope. The disclosure is therefore to be limited only by the terms of the appended claims along with the full scope of equivalents to which those claims are entitled.

Example 1: Preparation of VSV Expressing Spike(S) Glycoprotein Constructs

Infectious clones of Indiana strain VSV were used to generate four recombinant VSV constructs, wherein the VSV (G) glycoprotein was deleted and replaced by codon optimized sequences suitable for expression in human cells and encoding: (1) the full length SARS-CoV-2 spike(S) glycoprotein sequence (NCBI Reference Sequence: NC_045512.2; Protein_ID: YP_009724390.1) (variant 1; VSV SARS-CoV-2 dG=VSV-SARS-CoV-2-S; amino acid sequence SEQ ID NO: 1; codon optimized coding nucleotide sequence SEQ ID NO: 2); (2) the SARS-CoV-2 S glycoprotein sequence with a deletion of 19 amino acids KFDEDDSEPVLKGVKLHYT (SEQ ID NO: 20) at the C terminus (variant 2; VSV SARS-CoV-2 Δ19CT dG=VSV-SARS-CoV-2-S-Δ19CT; amino acid sequence SEQ ID NO: 3; codon optimized coding nucleotide sequence SEQ ID NO: 4); (3) the SARS-CoV-2 S glycoprotein sequence with a replacement of the S glycoprotein cytoplasmic tail with VSV G cytoplasmic tail KLKHTKKRQIYTDIEMNRLGK (SEQ ID NO: 21) (variant 3; VSV SARS-CoV-2 VSV-G CT dG; amino acid sequence SEQ ID NO: 5; codon optimized coding nucleotide sequence SEQ ID NO: 6), or (4) variant 4-the full length SARS-CoV-2 S glycoprotein sequence (VSV-SARS-CoV-2-S; amino acid sequence SEQ ID NO: 1;

codon optimized coding nucleotide sequence SEQ ID NO: 2) with the wild-type VSV Kozak sequence (cActATG; SEQ ID NO: 11) in place of the optimized Kozak sequence (caccATG; SEQ ID NO: 12) used in the other three constructs. One set of variant 1-4 constructs (constructs 1-4) was prepared that encoded wild-type VSV M protein (amino acid sequence SEQ ID NO: 9; nucleotide sequence SEQ ID NO: 10). A second set of variant 1-4 constructs (constructs 5-8) was prepared that encoded M protein with the substitution M51R (amino acid sequence SEQ ID NO: 7; nucleotide sequence SEQ ID NO: 8) resulting in virus attenuation. See FIG. 1.

The variant 1-4 recombinant viral particles were produced using standard published protocol using transfection with vaccinia-T7 virus (expressing T7 polymerase) followed by co-transfection with N, P and L expression plasmids (with respective genes under the control of T7 promoter) and the viral genome plasmid. A plasmid expressing VSV G was also transfected into the cells to facilitate rescue. The viruses were amplified and propagated in Vero cells. The amplified recombinant viruses do not have VSV (G) glycoprotein and depend on SARS-CoV-2 spike(S) glycoprotein for entry and infection.

Figure 3:
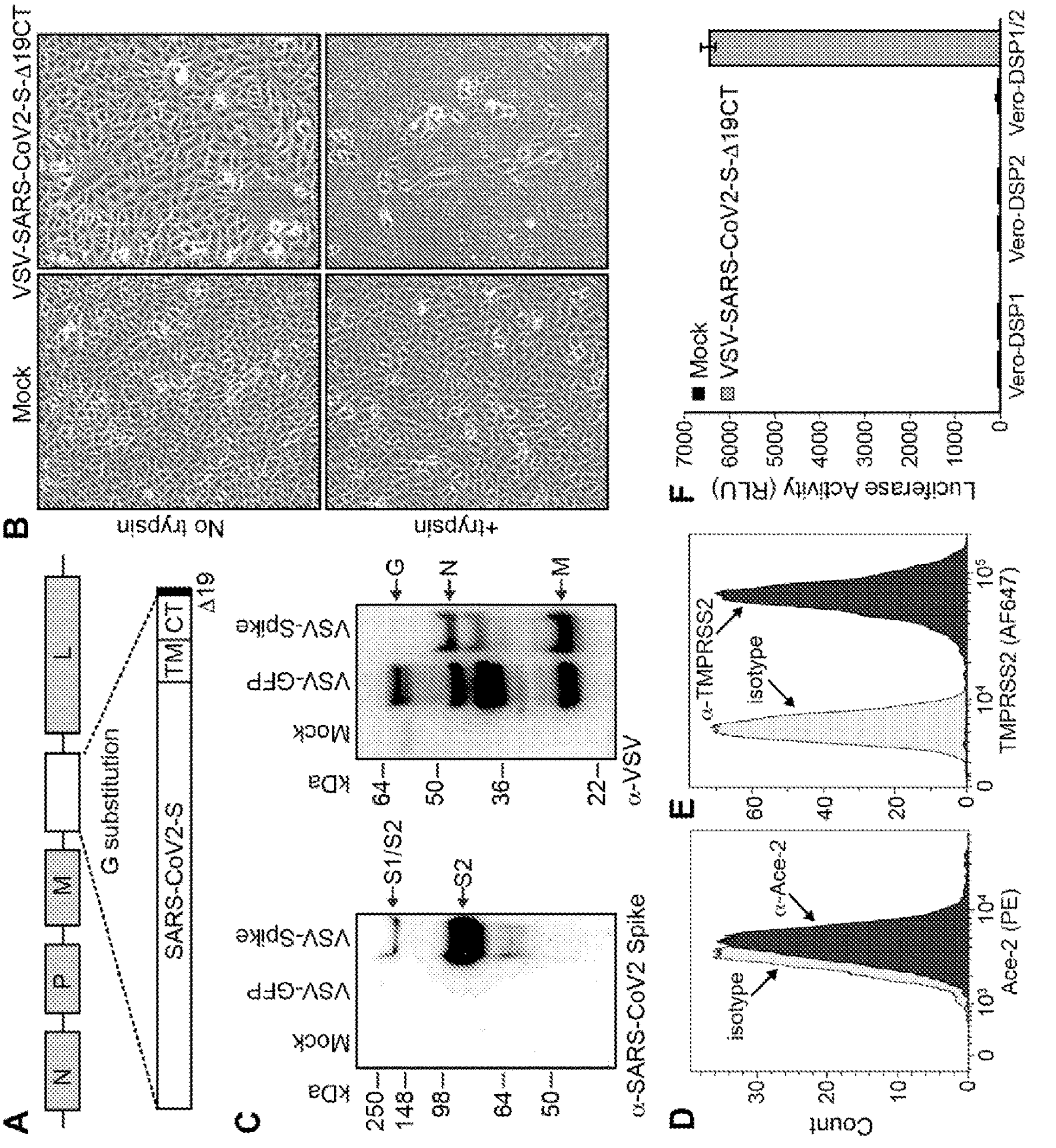
FIGS. 3A-F. (A) A schematic representation of the VSV-SARS-CoV-2-S-A19CT genome used in the assay. The location of the VSV N, P, M, and L genes are shown. VSV-G is replaced with a codon optimized SARS-CoV-2 spike gene with a 19 amino acid C-terminal (CT) deletion (A19CT). TM is transmembrane domain, CT is C-terminal domain. Not drawn to scale. (B) VSV-SARS-CoV-2-S-A19CT induces syncytia formation in Vero cell monolayers. Vero monolayers were infected with VSV-SARS-CoV-2-S-A19CT or mock-infected. After 4 hours, the inoculums were removed and replaced with fresh media±0.4 μg/mL trypsin. Images were taken 20 hours post infection at 100× magnification. (C) Immunoblot analysis. Viral supernatants prepared from Vero cells infected with VSV-GFP (encodes VSV-G) or VSV-SARS-CoV-2-S-Δ19CT or mock-infected were subjected to immunoblot analysis using anti-SARS-CoV-2-spike antibody (left) and rabbit anti-VSV antiserum (right). Arrows indicate the full-length S1/S2 variant and proteolytically cleaved S2 variant of SARS-CoV-2 spike protein and the VSV-G, VSV-N, and VSV-M proteins. (D and E) Flow cytometry. Monolayers of Vero-DSP1 cells were dislodged with versene, permeabilized (for TMPRSS2 staining only), stained with isotype control (grey), anti-ACE2 (D, black) or anti-TMPRSS2 (E, black) antibody, fixed, and subjected to flow cytometry analysis. (F) VSV-SARS-CoV-2-S-Δ19CT induced luciferase activity. Monolayers of Vero-DSP1, Vero-DSP2, or mixed Vero-DSP1/Vero-DSP2 cells were infected (10,000 TCID50 units/well) with VSV-SARS-CoV-2-S-Δ19CT or mock infected. Luciferase activity was measured as a marker of cell fusion at 24 hours after infection. Values represent the average (mean) RLU±standard deviation from duplicate wells.

Correct incorporation of VSV G, N and M proteins and SARS-CoV-2 S glycoprotein in the recombinant variant 2 VSV-SARS-CoV-2-S-Δ19CT construct 6 (VSV-M51R-nCOV19-S Δ19CT) virions was analyzed by Western blotting. The results are shown in FIG. 3C. Viral supernatants prepared from Vero cells infected with VSV-GFP (encodes VSV-G) or VSV-SARS-CoV-2-S-Δ19CT or mock-infected were subjected to immunoblot analysis using anti-SARS-CoV-2-spike antibody (left) and rabbit anti-VSV antiserum (right). SARS-CoV-2-S-Δ19CT S glycoprotein produced two bands corresponding to the full-length S1/S2 variant (180 kDa) and the proteolytically cleaved S2 variant (75 kDa) glycoprotein. The Western blot shows the presence of VSV N, M and G proteins in the VSV-GFP virus and the presence of VSV N and M proteins (but not VSV G glycoprotein) in the variant 2 VSV-SARS-CoV-2-S-Δ19CT virus. The Western blot for variant 2 VSV-SARS-CoV-2-S-Δ19CT virus also shows efficient incorporation of VSV-SARS-CoV-2-S-Δ19CT S glycoprotein in place of the VSV G glycoprotein.

Example 2: Development of a High-Throughput IMMUNO-CoV v. 1 Assay for Detecting Antibodies that Neutralize SARS-CoV-2

INTRODUCTION

Laboratory assays to detect SARS-CoV-2 neutralizing antibodies have been developed using clinical isolates of SARS-CoV-2, pseudotyped lentiviral vectors, and pseudotyped Vesicular stomatitis viruses (VSVs). Describe herein is a high-throughput, scalable clinical assay for the detection and quantitation of SARS-CoV-2-neutralizing antibodies using a recombinant VSV engineered to express the SARS-CoV-2 spike(S) glycoprotein in place of the VSV-G glycoprotein. The SARS-CoV-2 spike(S) glycoprotein binds to angiotensin converting enzyme-2 (ACE2) on the cell surface to initiate virus entry into the cell (Hoffman 2020, Walls 2020, Wan 2020). As the primary surface exposed viral protein, the coronavirus spike is a major target of the host immune system (Corman 2016, Liu 2006, Nie 2004, Zhao 2017). Blocking spike interaction with ACE2 prevents virus entry, making spike the primary target of neutralizing antibodies (Walls 2020, Wu 2020). Therefore, the present inventors hypothesized that the detection of antibodies capable of neutralizing VSV expressing spike(S) glycoprotein should directly reflect the level of SARS-CoV-2 neutralizing antibodies present in a sample. Importantly, using spike-expressing VSV in place of SARS-CoV-2 significantly increases assay safety and scalability.

Figure 2:
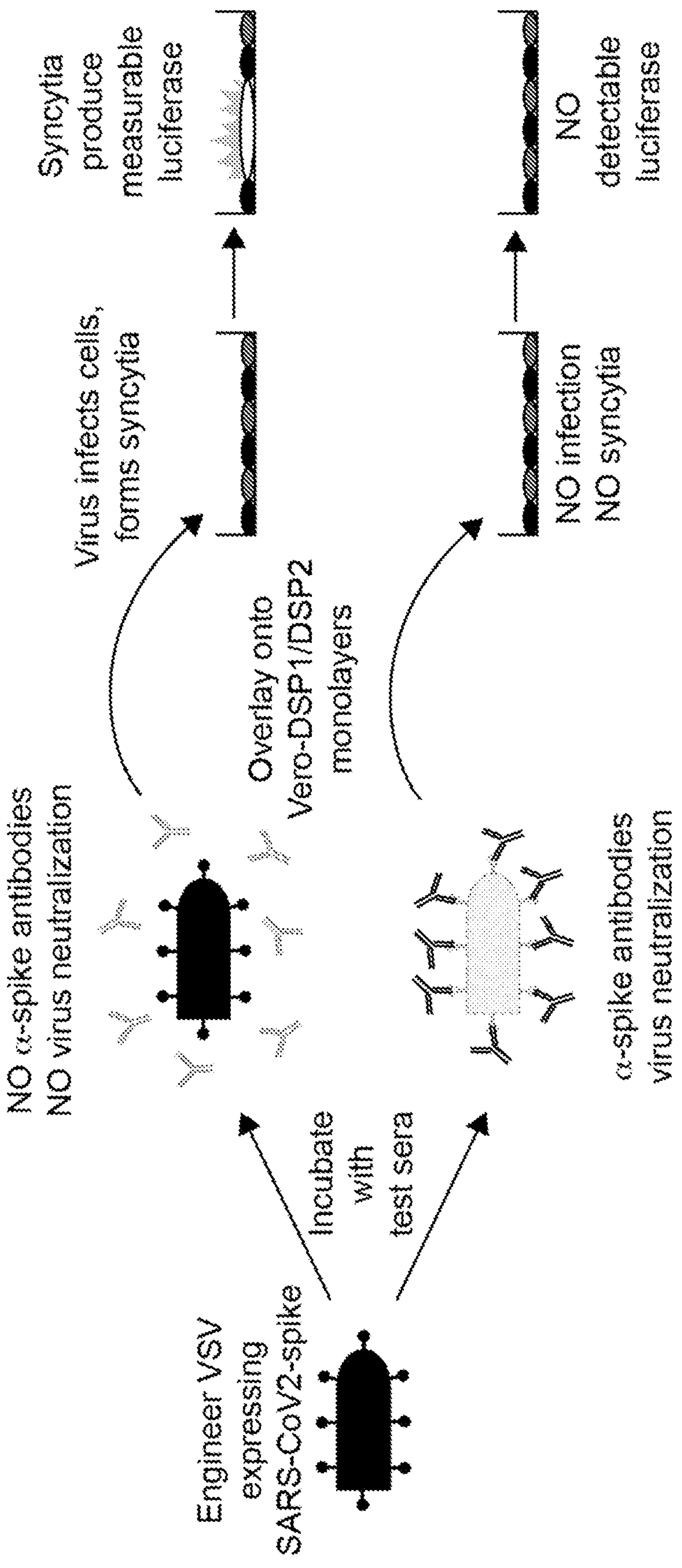
FIG. 2 represents an overview of a DSP Vero luciferase assay of the invention. A VSV expressing SARS-CoV-2 spike (e.g., VSV-SARS-CoV-2-S-A19CT or VSV-SARS-CoV-2-S) is incubated with test sera samples. In the absence of SARS-CoV-2 neutralizing antibodies (top) the virus retains infectivity and infects Vero-DSP1/Vero-DSP2 monolayers. If the test sample contains SARS-CoV-2 neutralizing antibodies (bottom), the antibodies bind to the spike protein causing virus neutralization by blocking cell entry. VSV-SARS-CoV-2-S-A19CT induces syncytia formation in Vero-DSP1/Vero-DSP2 monolayers, which reconstitutes a fully functional luciferase reporter that is used to quantitate virus-induced syncytia formation. High luciferase signal means the test sample did not neutralize the virus, while decreased luciferase indicates the presence of SARS-CoV-2-neutralizing antibodies in the test sample.

The present assay (IMMUNO-CoV v. 1) exploits the fusion phenotype of SARS-CoV-2 spike glycoprotein-expressing VSV by using a dual split protein (DSP) luciferase reporter system to quantitate virus-induced cell fusion and thereby the level of virus neutralization (FIG. 2). The DSP system of the present embodiment uses a chimeric split engineered green fluorescent protein (GFP) and split *Renilla* luciferase mutant Rluc8. Fusion between two cell lines expressing complementary pieces of the split reporter facilitates reassociation of fully functional GFP and Rluc8 luciferase. Thus, luciferase activity can be used to measure virus-induced cell fusion in a high-throughput 96-well plate format. Described herein is the development of the assay, including optimization of assay conditions and validation of the final clinical assay. Excellent correlation was observed between the assay results, clinical symptoms, and results from other serological tests. In particular, quantitation of SARS-CoV-2 neutralizing antibody levels correlated closely with plaque reduction neutralization IC50 values from an assay using a clinical isolate of SARS-CoV-2. Thus, the present assay accurately quantitates SARS-CoV-2 neutralizing antibodies, making it a valuable tool for assessing plasma therapies and immune responses to new SARS-CoV-2 vaccines.

The IMMUNO-CoV v. 1 assay exhibited 100% specificity in validation tests, and across all tests no false positives were detected. In blinded analyses, assay results demonstrated near-perfect correlation (196/197) with available clinical data and qRT-PCR or other serological testing results (commercially available ELISA). To quantitate the strength of the anti-viral response, a calibration curve was developed consisting of different concentrations of anti-SARS-CoV-2-spike monoclonal antibody spiked into pooled SARS-CoV-2 seronegative serum or plasma matrix. Using the calibration curve, neutralizing antibody levels were quantitated in the assay from a single 1:100 serum test dilution, determined to be the minimum recommended dilution. For samples with high levels of SARS-CoV-2-neutralizing antibodies, a second dilution facilitated more precise quantitation. The virus neutralization units (VNUs) calculated using this calibrator method correlated closely ($p<0.0001$) with plaque reduction neutralization titer-EC50 ($PRNT_{EC50}$) values determined by plaque reduction neutralization test against a clinical isolate of SARS-CoV-2. Taken together, these results demonstrate that the present IMMUNO-CoV v. 1 assay accurately quantitates SARS-CoV-2 neutralizing antibodies in samples (e.g., sera or plasma) in biosafety level 2 (BSL2), high-throughput format and can provide vital information for, e.g., evaluating donor eligibility for convalescent plasma therapy programs and participant eligibility for various clinical trials, as well assessing immune responses to candidate SARS-CoV-2 vaccines.

Results

Measurement of VSV-SARS-CoV-2-S-Δ19CT Fusion Through Luciferase Assay

Biosafety level 3 (BSL3) contaminant and practices are required to safely perform neutralization assays utilizing SARS-CoV-2, making widespread testing of patient samples using these assays impractical. The present inventors therefore sought to develop a safer, scalable assay that could be used to detect SARS-CoV-2 neutralizing antibodies in blood samples. The present inventors designed an assay in which syncytia formation in Vero cells, induced by infection with SARS-CoV-2 spike(S) glycoprotein-expressing VSV, is detected using a dual split protein (DSP) luciferase reporter (FIG. 2). Using reverse genetics, a recombinant Vesicular stomatitis virus (VSV) was generated in which the VSV glycoprotein (G) was replaced by the SARS-CoV-2 spike(S) glycoprotein (FIGS. 1 and 3A). Deletion of the last 19 amino acids in the C-terminal (cytoplasmic) domain of SARS-CoV-2 spike(S) glycoprotein improved virus rescue and amplification. The resulting virus (variant 2 VSV-SARS-CoV-2-S-Δ19CT), induced syncytia formation in Vero cell monolayers, which was enhanced in the presence of 0.4 μg/mL trypsin (FIG. 3B). Virion incorporation of SARS-CoV-2-419CT spike glycoprotein was confirmed in viral supernatants by immunoblot analysis (FIG. 3C). SARS-CoV-2-419CT spike glycoprotein, but not VSV-G, was detected, confirming efficient replacement of VSV-G with SARS-CoV-2-S-419CT in the recombinant virus.

Since Vero cells were infected by VSV-SARS-CoV-2-S-Δ19CT and express both ACE2 and TMPRSS2 (FIGS. 3D and E), they were chosen as the reporter cell line for the assay. Parental Vero cells were transduced with self-inactivating lentiviral vectors SFFV-DSP1-7-P2A-Puro or SFFV-DSP8-11-P2A-Puro expressing Rluc8 155-156DSP1-7 and Rluc8 155-156DSP8-11, respectively, under control of the spleen focus forming virus (SFFV) promoter and linked to the puromycin resistance gene via a P2A cleavage peptide. Vero-DSP1 cells express Rluc8 155-156DSP1-7 luciferase-GFP fusion protein (SEQ ID NO: 14) comprising RLuc8 mutant *Renilla* luciferase fragment amino acids 1-155 and engineered GFP fragment amino acids 1-156. Vero-DSP2 cells express Rluc8 155-156DSP8-11 luciferase-GFP fusion protein (SEQ ID NO: 16) comprising RLuc8 mutant *Renilla* luciferase fragment amino acids 157-311 and engineered GFP fragment amino acids 157-231. RLuc8 mutant *Renilla* luciferase contains the mutations A55T, C124A, S130A, K136R, A143M, M185V, M253L, and S287L (see SEQ ID NO: 19). The sequence of engineered GFP is provided in SEQ ID NO: 18.

When mixed monolayers of Vero-DSP1 and Vero-DSP2 cells seeded at a 1:1 ratio were infected with VSV-SARS-CoV-2-S-Δ19CT, syncytia formation was observed and luciferase activity was readily detected at 24 hours post infection (FIG. 3F). In contrast, luciferase activity was not detected in infected monolayers of Vero-DSP1 alone or Vero-DSP2 alone, or in mock-infected Vero-DSP1/Vero-DSP2 monolayers. Thus, luciferase activity was specific to virus-induced cell fusion of mixed Vero-DSP1/Vero-DSP2 monolayers.

Optimization of VSV-SARS-CoV-2-S-Δ19CT Fusion

Figure 4:
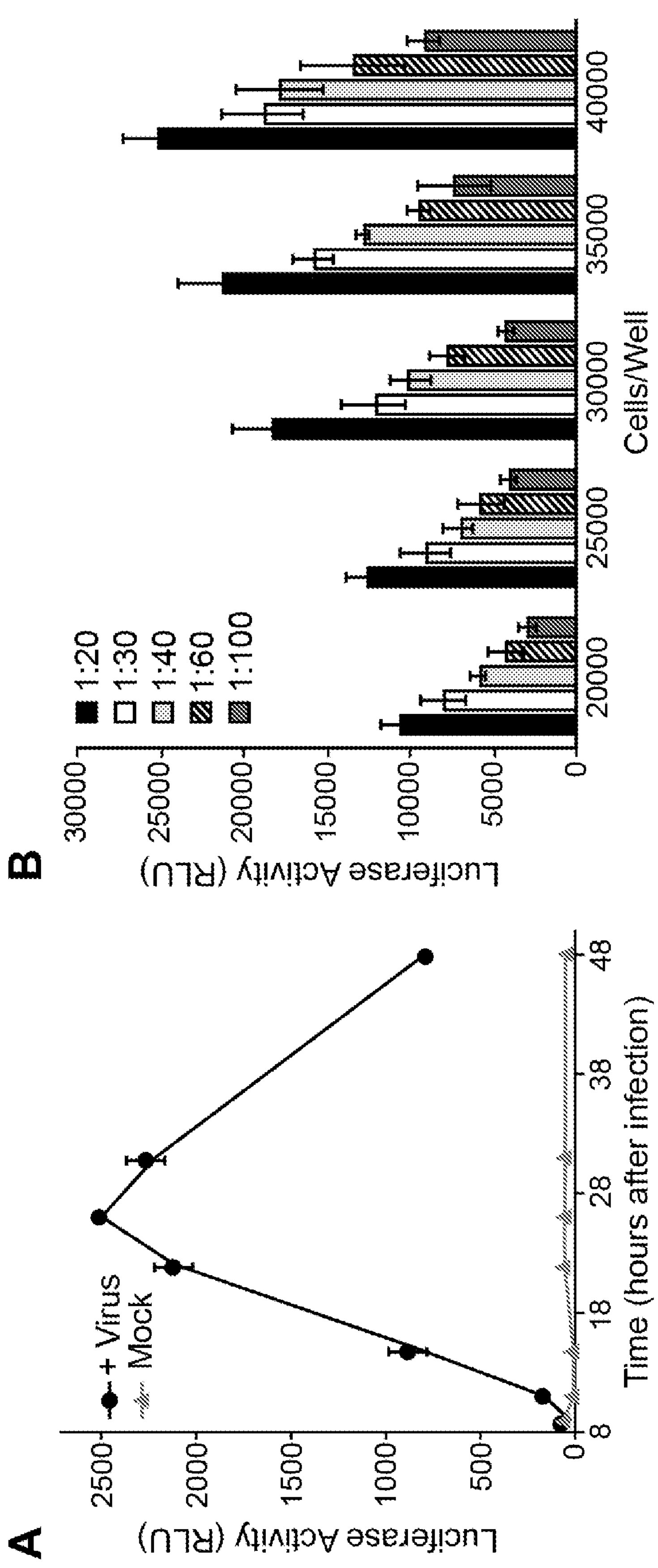
FIGS. 4A-B. Optimization of assay luciferase signal. (A) Kinetics of VSV-SARS-CoV-2-S-Δ19CT-induced luciferase activity. VSV-SARS-CoV-2-S-Δ19CT (2360 TCID50 units/well) or OptiMEM alone (mock) was overlaid onto monolayers of Vero-DSP1/Vero-DSP2 cells. Luciferase substrate EnduRen™ was added to wells and luciferase activity was measured at the indicated times (h) thereafter. Values represent the average (mean) RLU±standard deviation from duplicate wells. (B) Optimization of Vero-DSP1/Vero-DSP2 cell density. The indicated numbers of Vero-DSP1/Vero-DSP2 cells were seeded in 96-well plates. The following day, VSV-SARS-CoV-2-S-Δ19CT was diluted in OptiMEM to the indicated dilutions and overlaid onto the cell monolayers. Luciferase substrate EnduRen™ was added to wells and luciferase activity was measured 28 hours after infection. Values represent the average (mean) RLU±standard deviation from two separate experiments run in duplicate.

Syncytia formation is required to produce functional luciferase in the present assay. However, complete destruction of the cell monolayer following syncytia formation reduces luciferase activity due to loss of cell viability. The inventors therefore determined the optimal time after VSV-SARS-CoV-2-S-Δ19CT infection to measure luciferase. EnduRen™ Live Cell Substrate (EnduRen™) is an engineered "pro-substrate", which must be cleaved by cellular esterases to produce the luciferase substrate coelenterazine. Because the pro-substrate is highly stable, luciferase activity can be measured repeatedly at any time between 2 and 24 hours after EnduRen™ I'M addition to cells. By 15 hours after infection, luciferase activity in infected Vero-DSP1/Vero-DSP2 monolayers was readily distinguished from background signal in mock-infected cells (FIG. 4A). Luciferase activity continued to rise, reaching peak levels around 26 hours after infection. Thus, optimal luciferase readout in the assay was between 24 to 30 hours after infection.

To enhance cell fusion and luciferase activity, and thereby increase assay sensitivity, the optimal cell density and virus concentration were also determined. Vero-DSP1/Vero-DSP2 cells were seeded at increasing cell densities and after 24 hours the monolayers were infected with increasing concentrations of VSV-SARS-CoV-2-S-Δ19CT. At all virus dilutions, increasing cell density improved luciferase signal (FIG. 4B). As expected, syncytia formation and luciferase activity also increased when more virus was used to inoculate the monolayers. It was concluded that $6\times10^4$ cells/well should be used for the assay. It was also noted that for the best results cells should be seeded from flasks that are "under-confluent" and that cells can be seeded directly from cryopreserved stocks if given 2 days to recover.

Not surprisingly, additional studies across many experiments indicated that different lots of VSV-SARS-CoV-2-S-Δ19CT exhibited different potencies for inducing fusion. An appropriate concentration of virus for assay was therefore determined for each lot of virus based on performance against a set of contrived controls (see below).

Figure 5:
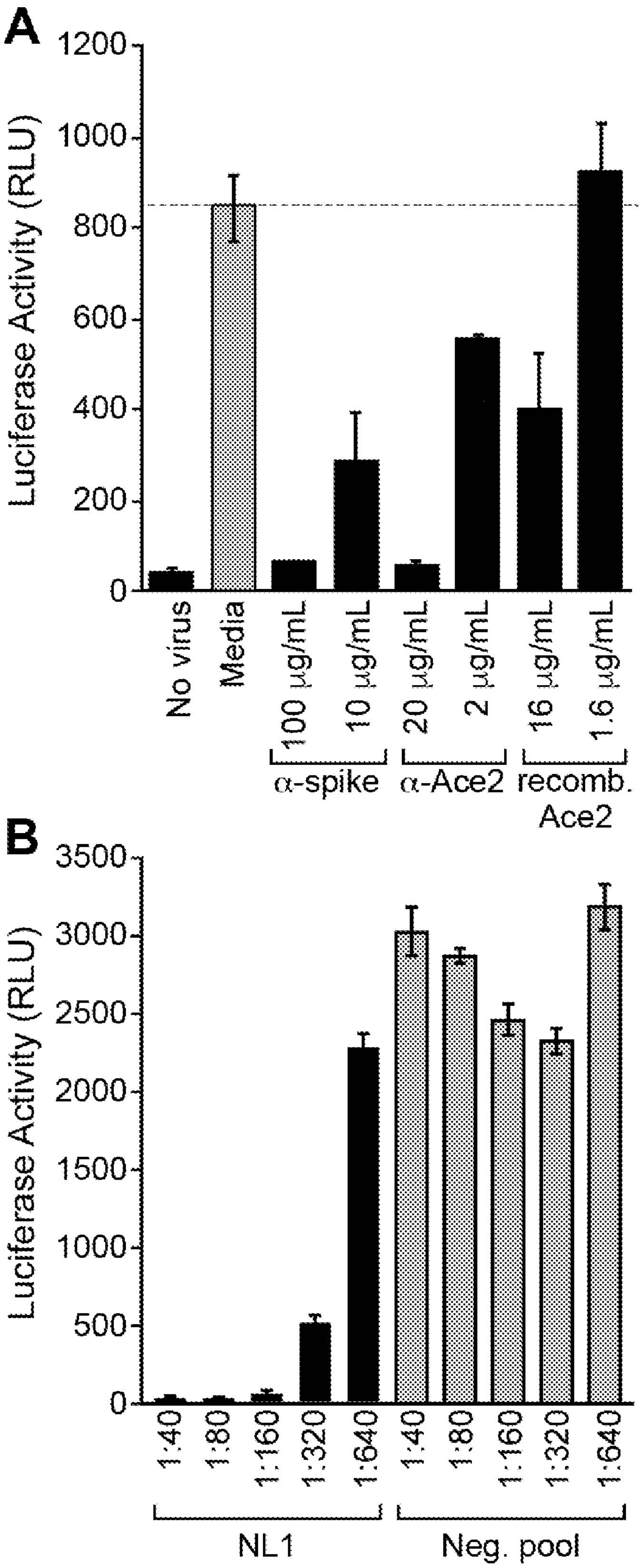
FIGS. 5A-B. Neutralization of VSV-SARS-CoV-2-S-Δ19CT-induced luciferase activity. (A) Inhibition by purified molecules. VSV-SARS-CoV-2-S-Δ19CT was incubated with media alone or the indicated concentrations of polyclonal anti-SARS-CoV-2-spike antibody, monoclonal anti-ACE2 antibody, or recombinant ACE2. After 1 hour at 37° C., the virus mixes were overlaid on Vero-DSP1/Vero-DSP2 monolayers. Control wells received media alone (no virus). Luciferase substrate EnduRen™ was added to wells and luciferase activity was measured 24 hours after infection. Values represent the average (mean) RLU±standard deviation from duplicate wells. (B) Inhibition by COVID-19 convalescing plasma. VSV-SARS-CoV-2-S-Δ19CT was incubated with the indicated dilutions of plasma from a COVID-19 convalescing individual (NL1) or pooled plasma from three presumptive SARS-CoV-2 seronegative individuals. Plasma dilutions represent final dilutions after addition of virus. After 1 hour at 37° C., the virus mixes were overlaid on Vero-DSP1/Vero-DSP2 monolayers. Luciferase substrate EnduRen™ was added to wells and luciferase activity was measured 28 hours after infection. Values represent the average (mean) RLU±standard deviation from duplicate wells.

Detection of VSV-SARS-CoV-2-S-Δ19CT Neutralization Using the Vero-DSP Reporter Assay To demonstrate that virus neutralization could be detected using the present assay, the capacity of several purified proteins to inhibit virus-induced fusion was first tested. Affinity-purified polyclonal anti-SARS-CoV-spike antibody and soluble recombinant Ace2 protein bind spike on the virus surface and block entry into cells. Similarly, monoclonal anti-Ace2 antibody blocks the cellular receptors and limits virus entry. All three inhibitors successfully blocked VSV-SARS-CoV-2-S-Δ19CT-induced fusion in a dose-dependent manner (FIG. 5A), demonstrating that the present assay can detect inhibition of VSV-SARS-CoV-2-S-Δ19CT infection. Importantly, VSV-SARS-CoV-2-S-Δ19CT neutralization by plasma acquired from a SARS-CoV-2 convalescing individual (NL1) was also detected. Compared to pooled plasma from three presumed SARS-CoV-2 seronegative individuals, heat-inactivated NL1 plasma neutralized VSV-SARS-CoV-2-S-Δ19CT in a dose-dependent manner (FIG. 5B). Thus, the present assay was able to detect VSV-SARS-CoV-2-S-Δ19CT-neutralizing antibodies in convalescing plasma.

Optimization of VSV-SARS-CoV-2-S-Δ19CT Neutralization Time

Figure 6:
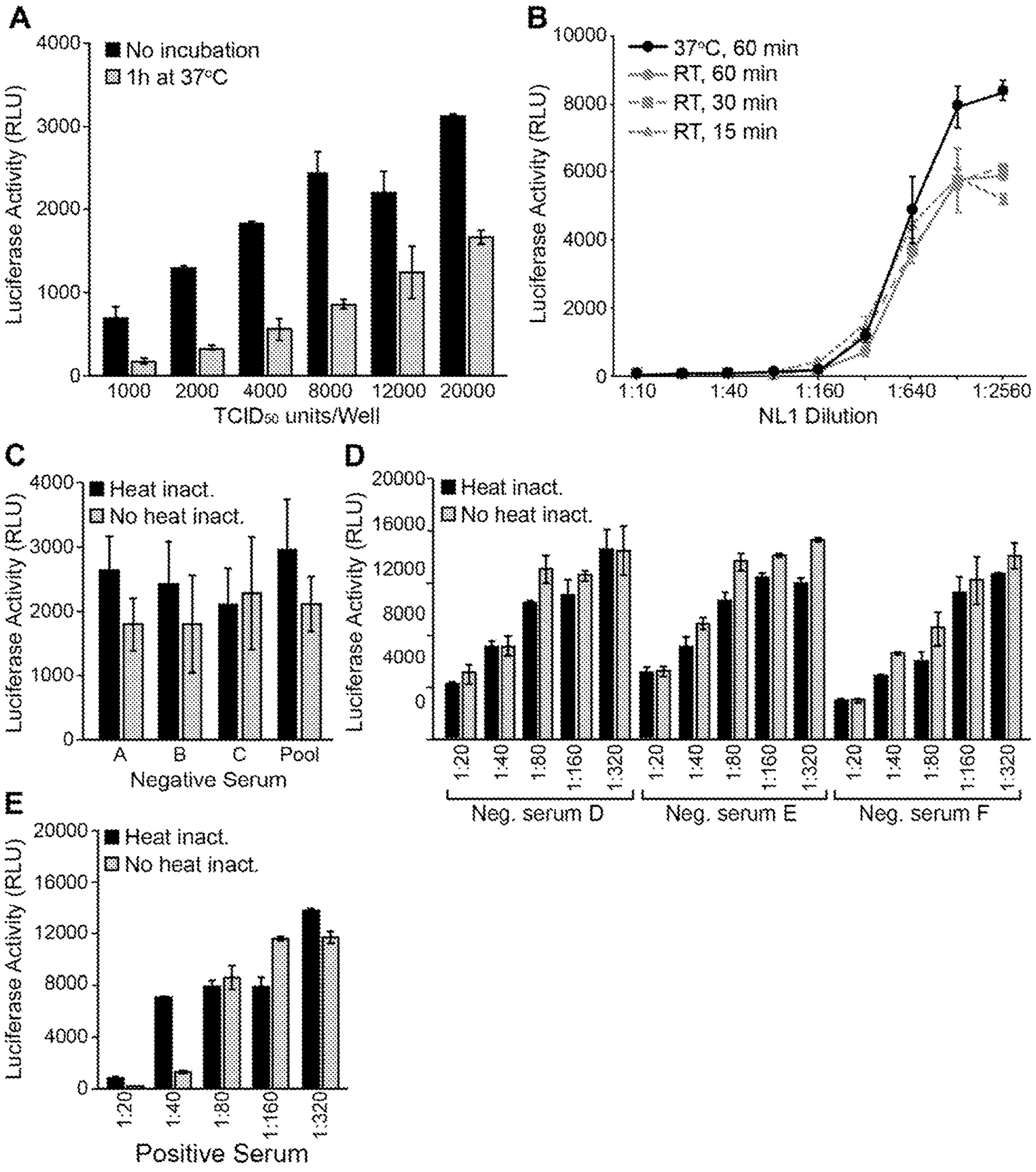
FIGS. 6A-E. Optimization of assay neutralization conditions. (A) Incubation of virus decreases syncytia formation. VSV-SARS-CoV-2-S-Δ19CT was thawed and diluted to the indicated TCID50 units/100 μL in OptiMEM. Duplicate samples were prepared; one set was immediately overlaid onto Vero-DSP1/Vero-DSP2 monolayers, while the other was incubated at 37° C. for 1 hour before being overlaid onto Vero-DSP1/Vero-DSP2 monolayers. Luciferase substrate EnduRen™ was added to wells and luciferase activity was measured 27 hours after infection. Values represent the average (mean) RLU±standard deviation from duplicate wells. (B) NL1 inhibition under different conditions. Dilutions of NL1 convalescing plasma were prepared and incubated with VSV-SARS-CoV-2-S-Δ19CT for the times and at the temperatures indicated, before being overlaid onto Vero-DSP1/Vero-DSP2 monolayers. Dilutions represent NL1 dilutions in the final virus/plasma mixes. Luciferase substrate EnduRen™ was added to wells and luciferase activity was measured 25 hours after infection. Values represent the average (mean) RLU±standard deviation from duplicate wells. (C and D) Effect of heat inactivation on negative sera. Presumptive negative serum samples A, B, C, D, E, F, G, and a commercial SARS-CoV-2 seronegative pooled sera (Pool) were prepared as duplicate aliquots. One aliquot was stored on ice while the other was incubated for 30 minutes at 56° C. Each aliquot was then diluted in OptiMEM and mixed with VSV-SARS-CoV-2-S-Δ19CT to a final dilution of 1:100 (C) or the dilutions indicated (D). Following a 30-minute incubation at room temperature, the virus/sera mixes were overlaid onto Vero-DSP1/Vero-DSP2 monolayers. Luciferase substrate EnduRen™ was added to wells and luciferase activity was measured 23 hours after infection. Values represent the average (mean) RLU±standard deviation from duplicate wells. (E) Effect of heat inactivation on COIVD-19 convalescing serum. A presumptive SARS-CoV-2 seropositive sample was thawed and assayed as described in Panel D.

In an early experiment it was observed that even in the absence of any neutralizing serum or inhibitors, incubation of VSV-SARS-CoV-2-S-Δ19CT at 37° C. for 1 hour resulted in a loss of luciferase activity (FIG. 6A). This loss of activity was partially abrogated at higher concentrations of virus. Nevertheless, the present inventors explored whether a shorter incubation time at room temperature could facilitate efficient virus neutralization. Two-fold serial dilutions of neutralizing NL1 plasma were prepared and incubated with VSV-SARS-CoV-2-S-Δ19CT for 60 minutes at 37° C. or for 15, 30, or 60 minutes at room temperature. Relative to the other conditions, luciferase activity was slightly higher at the 1:160 dilution in the sample that had been incubated for 15 minutes at room temperature (FIG. 6B), suggesting that this condition may not be sufficient for complete neutralization. However, NL1 neutralized VSV-SARS-CoV-2-S-Δ19CT as well, if not more efficiently, when incubated at room temperature for 30 or 60 minutes, relative to incubation at 37° C. for 1 hour. It was concluded that a 30-minute incubation at room temperature is sufficient for virus neutralization.

Heat Inactivation is not Necessary for Assay Compatibility

To further streamline the assay workflow, it was determined whether heat inactivation of samples is necessary to achieve reliable results. Serum samples were used for testing, due to their more ready availability compared to plasma samples. The inventors initially tested three presumptive SARS-CoV-2 seronegative samples and a commercially available sera pool (generated before fall of 2019) at a 1:100 dilution. In the sera pool, and two of the three negative sera, heat-inactivation lead to a modest decrease in luciferase activity (FIG. 6C), possibly due to low-levels of virus inactivation by complement. Yet overall, heat-inactivation had little effect on VSV-SARS-CoV-2-S-Δ19CT-induced cell fusion and luciferase activity. When three additional presumptive negative sera were tested at multiple dilutions, there was again little difference in luciferase activity between heat-inactivated and non-heat-inactivated samples (FIG. 6D). In contrast, heat inactivation reduced the capacity of a SARS-CoV-2 convalescing serum to neutralize VSV-SARS-CoV-2-S-Δ19CT (FIG. 6E). It was therefore concluded that using non-heat inactivated samples is preferred, as it streamlines assay workflow and increases assay sensitivity.

Determination of the Minimum Recommended Dilution

Sample interference is common in serological assays at high sample concentrations. Therefore, the inventors defined the minimum recommended dilution for assay samples, in which false positives due to sample interference are nearly eliminated. To this end, 39 presumptive SARS-CoV-2 seronegative samples were assayed at 2-fold serial dilutions ranging from 1:10 through 1:320. As expected, interference with virus fusion and luciferase activity was observed at higher serum concentrations (FIG. 7A) but disappeared as the samples were further diluted. Statistical analyses indicated that the minimum recommended dilution was approximately 1:100. At this dilution there is greater than 95% confidence that the luciferase signal from a negative serum sample will be >50%. In all future studies, therefore, 1:100 was used as the dilution for both test serum samples as well as pooled SARS-CoV-2 seronegative sera controls.

Development of a Contrived Positive Control

Figure 7:
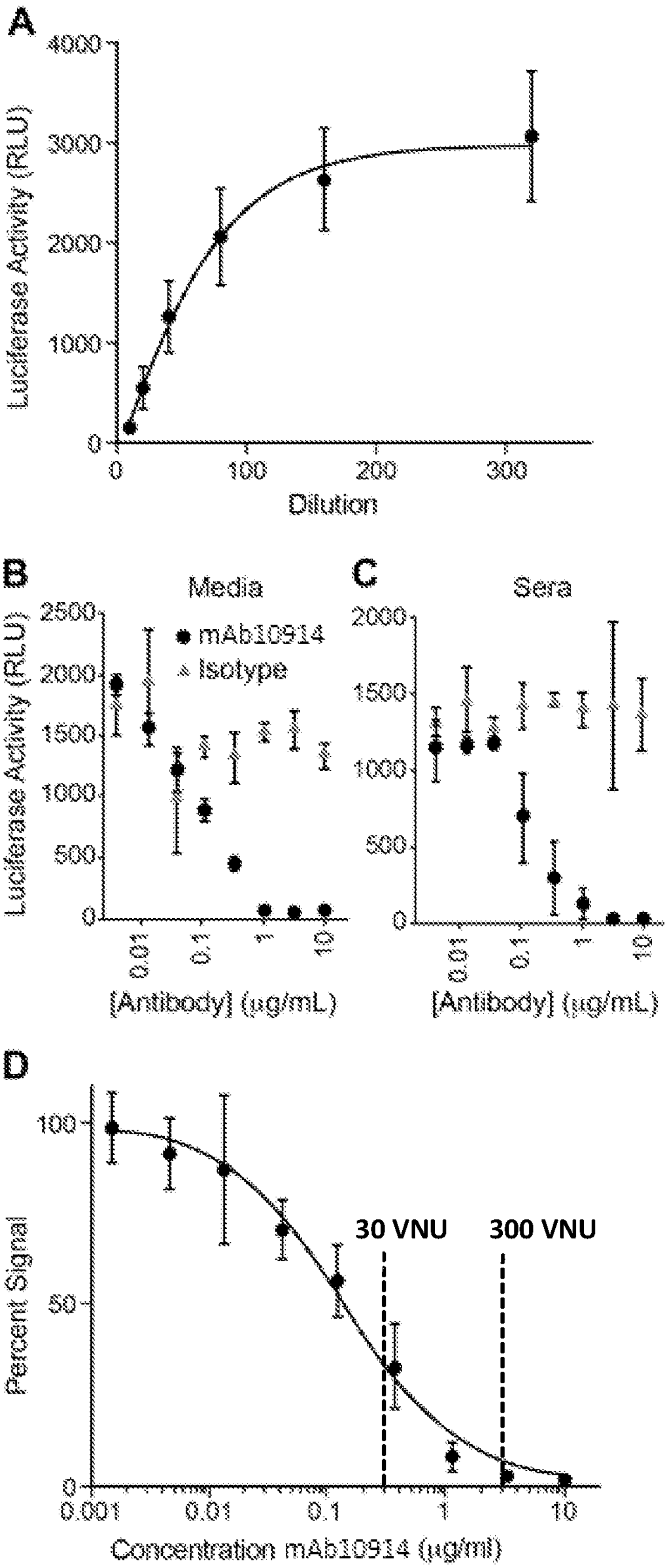
FIGS. 7A-D. Development of a contrived positive control. (A) Minimum recommended dilution. Thirty-nine sera from presumed SARS-CoV-2 seronegative individuals were serially diluted and mixed with VSV-SARS-CoV-2-S-Δ19CT in singlet. Dilutions represent serum dilution in the virus/serum mix. After 30 minutes at room temperature, the virus/serum mixes were overlaid on Vero-DSP1/Vero-DSP2 monolayers. Luciferase substrate EnduRen™ was added to wells and luciferase activity was measured 22 hours after infection. Values represent the average (mean) RLU±standard deviation fit with a non-linear regression curve. (B and C) Neutralization of VSV-SARS-CoV-2-S-Δ19CT by mAb10914. mAb10914 or isotype control antibody were diluted in OptiMEM (B) or pooled SARS-CoV-2 seronegative sera (C) and incubated with VSV-SARS-CoV-2-S-Δ19CT. Concentrations represent the antibody concentration in the virus/antibody mixes; sera concentration was 1:100. After 30 minutes at room temperature, the virus mixes were overlaid onto Vero-DSP1/Vero-DSP2 monolayers. Luciferase substrate EnduRen™ was added to wells and luciferase activity was measured 24 hours after infection. Values represent the average (mean) RLU±standard deviation from duplicate wells. (D) Establishment of contrived positive control values. mAb10914 was diluted in pooled SARS-CoV-2 seronegative sera as described in panel C and assayed as in panel C in triplicate runs performed by three different operators. Diluted pooled negative sera was used as a control (0 μg/mL mAb10914). Percent signal relative to the control was determined for each sample. Values represent the average (mean) percent signal+standard deviation from three independent experiments performed in duplicate, fit with a non-linear regression curve. Percent luciferase signal: luciferase signal from test sample relative to that in a negative control (pooled negative sera): above 50%=negative sample; below 50%=positive or borderline. A virus neutralizing unit (VNU): an arbitrary unit equal to 100 times the mAb10914 concentration with equivalent percent luciferase signal. Samples must have a VNU of 30 to be positive.

Due to the limited availability of large quantities of qualified SARS-CoV-2 seropositive sera, the inventors sought to develop a contrived positive control for the assay. To this end, various concentrations of mAb10914, a monoclonal antibody that binds to the SARS-CoV-2 spike(S) glycoprotein, were spiked into pooled SARS-CoV-2 seronegative serum or media alone. As a control, isotype antibody was also used. As expected, mAb10914 caused dose-dependent neutralization of VSV-SARS-CoV-2-S-Δ19CT in both media and pooled negative sera (FIGS. 7B and C). In contrast, the isotype control antibody did not significantly alter virus-induced luciferase activity, indicating that neutralization by mAb10914 was specific to spike binding. To establish appropriate concentrations to use for contrived controls in validation studies, a total of nine 3-fold serial dilutions of mAb10914 (from 10 μg/mL through ~0.0015 μg/mL) were tested in duplicate on three separate runs performed by three separate analysts. Because of variability in raw RLU (relative light unit) values between plates, results were normalized as percent luciferase signal relative to the luciferase signal in control wells containing pooled SARS-CoV-2 seronegative sera. The average (mean) percent luciferase signal at each concentration was plotted and a non-linear regression curve was generated (FIG. 7D). The linear range of the assay was between approximately 10% to 80% signal or 0.01 to 0.6 μg/mL mAb10914. 2 μg/mL mAb10914 was selected as a contrived positive control high (CPC High), which consistently reduces signal to <20%. Based on a 95% confidence of the response curve, the concentration of mAb10914 that should elicit a signal below 50% was calculated as 0.18 μg/mL, which thus represents an approximate limit of detection of the assay.

Examination of Assay Specificity and Sensitivity

CPC High value was used to define assay specificity and sensitivity. To measure specificity, 30 presumptive SARS-CoV-2 seronegative samples were tested alone or spiked with 2 μg/mL (CPC High) of mAb10914. This evaluation was conducted to verify that at the optimized 1:100 serum dilution no false positives were obtained and that all contrived positive controls showed virus neutralization. In two separate analytical runs performed by different analysts, no false positives or negatives were observed (Table 1). One negative sample was qualified as indeterminant in the first assay due to one replicate having signal <50%. However, in the second assay the sample was correctly identified as negative. Thus, in this validation IMMUNO-CoV v. 1 assay sensitivity and specificity was 100%. To measure assay specificity near the limit of detection, 30 presumptive SARS-CoV-2 seronegative samples (at 1:100 serum dilution) were tested alone; and 19 of the samples were also measured after spike with 0.35 μg/mL of mAb10914. 11 of the samples were spiked with 2 μg/mL mAb10914, which is not near the limit of detection. The experiment demonstrated 68% sensitivity near the limit of detection (Table 2).

To evaluate assay sensitivity, a similar, but single-blinded analysis was performed using the same 30 presumptive SARS-CoV-2 seronegative samples. Duplicate samples were assayed at 1:100, where one replicate sample was spiked with mAb10914 at 2 μg/mL (CPC High) or 0.35 μg/mL (borderline inhibition), before being assigned blinded IDs. Of the 30 negative samples, 26 were identified as negative and 4 as indeterminant (Table 2). 10 of the 11 CPC High samples were detected, and sample preparation error was suspected in the single positive not identified. From the 19 borderline samples, 13 were identified as positive, 4 as negative, and 2 as indeterminant, concordant with the samples containing only a low-level of neutralizing antibody and 0.35 μg/mL being close to the previously estimated assay limit of detection.

To further evaluate assay specificity, samples from patients who had recovered from documented infections with four common coronaviruses (HCoV-NL63, HCOV-229E, HCoV-OC43 and HKU1) prior to December 2019 were tested. No cross-reactivity with the common coronaviruses was observed demonstrating strong IMMUNO-CoV v. 1 assay specificity for SARS-CoV-2.

Demonstration of Clinical Agreement

Given that the present assay performed well with the contrived controls, the inventors proceeded with blinded studies to determine whether results correlated well with clinical symptoms. Serum samples were acquired from negative donors (symptomless, negative for SARS-CoV-2 by PCR, or SARS-CoV-2 seronegative by ELISA), positive donors (positive for SARS-CoV-2 by PCR or SARS-CoV-2 seropositive by ELISA), and contact positive donors (not tested, but in direct contact with someone positive for SARS-CoV-2 by PCR). A total of 230 samples were received and blinded to the assay analysts until after testing was complete. Of the 125 negative samples received, all 125 tested negative in the assay (Table 3), providing further evidence of the assay's excellent specificity. All 38 of the known SARS-CoV-2 seropositive samples also tested positive in the assay. From the 34 samples obtained from donors that had previously tested positive for SARS-CoV-2 by PCR, neutralizing antibodies were identified in 31 samples. Upon closer examination, one sample was expected to be negative because it was collected only 8 days after positive PCR test, which is not sufficient time for a strong antibody response to develop. From donors who had contact with someone positive for SARS-CoV-2, 13 of 33 samples (39.4%) were identified as positive for neutralizing antibodies. Taken together, the present data indicate that the assay has excellent clinical agreement.

Correlation Between VSV-SARS-CoV-2-S-Δ19CT and SARS-CoV-2 Neutralization

The strong clinical agreement observed for the assay supported the inventors' premise that neutralization of VSV-SARS-CoV-2-S-Δ19CT accurately reflects neutralization of SARS-CoV-2. In order to directly demonstrate this correlation, 20 of the serum samples from above were also tested against a clinical isolate of SARS-CoV-2 in a BSL-3 plaque reduction neutralization test (PRNT) (PRNT is described, e.g., in Wang et al., Nat Commun 11, 2251 (2020) doi.org/10.1038/s41467-020-16256-y; Okba et al., Emerg Infect Dis. 2020 July doi.org/10.3201/eid2607.200841; Ranawaka et al., Euro Surveill. 2020; 25 (16): pii=2000421. doi.org/10.2807/1560-7917.ES.2020.25.16.2000421). Each of the 5 samples that tested negative in the present assay were also below the limit of detection in the PRNT assay (Table 4). Likewise, the 15 samples that tested positive in the present assay also were positive in the PRNT assay. Moreover, quantitative virus neutralizing units (VNUs) determined in the present assay correlated closely with PRNT50% and $PRNT_{EC50}$ values (Tables 4-5 and FIG. 8A). To calculate VNUs, a calibration curve consisting of a five-point dilution series of mAb10914 in 1:100 pooled SARS-CoV-2 seronegative sera was included on each assay plate. Based on percent luciferase signal, the equivalent mAb10914 concentration for each sample was determined and multiplied by 100 to give the VNUs for that sample. Strong correlation (Pearson p=0.8902, p<0.0001) was observed between VNUs and $PRNT_{EC50}$ values. The relationship between VNU and virus neutralization titer (VNT) EC50 values was also examined. Five 2-fold serial dilutions of forty-four SARS-CoV-2 positive samples were prepared and tested in the assay. The percent luciferase signal for each dilution was plotted and the resulting curves were used to determine the $VNT_{EC50}$ values. Statistical comparison of the VNU and $VNT_{EC50}$ indicated excellent correlation (Spearman p=0.8327, p<0.0001) between the two values (FIG. 8B), providing additional demonstration of the accuracy of the VNU values. It was concluded that neutralization of VSV-SARS-CoV-2-S-Δ19CT closely replicates neutralization of SARS-CoV-2 and that VNUs provide an accurate method to quantitate the strength of the anti-SARS-CoV-2 antibody response. FIG. 8C depicts representative VNUs from PCR-positive samples showing that convalescent samples exhibit a range of VNUs.

Correlation between VNU values and symptom severity was investigated for 31 positive samples for which clinical symptoms were self-reported (FIG. 8D). 3 patients reported being asymptomatic: two were in lowest VNU quadrant and one in the second-lowest VNU quadrant. One patient who experienced only chills generated over 1000 VNUs of neutralizing antibodies. It follows that individuals with severe disease are more likely to develop strong neutralizing antibody responses, but severe disease is not required for a strong neutralizing antibody response.

Example of a 96-Well Plate Layout for the Assay

Figure 9:
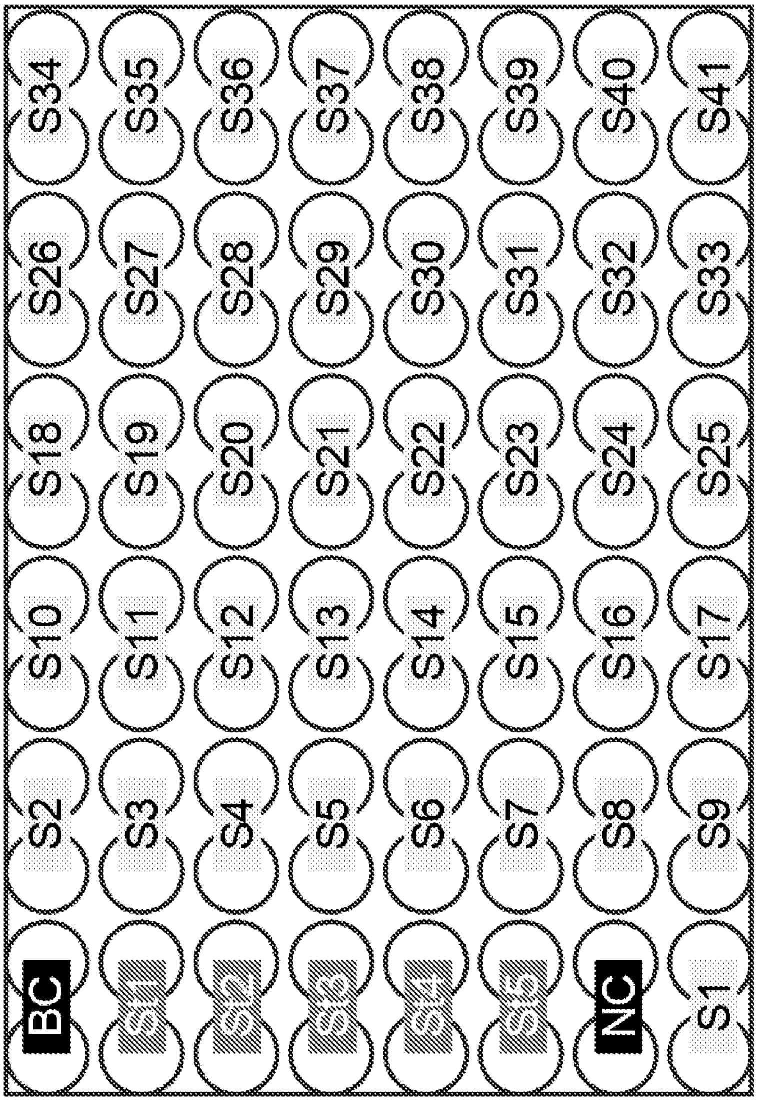
FIG. 9 shows an example of an assay plate layout for the DSP Vero luciferase assay. Example assay plate layout. All controls and samples are assayed in duplicate. A total of 41 samples (S1 to S41) can be run on a single plate using a single dilution for each sample. BC (background control) consists of pooled SARS-CoV-2 seronegative serum at 1:100 without virus. NC (negative control), consists of pooled SARS-CoV-2 seronegative serum at 1:100 with VSV-SARS-CoV-2-S-Δ19CT. NC is used to determine 100% luciferase signal in the assay. St1 through St5 are standards for the calibration curve. All standards are pooled SARS-CoV-2 seronegative serum at 1:100 with VSV-SARS-CoV-2-S-Δ19CT and mAb10914 spiked into each standard at different concentrations: Std1 is 3 μg/mL, Std2 is 1 μg/mL, Std3 is 0.33 μg/mL, Std4 is 0.11 μg/mL, and Std5 is 0.037 μg/mL.

A non-limiting example of a 96-well plate layout for the assay is shown in FIG. 9. Each sample and control is prepared in singlet in u-well plates or tubes and then transferred to duplicate wells of the Vero-DSP1/DSP2 mixed cells in 96-well black-walled, clear-bottom plates. Samples S1 to S41 are shown. Each sample is assayed at 1:100 in OptiMEM. It is possible to change the plate location of the samples and controls. The important part is to ensure that all of the controls are included on each plate. The controls include BC, NC, and Standards (St) 1 to 5.

BC is negative (matrix) pooled serum at a 1:100 dilution and NO virus

NC is negative (matrix) pooled serum at a 1:100 dilution+VSV-SARS-CoV-2-S-Δ19CT

Each Standard contains 3 components:

- Negative (matrix) pooled serum at 1:100 dilution
- VSV-SARS-CoV-2-S-Δ19CT
- Positive control (e.g., mAb10914) antibody at a specified concentration The final concentration of mAb10914 for each standard is currently: St1=3 μg/mL, St2=1 μg/mL, St3=0.3333 μg/mL, St4=0.1111 μg/mL, St5=0.0370 μg/mL (An alternative standard curve can contain 6 standards and the range will be: St1=2 μg/mL, St2=1 μg/mL, St3=0.5 μg/mL, St4=0.25 μg/mL, St5=0.125 μg/mL, St6 =0.0625 μg/mL)

To determine the result the following steps are performed:

1. Luciferase activity is measured (2000 ms integration/well, 200 ms settle time between wells) and the output unit is relative light unit (RLU).
2. The average (mean) RLU from the BC wells is determined and subtracted from each other to give background-corrected RLU values.
3. The mean corrected RLUs from the NC wells is determined.
4. Controls are examined for any obvious outliers, which are removed from mean values.
5. The percent luciferase signal is determined for each sample and standard (calculated for each replicate well individually). Percent luciferase signal is:

$$\text{percent luciferase signal} = \frac{\text{corrected } RLU \text{ of sample}}{\text{corrected mean } RLU \text{ of } NC} \times 100\%$$

6. To determine qualitative result the percent signal for each sample replicate is examined and resulted as follows:
   - Negative: both sample replicates have percent luciferase signal ≥50%
   - Positive both sample replicates have percent luciferase signal <50%
   - Indeterminant: one sample replicate has percent luciferase signal ≥50% and other <50%.
7. To calculate the quantitative virus neutralizing units (VNUs) for positive samples, the following steps are performed within the Magellan software automatically following reading of the luciferase signal:
   a. The standards are converted to arbitrary VNUs by multiplying their values by 100 (e.g. 3 μg/mL mAb10914 becomes 300 VNUs and 0.33 μg/mL become 33 VNUs).

b. The VNUs are plotted relative to background-corrected RLU values and a 4-parameter fit curve from the standards is generated.
c. Using the standard curve, the VNU value for each sample replicate and the mean of duplicate samples is determined.
d. VNUs above 300 are above the limit of quantification. They can either be reported as >300 VNUs or the samples can be assayed again at a higher dilution to get the sample within the linear range of the standard curve. After assay, the VNU is then multiplied by the increased dilution factor. (For example, a sample assayed at a 1:1000 dilution that reads as 180 VNUs is multiplied by 10 to give 1800 VNUs because the 1:1000 dilution is 10 times more dilute than a 1:100 dilution). Informal parallelism testing has been conducted, and dilutions have been performed out to 1:3200 for use in the assay (a dilution factor of 32).

DISCUSSION

High demand for serological tests to detect anti-SARS-CoV-2 antibodies is fueled by necessity to understand past rates of infection and evaluate the efficacy of vaccines and plasma therapies. Numerous ELISA and rapid diagnostic tests have been developed to detect anti-SARS-CoV-2 antibodies, and several are approved in various countries for diagnostic testing. Yet, an easily scalable serological assay for detecting antibodies capable of neutralizing SARS-CoV-2 has remained elusive. Described herein is IMMUNO-CoV v. 1 assay for the detection of SARS-CoV-2 neutralizing antibodies that is high-throughput, performed under lower biosafety (BSL2) conditions, scalable, and quantitative. The present assay is useful, e.g., for screening donor samples for SARS-CoV-2 plasma therapy trials, evaluating immune responses to candidate vaccines, and better understanding how antibody responses relate to SARS-CoV-2 immunity.

Figure 8:
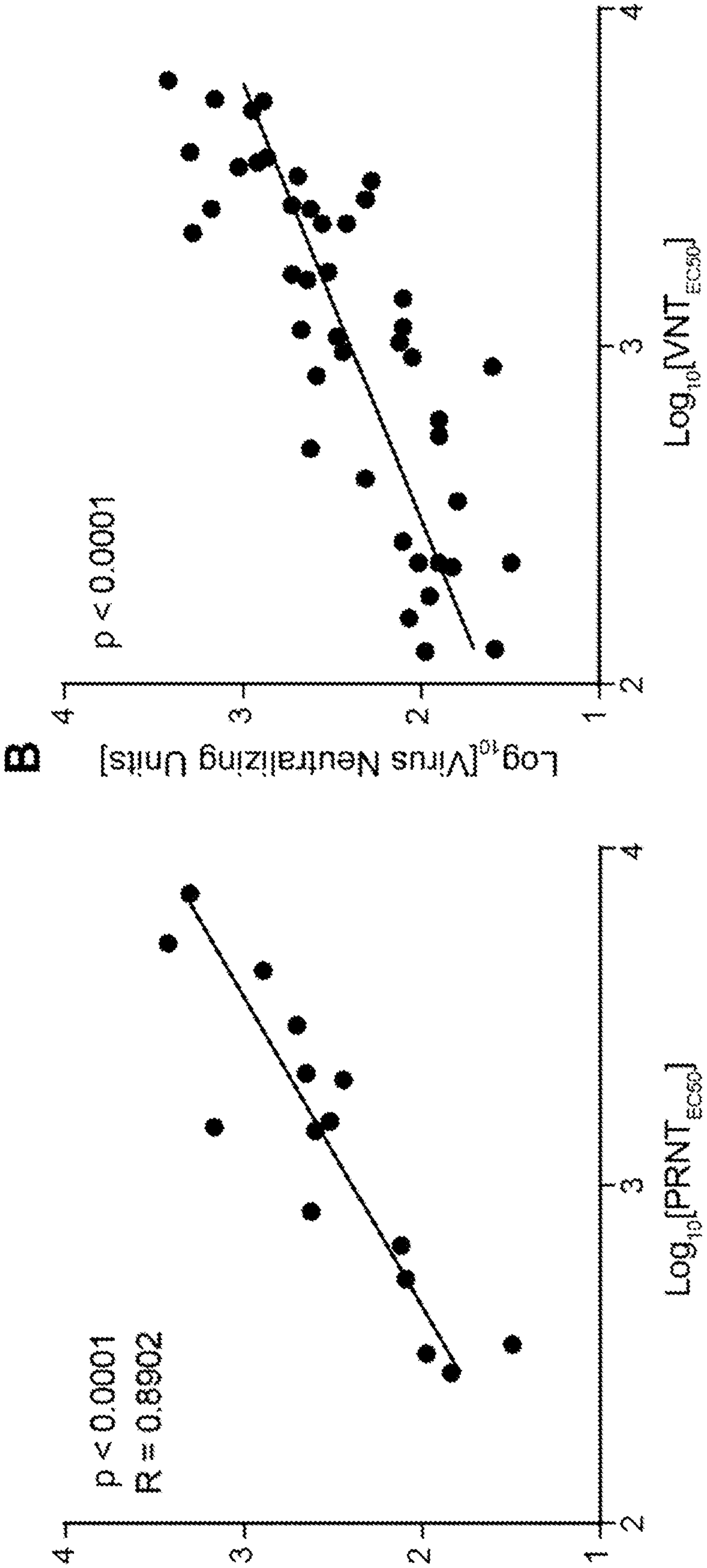
FIGS. 8A-D. Correlation of virus neutralizing units to $PRNT_{EC50}$ and $VNT_{EC50}$. SARS-CoV-2 seropositive sera samples were serially diluted in OptiMEM and mixed with VSV-SARS-CoV-2-S-Δ19CT. After 30 minutes at room temperature, the virus/serum mixes were overlaid onto Vero-DSP1/Vero-DSP2 monolayers. Luciferase substrate EnduRen™ was added to wells and luciferase activity was measured between 23 and 27 hours after infection. Each assay plate also included a calibration curve in which mAb10914 was spiked into pooled SARS-CoV-2 seronegative sera and mixed with virus. The concentrations of mAb10914 in the virus mixes for the calibration curve were 3, 1, 0.33, 0.11, and 0.037 μg/mL. The percent signal for each test sample and calibration curve point were determined. A virus neutralizing unit (VNU) was then determined for each sample based on its percent signal relative to the calibration curve, where a VNU equals the concentration of mAb10914 for the given percent signal multiplied by 100. Samples must have a VNU of 30 to be positive. (A) Comparison with $PRNT_{EC50}$. Of the positive samples tested, 15 serum samples were subjected to a plaque reduction neutralization test (PRNT) using a clinical isolate of SARS-CoV-2. Two-fold serial dilutions of samples were tested in the PRNT50 assay from 1:20 through 1:40960. For each sample, the number of plaques at each dilution was plotted and used to determine the $PRNT_{EC50}$ value for each sample. Statistical comparison of VNU relative to $PRNT_{EC50}$ was performed. Data was transformed due to non-normal distribution ($p<0.0001$). (B) Comparison with $VNT_{EC50}$. The percent signal for each sample dilution was plotted and used to determine the $VNT_{EC50}$. Statistical comparison of VNU relative to $VNT_{EC50}$ was performed. Data was transformed due to non-normal distribution (p<0.0001). (C) Representative distribution of VNUs in PCR-positive cohort. (D) Correlation between VNU values and symptom severity in 31 positive samples for which clinical symptoms were self-reported.
Figure 8:
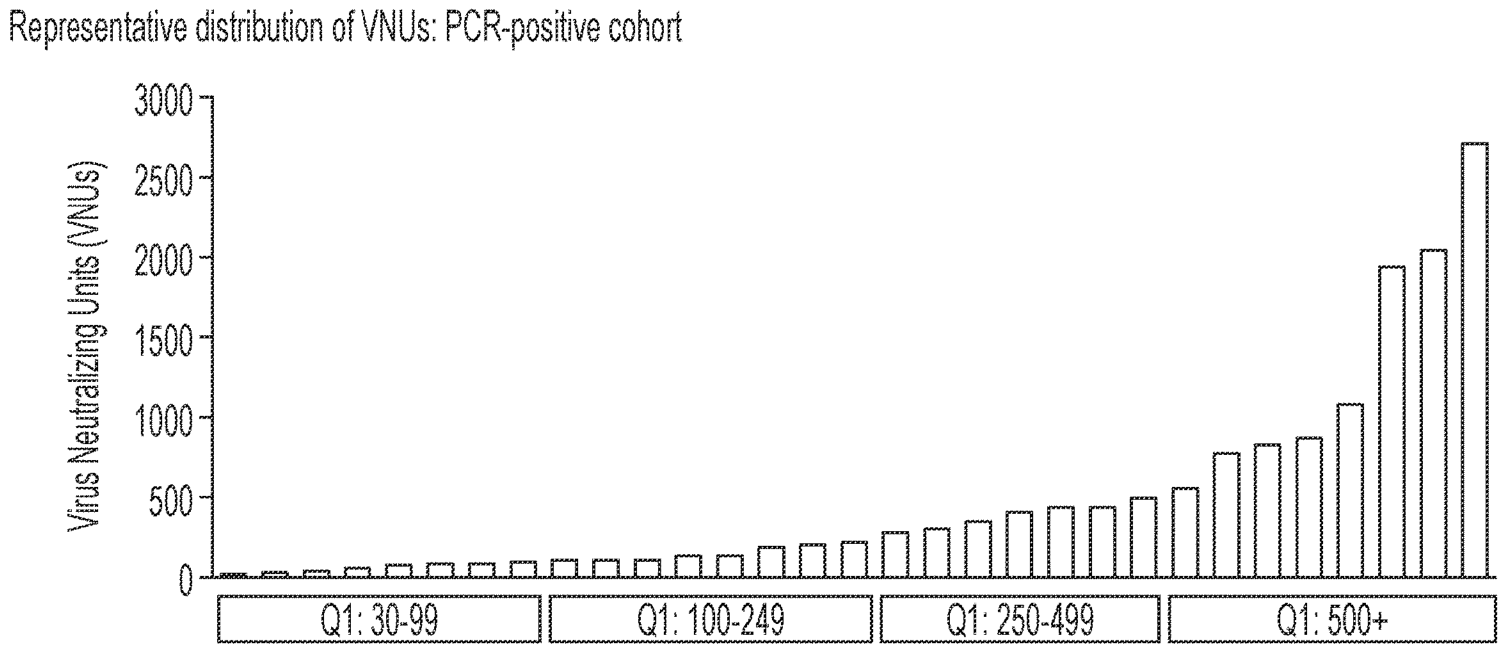

The present assay exploits the fusion phenotype of recombinant VSV-SARS-CoV-2-S-Δ19CT (or other similar constructs such as VSV-SARS-CoV-2-S) to produce quantitative luciferase signal in a 96-well plate format (FIGS. 2, 3, 9, and 10). Virus neutralization by test serum samples is then detected as a reduction in luciferase activity. Importantly, results from the present assay correlate closely (p=0.8987) with virus neutralization titers determined using a clinical isolate of SARS-CoV-2 (FIG. 8). Interestingly, when positive control antibody mAb10914 was tested in the SARS-CoV-2 plaque reduction neutralization test, it had a PRNT50% titer of 40960, which corresponds to a concentration of 0.026 μg/mL. In the present assay, it was determined that the lowest concentration of mAb10914 that could inhibit >50% of VSV-SARS-CoV-2-S-Δ19CT was approximately 0.18 μg/mL (FIG. 8). The present data indicate that even though the present assay uses a different virus (VSV-SARS-CoV-2-S-Δ19CT), it accurately measures anti-SARS-CoV-2 neutralizing antibodies and is unlikely to detect positives that are not also able to inhibit SARS-CoV-2. The present assay also demonstrated perfect correlation with the EUROIMMUN assay.

During testing, three samples collected from donors that were positive for SARS-CoV-2 by PCR test were negative using the present assay (Table 4). One of these samples was deemed a true negative, as it was received only 8 days after the positive PCR test, earlier than a strong antibody immune response is expected, and the sample also tested negative in the SARS-CoV-2 PRNT50 assay. Whether the other two samples represent false or true negatives has not yet been determined. Possibly, the samples indeed lacked any significant level of neutralizing antibodies, which supports the hypothesis that a positive PCR test results alone do not guarantee a protective antibody response. Alternatively, the samples may have only possessed low levels of neutralizing antibodies that were missed by the present assay. Studies performed using the contrived control spiked into negative pooled sera at a low level, suggested that near the limit of detection assay sensitivity is 68% (Table 2). However, sensitivity was 90.9% when the contrived control was spiked in at a higher concentration (2 μg/mL). Over half of the clinical samples tested exhibited virus neutralization units (VNUs) equivalent to at least 2 μg/mL neutralizing antibody. It is not surprising, therefore, that when calculating sensitivity based on blinded tests, a much higher degree of sensitivity (97.2%) is observed. Signal below 50% is cutoff. Variability was within acceptable limits.

The RBD of spike is likely the primary target of neutralizing antibodies, yet additional studies are needed to determine whether the assay, which only measures disruption of RBD-ACE2 binding, will accurately quantitate total SARS-CoV-2 neutralizing antibodies. Notably, the RBD domain of coronaviruses constantly switches between a standing-up and lying-down position (Yuan 2017 and Gui 2017), suggesting that some neutralizing antibody targeting may be context dependent. As proteolytic activation of spike is also required for membrane fusion and virus entry into cells the S1/S2 cleavage boundary may also be a target for neutralizing antibodies. Several recently developed assays use viral vectors pseudotyped with SARS-CoV-2 spike glycoprotein. However, scalability of pseudotyped viruses is more challenging than with live-replicating viruses (as used in the present assay), offering the present assay an advantage for widespread diagnostic testing.

Another advantage of the present assay is that the level of SARS-CoV-2 neutralizing antibodies is quantitated without the need for a full dilution series of the test samples. A minimum recommended dilution of 1:100 was determined for the assay. At this dilution, about 16.9% of samples fell above the linear range of the calibration curve. For samples containing high levels of SARS-CoV-2 neutralizing antibodies, a second dilution (e.g., 1:1000) can facilitate a more precise quantitation of antibody levels.

Additional testing has indicated that the Vero-DSP1 and Vero-DSP2 cell lines can be passaged for at least three weeks without impact on assay performance and that the SARS-CoV-2 neutralizing antibodies detected using this assay are stable under a number of storage conditions, including refrigeration for up to one week and multiple freeze-thaw cycles. Experiments with NL1 and a small pool of presumptive SARS-CoV-2 seronegative plasma (FIGS. 5B and 6B) suggest the assay is also compatible with plasma samples.

Studies with MERS and SARS-CoV have demonstrated antibody dependent enhancement of infection in vitro (Yip, Wang, Wan, and Jaume). Studies in NHP also suggest possible disease augmentation with increasing antibody levels for SARS-CoV (Liu et al. 2019). Some evidence supports antibody dependent enhancement in clinical cases of SARS (Ho 2005, Peiris 2003). Yet early studies using COVID-19 convalescing plasma to treat severe cases of COVID-19 have shown great promise. As researchers work to further refine convalescing plasma therapies, develop monoclonal antibody therapies, and engineer effective vaccines that produce strong anti-SARS-CoV-2 immune responses, there is clearly still much to be learned about the interaction between SARS-CoV-2 and the immune system. How total anti-SARS-CoV-2 antibody levels relate to neutralizing antibody levels is a key piece of this puzzle. A piece that the present assay can help to answer.

Materials and Methods

Cells. African green monkey Vero cells, Vero-αHis, and baby hamster kidney BHK-21 cells were maintained in high-glucose DMEM supplemented with 5% fetal bovine serum and 1X penicillin/streptomycin (complete media) at 37° C./5% $CO_2$.

Vero-DSP1 (Vero-DSP-1-Puro; CLR-73) and Vero-DSP2 (Vero-DSP-2-Puro; CLR-74) cells were generated by transducing Vero cells (African green monkey-derived kidney epithelial cells) with self-inactivating lentiviral vectors SFFV-DSP1-7-P2A-Puro or SFFV-DSP8-11-P2A-Puro expressing Rluc8 155-156DSP1-7 and Rluc8 155-156DSP8-11, respectively, under control of the spleen focus forming virus (SFFV) promoter and linked to the puromycin resistance gene via a P2A cleavage peptide. Transduced cells were selected using 10 μg/mL puromycin. Following selection Vero-DSP cells were maintained in complete media supplemented with 5 μg/mL puromycin. Puromycin was excluded removed when cells were seeded for assays.

Vero-DSP1 cells express Rluc8 155-156DSP1-7 luciferase-GFP fusion protein (SEQ ID NO: 14) comprising RLuc8 mutant *Renilla* luciferase fragment amino acids 1-155 and engineered GFP fragment amino acids 1-156. Vero-DSP2 cells express Rluc8 155-156DSP8-11 luciferase-GFP fusion protein (SEQ ID NO: 16) comprising RLuc8 mutant *Renilla* luciferase fragment amino acids 157-311 and engineered GFP fragment amino acids 157-231. RLuc8 mutant *Renilla* luciferase contains the mutations A55T, C124A, S130A, K136R, A143M, M185V, M253L, and S287L (see SEQ ID NO: 19). The sequence of engineered GFP is provided in SEQ ID NO: 18.

Generation of VSV-SARS-CoV-2-S-419CT. As discussed in Example 1, above, the full length SARS-CoV-2 spike(S) glycoprotein sequence (NCBI Reference Sequence: NC_045512.2; Protein_ID: YP_009724390.1) (variant 1; VSV SARS-CoV-2 dG=VSV-SARS-CoV-2-S; amino acid sequence SEQ ID NO: 1; codon optimized coding nucleotide sequence SEQ ID NO: 2); (2) the SARS-CoV-2 S glycoprotein sequence with a deletion of 19 amino acids KFDEDDSEPVLKGVKLHYT (SEQ ID NO: 20) at the C terminus (variant 2; VSV SARS-CoV-2 Δ19CT dG=VSV-SARS-CoV-2-S-Δ19CT; amino acid sequence SEQ ID NO: 3; codon optimized coding nucleotide sequence SEQ ID NO: 4). Full-length human codon-optimized SARS-CoV-2 spike(S) glycoprotein (NC_045512.2) was cloned in pUC57. The plasmid was used as a PCR template to generate a cDNA encoding SARS-CoV-2-S with a deletion in the nucleotides encoding the C-terminal 19 amino acids (S-Δ19CT) and 5' MluI and 3' NheI restriction sites. To generate the viral genome, the amplified PCR product containing S-Δ19CT was cloned into pVSV-M51R in place of VSV-G using the MluI and NheI restriction sites (FIGS. 1 and 3A). Plasmid was sequence verified and used for infectious virus rescue on BHK-21 cells as previously described. VSV-G was co-transfected into the BHK-21 cells to facilitate rescue but was not present in subsequent passages of the virus. The virus was propagated in Vero-αHis cells by inoculating 80% confluent monolayers in 10-cm plates with 1 mL of virus. Viruses were harvested 48 hours after inoculation, aliquoted, and stored at −80° C. until use. Aliquots were used for tissue culture infectious dose 50 (TCID50) assay on Vero-αHis cells.

Infections. Vero monolayers in 6-well plates were inoculated with 2 mL of passage 3 VSV-SARS-CoV-2-S-Δ19CT in OptiMEM or OptiMEM alone (mock). After 4 hours at 37° C./5% $CO_2$, the inoculums were removed and the cells were rinsed once with OptiMEM. Fresh OptiMEM alone or OptiMEM containing 4 μg/mL trypsin were added to wells. Cells were returned to the 37° C./5% $CO_2$ incubator until 20 hours after infection, when they were photographed at 100× magnification using an inverted microscope.

Reagents. EnduRen™ live cell substrate was prepared according to manufacturer's instructions (Promega #E6482). For inhibition studies, mouse anti-SARS-CoV-2 spike antibody (GeneTex #GTX632604), affinity-purified, polyclonal anti-human-ACE2 antibody (R&D Systems #AF933), and recombinant human ACE2 (R&D Systems #933-ZN-010) were diluted in OptiMEM to the desired concentrations.

Luciferase Assays. Assays were performed in 96-well black-walled plates with clear bottoms. EnduRen™ substrate was added to wells (final concentration of 7.5 μM) at various times after infection, but at least 2 hours before reading bioluminescence on a Tecan Infinity or Tecan M Plex instrument (2000 ms integration, 200 ms settle time). For kinetic experiments, repeated bioluminescence reads were performed without the addition of more EnduRen™ for up to 24 hours after initial EnduRen™ addition; at later time points additional EnduRen™ was added to wells at least 2 hours prior to reading bioluminescence.

Collection of plasma and sera samples. A clinical protocol to collect blood samples for assay validation was reviewed and approved by Western IRB (study ID: VYR-CoV-001). Serum and plasma samples were collected from patients who had previously tested positive for SARS-CoV-2 infection by a PCR test, from patients who had known exposure to individuals infected with SARS-CoV-2 and symptoms of COVID-19, as well as a cohort of patients of were presumed negative for antibodies, i.e. individuals who never had symptoms of COVID-19 disease and were likely never exposed. A total of 150 adults were enrolled at BioTrial based in Newark, New Jersey and Olmsted Medical Center in Rochester, Minnesota. Eighty additional sera aliquots from samples that had been tested using the EUROIMMUN assay.

Blinded sample testing. Sera samples were assigned a random ID prior to being given to analysts for assay testing. Samples were assayed in batches, with an unknown number of expected positive and negative samples in each batch. Each sample was assayed at a 1:100 dilution, with all positive and some negative samples being further assayed in a dilution series including 1:100, 1:200, 1:400, 1:800, and 1:1600.

PRNT Assay. Sera was heat-inactivated for 30 minutes at 56° C. and serially diluted in X. SARS-CoV-2 was diluted to 800 PFU/mL and mixed with an equal volume of diluted sera (final dilutions of serum with virus 1:20, 1:40, 1:80, 1:160, 1:320, 1:640, 1:1280, 1:2560, 1:5120, 1:10240, 1:20480, 1:40960). Virus mixed with an equal volume of media alone was used as a control. After a 1 hour incubation at 37° C., 250 μL of virus/serum or virus/media mixes were used to inoculate Vero-E6 monolayers in 6-well plates. Inoculations proceeded for 1 hour at 37° C. with occasional rocking, before monolayers were overlaid with 3 mL of 0.4% low-melting agarose in Minimal Essential Media supplemented with 2% fetal bovine serum and 1X penicillin/streptomycin. Plates were incubated at 37° C. until plaques appeared, then fixed with 10% formaldehyde, and stained with 0.25% crystal violet. Plaques were counted and the number of plaques at each dilution was plotted and used to determine the $PRNT_{EC50}$ value for each sample by a non-linear regression model. Plaque counts greater than 30 were too numerous to count and were considered as equivalent to the virus/media control. The PRNT50% titer was determined as the highest dilution (represented as the reciprocal) of serum that inhibited 50% of plaques relative to the virus/media control well.

Flow cytometry. Vero-DSP1 cells were dislodged using Versene, counted, and transferred to microcentrifuge tubes ($5\times10^5$ cells/tube was used for ACE2 staining and $1.5\times10^6$ cells/tube was used for TMPRSS2 staining). For ACE2 staining, cells were pelleted and resuspended in 100 μL FACS buffer (2% FBS in DPBS) containing 0.2 μg goat-anti-human ACE2 (R&D Systems #AF933). After 30 minutes on ice, cells were rinsed with 1 mL FACS buffer and resuspended in 100 μL FACS buffer containing 5 μL donkey-anti-goat IgG-PE secondary antibody. After 30 minutes on ice, cells were rinsed with 1 mL FACS buffer and fixed with 1% paraformaldehyde for 15 minutes on ice. Cells were washed twice with FACS buffer, resuspended in 500 μL FACS buffer and analyzed on a CYTOFLEX flow cytometer (Beckman Coulter). For TMPRSS2 staining cells were resuspended in 1 mL ice-cold 70% ethanol in DPBS and incubated on ice for 10 minutes. Cells were centrifuged, washed once with 1 mL FACS buffer, and resuspended in 100 μL of a 0.5% saponin solution containing 4 μg rabbit anti-TMPRSS2 (Invitrogen #PA5-14264). After 30 minutes on ice, samples were washed twice with 1 mL FACS buffer and resuspended in 100 μL of a 0.5% saponin solution containing 2 μL goat anti-rabbit IgG-AF647 secondary antibody. After 30 minutes on ice, cells were washed twice with FACS buffer and fixed with 1% paraformaldehyde for 15 minutes on ice. Cells were washed twice with FACS buffer, resuspended in 500 μL FACS buffer and analyzed on a CYTOFLEX flow cytometer (Beckman Coulter). For both ACE2 and TMPRSS2 staining, secondary antibody only controls were used for isotype.

Immunoblot. Total cells and culture supernatants of Vero cells infected with VSV-GFP or VSV-SARS-CoV-2-S-Δ19CT or mock-infected were harvested 48 hours after infection. Virus was released from the cell membranes by freeze-thaw and cell debris was removed by centrifugation. Samples were diluted in duplicate in LDS sample buffer (Invitrogen #B0007) and reducing agent (Invitrogen #B0009) according to the manufacturer's directions, incubated at 70° C. for 10 minutes, and 40 μL of each sample was ran on duplicate 4-12% Bis-Tris 15-well gels (Invitrogen #NW04125Box) along with precision plus protein dual color standard (Bio-Rad #161-0374). Proteins were transferred to nitrocellulose membranes using a Power Blotter XL. Membranes were blocked in 5% non-fat dry milk in TBST, washed three times with TBST, and incubated for 1 hour at room temperature with primary antibody mouse anti-SARS-CoV-2 spike (1:1000, GeneTex #GTX632604) or rabbit polyclonal anti-VSV (1:5000, Imanis Life Sciences #REA005). Membranes were washed three times with TBST and incubated for 1 hour at room temperature with secondary antibody goat anti-mouse IgG-HRP (Prometheus #20-304) or goat anti-rabbit IgG-HRP (Prometheus #20-303) at 1:20,000. Membranes were washed three times with TBST, and protein bands were developed for 2 minutes at room temperature using ProSignal® Dura ECL Reagent (Prometheus #20-301). Protein bands were imaged using a Bio-Rad ChemiDoc™ Imaging System.

Determination of percent response and virus neutralization units. Raw relative light unit (RLU) values for each well were blank corrected using the mean RLU value from background wells receiving pooled SARS-CoV-2 seronegative serum at 1:100 but not virus. The percent response was determined for each sample well as the corrected RLU value divided by the mean corrected RLU value from negative control wells receiving virus and pooled SARS-CoV-2 seronegative serum at 1:100 multiplied by 100%. Samples with a percent response <50% for both sample replicates were classified as positive. Samples with a percent response ≥50% for both sample replicates were classified as negative. When one replicate exhibited a positive response and the other a negative response, the sample was classified as indeterminant and assay was repeated. Virus neutralizing titers (VNUs) were determined for positive samples based on a calibration curve. The calibration curve was run on each plate and consisted of mAb10914 spiked into pooled SARS-CoV-2 seronegative sera at 3, 1, 0.33, 0.11, and 0.037 μg/mL. From the calibration curve, the equivalent concentration of neutralizing antibody for a given percent response was determined. To convert to VNU, the antibody equivalent concentration was multiplied by 100.

Statistical Analyses. Descriptive statistics, comparisons, and regression analyses were performed in Graph Pad Prism, v8.4.0 (San Diego, CA). Tests for normality of variance were conducted, and whenever possible parametric comparisons were used. For non-normal datasets, non-parametric approaches were used. A four-parameter non-linear regression was used for the calibration curve of the virus neutralizing units within the assay. For correlation analyses, Spearman's rank-order correlation analysis was conducted.

TABLE 1

Assay specificity and sensitivity

| | Analyst A | | Analyst B | |
|---|---|---|---|---|
| | Diluted Matrix | CPC spike* | Diluted Matrix | CPC spike |
| Total Tested | 30 | 30 | 30 | 30 |
| Number Positive | 0 | 30 | 0 | 30 |
| Number Negative | 29 | 0 | 30 | 0 |
| Number indeterminant | 1† | 30 | 0 | 0 |

*CPC spike: mAb10914 spiked into diluted matrix sample at 2 μg/mL.

†Sample identified as indeterminant due to one replicate with signal <50%.

TABLE 2

Assay specificity near the limit of detection

| | Sample Type* | | |
|---|---|---|---|
| | Negative | Borderline | Positive |
| Number of samples | 30 | 19 | 11 |
| Result positive | 0 | 13 | 10 |
| Result negative | 26 | 4 | 1† |
| Result indeterminant$ | 4 | 2 | 0 |

*Sample Type: Negative is diluted seronegative (matrix) sample; borderline is diluted matrix spiked with mAb10914 at 0.35 μg/mL; positive is diluted matrix spiked with mAb10914 at 2 μg/mL.

$Indeterminant: one replicate with signal >50%, other replicate with signal <50%.

†Technical error during sample preparation is suspected.

TABLE 3

| Clinical correlation-blinded studies | | | |
|---|---|---|---|
| | Total tested | Number Negative Results | Number Positive Results |
| Negatives | 125 | 125 | 0 |
| Presumptive (not tested) | 83 | 83 | 0 |
| Negative by ELISA* | 42 | 42 | 0 |
| Positives | 72 | 3† | 69 |
| Positive by PCR | 34 | 3† | 31 |
| Positive by ELISA | 38 | 0 | 38 |
| Contact Positives$ | 33 | 20 | 13 |

$Donors were not tested but had contact with someone confirmed positive by PCR.
†One sample received only 8 days after positive PCR result.
*Samples also tested by EPITOPE IgG ELISA (clinically validated

TABLE 4

| Correlation between IMMUNO-COV v. 1 and SARS-CoV2 Plaque Reduction Neutralization Test | | | | |
|---|---|---|---|---|
| Random ID | IMMUNO-COV Result | IMMUNO-COV VNU* | $PRNT_{EC50}$† | Clinical Correlation |
| RID-165 | Negative | N/A | <20$ | Presumed Negative |
| RID-152 | Negative | N/A | <20 | Presumed Negative |
| RID-121 | Negative | N/A | <20 | Contact positive |
| RID-195 | Negative | N/A | <20 | Contact positive |
| RID-239 | Negative | N/A | <20 | PCR positive 8-days before testing |
| RID-142 | Positive | 31.8 | 340.0 | PCR Positive |
| RID-168 | Positive | 69.9 | 277.7 | Contact tested positive |
| RID-272 | Positive | 95.2 | 319.8 | PCR Positive |
| RID-288 | Positive | 125.5 | 530.7 | Contact tested positive |
| RID-144 | Positive | 134.2 | 665.8 | PCR Positive |
| RID-138 | Positive | 281.7 | 2061 | Contact tested positive |
| RID-193 | Positive | 345.4 | 1545 | PCR Positive |
| RID-183 | Positive | 402.6 | 1449 | PCR Positive |
| RID-167 | Positive | 430.7 | 845.6 | Contact tested positive |
| RID-287 | Positive | 447.8 | 2130 | PCR Positive |
| RID-290 | Positive | 491.0 | 2999 | Contact tested positive |
| RID-192 | Positive | 775.7 | 4362 | Contact tested positive |
| RID-194 | Positive | 1504.9 | 1502 | Contact tested positive |
| RID-235 | Positive | 2046.6 | 7311 | PCR Positive |
| RID-236 | Positive | 2702.5 | 5203 | PCR Positive |

*VNU: Virus Neutralization Unit. Arbitrary quantitative value assigned based on calibration curve; higher VNUs represent higher neutralizing antibody levels.
$The limit of detection for this assay is 20.
†PRNT50: Plaque Reduction Neutralization Titer 50%. Highest sample dilution able to inhibit at least 50% of plaque formation; expressed as the recipricol value.

TABLE 5

| Correlation between IMMUNO-COV v. 1 and SARS-CoV2 Plaque Reduction Neutralization Test | | |
|---|---|---|
| VNU | PRNT | Result |
| <10 | <1:40 | Negative |
| 10 to 30 | 1:40 to 1:80 | Borderline |
| 30 to 75 | 1:160 | Positive |
| 75 to 150 | 1:320 | Positive |
| 150 to 300 | 1:640 | Positive |
| 300 to 600 | 1:1280 | Positive |

TABLE 5-continued

| Correlation between IMMUNO-COV v. 1 and SARS-CoV2 Plaque Reduction Neutralization Test | | |
|---|---|---|
| VNU | PRNT | Result |
| 600 to 1500 | 1:2560 | Positive |
| 1500 to 3000 | 1:5120 | Positive |
| >3000 | >10240 | Positive |

Core Validation

Core specificity is tested as follows. At least 30 sera samples from assumed SARS-CoV-2 seronegative individuals are analyzed on the assay in duplicate at their MRD. Additionally, for each serum sample analyzed, a corresponding CPCH sample is prepared by spiking into each sample at the concentration determined in the above section on optimized sample dilution, and then analyzed in duplicate. This assessment should be completed on at least two assay runs by two separate analysts. The mean response and % CV for each replicate dilution is reported.

A false positive rate is determined by the percentage of control matrix samples that generate a response below 50%. Acceptance criteria for false positive rate is below 5%.

A false negative rate is determined by the percentage of CPCH samples that generate a response above 50%. The false negative rate is reported in the final assay validation summary but does not have acceptance criteria.

Clinical agreement is determined as follows. At least three sera samples from convalescent patients who previously tested positive for SARS-CoV-2 by a molecular diagnostic test or another serological method, or were declared presumed positive by a medical professional due to onset of symptoms is tested on the assay. Information from presumed-positive patients is self-reported. This assessment is completed by plating the diluted samples in duplicate on at least one assay run, performed by one analyst. If possible, due to available sample volumes, this analysis is completed with three assay runs by at least two analysts. Submission of samples is conducted single-blinded to the analyst(s) with a mix a presumed positive and presumed negative samples. Presumed positive samples is analyzed by another serological method to allow for an accuracy assessment.

The mean response and % CV for each replicate dilution is reported. Clinical agreement is reported if response is observed below 50% at the MRD for all presumed positive samples tested. Following the initial screen, the samples are analyzed in a dilution series starting at the MRD, and determining the dilution titer result may be performed. Obtaining a dilution titer result is optional, and is not required for the assay validation. There should be 90% agreement for positive versus negative determination for samples compared to results obtained by the alternative serological method.

Intra-assay precision is determined as follows. The intra-operator and intra-assay precision is tested by preparing CPCH, CPCL, and untreated serum matrix pool for use as quality control (QC) samples. Twenty replicates of each QC sample are tested by one operator within a single assay run. An assay run may consist of sample plates due to sample capacity. All twenty replicates for each QC sample may be analyzed on the same assay plate, but this is not required.

The mean response, SD, and % CV are reported. The acceptance for each QC sample is based on the % CV, with an acceptance level of 20%. For the CPCH sample, acceptance criteria of 30% CV or within a reference range of Mean Response±3SD is accepted. This measure is chosen due to the high % CV expected in low response outputs. An error rate of up to 10% is accepted.

Inter-assay precision and inter-analyst precision are determined as follows. CPCH, CPCL and the untreated serum matrix pool is prepared and analyzed in duplicate for at least three assay runs by at least two analysts across multiple days.

The mean response, SD, and % CV is reported. The acceptance for each QC sample is based on the % CV, with an acceptance level of 20%. For the CPCH sample, acceptance criteria of 30% CV or within a reference range of Mean Response±3SD is accepted. This measure was chosen due to the high % CV expected in low response outputs. An error rate of up to 10% is accepted.

Inter-laboratory precision is determined as follows. CPCH, CPCL and untreated serum matrix pool is prepared at the testing facility. Sample levels is single-blinded and sent with reagents to complete the assay at an alternate test site. At least one assay run should be completed with the samples analyzed in duplicate. The alternate test site and responsible personnel for the alternate test site is identified in the final assay validation report.

Mean response, SD, and % CV are reported. Acceptance for each QC sample is based on the % CV, with an acceptance level of 520%. For the CPCH sample, acceptance criteria of 530% CV or within a reference range of Mean Response±3SD is accepted. This measure was chosen due to the high % CV expected in low response outputs. An error rate of up to 10% is accepted.

The robustness of stability of a first cell line is determined as follows. Analysis of ACE-2 expression on Vero-DSP1 and Vero-DSP2 cell lines is determined by flow cytometry. Based on the anticipated use of the cells, each cell line is tested at multiple intervals to determine consistent receptor expression throughout the anticipated use of the cells. Cells initially are tested within 48 hours after plating from frozen stocks at an initial passage after thawing. Repeat analyses take place at multiple passages out to a minimum of 6 passages or to a minimum time length of 3 weeks from thaw. The specific intervals tested and determined interval for acceptable stability is indicated in the final assay validation report. A single analysis run consisting of an anti-ACE-2 stained sample and an appropriate flow cytometry negative control sample is obtained at each interval tested.

The median fluorescence intensity (MFI) and Half-Peak % CV is reported for both the ACE-2 stained cells, and for the negative staining control. The staining index is calculated at each interval and reported in the final assay validation report. Acceptance criteria for the flow cytometry assessment is described as follows.

The median fluorescence intensity (MFI) and Half-Peak % CV is reported for both the ACE-2 stained cells, and for the negative staining control. The acceptance range is calculated from data collected at the first cell passage, within 48-hours of the cells being thawed. The acceptable MFI range is calculated as follows:

$$\text{Range} = MFI_{1st\ Passage} \pm \left(\frac{\%\ CV_{hp}}{100\%} \times MFI_{1st\ Passage}\right)$$

Where % CVhp is defined as the half-peak % CV from the flow cytometer instrument. All analyses conducted at other intervals should fall within MFI range established from this calculation for both the ACE-2 stained cells, and for the negative staining control.

The robustness of stability of a second cell line is determined as follows. Analysis of functional DSP on Vero-DSP1 and Vero-DSP2 cell lines is determined by level of luminescence generated in presence of CPCH, CPCL, and CM. An assay run is conducted on cells thawed from a cryovial aliquot, allowed to expand for two days, and then passaged for use in the assay. The time from thawing of cells to reading of the assay plate would be 4 total days. The assay run should include CPCH, CPCL and untreated matrix pool prepared and analyzed in duplicate. For each successive split of the cells, assay plates are prepared, and an assay run is completed including CPCH, CPCL and untreated matrix pool prepared and analyzed in duplicate. The specific number of passages and assay runs is not known, but cells are carried for a period of at least three weeks from when the cells initially thawed, and at each split, an assay plate is plated to conduct an assay run, setup on the next day, and read two days after plating.

Mean response, SD, and % CV are reported. Performance at each level is compared to the mean response obtained from the first assay run on the cells (read 4 days cell thaw). Percent Relative Error (% RE) from the first assay run on the cell is calculated. Acceptance criteria are defined as +30% RE obtained from the CPCL sample. The CPCL sample was chosen to evaluate stability when it is suspected the CPCL response falls within the linear range of the assay.

The robustness of viral stock stability is determined as follows. A virus stock tube is thawed for use in the assay, and then stored on wet ice or refrigerated conditions (2 to 8° C.) for up to 24-hours. At least three assay runs are prepared from this single tube at multiple intervals. Each assay run includes CPCH, CPCL and untreated matrix pool plated in duplicate. The specific timed intervals tested includes an assay plate prepared within 1 hour of thawing ("fresh virus"), an assay plate prepared between 22 and 24 hours after thawing, and at least one intermediate time interval (i.e. within 12 hours of thawing).

Mean response, SD, and % CV are reported. Performance at each level is compared to the mean response obtained from the less than one hour interval. The percent relative error (% RE) from the less than one hour interval is calculated. Acceptance criteria are defined as +30% RE obtained from the CPCL sample. The CPCL sample was chosen to evaluate stability as it is suspected the CPCL response falls within the linear range of the assay.

The robustness of sample matrix stability is determined as follows. From the minimum three samples obtained above, analysis is conducted as quickly as possible following collection. Duration of time from collection to analysis is reported. During the analysis procedure, additional matrix aliquots is prepared to be used for stability assessment. Stability is conducted for samples stored in a freezer set to maintain a temperature −20° C., as well as the other conditions described.

Time/Temperature: Due to variability in sample volume, the specific number of aliquots able be prepared is unknown but is reported in the validation assay report. Minimum stability assessments are prepared at the following intervals as shown in Table 6, below.

TABLE 6

| | Refrigerator | Freezer | | Benchtop |
|---|---|---|---|---|
| Time | 1-week | 1-week | 1-month | hours |
| Temperature | 2 to 8° C. | 5-20° C. | 5-20° C. | 19 to 28° C. |

A freeze-thaw (FT) cycle is defined as allowing frozen sample to thaw completely (>_15 minutes removal from freezer, and visual determination of sample appearance as completely liquid state), and then returning sample to freezer 6 hours prior to thawing again to conduct analysis. Three FT cycles are performed.

Samples are analyzed in duplicate at each of the described intervals listed above. The mean response, SD, and % CV are reported. Performance at each level is compared to the mean response obtained from the initial analysis result. Percent Relative Error (% RE) from the initial analysis is calculated. Acceptance criteria are defined as +30% RE.

Statistical Analysis

A negative threshold determination is performed as follows. Biological outliers are identified using a Tukey Boxplot1. The first quartile, the third quartile, interquartile range or IQR (third quartile−first quartile), upper fence (third quartile+k*IQR), and lower fence (first quartile−k*IQR) are calculated. The constant k are defined as equal to 3. Biological outliers are excluded from further calculation of the negative threshold determination.

Non-excluded data from all runs are pooled. Variance in normality is analyzed using an appropriate statistical test such as the Shapiro-Wilk test or the Anderson-Darling test. See, John W. Tukey, Journal of Computational and Graphical Statistics, 1993, 2:1-33 and Shapiro, S. S. and Wilk, M. B., Biometrika, 1965, 52 (3-4): 591-611. See, Anderson, T. W. and Darling, D. A., A Test of Goodness of Fit. Journal of the American Statistical Association, 1954, 49 (268): 765-769.

If the data distribution is normal, use a parametric approach with $\alpha=0.05$:

Negative Threshold Determination=mean normalized response±1.646×SD

If the data distribution is non-normal, use a non-parametric approach:

Negative Threshold Determination=95th percentile of the data

The flow cytometry cell analysis acceptance criteria is as follows. The median fluorescence intensity (MFI) and Half-Peak % CV is reported for both the ACE-2 stained cells, and for the negative staining control. The acceptance range is calculated from data collected at the first cell passage, within 48-hours of the cells being thawed. The acceptable MFI range is calculated as follows:

$$\text{Range} = MFI_{1st\ Passage} \pm \left(\frac{\%\ CV_{hp}}{100\%} \times MFI_{1st\ Passage}\right)$$

The % CVhp is defined as the half-peak % CV from the flow cytometer instrument. All analyses conducted at other intervals should fall within MFI range established from this calculation for both the ACE-2 stained cells, and for the negative staining control.

Example 3: The Use of IMMUNO-CoV v. 1 Assay to Detect SRS-CoV-2-Neturalizing Antibodies in Plasma The present Example demonstrates compatibility of plasma with the IMMUNO-CoV v. 1 assay of the invention.

Figure 11:
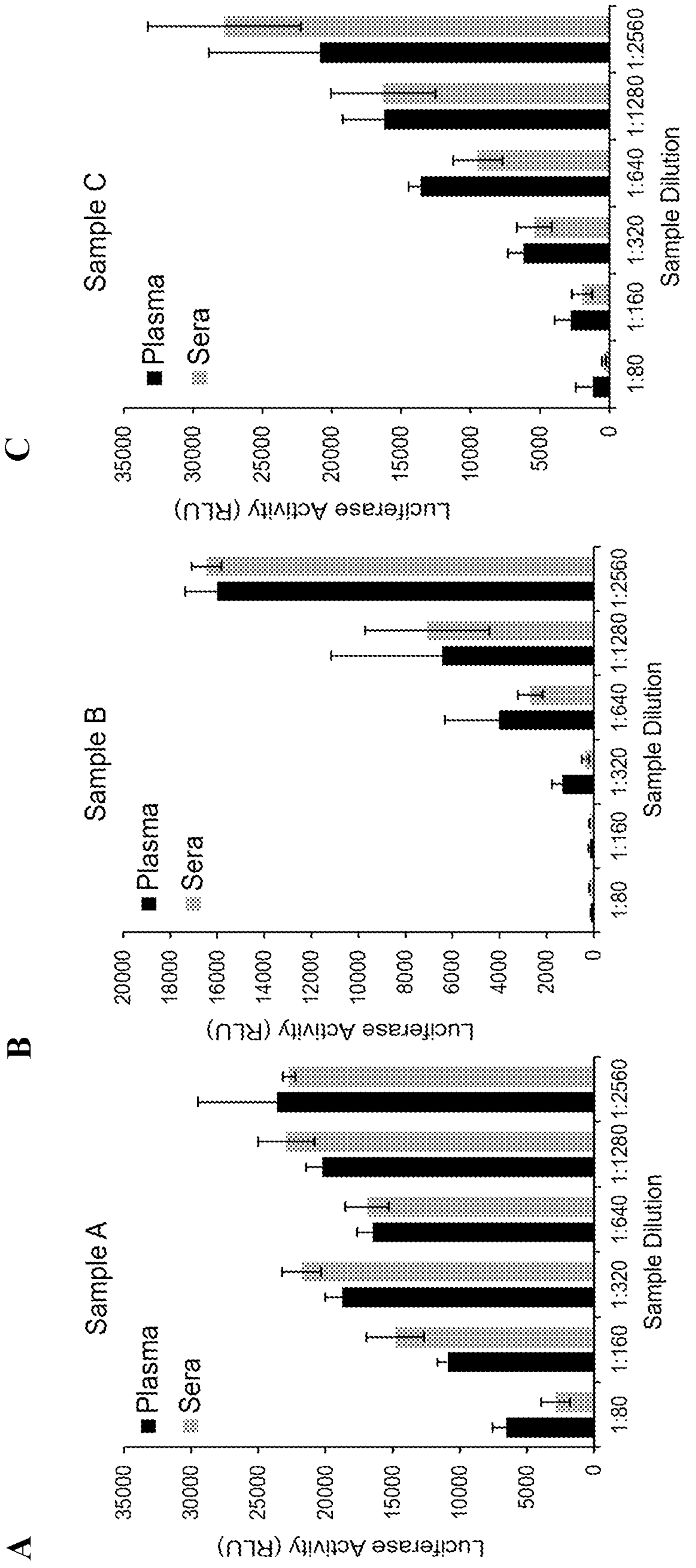
FIGS. 11A-C show luciferase activity in plasma and serum of three subjects at different dilutions. Plasma and serum from three COVID-19 convalescing individuals were heat inactivated for 30 min at 56° C. Serial dilutions were then prepared and incubated with VSV-SARS-CoV-2-S-Δ19CT for 30 minutes at room temperature before being overlaid onto Vero-DSP1/DPS2 monolayers. Luciferase activity was measured after approximately 24 hours.
FIG. 11D shows luciferase activity in pooled SARS-CoV-2 seronegative plasma containing stepped concentrations of anti-SARS-CoV-2 spike antibody mAb10914 mixed with VSV-SARS-CoV2 v1.0 (VSV-SARS-CoV-2-S-Δ19CT) virus. After a 30-minute incubation at room temperature, the plasma/virus mixes were overlaid onto Vero-DSP1/DSP2 monolayers. Luciferase activity was measured after approximately 24 hours.
FIG. 11E shows luciferase activity in dilutions of pooled SARS-CoV-2 seronegative plasma or plasma from a COVID-19 convalescing individual (NL1) mixed with VSV-SARS-CoV2 v.1.0 (VSV-SARS-CoV-2-S-Δ19CT) virus. After a 1 hour incubation at 37° C., the plasma/virus mixes were overlaid onto Vero-DSP1/DSP2 cell monolayers. Luciferase activity was measured approximately 24 hours later.
FIG. 11F shows the effect of heat inactivation on plasma samples. One aliquot was stored on ice while the other was incubated for 30 minutes at 56° C. Each aliquot was then diluted in OptiMEM and mixed with VSV-SARS-CoV-2-S-Δ19CT to a final dilution indicated in the graph. Following a 30-minute incubation at room temperature, the virus/plasma mixes were overlaid onto Vero-DSP1/Vero-DSP2 monolayers. Luciferase activity was measured after approximately 24 hours.
Figure 11:
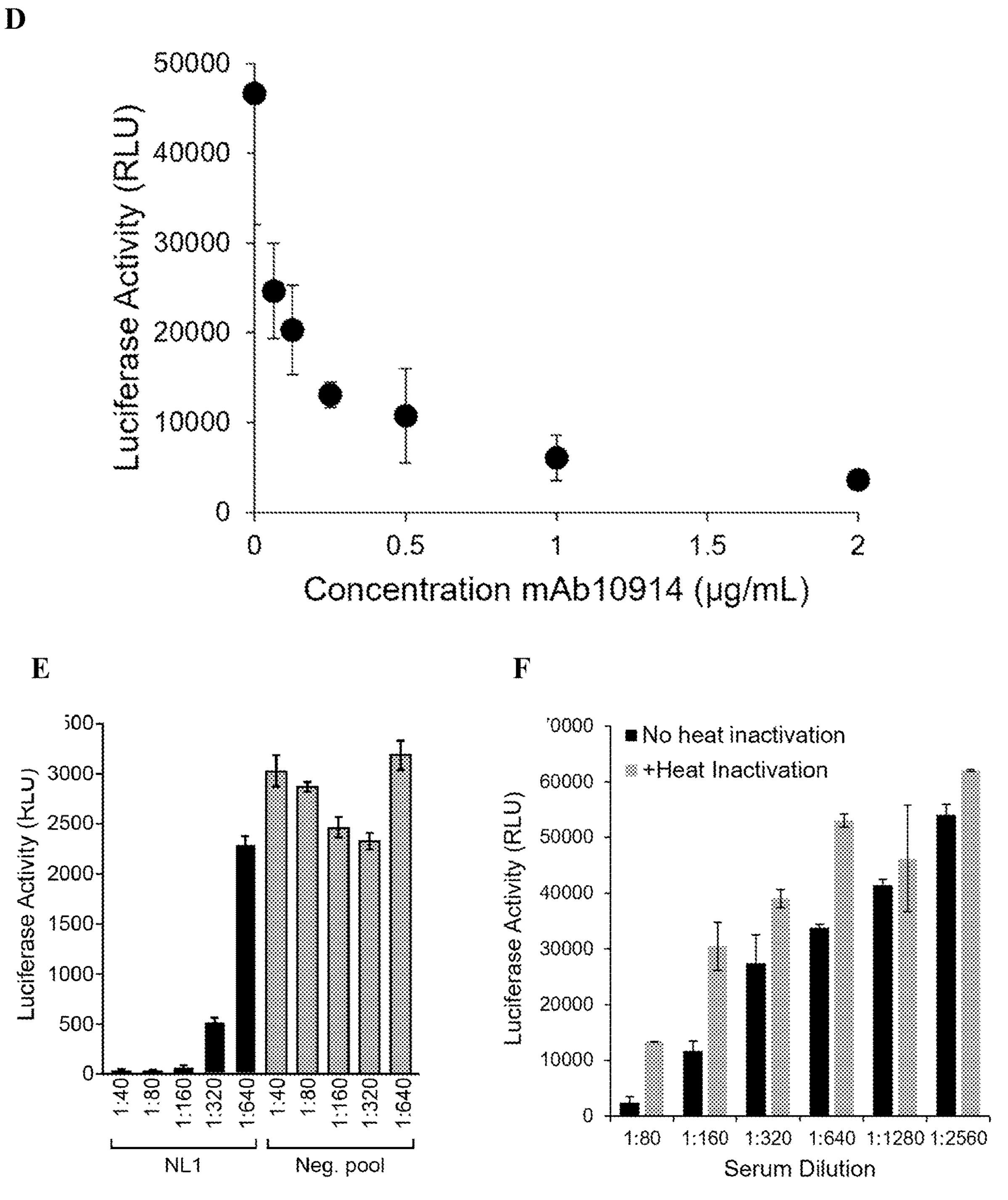

FIGS. 11A-C show luciferase activity in plasma and serum of three subjects at different dilutions. Plasma and serum from three COVID-19 convalescing individuals were heat inactivated for 30 min at 56° C. Serial dilutions were then prepared and incubated with VSV-SARS-CoV-2-S-Δ19CT for 30 minutes at room temperature before being overlaid onto Vero-DSP1/DPS2 monolayers. Luciferase activity was measured after approximately 24 hours. The figures show that virus neutralizing titers are similar between plasma and sera.

Pooled SARS-CoV-2 seronegative plasma (not heat-inactivated) containing stepped concentrations of anti-SARS-CoV-2 spike antibody mAb10914 was mixed with VSV-SARS-CoV2 v1.0 (VSV-SARS-CoV-2-S-Δ19CT). After a 30-minute incubation at room temperature, the plasma/virus mixes were overlaid onto Vero-DSP1/DSP2 monolayers. Luciferase activity was measured after approximately 24 hours. As shown in FIG. 11D, the addition of stepped concentrations of anti-SARS-CoV-2 spike antibody mAb10914 to pooled SARS-CoV-2 seronegative plasma showed a dose-dependent capacity to block the VSV-SARS-CoV2 v.1.0 virus (VSV-SARS-CoV-2-S-Δ19CT) used in the assay.

In another experiment, dilutions of pooled SARS-CoV-2 seronegative plasma or plasma from a COVID-19 convalescing individual (NL1) were mixed with VSV-SARS-CoV2 v.1.0 virus (VSV-SARS-CoV-2-S-Δ19CT). After a 1-hour incubation at 37° C., the plasma/virus mixes were overlaid onto Vero-DSP1/DSP2 cell monolayers. Luciferase activity was measured approximately 24 hours later. As shown in FIG. 11E, COVID-19 convalescing plasma was able to block the virus and luciferase activity in the assay. Both heat-inactivated (56° C., 30 min) and non-heat-inactivated plasma samples were tested and demonstrated assay compatibility, though non-heat-inactivated samples demonstrated higher background.

The effect of heat inactivation on plasma samples was also investigated. One aliquot was stored on ice while the other was incubated for 30 minutes at 56° C. Due to plasma thermal coagulation, samples were clarified by centrifugation before they were used in the assay. Each aliquot was then diluted in OptiMEM and mixed with VSV-SARS-CoV-2-S-Δ19CT to a final dilution of 1:80, 1:160, 1:320, 1:640, 1:1280, and 1:2560. Following a 30-minute incubation at room temperature, the virus/plasma mixes were overlaid onto Vero-DSP1/Vero-DSP2 monolayers. Luciferase activity was measured after approximately 24 hours. The results are shown in FIG. 11F. It appears that heat inactivation has less of an effect on the neutralizing capacity of plasma samples as compared to serum samples. In some plasma samples, heat inactivation lead to reduced sensitivity for borderline samples.

Example 4: The Use of IMMUNO-CoV v. 1 Assay to Detect SRS-CoV-2-Neturalizing Antibodies in Saliva Compatibility of saliva with the IMMUNO-CoV v. 1 assay was demonstrated by spiking pooled human saliva with anti-SARS-CoV-2 spike antibody mAb10914. Specifically, pooled saliva prepared from individuals prior to the COVID pandemic spiked with mAb10914 at stepped concentrations (QC-High, Mid, and Low). In order to prevent bacterial contamination associated with the use of saliva, all saliva samples were spiked with an Antibiotic/Antimycotic (Ab/Am) mix, diluted to a final dilution of 1:6.25 in OptiMEM, and filtered through a 0.22 um filter pre-wet with OptiMEM containing Ab/Am mix. The final concentrations of the Ab/Am components in the saliva were as follows: 0.2 mg/mL Ampicillin, 0.1 mg/mL Gentamicin sulfate, 4 μg/mL Amphotericin B. Contrived positive control samples with various concentrations of mAb10914 were prepared by adding the mAb10914 to the saliva before the addition of Ab/Am or filtration, to ensure that the filtration did not remove inhibitory antibody from the saliva samples.

The filtered samples were further diluted serially in OptiMEM before being mixed with VSV-SARS-CoV2 v.1.0 virus (VSV-SARS-CoV-2-S-Δ19CT). After a 30-minute incubation at room temperature the saliva/virus mixes were overlaid onto Vero-DSP1/Vero-DSP2 monolayers. Luciferase activity was measured approximately 24 hours later. The concentration of mAb10914 in the samples after mix with virus at the 1:100 dilution shown were: 2 μg/mL (QC-High), 0.6 μg/mL (QC-Mid), and 0.4 μg/mL (QC-Low). At higher saliva concentrations sample interference was observed.

Figure 12:
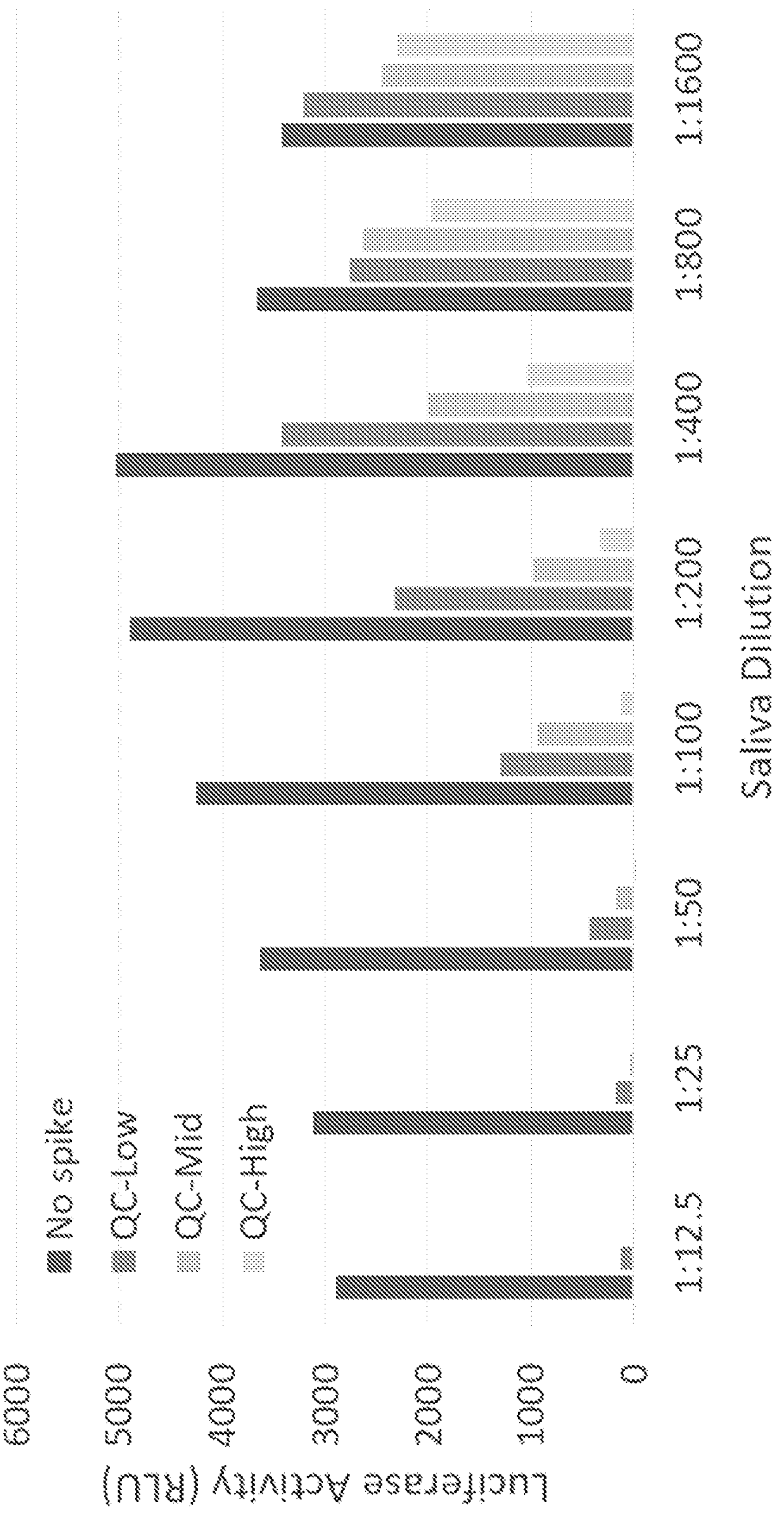
FIG. 12 shows luciferase activity in pooled saliva prepared from individuals prior to the COVID pandemic spiked with mAb10914 at stepped concentrations (2 μg/mL (QC-High), 0.6 μg/mL (QC-Mid), and 0.4 μg/mL (QC-Low)) mixed with VSV-SARS-CoV2 v.1.0 (VSV-SARS-CoV-2-S-Δ19CT) virus at 1:100 dilution. After a 30-minute incubation at room temperature the saliva/virus mixes were overlaid onto Vero-DSP1/Vero-DSP2 monolayers. Luciferase activity was measured approximately 24 hours later. Bars corresponding to data generated using No Spike, QC-Low, QC-Mid, QC-High are shown in order of appearance (from left to right) for each dilution tested.

As demonstrated in FIG. 12, the IMMUNO-CoV v. 1 assay works well with saliva samples.

Example 5: Development of IMMUNO-CoV assay v. 2

Figure 13:
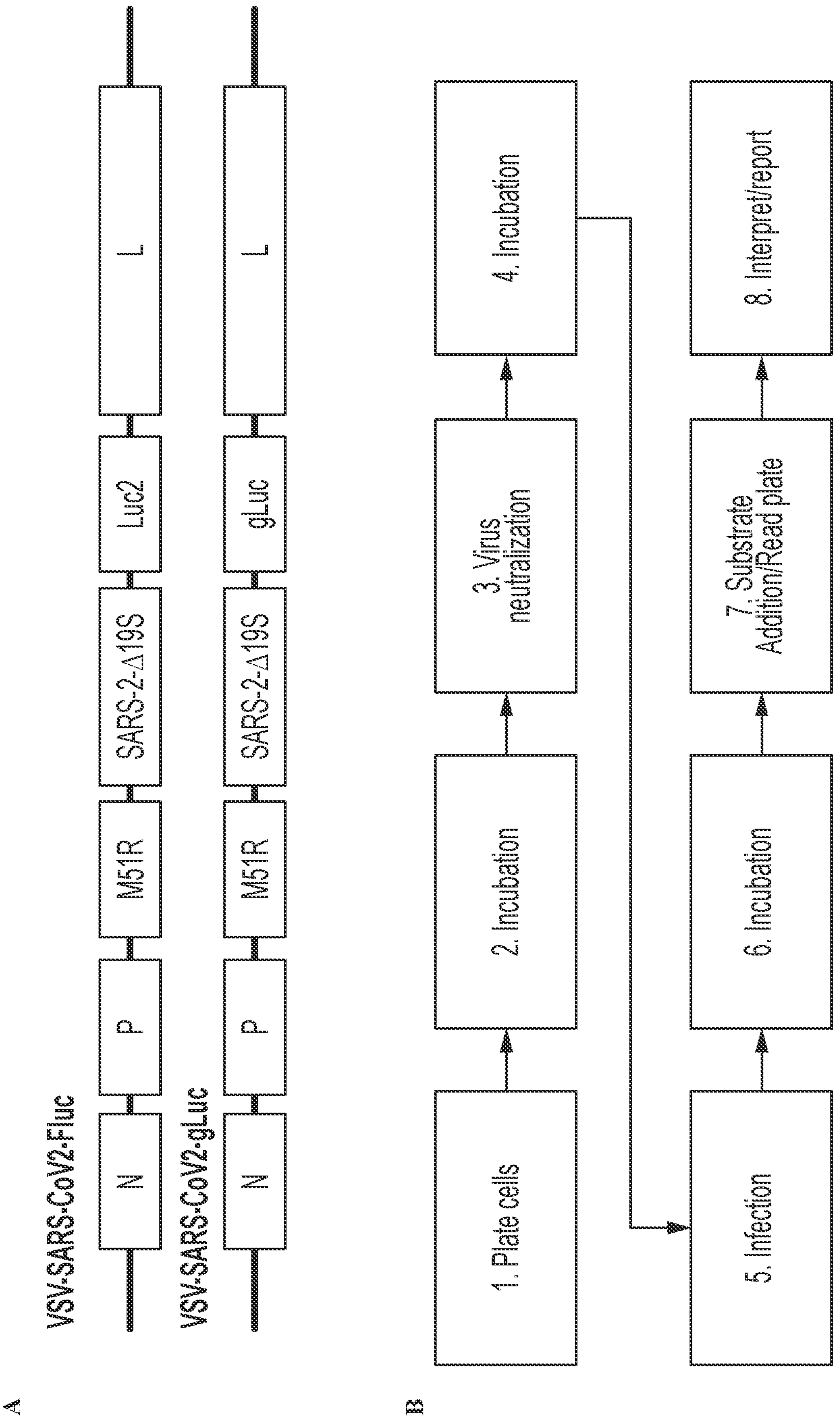
FIG. 13A is a schematic representation of VSV-SARS-CoV-2-Fluc and VSV-SARS-CoV-2-S-Δ19CT-gLuc. VSV-SARS-CoV-2-Fluc encodes a mutant Luc2 variant of firefly luciferase (GenBank Accession No. AY738222). VSV-SARS-CoV-2-S-Δ19CT-gLuc encodes a secreted *Gaussia* luciferase (gLuc).
FIG. 13B shows the workflow of IMMUNO-CoV assay version 2.

As depicted in FIG. 13A, version 2 (v. 2) of the IMMUNO-CoV assay uses a recombinant VSV encoding the SARS-CoV-2 spike glycoprotein (e.g., VSV-SARS-CoV-2-S-Δ19CT or VSV-SARS-CoV-2-S) in place of the VSV-G glycoprotein in addition to a reporter gene (e.g., firefly luciferase (Luc2/Fluc) gene or *Gaussia* luciferase (gLuc) gene). Because the virus itself encodes the reporter, Vero-DSP cells are no longer used for the assay. The assay principle is as follows: the recombinant virus (VSV-SARS-CoV-2-S-Δ19CT-luc or VSV-SARS-CoV-2-S-luc) infects Vero cells, delivering a luciferase gene, which causes the cells to make luciferase protein. The presence of luciferase can be detected using a substrate such as, e.g., d-luciferin for Fluc (available at Gold Biotechnology goldbio.com) or coelenterazine for gLuc (Cat. #3031, NanoLight Technology; nanolight.com/product/coelenterazine-in-vivo/). *Gaussia* luciferase is a secreted form of luciferase that uses coelenterazine as a substrate in an ATP independent reaction.

In IMMUNO-CoV assay v. 2, serum or plasma samples are incubated with the virus (e.g., VSV-SARS-CoV-2-S-Δ19CT-luc or VSV-SARS-CoV-2-S-luc), and the mixtures are then combined with or overlaid onto Vero cells (or other susceptible cells). In the absence of SARS-CoV-2-neutralizing antibodies, the virus infects cells and reporter (e.g., luciferase) activity is detected. If the test samples contain SARS-CoV-2-neutralizing antibodies, virus infection is inhibited and reporter (e.g., luciferase) activity is reduced. Controls such as pooled SARS-CoV-2 seronegative serum/plasma or serum/plasma alone or serum/plasma mixed with stepped concentrations of anti-SARS-CoV-2 spike monoclonal antibody mAb10914 are used to quantitate the level of the neutralizing response. The IMMUNO-CoV assay v. 2 workflow is shown in FIG. 13B.

Figure 14:
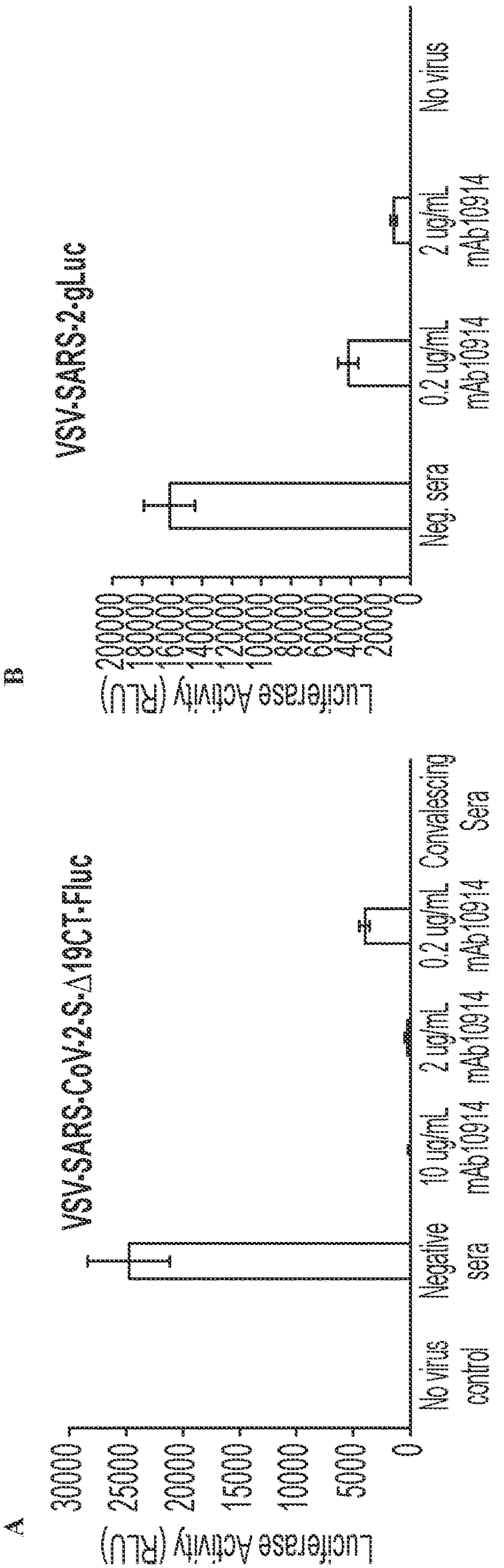
FIG. 14A shows luciferase activity upon incubation of VSV-SARS-CoV-2-S-Δ19CT-Fluc encoding a mutant Luc2 variant of firefly luciferase with pooled negative sera (at 1:80 dilution), COVID-19 convalescing sera (at 1:80 dilution), or pooled negative sera (at 1:80 dilution) mixed with 10, 2, or 0.2 μg/mL mAb10914. After a 45-minute incubation at room temperature, the virus/sera mixes were overlaid onto Vero cell monolayers. After an additional 18 hours, d-luciferin substrate was added to wells and luciferase activity (RLUs) were measured using a luminometer.
FIG. 14B shows luciferase activity upon incubation of VSV-SARS-CoV-2-S-Δ19CT-gLuc encoding secreted *Gaussia* luciferase (1:48 dilution of virus stock) with pooled SARS-CoV-2 seronegative sera (at 1:80 dilution) alone or spiked with 0.2 or 2 μg/mL mAb10914. After 30-minute incubation at room temperature, the virus/sera mixes were overlaid onto Vero-Ace-2 monolayers. After an additional 24 hours, coelenterazine (20 μL of a 5 μM stock) was added and luciferase activity was measured.

In the experiment shown in FIG. 14A, VSV-SARS-CoV-2-S-Δ19CT-Fluc encoding a mutant Luc2 variant of firefly luciferase (GenBank Accession No. AY738222) was incubated with pooled negative sera (at 1:80 dilution), COVID-19 convalescing sera (at 1:80 dilution), or pooled negative sera (at 1:80 dilution) mixed with 10, 2, or 0.2 μg/mL mAb10914. After a 45-minute incubation at room temperature, the virus/sera mixes were overlaid onto Vero cell monolayers (an alternative incubation time can be 30 minutes). After an additional 18 hours (can be 24 hours or even longer for a stronger signal), d-luciferin substrate was added to wells and luciferase activity (RLUs) were measured using a luminometer. As shown in FIG. 14A, VSV-SARS-CoV-2-S-Δ19CT-Fluc virus induces luciferase expression and activity in Vero cells that can be blocked by COVID-19 convalescing serum as well as mAb10914 in a dose dependent manner.

In the experiment shown in FIG. 14B, pooled SARS-CoV-2 seronegative sera (at 1:80 dilution) was incubated with media only (no virus) or VSV-SARS-CoV-2-S-Δ19CT-gLuc (1:48 dilution of virus stock) alone or spiked with 0.2 or 2 μg/mL mAb10914. After 30 minutes at room temperature, the virus/sera mixes were overlaid onto Vero-Ace-2 monolayers (see below for the generation of Vero-Ace-2 cells) seeded the day before in black, clear-bottomed 96-well plates at 1e4 cells/well. After an additional 24 hours, luciferase activity in the wells was measured. Coelenterazine (20 μL of a 5 μM stock) was added to each well using an injector in the TECAN (luminescence plate reader) that added the substrate and proceeded to immediately measure luminescence. The results shown in FIG. 14B indicate that luciferase activity can be detected in Vero-Ace-2 cells that are infected (24 hour previously) with VSV-SARS-CoV-2-S-Δ19CT-gLuc in the presence of pooled SARS-CoV-2 seronegative sera. The luciferase activity can be reduced by the addition of mAb10914 to the pooled sera. While mAb10914 was able to inhibit luciferase activity, the level of inhibition was slightly lower than that observed when using VSV-SARS-CoV-2-S-Δ19CT-Fluc. However, the main advantage of VSV-SARS-CoV-2-S-Δ19CT-gLuc is that the gLuc gene is significantly smaller than the Fluc gene, which may result in increased stability and manufacturability of the gLuc-containing virus.

Additional experiments were directed to optimizing IMMUNO-CoV assay v. 2 conditions, including determining whether Vero-αHis, Vero-E6, or engineered Vero cells that overexpress Ace-2 and/or TRMPSS2 work best in the assay.

For generation of Vero-Ace-2 and Vero-TRMPSS2 cells, plasmids with Ace-2 (GenBank Accession No. BC039902) and/or TMPRSS2 (GenBank Accession No. BC051839) were purchased from ABM (Cat. #1116701; abmgood.com/ACE2-ORF-Vector-1116701.html #Ace2 and Cat. #471480110000; abmgood.com/TMPRSS2-ORF-Vector-4714801.html #471480110000). The Ace-2 and TMPRSS2 were subcloned into a lentiviral vector construct. Vero cells were then transduced with the lentiviral vector(s) and selected with appropriate selection antibiotic.

Figure 15:
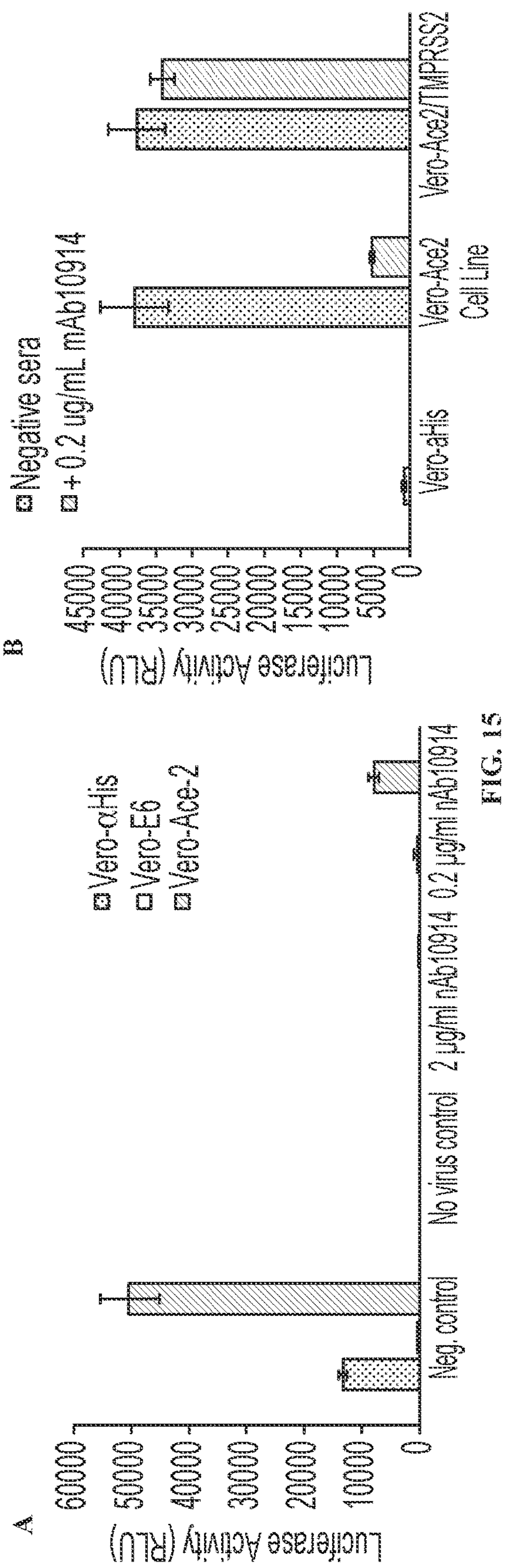
FIGS. 15A-B demonstrate that Vero-Ace-2 cells are particularly effective in IMMUNO-CoV assay v. 2.

FIGS. 15A-B demonstrate that Vero-Ace-2 cells are particularly effective in IMMUNO-CoV assay v. 2. In the experiment shown in FIG. 15A, VSV-SARS-CoV-2-S-Δ19CT-Fluc or media alone (no virus control) was incubated with pooled SARS-CoV-2 seronegative sera (at a dilution of 1:80) mixed with 2 or 0.2 μg/mL of mAb10914. After a 30-minute room temperature incubation, the virus/sera mixes were overlaid onto monolayers of cells (Vero-αHis, Vero-E6 or Vero-Ace-2). After an additional 26 hours, d-luciferin substrate was added to the wells and luciferase activity (RLUs) was measured using a luminometer. As shown in FIG. 15A, both Vero-Ace-2 and Vero-αHis worked well in the assay, with Vero-Ace-2 generating a higher luciferase signal in the absence of SARS-CoV-2-neutralizing antibodies.

In the experiment shown in FIG. 15B, pooled SARS-CoV-2 seronegative sera (at 1:80 dilution) was incubated with VSV-SARS-CoV-2-S-Δ19CT-gLuc (4800 TCID50/well) alone or spiked with 0.2 μg/mL mAb10914. After 30 min at room temperature, the virus/sera mixes were overlaid onto Vero-αHis, Vero-Ace-2, or Vero-Ace-2/TMPRSS2 cell monolayers seeded the day before in black, clear-bottomed 96-well plates at 1e4 cells/well. After an additional 24 hours, luciferase activity in the wells was measured after the addition of d-luciferin. Although both Vero-Ace-2 and Vero-Ace2/TMPRSS2 cells gave similarly high levels of luciferase expression in the presence of pooled negative sera, luciferase signal and therefore virus was only inhibited by mAb10914 effectively in the Vero-Ace2 cell line.

Figure 16:
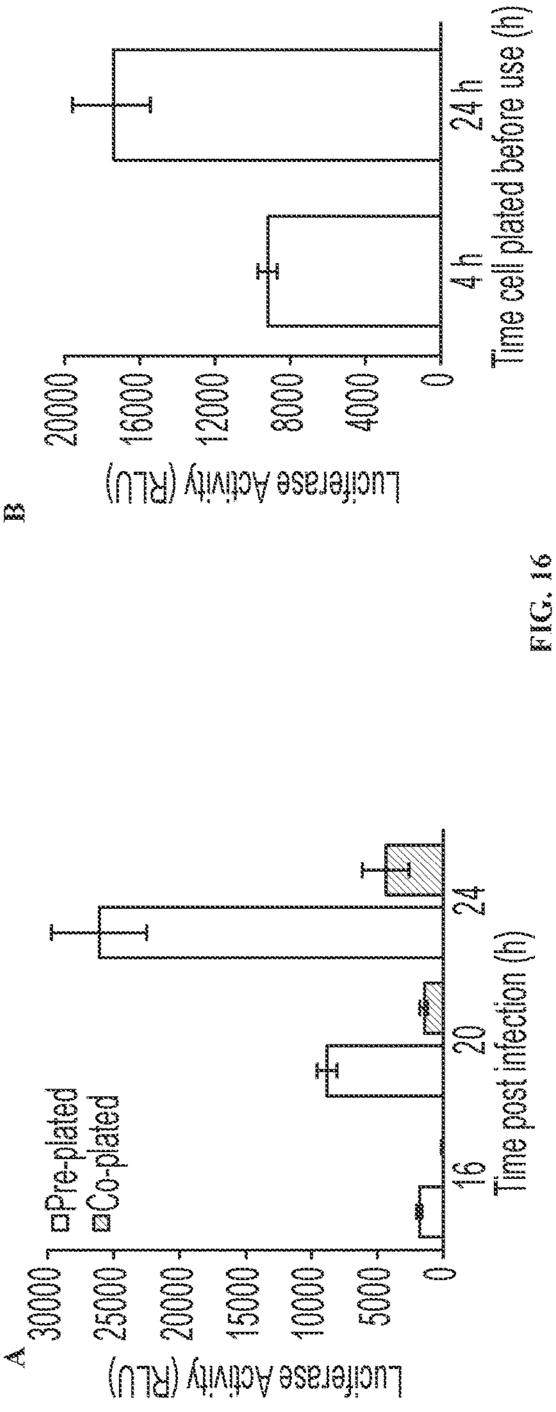
FIGS. 16A-B shows that luciferase signal is substantially lower when cells are co-plated with virus (as compared to when cells are pre-plated), but significantly recovers when given a 4 hour recovery time. (A) Virus was incubated with pooled SARS-CoV-2 seronegative sera (1:80) for 30 minutes at room temperature then overlaid onto Vero cell monolayers or mixed with Vero cells at a similar density. At the indicated times after cell overlay, luciferase activity was measured. (B) Virus was incubated with pooled SARS-CoV-2 seronegative sera (1:80) for 30 minutes at room temperature then overlaid onto Vero cell monolayers plated either 4 or 24 hours prior. After an additional 24 hours luciferase activity was measured.

As shown in FIGS. 16A-B, luciferase signal is substantially lower when cells are co-plated with virus (as compared to when cells are pre-plated), but significantly recovers when given a 4 hour recovery time. In FIG. 16A, virus was incubated with pooled SARS-CoV-2 seronegative sera (1:80) for 30 minutes at room temperature then overlaid onto Vero cell monolayers or mixed with Vero cells at a similar density. At the indicated times after cell overlay, luciferase activity was measured. In FIG. 16B, virus was incubated with pooled SARS-CoV-2 seronegative sera (1:80) for 30 minutes at room temperature then overlaid onto Vero cell monolayers plated either 4 or 24 hours prior. After an additional 24 hours luciferase activity was measured.

Figure 17:
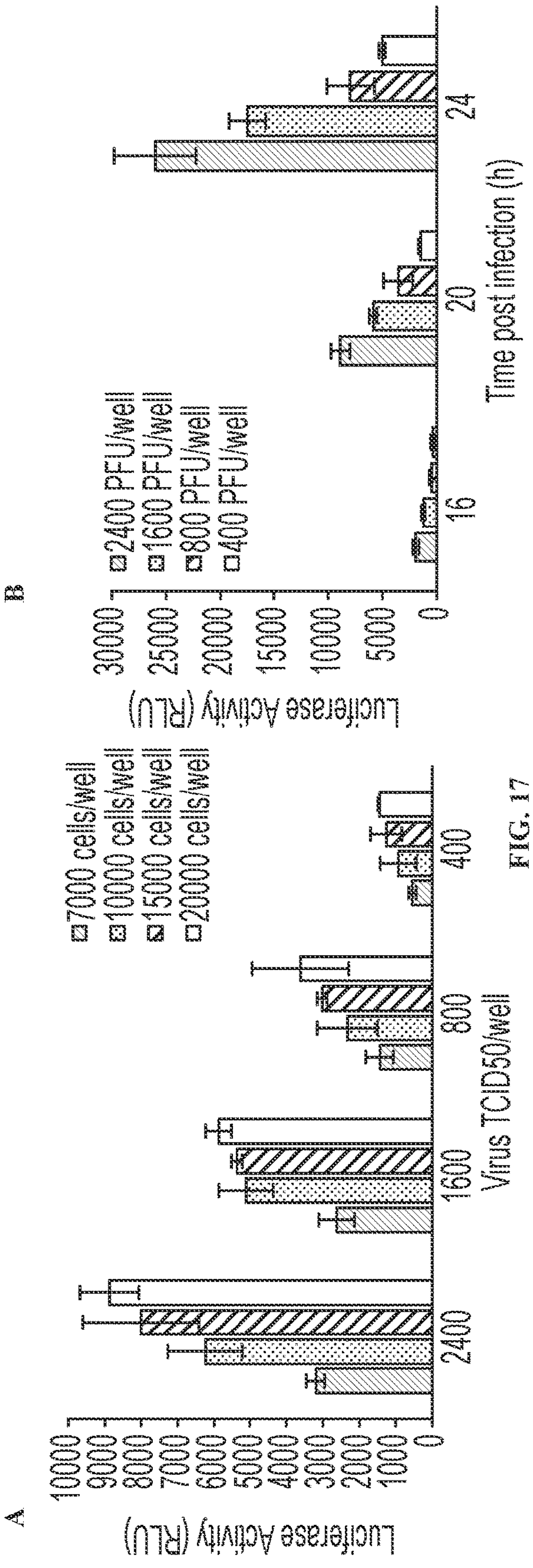
FIGS. 17A-B show that luciferase activity increases with increased cell density (A) and virus quantity/well (B). Virus was diluted in OptiMEM to the indicated TCID50 per well and overlaid onto Vero cell monolayers plated at the indicated cells/well the day before. After an additional 16, 20, and 24 hours luciferase activity was measured. Data in panel A are from 24 hours. In panel A, bars corresponding to data generated using 7000 cells/well, 10000 cells/well, 15000 cells/well, and 20000 cells/well are shown in order of appearance (from left to right) for each virus TCID50 condition tested. In panel B, bars corresponding to data generated using 2400 PFU/well, 1600 PFU/well, 800 PFU/well, and 400 PFU/well are shown in order of appearance (from left to right) for each time point tested.

The experiments shown in FIGS. 17A-B tested the effects of cell density and virus TCID50 on luciferase activity. Virus was diluted in OptiMEM to the indicated TCID50 per well and overlaid onto Vero cell monolayers plated at the indicated cells/well the day before. After an additional 16, 20, and 24 hours luciferase activity was measured. Data in FIG. 17A are from 24 hours. FIG. 17A shows that luciferase activity increases with increased cell density. FIG. 17B shows that luciferase activity increases with increased virus quantity/well.

Figure 18:
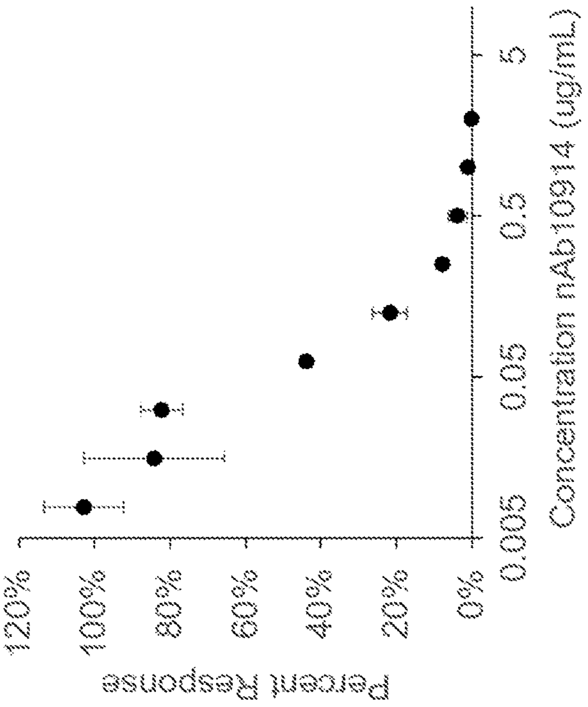
FIG. 18 shows that IMMUNO-CoV assay v. 2 is highly sensitive and shows dose-dependent inhibition of VSV-SARS-CoV-2-S-Δ19CT-Fluc. Virus was incubated with pooled negative serum containing stepped concentrations of mAb10914 for 30 minutes at room temperature. The virus/serum mixes were then overlaid onto Vero cell monolayers. Luciferase activity was measured after an additional 24 hours.

As shown in FIG. 18, IMMUNO-CoV assay v. 2 is highly sensitive allowing to detect weak neutralizing antibody responses and shows dose-dependent inhibition of VSV-SARS-CoV-2-S-Δ19CT-Fluc. Virus was incubated with pooled negative serum containing stepped concentrations of mAb10914 for 30 minutes at room temperature. The virus/serum mixes were then overlaid onto Vero cell monolayers. Luciferase activity was measured after an additional 24 hours.

TABLE 7

Comparison of percent responses in IMMUNO-COV Assay versions 1 and 2

| Concentration of mAb10914 | % Luciferase Signal | |
|---|---|---|
| | Version 1 | Version 2 (Flue) |
| 0.6 μg/mL | 32.5% | 1.2% |
| 0.4 μg/mL | 47.5% | 2.6% |

Percent Response=(luciferase signal=luciferase signal from negative control)×100% Lower percent response indicates a greater reduction in luciferase and virus inhibition Values represent the average (mean) from 24 wells run on 6 different plates for each sample.

Figure 19:
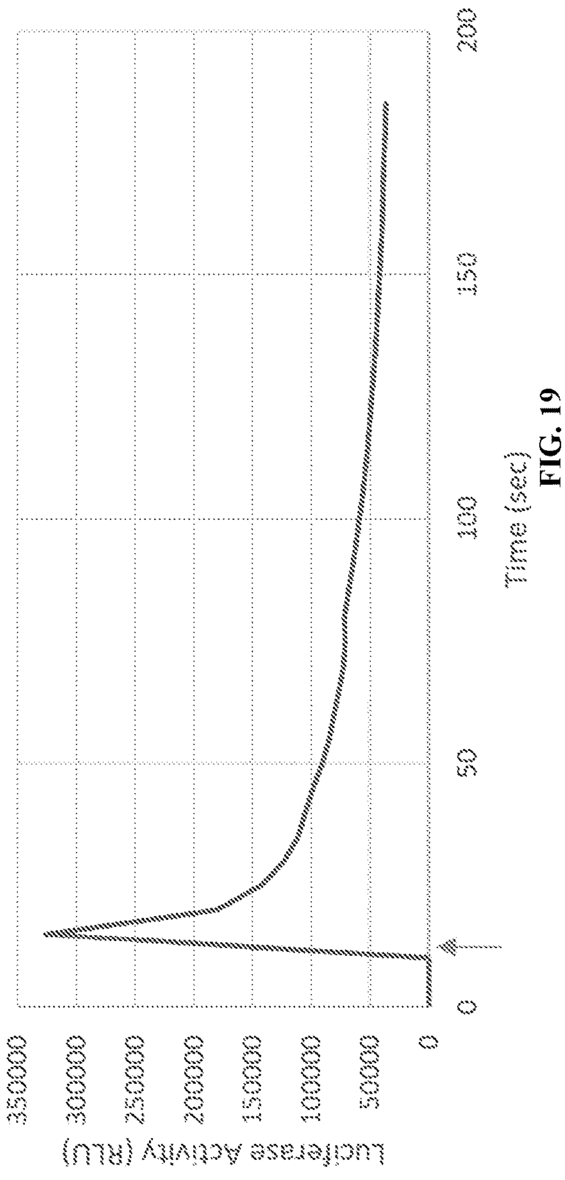
FIG. 19 shows kinetic curve of Fluc activity in VSV-SARS-CoV-2-S-Δ19CT-Fluc-infected Vero-Ace-2 cells following d-luciferin addition. Vero-Ace-2 cell monolayers (seeded at 1e4 cells/well the day before infection) were infected with 4800 TCID50 units of VSV-SARS-CoV-2-S-Δ19CT-Fluc. After 24 hours the plate was loaded in the TECAN instrument (luminescence plate reader) that was fitted with an injector. The injector was programmed to inject the desired quantity of substrate (20 μL of a 3.75 mg/mL solution of d-luciferin) into each well, and then after 0.5 sec read luminescence (1000 ms integration time). Additional luciferase reads were performed every 5 seconds for 3 min to generate a kinetic curve of luciferase activity (two reads done, d-luciferin added (final concentration 0.44 mg/mL in well) at 9 sec (arrow), additional reads done through 3 min).

FIG. 19 shows kinetic curve of Fluc activity in VSV-SARS-CoV-2-S-Δ19CT-Fluc-infected Vero-Ace-2 cells following d-luciferin addition. Because Fluc exhibits flash kinetics, the expected peak luminescence signal is expected to be 0.5 sec after the addition of d-luciferin to wells. This was confirmed to be true for VSV-SARS-CoV-2-S-Δ19CT-Fluc-infected Vero-Ace-2 cells as shown in FIG. 19. For this experiment, Vero-Ace-2 cell monolayers (seeded at 1e4 cells/well the day before infection) were infected with 4800 TCID50 units of VSV-SARS-CoV-2-S-Δ19CT-Fluc. After 24 hours the plate was loaded in the TECAN instrument (luminescence plate reader) that was fitted with an injector. The injector was programmed to inject the desired quantity of substrate (in this experiment 20 μL of a 3.75 mg/mL solution of d-luciferin) into each well, and then after 0.5 sec read luminescence (1000 ms integration time). Additional luciferase reads were performed every 5 seconds for 3 min to generate a kinetic curve of luciferase activity (two reads done, d-luciferin added (final concentration 0.44 mg/mL in well) at 9 sec (arrow), additional reads done through 3 min). As expected, activity peaked immediately (0.5 sec) after the addition of d-luciferin.

REFERENCES

Casadevall A, Pirofski LA. The convalescent sera option for containing COVID-19. 379 J Clin Invest 2020 Mar. 13. pii: 138003. doi: 10.1172/JCI138003 Corman et al., 2016. Viral shedding and antibody response in 37 patients with Middle East respiratory syndrome coronavirus infection. Clin Infect Dis 62:477-483.

Gui, M et al. (2017) Cryo-electron microscopy structure of the SARS-CoV spike flycoprotein reveal a prerequisite conformational state for receptor binding. Cell Res. 27:119-129.

Ho M. S., Chen W. J., Chen H. Y. Neutralizing antibody response and SARS severity. Emerg Infect Dis. 2005; 11 (11): 1730-1737.

Hoffmann, M., Kleine-Weber, H., Schroeder, S., Kruger, N., Herrler, T., Erichsen, S., Schiergens, T. S., Herrler, G., Wu, N. H., Nitsche, A., et al. (2020). SARS-CoV-2 Cell Entry Depends on ACE2 and TMPRSS2 and Is Blocked by a Clinically Proven Protease Inhibitor. Cell.181:271-280

Jaume M., Yip M. S., Cheung C. Y. Anti-severe acute respiratory syndrome coronavirus spike antibodies trigger infection of human immune cells via a pH- and cysteine protease-independent FcgammaR pathway. J Virol. 2011; 85 (20): 10582-10597.

Koff W C, Burton D R, Johnson P R, et al. Accelerating next-generation vaccine development for global disease prevention. Science. 2013; 340 (6136).

Liu, W., Fontanet, A., Zhang, P. H., Zhan, L., Xin, Z. T., Baril, L., Tang, F., Lv, H., and Cao, W. C. (2006). Two-year prospective study of the humoral immune response of patients with severe acute respiratory syndrome. J. Infect. Dis. 193, 792-795.

Liu, L et al. (2019) Anti-spike IgG causes severe acute lung injury by skewing macrophage responses during acute ARS-CoV infection. JCI Insight. 4 (4): e123158.

Nie Y, Wang G, Shi X, Zhang H, Qiu Y, He Z, et al. Neutralizing antibodies in patients with severe acute respiratory syndrome-associated coronavirus infection. J Infect Dis. 2004; 190:1119-26.

Peiris J. S., Chu C. M., Cheng V. C. Clinical progression and viral load in a community outbreak of coronavirus-associated SARS pneumonia: a prospective study. Lancet. 2003; 361 (9371): 1767-1772.

Walls, A. C., Park, Y. J., Tortorici, M. A., Wall, A., McGuire, A. T., and Veesler, D. (2020). Structure, Function, and Antigenicity of the SARS-CoV-2 Spike Glycoprotein. Cell.181:281-292.

Wan, Y., Shang, J., Graham, R., Baric, R. S., and Li, F. (2020). Receptor recognition by novel coronavirus from Wuhan: An analysis based on decade-long structural studies of SARS. Journal of Virology, JVI.00127-00120.

Wang S. F., Tseng S. P., Yen C. H. Antibody-dependent SARS coronavirus infection is mediated by antibodies against spike proteins. Biochem Biophys Res Commun. 2014; 451 (2): 208-214.

Yip M. S., Leung H. L., Li P. H. Antibody-dependent enhancement of SARS coronavirus infection and its role in the pathogenesis of SARS. Hong Kong Med J. 2016; 22 (3 Suppl 4): 25-31.

Yuan, Y. et al. (2017) Cryo-EM structure of MERS-CoV and SARS-CoV spike flyocpoteins reveal the dynamic receptor binding domains. Natu. Commun. 8:15092.

Zhao J et al Recovery from the Middle East respiratory syndrome is associated with antibody and T-cell responses (2017). Sci Immunol 2:5393.

Example 6: Generation of Variants of SARS-CoV-2

The SARS-CoV-2 spike glycoprotein mutants were human codon optimized and synthesized with a deletion in the nucleotides encoding the C-terminal 19 amino acids (S-Δ19CT). The variants of SARS-CoV-2 were cloned into a plasmid encoding the VSV genome using the restriction sites MluI and NheI. The plasmid was sequence verified and used for infectious virus rescue on BHK-21 cells. VSV-G was co-transfected into the BHK-21 cells to facilitate rescue but was not present in subsequent passages of the virus.

TABLE 8

Non-Limiting Examples of Amino Acid Residue Positions for Insertion, Deletion, and/or Substitution to Generate Recombinant VSV Particle Variants

| Mutations | Location | Phenotypes | References |
|---|---|---|---|
| COVID VARIANT: B.1.1.7 lineage, (20I/501Y.V1 or VOC 202012/01) Origin: UK hCoV-19/England/SHEF-10C8326/2021 | | | |
| N501Y | RBD | One of the six key amino acids interacting with ACE-2 receptor. Associated with increased transmissibility (more efficient/rapid transmissibility). | Horby P, Huntley C, Davies N, Edmunds J, Ferguson N, Medley G, et al. NERVTAG paper on COVID-19 variant of concern B.1.1.7 (2021) [www.gov.uk/government/publications/nervtag-paper-on-covid-19-variant-ofconcern-b117] Accession number: SAMN17373206 |
| 69-70 deletion | | Potential conformational change in spike protein. Reduced sensitivity to neutralizing antibodies. Associated with increased transmissibility (more efficient/rapid transmissibility). | Wu K, Werner AP, Moliva JI, et al. mRNA-1273 vaccine induces neutralizing antibodies against spike mutants from global SARS-CoV-2 variants. [Preprint Posted Jan. 25, 2021] GenBank: MW487270.1 |
| P681H | Near S1/S2 furin cleavage site | Associated with increased transmissibility (more efficient/rapid transmissibility). | Xie X, Zou J, Fontes-Garfias CR, et al. Neutralization of N501Y mutant SARS-CoV-2 by BNT162b2 vaccine-elicited sera. [Preprint Posted Jan. 7, 2021] Greaney AJ, Loes AN, Crawford KHD, et al. Comprehensive mapping of mutations to the SARS-CoV-2 receptor-binding domain that affect recognition by polyclonal human serum antibodies. [Preprint Posted Jan. 4, 2021] Severe acute respiratory syndrome coronavirus 2 isolate SARS-CoV-2/human/USA/NYI.B1-7.01-21/2021, complete genome |
| Y144 del | | | Weisblum Y, Schmidt F, Zhang F, et al. Escape from neutralizing antibodies by SARS-CoV-2 spike protein variants [eLife 2020;9:e61312] |
| A570D T716I S982A D1118H | | | |
| COVID VARIANT: B.1.351 (20H/501Y.V2) Origin: South Africa | | | |
| K417N | RBD | Resistant to neutralizing antibodies. | Weisblum Y, Schmidt F, Zhang F, et al. Escape from neutralizing antibodies by SARS-CoV-2 spike protein variants [eLife 2020;9:e61312] hCoV-19/Belgium/AZDelta05413-2105R/2021 |
| E484K | RBD | Resistant to neutralizing antibodies. E484K may affect neutralization by some polyclonal and mAb, potentially by disrupting the | Resende PC, Bezerra JF, de Vasconcelos RHT, at al. Spike E484K mutation in the first SARS-CoV-2 reinfection case confirmed in Brazil, 2020external icon. [Posted on www.virological.orgexternal icon on Jan. 10, 2021] |

TABLE 8-continued

| Non-Limiting Examples of Amino Acid Residue Positions for Insertion, Deletion, and/or Substitution to Generate Recombinant VSV Particle Variants | | | |
|---|---|---|---|
| Mutations | Location | Phenotypes | References |
| | | immunodominant B cell epitope, and is thought to be the mutation that drives immune escape. | |
| N501Y | RBD | Resistant to neutralizing antibodies, increased transmissibility. | |
| D614G | | | |
| A701V | | | |
| L18F | NTD | | |
| D80A | NTD | | |
| D215G | NTD | | |
| L242-244 del | NTD | | |
| R246I | NTD | Disrupts N5-loop (large, solvent exposed loop in NTD) and displaces the loop | |
| COVID VARIANT: (B1.1.28.1 or 20J/501.V3, 484K.V2) Origin: Brazil | | | |
| K417T<br>E484K<br>N501Y<br>L18F<br>T20N<br>P26S<br>D138Y<br>R190S<br>D614G<br>H655Y<br>T1027I | RBD<br>RBD<br>RBD<br>NTD<br>NTD | altered transmissibility and antigenic profile, which may affect ability of Ab generated through previous natural infection or vaccination to recognize and neutralize virus | Resende PC, Bezerra JF, de Vasconcelos RHT, at al. Spike E484K mutation in the first SARS-CoV-2 reinfection case confirmed in Brazil, 2020external icon. [Posted on www.virological.orgexternal icon on Jan. 10, 2021] hCoV-19/Brazil/RR-1087/2021 |
| COVID VARIANT: B.1.429 (CAL.20C, CA VUI) Origin: California | | | |
| S131 | | | |
| W152C | | | |
| L452R | | | |
| D614G | | | |
| COVID VARIANT: B.1.2 lineage 20C-US | | | |
| Q677H | Adjacent to furin cleavage site | | Adrian A. Pater et al., Emergence and Evolution of a Prevalent New SARS-CoV-2 Variant in the United States [doi.org/10.1101/2021.01.11.426287] |
| Other mutations in ORFs | | | |
| COVID VARIANT: B1.1.17 | | | |
| | | | Weisblum Y, Schmidt F, Zhang F, et al. Escape from neutralizing antibodies by SARS-CoV-2 spike protein variants [eLife 2020;9:e61312] |
| COVID VARIANT: 20E (EU1) | | | |
| A22V | | | |
| D614G | | | |
| COVID VARIANT: 20A.EU2 | | | |
| S477N | | | |
| D614G | | | |
| COVID VARIANT: N439K-D614G | | | |
| N439K | | | |
| D614G | | | |
| COVID VARIANT: Mink Cluster 5 variant | | | |
| H69 del | | | |
| V70 del | | | |
| Y453F | RBD | Increased binding affinity for mink Ace2. | |

TABLE 8-continued

| Non-Limiting Examples of Amino Acid Residue Positions for Insertion, Deletion, and/or Substitution to Generate Recombinant VSV Particle Variants | | | |
|---|---|---|---|
| Mutations | Location | Phenotypes | References |
| D614G | | | |
| I692V | | | |
| M1229I | | | |

TABLE 9

| Non-Limiting Examples of Recombinant VSV Particle Variants | |
|---|---|
| Variant Name | Mutations |
| VSV-SARS-CoV2-S_E484K | E484K |
| VSV-SARS-CoV2-S_B.1.351_NTD | L18F, D80A, D215G, 242-244 del, R246I, A701V |
| VSV-SARS-CoV2-S_B.1.351_RBD | K417N, E484K, N501Y, D614G |
| VSV-SARS-CoV2-S_B.1.351 | K417N, E484K, N501Y, D614G, L18F, D80A, D215G, 242-244 del, R246I, A701V |
| VSV-SARS-CoV2-S_B.1.1.7_RBD | N501Y, 69-70 del, P681H |
| VSV-SARS-CoV2-S_B.1.1.7 | N501Y, 69-70 del, P681H, Y144 del, A570D, T716I, S982A, D1118H |
| VSV-SARS-CoV2-S_B.1.1.28_RBD | K417T, E484K, N501Y |

Example 7: Sample Collection Kits for Dried Bloodspot (DBS) Sampling

A non-limiting example of a standard Dried Bloodspot (DBS) collection procedure was performed as described below. Sample collection kits for DBS sampling contained all of the necessary components to perform the sample collection.

Figure 20:
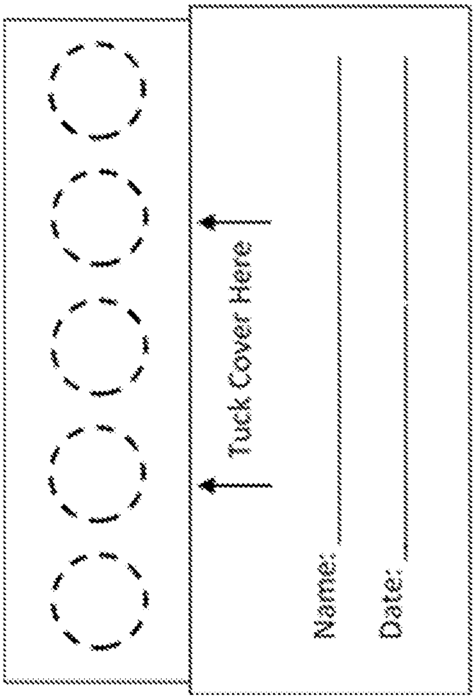
FIG. 20 shows a description of an exemplar Dried Bloodspot (DBS) collection card. Droplets of blood are allowed to fall onto the filter paper, which is printed with 5 circles.

For the DBS collection procedure, the following steps were performed:

1. A bloodspot collection card was prepared for collection:
   a. The bloodspot collection card contained Whatman 903TM filter paper, which was protected by a paper cover.
   b. The cover was folded back and creased to keep the filter paper portion of the card exposed.
   c. If self-performing the collection, the card was taped to the edge of a table with the exposed filter paper overhanging the table.
2. The sample collection site was wiped with an alcohol prep pad, and then the skin was allowed to dry for about 30 seconds.
   a. The Recommended collection site was on the finger pad of a preferred finger, near the fingertip.
3. A contact-activated lancet (BD Microtainer®, Ref #: 366594) was provided as the recommended lancet.
   a. Blue-color contact-activated lancet was considered "high flow" and comprised either a 14-guage needle or 1.5 mm wide blade with a 2.0 mM incision depth.
   b. There was a blue twist-off cover that was removed for the lancet to be activated.
   c. With the cover removed, the activation area of the lancet was firmly pushed against collection site, which resulted in a minor incision.
4. A gauze square (included in the kit) was used to wipe the first drop of blood away.
5. A droplet of blood on fingertip was then allowed to fall onto the filter paper, which was printed with 5 circles. A description of the DBS collection card comprising the 5 printed circles is provided in FIG. 20.
6. When possible all 5 circles were completely filled with sample. The finger was not directly touched to the card, but if a large blood droplet was not falling on its own onto the card, the droplet was touched to the paper (but touching the paper with finger was avoided).
7. After circles on card were filled, pressure was applied with a gauze pad at the collection site to slow/stop bleeding, and then an included band aid apply was applied.
8. The collection card was left open and allowed to dry. Once dry, samples were then shipped to analysis laboratory.
   a. CDC recommendations for dried bloodspot collections are to allow samples to dry for 3 hours prior to shipment.
   b. Collection card may be stored at room temperature (≤75° F., ≤24° C.) or refrigerated condition once dry (34-46° F., 2-8° C.). Avoid extreme heat conditions or storing in direct sunlight.
   c. Sample was shipped within 3 days of collection, and received within 2 weeks from collection date.

Example 8: IMMUNO-CoV V2 Bloodspot Assay Sample Analysis Protocol

The present example provides a IMMUNO-CoV V2 Bloodspot Assay Setup and Bloodspot Assay Maps, which describe the Dried Bloodspot Assay Sample Analysis protocol. Specifically, the procedure describes assaying of 6 bloodspot samples using 6 dilutions beginning at a 1:4 and diluting serial 2-fold out to a 1:128 dilution. Exemplar Bloodspot Assay Maps showing various bloodspot sample dilutions are described for a U-well (or U-bottom) Plate (FIG. 23) and an Assay Plate (FIG. 24).

The following is a list of reagents was needed to perform the procedure: VSV-SARS2-Fluc OptiMEM mAb10914 mAb10922

Pooled negative serum

D-luciferin

For the IMMUNO-CoV V2 Bloodspot Assay Setup, the following steps were performed:

Cells were seeded according to IMMUNO-CoV V2 Cell Preparation procedures of the present disclosure. Cells were seeded 16 to 24 hours before being used for assay.

1. Dried Bloodspot (DBS) sample processing was started approximately 1.5 hours before assay plating began.
2. For each DBS sample, a ¼ inch (6 mm) hole punch was used to punch a single punch/spot into an appropriately labeled 1.7 mL microcentrifuge tube. Bloodspot collection cards were viewed from the back when punching to ensure the punchout location was being taken from a location where capillary whole blood had saturated through the entire area of the filter paper being sampled.

3. Once all sample punches were added to tubes, 400 μL OptiMEM was added to each sample tube. For DBS sampling clarification, extractions were conducted using 200 μL, the assay recommended minimum volume to use per each 6 mm spot. Because 400 μL was used in the present extraction, this was considered a 1:2 dilution, which after mixing with the virus resulted in a 1:4 starting dilution. This provided adequate volume to transfer 240 μL of eluent to a U-bottom plate at later steps.
4. The tubes were incubated at room temperature for 1 hour on a plate shaker, shaking at 450 rpm setting.
5. Following 1 hour incubation, a micropipette was used to transfer supernatant to a new tube. The filter paper punch was pushed to the side with the pipette tip, and the extracted whole blood eluent was easily collected.
6. A brief centrifugation step (1000 x g for approximately 30 seconds) was performed before sampling bloodspot eluent to reduce the frequency of small filter paper debris from transferring to the U-bottom plate during assay setup.
7. 120 μL OptiMEM was placed in wells of U-bottom suspension 96-well culture plates indicated by grey shading according to plate layout maps, as shown in FIG. 23.
8. A working stock of mAb10914 antibody was prepared at 0.μg/μL by diluting 10 μL mAb10914 stock in 98 μL OptiMEM. The working stock was mixed by pipetting.
9. ST1 (standard) was prepare at 1.6 μg/mL mAb10914 (0.8 μg/mL after virus addition) as follows:

For 2 plates: 9.6 μL working stock mAb10914 was combined with 590.4 μL OptiMEM.

10. Working stock of mAb10922 antibody was prepared at 0.01 μg/μL by diluting 5 μL mAb10922 stock in 245 μL OptiMEM. The working stock was mixed by pipetting.
11. Assay controls (NC, negative control; PC, positive control) were prepared as follows, mixed by pipetting:

| Mix | Pooled negative serum | Working stock mAb10922 | OptiMEM |
|---|---|---|---|
| NC | 8 μL | None | 312 μL |
| PC | 12.5 μL | 3.1 μL | 484.4 μL |

12. 120 μL of controls were added to U-bottom plates according to the plate layout map (FIG. 23).
13. 240 μL of ST1 was added to wells labeled ST1 in the plate layout map (FIG. 23).
14. 240 μL of bloodspot sample eluent was added to sample wells A1, B1, C1 and A7, B7, C7 according to the plate layout map (FIG. 23).
15. Six-point 2-fold serial dilutions were performed as follows:

120 μL were transferred from Column 1 wells to Column 2 wells and mixed by pipetting. 120 μL were transferred from Column 2 wells to Column 3 wells and mixed by pipetting.

120 μL were transferred from Column 3 wells to Column 4 wells and mixed by pipetting.

120 μL were transferred from Column 4 wells to Column 5 wells and mixed by pipetting.

120 μL were transferred from Column 5 wells to Column 6 wells and mixed by pipetting.

120 μL from Column 6 wells was discarded.

The entire process was repeated for Samples S4, S5, S6, on right side of the plate (Column 7 through 12; NC, POS, or Media controls were not diluted).

16. The virus was thawed. Once completely thawed, the virus was stored on ice.
17. The virus was diluted to 6000 pfu/mL. Actual volume of OptiMEM needed for dilution can be calculated based on virus lot and titer using the following table:

| Virus Lot | Virus Titer | Vol. Virus ($8.4 \times 10^4$ ÷ titer) | Vol. OptiMEM (14-vol. virus) |
|---|---|---|---|
| | | mL | mL |

18. 120 μL of prepared virus was added to all wells of U-well plates and mixed by pipetting.
19. Plates were incubated at room temperature for 30 to 45 min.
20. 100 μL of samples were transferred from U-bottom plates to a plate of cells in duplicate according to Assay Plate layout maps (FIG. 24). Cells were placed in 37° C./5% $CO_2$ incubator.
21. Between 24 and 28 hours after the sample was overlayed onto the cells, the luciferase activity was read as follows:
    a. 15 mg/mL d-luciferin was diluted 1:10 (to 1.5 mg/mL) in DPBS. As a non-limiting example, 1 mL of 15 mg/mL d-luciferin was combined with 9 mL DPBS. Mixing was performed by inversion.

It was acceptable to prepare a larger volume of diluted (1.5 mg/mL) d-luciferin if reading luciferase from multiple plates/assays at the same time.

b. A 12-channel electronic or manual pipette was used to add 50 μL of 1.5 mg/mL d-luciferin to each well of assay plates.

D-luciferin was added to rows in order (i.e., A, B, C, D, E, F, G, H).

The timing of d-luciferin addition to rows was 4 to 8 seconds between each row.

c. One at a time, plates were placed in TECAN, and read using an appropriate program.

Initiation of the plate read occurred within 1 min of the addition of d-luciferin to the last row of the cell plate.

The assay was reviewed and reviewer details and date were recorded.

Figure 21:
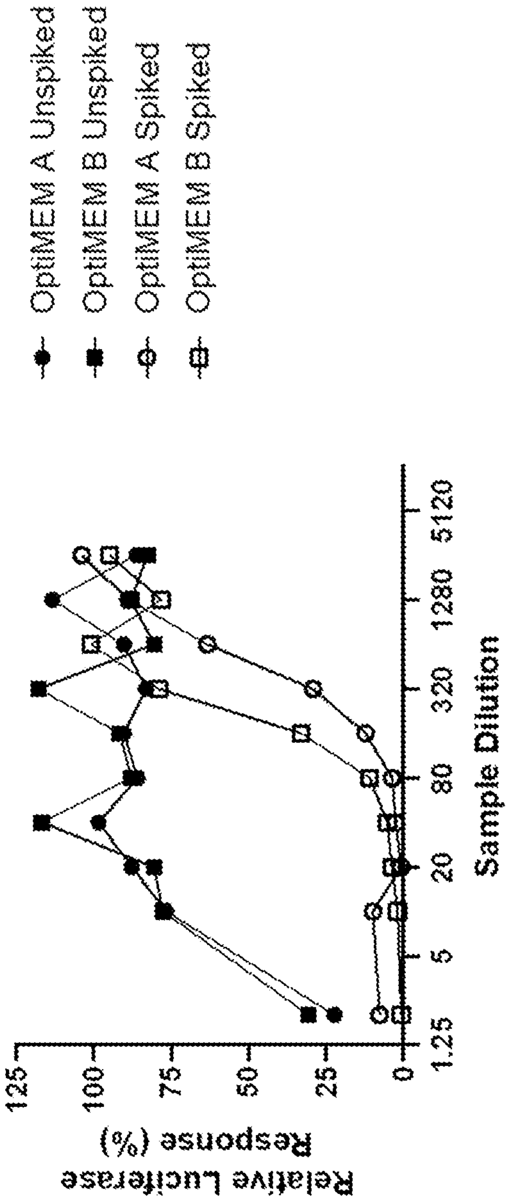
FIG. 21 shows a graphical summary of exemplar percent relative luciferase response data generated by extracting the bloodspots using OptiMEM across various sample dilutions. OptiMEM A and B are independent samples of OptiMEM.

As a non-limiting example, extracting of the blood spots was performed with either OptiMEM or PBST. For OptiMEM conditions, the OptiMEM started at 1:2 dilutions in the assay (neat elution, 1:2 when diluted with virus) and PBST started at a 1:10 dilution (1:10 after virus addition). FIG. 21 shows a graphical summary of exemplar percent relative luciferase response data generated by extracting bloodspots using OptiMEM across various sample dilutions in accordance with above-described methods.

Figure 22A:
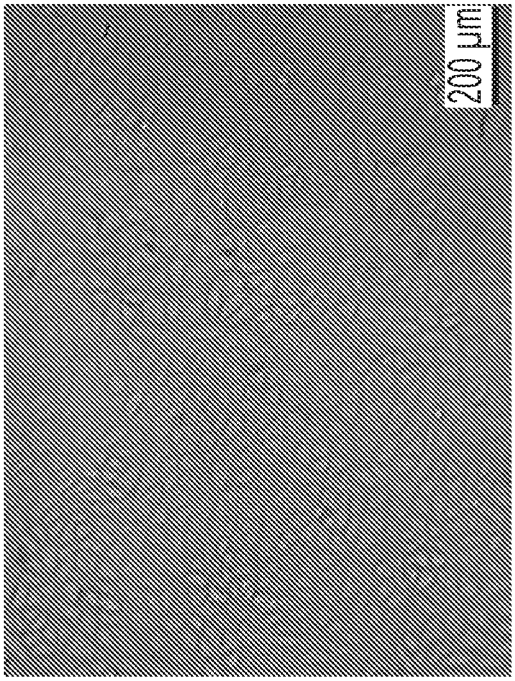
FIGS. 22A-B show exemplar photomicrographs of bloodspot matrixes. (A) B7 Opti-20x Positive Matrix A and (B) A7 Opti 20x Negative Matrix A. Bloodspot matrix was compatible at a 1:20 dilution of matrix. No issues were seen regarding either cell health or virus infectivity in the bloodspot samples that were tested.
Figure 22B:
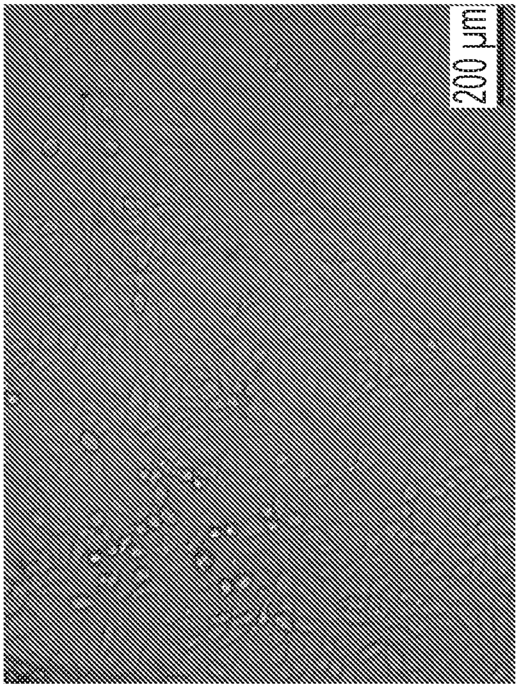

A proof-of-concept experiment demonstrated that the bloodspot matrix was completely compatible at a 1:20 dilution of matrix (FIGS. 22A-B). No major issues were seen regarding either cell health or virus infectivity in the bloodspot samples that were tested.

Sequences

Amino Acid Sequence of SARS-CoV-2 full-length S glycoprotein (SEQ ID NO: 1; variant 1 and variant 4; NCBI Reference Sequence: YP_009724390.1; S1 subunit is underlined; RBD site is shown in bold)

MFVFLVLLPLVSSQCVNLTTRTQLPPAYTNSFTRGVYYPDKVFRSSVLHSTQDLFLPFFSNVTW

FHAIHVSGTNGTKRFDNPVLPFNDGVYFASTEKSNIIRGWIFGTTLDSKTQSLLIVNNATNVVI

KVCEFQFCNDPFLGVYYHKNNKSWMESEFRVYSSANNCTFEYVSQPFLMDLEGKQGNFKNLREF

VFKNIDGYFKIYSKHTPINLVRDLPQGFSALEPLVDLPIGINITRFQTLLALHRSYLTPGDSSS

GWTAGAAAYYVGYLQPRTFLLKYNENGTITDAVDCALDPLSETKCTLKSFTVEKGIYQTSNFRV

QPTESIVRFPNITNLCPFGEVFNATRFASVYAWNRKRISNCVADYSVLYNSASFSTFKCYGVSP

TKLNDLCFTNVYADSFVIRGDEVRQIAPGQTGKIADYNYKLPDDFTGCVIAWNSNNLDSKVGGN

YNYLYRLFRKSNLKPFERDISTEIYQAGSTPCNGVEGFNCYFPLQSYGFQPTNGVGYQPYRVVV

LSFELLHAPATVCGPKKSTNLVKNKCVNFNFNGLTGTGVLTESNKKFLPFQQFGRDIADTTDAV

RDPQTLEILDITPCSFGGVSVITPGTNTSNQVAVLYQDVNCTEVPVAIHADQLTPTWRVYSTGS

NVFQTRAGCLIGAEHVNNSYECDIPIGAGICASYQTQTNSPRRARSVASQSIIAYTMSLGAENS

VAYSNNSIAIPTNFTISVTTEILPVSMTKTSVDCTMYICGDSTECSNLLLQYGSFCTQLNRALT

GIAVEQDKNTQEVFAQVKQIYKTPPIKDFGGFNFSQILPDPSKPSKRSFIEDLLFNKVTLADAG

FIKQYGDCLGDIAARDLICAQKFNGLTVLPPLLTDEMIAQYTSALLAGTITSGWTFGAGAALQI

PFAMQMAYRFNGIGVTQNVLYENQKLIANQFNSAIGKIQDSLSSTASALGKLQDVVNQNAQALN

TLVKQLSSNFGAISSVLNDILSRLDKVEAEVQIDRLITGRLQSLQTYVTQQLIRAAEIRASANL

AATKMSECVLGQSKRVDFCGKGYHLMSFPQSAPHGVVFLHVTYVPAQEKNFTTAPAICHDGKAH

FPREGVFVSNGTHWFVTQRNFYEPQIITTDNTFVSGNCDVVIGIVNNTVYDPLQPELDSFKEEL

DKYFKNHTSPDVDLGDISGINASVVNIQKEIDRLNEVAKNLNESLIDLQELGKYEQYIKWPWYI

WLGFIAGLIAIVMVTIMLCCMTSCCSCLKGCCSCGSCCKFDEDDSEPVLKGVKLHYT

Codon Optimized Nucleotide Sequence of SARS-CoV-2 full-length S glycoprotein (SEQ ID NO: 2; variant 1 and variant 4)

atgttcgtcttcctggtcctgctgcctctggtctcctcacagtgcgtcaatctgacaactcgga ctcagctgccacctgcttatactaatagcttcaccagaggcgtgtactatcctgacaaggtgtt tagaagctccgtgctgcactctacacaggatctgtttctgccattctttagcaacgtgacctgg ttccacgccatccacgtgagcggcaccaatggcacaaagcggttcgacaatcccgtgctgcctt ttaacgatggcgtgtacttcgcctctaccgagaagagcaacatcatcagaggctggatctttgg caccacactggactccaagacacagtctctgctgatcgtgaacaatgccaccaacgtggtcatc aaggtgtgcgagttccagttttgtaatgatcccttcctgggcgtgtactatcacaagaacaata agagctggatggagtccgagtttagagtgtattctagcgccaacaactgcacatttgagtacgt gagccagcctttcctgatggacctggagggcaagcagggcaatttcaagaacctgagggagttc gtgtttaagaatatcgacggctacttcaaaatctactctaagcacacccccatcaacctggtgc gcgacctgcctcagggcttcagcgccctggagcccctggtggatctgcctatcggcatcaacat cacccggtttcagacactgctggccctgcacagaagctacctgacacccggcgactcctctagc ggatggaccgccggcgctgccgcctactatgtgggctacctccagccccggaccttcctgctga agtacaacgagaatggcaccatcacagacgcagtggattgcgccctggacccccctgagcgagac aaagtgtacactgaagtcctttaccgtggagaagggcatctatcagacatccaatttcagggtg cagccaaccgagtctatcgtgcgctttcctaatatcacaaacctgtgcccatttggcgaggtgt tcaacgcaacccgcttcgccagcgtgtacgcctggaataggaagcggatcagcaactgcgtggc cgactatagcgtgctgtacaactccgcctctttcagcacctttaagtgctatggcgtgtccccc -continued acaaagctgaatgacctgtgctttaccaacgtctacgccgattctttcgtgatcaggggcgacg aggtgcgccagatcgcccccggccagacaggcaagatcgcagactacaattataagctgccaga cgatttcaccggctgcgtgatcgcctggaacagcaacaatctggattccaaagtgggcggcaac tacaattatctgtaccggctgtttagaaagagcaatctgaagcccttcgagagggacatctcta cagaaatctaccaggccggcagcaccccttgcaatggcgtggagggctttaactgttatttccc actccagtcctacggcttccagcccacaaacggcgtgggctatcagccttaccgcgtggtggtg ctgagctttgagctgctgcacgccccagcaacagtgtgcggccccaagaagtccaccaatctgg tgaagaacaagtgcgtgaacttcaacttcaacggcctgaccggcacaggcgtgctgaccgagtc caacaagaagttcctgccatttcagcagttcggcagggacatcgcagataccacagacgccgtg cgcgacccacagaccctggagatcctggacatcacaccctgctctttcggcggcgtgagcgtga tcacacccggcaccaatacaagcaaccaggtggccgtgctgtatcaggacgtgaattgtaccga ggtgcccgtggctatccacgccgatcagctgaccccaacatggcgggtgtacagcaccggctcc aacgtcttccagacaagagccggatgcctgatcggagcagagcacgtgaacaattcctatgagt gcgacatcccaatcggcgccggcatctgtgcctcttaccagacccagacaaactctcccagaag agcccggagcgtggcctcccagtctatcatcgcctataccatgtccctgggcgccgagaacagc gtggcctactctaacaatagcatcgccatcccaaccaacttcacaatctctgtgaccacagaga tcctgcccgtgtccatgaccaagacatctgtggactgcacaatgtatatctgtggcgattctac cgagtgcagcaacctgctgctccagtacggcagcttttgtacccagctgaatagagccctgaca ggcatcgccgtggagcaggataagaacacacaggaggtgttcgcccaggtgaagcaaatctaca agacccccccctatcaaggactttggcggcttcaatttttcccagatcctgcctgatccatccaa gccttctaagcggagctttatcgaggacctgctgttcaacaaggtgaccctggccgatgccggc ttcatcaagcagtatggcgattgcctgggcgacatcgcagccagggacctgatctgcgcccaga agtttaatggcctgaccgtgctgccacccctgctgacagatgagatgatcgcacagtacacaag cgccctgctggccggcaccatcacatccggatggaccttcggcgcaggagccgccctccagatc ccctttgccatgcagatggcctataggttcaacggcatcggcgtgacccagaatgtgctgtacg agaaccagaagctgatcgccaatcagtttaactccgccatcggcaagatccaggacagcctgtc ctctacagccagcgccctgggcaagctccaggatgtggtgaatcagaacgcccaggccctgaat accctggtgaagcagctgagcagcaacttcggcgccatctctagcgtgctgaatgacatcctga gccggctggacaaggtggaggcagaggtgcagatcgaccggctgatcaccggccggctccagag cctccagacctatgtgacacagcagctgatcagggccgccgagatcagggccagcgccaatctg gcagcaaccaagatgtccgagtgcgtgctgggccagtctaagagagtggacttttgtggcaagg gctatcacctgatgtccttccctcagtctgccccacacggcgtggtgtttctgcacgtgaccta cgtgcccgcccaggagaagaacttcaccacagcccctgccatctgccacgatggcaaggcccac tttccaagggagggcgtgttcgtgtccaacggcacccactggtttgtgacacagcgcaatttct acgagccccagatcatcaccacagacaacaccttcgtgagcggcaactgtgacgtggtcatcgg catcgtgaacaataccgtgtatgatccactccagcccgagctggacagctttaaggaggagctg gataagtatttcaagaatcacacctcccctgacgtggatctgggcgacatcagcggcatcaatg cctccgtggtgaacatccagaaggagatcgaccgcctgaacgaggtggctaagaatctgaacga gagcctgatcgacctccaggagctgggcaagtatgagcagtacatcaagtggccctggtacatc -continued tggctgggcttcatcgccggcctgatcgccatcgtgatggtgaccatcatgctgtgctgtatga catcctgctgttcttgcctgaagggctgctgtagctgtggctcctgctgtaagtttgacgagga tgactctgaacctgtgctgaagggcgtgaagctgcattacacctaa Amino Acid Sequence of SARS-CoV-2 Δ19CT S glycoprotein
(SEQ ID NO: 3; variant 2; S1 subunit is underlined; RBD site is shown in bold)

MFVFLVLLPLVSSQCVNLTTRTQLPPAYTNSFTRGVYYPDKVFRSSVLHSTQDLFLPFFSNVTW

FHAIHVSGTNGTKRFDNPVLPFNDGVYFASTEKSNIIRGWIFGTTLDSKTQSLLIVNNATNVVI

KVCEFQFCNDPFLGVYYHKNNKSWMESEFRVYSSANNCTFEYVSQPFLMDLEGKQGNFKNLREF

VFKNIDGYFKIYSKHTPINLVRDLPQGFSALEPLVDLPIGINITRFQTLLALHRSYLTPGDSSS

GWTAGAAAYYVGYLQPRTFLLKYNENGTITDAVDCALDPLSETKCTLKSFTVEKGIYQTSNFRV

QPTESIVRFPNITNLCPFGEVFNATRFASVYAWNRKRISNCVADYSVLYNSASFSTFKCYGVSP

TKLNDLCFTNVYADSFVIRGDEVRQIAPGQTGKIADYNYKLPDDFTGCVIAWNSNNLDSKVGGN

YNYLYRLFRKSNLKPFERDISTEIYQAGSTPCNGVEGFNCYFPLQSYGFQPTNGVGYQPYRVVV

LSFELLHAPATVCGPKKSTNLVKNKCVNFNFNGLTGTGVLTESNKKFLPFQQFGRDIADTTDAV

RDPQTLEILDITPCSFGGVSVITPGTNTSNQVAVLYQDVNCTEVPVAIHADQLTPTWRVYSTGS

NVFQTRAGCLIGAEHVNNSYECDIPIGAGICASYQTQTNSPRRARSVASQSIIAYTMSLGAENS

VAYSNNSIAIPTNFTISVTTEILPVSMTKTSVDCTMYICGDSTECSNLLLQYGSFCTQLNRALT

GIAVEQDKNTQEVFAQVKQIYKTPPIKDFGGFNFSQILPDPSKPSKRSFIEDLLFNKVTLADAG

FIKQYGDCLGDIAARDLICAQKFNGLTVLPPLLTDEMIAQYTSALLAGTITSGWTFGAGAALQI

PFAMQMAYRFNGIGVTQNVLYENQKLIANQFNSAIGKIQDSLSSTASALGKLQDVVNQNAQALN

TLVKQLSSNFGAISSVLNDILSRLDKVEAEVQIDRLITGRLQSLQTYVTQQLIRAAEIRASANL

AATKMSECVLGQSKRVDFCGKGYHLMSFPQSAPHGVVFLHVTYVPAQEKNFTTAPAICHDGKAH

FPREGVFVSNGTHWFVTQRNFYEPQIITTDNTFVSGNCDVVIGIVNNTVYDPLQPELDSFKEEL

DKYFKNHTSPDVDLGDISGINASVVNIQKEIDRLNEVAKNLNESLIDLQELGKYEQYIKWPWYI

WLGFIAGLIAIVMVTIMLCCMTSCCSCLKGCCSCGSCC

Codon Optimized Nucleotide Sequence of SARS-CoV-2 A19CT S glycoprotein
(SEQ ID NO: 4; variant 2)

atgttcgtcttcctggtcctgctgcctctggtctcctcacagtgcgtcaatctgacaactcgga ctcagctgccacctgcttatactaatagcttcaccagaggcgtgtactatcctgacaaggtgtt tagaagctccgtgctgcactctacacaggatctgtttctgccattctttagcaacgtgacctgg ttccacgccatccacgtgagcggcaccaatggcacaaagcggttcgacaatcccgtgctgcctt ttaacgatggcgtgtacttcgcctctaccgagaagagcaacatcatcagaggctggatctttgg caccacactggactccaagacacagtctctgctgatcgtgaacaatgccaccaacgtggtcatc aaggtgtgcgagttccagttttgtaatgatcccttcctgggcgtgtactatcacaagaacaata agagctggatggagtccgagtttagagtgtattctagcgccaacaactgcacatttgagtacgt gagccagcctttcctgatggacctggagggcaagcagggcaatttcaagaacctgagggagttc gtgtttaagaatatcgacggctacttcaaaatctactctaagcacacccccatcaacctggtgc gcgacctgcctcagggcttcagcgccctggagcccctggtggatctgcctatcggcatcaacat cacccggtttcagacactgetggccctgcacagaagctacetgacacccggcgactcctctage ggatggaccgccggcgctgccgcctactatgtgggctacctccagccccggaccttcctgctga agtacaacgagaatggcaccatcacagacgcagtggattgcgccctggacccccctgagcgagac -continued aaagtgtacactgaagtcctttaccgtggagaagggcatctatcagacatccaatttcagggtg
cagccaaccgagtctatcgtgcgctttcctaatatcacaaacctgtgcccatttggcgaggtgt
tcaacgcaacccgcttcgccagcgtgtacgcctggaataggaagcggatcagcaactgcgtggc
cgactatagcgtgctgtacaactccgcctctttcagcacctttaagtgctatggcgtgtccccc
acaaagctgaatgacctgtgctttaccaacgtctacgccgattctttcgtgatcaggggcgacg
aggtgcgccagatcgcccccggccagacaggcaagatcgcagactacaattataagctgccaga
cgatttcaccggctgcgtgatcgcctggaacagcaacaatctggattccaaagtgggcggcaac
tacaattatctgtaccggctgtttagaaagagcaatctgaagcccttcgagagggacatctcta
cagaaatctaccaggccggcagcaccccttgcaatggcgtggagggctttaactgttatttccc
actccagtcctacggcttccagcccacaaacggcgtgggctatcagccttaccgcgtggtggtg
ctgagctttgagctgctgcacgccccagcaacagtgtgcggccccaagaagtccaccaatctgg
tgaagaacaagtgcgtgaacttcaacttcaacggcctgaccggcacaggcgtgctgaccgagtc
caacaagaagttcctgccatttcagcagttcggcagggacatcgcagataccacagacgccgtg
cgcgacccacagaccctggagatcctggacatcacaccctgctctttcggcggcgtgagcgtga
tcacacccggcaccaatacaagcaaccaggtggccgtgctgtatcaggacgtgaattgtaccga
ggtgcccgtggctatccacgccgatcagctgaccccaacatggcgggtgtacagcaccggctcc
aacgtcttccagacaagagccggatgcctgatcggagcagagcacgtgaacaattcctatgagt
gcgacatcccaatcggcgccggcatctgtgcctcttaccagacccagacaaactctcccagaag
agcccggagcgtggcctcccagtctatcatcgcctataccatgtccctgggcgccgagaacagc
gtggcctactctaacaatagcatcgccatcccaaccaacttcacaatctctgtgaccacagaga
tcctgcccgtgtccatgaccaagacatctgtggactgcacaatgtatatctgtggcgattctac
cgagtgcagcaacctgctgctccagtacggcagcttttgtacccagctgaatagagccctgaca
ggcatcgccgtggagcaggataagaacacacaggaggtgttcgcccaggtgaagcaaatctaca
agacccccccctatcaaggactttggcggcttcaatttttcccagatcctgcctgatccatccaa
gccttctaagcggagctttatcgaggacctgctgttcaacaaggtgaccctggccgatgccggc
ttcatcaagcagtatggcgattgcctgggcgacatcgcagccagggacctgatctgcgcccaga
agtttaatggcctgaccgtgctgccacccctgctgacagatgagatgatcgcacagtacacaag
cgccctgctggccggcaccatcacatccggatggaccttcggcgcaggagccgccctccagatc
ccctttgccatgcagatggcctataggttcaacggcatcggcgtgacccagaatgtgctgtacg
agaaccagaagctgatcgccaatcagtttaactccgccatcggcaagatccaggacagcctgtc
ctctacagccagcgccctgggcaagctccaggatgtggtgaatcagaacgcccaggccctgaat
accctggtgaagcagctgagcagcaacttcggcgccatctctagcgtgctgaatgacatcctga
gccggctggacaaggtggaggcagaggtgcagatcgaccggctgatcaccggccggctccagag
cctccagacctatgtgacacagcagctgatcagggccgccgagatcagggccagcgccaatctg
gcagcaaccaagatgtccgagtgcgtgctgggccagtctaagagagtggacttttgtggcaagg
gctatcacctgatgtccttccctcagtctgccccacacggcgtggtgtttctgcacgtgaccta
cgtgcccgcccaggagaagaacttcaccacagcccctgccatctgccacgatggcaaggcccac
tttccaagggagggcgtgttcgtgtccaacggcacccactggtttgtgacacagcgcaatttct
acgagccccagatcatcaccacagacaacaccttcgtgagcggcaactgtgacgtggtcatcgg
catcgtgaacaataccgtgtatgatccactccagcccgagctggacagctttaaggaggagctg gataagtatttcaagaatcacacctcccctgacgtggatctgggcgacatcagcggcatcaatg cctccgtggtgaacatccagaaggagatcgaccgcctgaacgaggtggctaagaatctgaacga gagcctgatcgacctccaggagctgggcaagtatgagcagtacatcaagtggccctggtacatc tggctgggcttcatcgccggcctgatcgccatcgtgatggtgaccatcatgctgtgctgtatga catcctgctgttcttgcctgaagggctgctgtagctgtggctcctgctgttaa Amino Acid Sequence of SARS-CoV-2 VSV G CT glycoprotein (SEQ ID NO: 5; variant 3; the sequence of VSV G cytoplasmic tail is shown in bold, underline)

MFVFLVLLPLVSSQCVNLTTRTQLPPAYTNSFTRGVYYPDKVFRSSVLHSTQDLFLPFFS

NVTWFHAIHVSGTNGTKRFDNPVLPFNDGVYFASTEKSNIIRGWIFGTTLDSKTQSLLIV

NNATNVVIKVCEFQFCNDPFLGVYYHKNNKSWMESEFRVYSSANNCTFEYVSQPFLMDLE

GKQGNFKNLREFVFKNIDGYFKIYSKHTPINLVRDLPQGFSALEPLVDLPIGINITRFQT

LLALHRSYLTPGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASVYAWNRKRISN

CVADYSVLYNSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTEIYQAGSTPC

NGVEGFNCYFPLQSYGFQPTNGVGYQPYRVVVLSFELLHAPATVCGPKKSTNLVKNKCVN

FNFNGLTGTGVLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCLIGAEHVNNSY

ECDIPIGAGICASYQTQTNSPRRARSVASQSIIAYTMSLGAENSVAYSNNSIAIPTNFTI

SVTTEILPVSMTKTSVDCTMYICGDSTECSNLLLQYGSFCTQLNRALTGIAVEQDKNTQE

VFAQVKQIYKTPPIKDFGGFNFSQILPDPSKPSKRSFIEDLLFNKVTLADAGFIKQYGDC

LGDIAARDLICAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQDVVNQNAQALN

TLVKQLSSNFGAISSVLNDILSRLDKVEAEVQIDRLITGRLQSLQTYVTQQLIRAAEIRA

SANLAATKMSECVLGQSKRVDFCGKGYHLMSFPQSAPHGVVFLHVTYVPAQEKNFTTAPA

ICHDGKAHFPREGVFVSNGTHWFVTQRNFYEPQIITTDNTFVSGNCDVVIGIVNNTVYDP

LQPELDSFKEELDKYFKNHTSPDVDLGDISGINASVVNIQKEIDRLNEVAKNLNESLIDL

QELGKYEQYIKWPWYIWLGFIAGLIAIVMVTIMLCCM<u>KLKHTKKRQIYTDIEMNRLGK</u>

Codon Optimized Nucleotide Sequence of SARS-CoV-2 VSV G CT glycoprotein (SEQ ID NO: 6; variant 3; the sequence encoding VSV G cytoplasmic tail is shown in CAPs)

atgttcgtcttcctggtcctgctgcctctggtctcctcacagtgcgtcaatctgacaactcgga ctcagctgccacctgcttatactaatagcttcaccagaggcgtgtactatcctgacaaggtgtt tagaagctccgtgctgcactctacacaggatctgtttctgccattctttagcaacgtgacctgg ttccacgccatccacgtgagcggcaccaatggcacaaagcggttcgacaatcccgtgctgcctt ttaacgatggcgtgtacttcgcctctaccgagaagagcaacatcatcagaggctggatctttgg caccacactggactccaagacacagtctctgctgatcgtgaacaatgccaccaacgtggtcatc aaggtgtgcgagttccagttttgtaatgatcccttcctgggcgtgtactatcacaagaacaata agagctggatggagtccgagtttagagtgtattctagcgccaacaactgcacatttgagtacgt gagccagcctttcctgatggacctggagggcaagcagggcaatttcaagaacctgagggagttc gtgtttaagaatatcgacggctacttcaaaatctactctaagcacacccccatcaacctggtgc gcgacctgcctcagggcttcagcgccctggagcccctggtggatctgcctatcggcatcaacat -continued cacccggtttcagacactgctggccctgcacagaagctacctgacacccggcgactcctctagc ggatggaccgccggcgctgccgcctactatgtgggctacctccagccccggaccttcctgctga agtacaacgagaatggcaccatcacagacgcagtggattgcgccctggacccctgagcgagac aaagtgtacactgaagtcctttaccgtggagaagggcatctatcagacatccaatttcagggtg cagccaaccgagtctatcgtgcgctttcctaatatcacaaacctgtgcccatttggcgaggtgt tcaacgcaacccgcttcgccagcgtgtacgcctggaataggaagcggatcagcaactgcgtggc cgactatagcgtgctgtacaactccgcctctttcagcacctttaagtgctatggcgtgtccccc acaaagctgaatgacctgtgctttaccaacgtctacgccgattctttcgtgatcaggggcgacg aggtgcgccagatcgcccccggccagacaggcaagatcgcagactacaattataagctgccaga cgatttcaccggctgcgtgatcgcctggaacagcaacaatctggattccaaagtgggcggcaac tacaattatctgtaccggctgtttagaaagagcaatctgaagcccttcgagagggacatctcta cagaaatctaccaggccggcagcaccccttgcaatggcgtggagggctttaactgttatttccc actccagtcctacggcttccagcccacaaacggcgtgggctatcagccttaccgcgtggtggtg ctgagctttgagctgctgcacgccccagcaacagtgtgcggccccaagaagtccaccaatctgg tgaagaacaagtgcgtgaacttcaacttcaacggcctgaccggcacaggcgtgctgaccgagtc caacaagaagttcctgccatttcagcagttcggcagggacatcgcagataccacagacgccgtg cgcgacccacagaccctggagatcctggacatcacaccctgctctttcggcggcgtgagcgtga tcacacccggcaccaatacaagcaaccaggtggccgtgctgtatcaggacgtgaattgtaccga ggtgcccgtggctatccacgccgatcagctgaccccaacatggcgggtgtacagcaccggctcc aacgtcttccagacaagagccggatgcctgatcggagcagagcacgtgaacaattcctatgagt gcgacatcccaatcggcgccggcatctgtgcctcttaccagacccagacaaactctcccagaag agcccggagcgtggcctcccagtctatcatcgcctataccatgtccctgggcgccgagaacagc gtggcctactctaacaatagcatcgccatcccaaccaacttcacaatctctgtgaccacagaga tcctgcccgtgtccatgaccaagacatctgtggactgcacaatgtatatctgtggcgattctac cgagtgcagcaacctgctgctccagtacggcagcttttgtacccagctgaatagagccctgaca ggcatcgccgtggagcaggataagaacacacaggaggtgttcgcccaggtgaagcaaatctaca agacccccccctatcaaggactttggcggcttcaatttttcccagatcctgcctgatccatccaa gccttctaagcggagctttatcgaggacctgctgttcaacaaggtgaccctggccgatgccggc ttcatcaagcagtatggcgattgcctgggcgacatcgcagccagggacctgatctgcgcccaga agtttaatggcctgaccgtgctgccacccctgctgacagatgagatgatcgcacagtacacaag cgccctgctggccggcaccatcacatccggatggaccttcggcgcaggagccgccctccagatc ccctttgccatgcagatggcctataggttcaacggcatcggcgtgacccagaatgtgctgtacg agaaccagaagctgatcgccaatcagtttaactccgccatcggcaagatccaggacagcctgtc ctctacagccagcgccctgggcaagctccaggatgtggtgaatcagaacgcccaggccctgaat accctggtgaagcagctgagcagcaacttcggcgccatctctagcgtgctgaatgacatcctga gccggctggacaaggtggaggcagaggtgcagatcgaccggctgatcaccggccggctccagag cctccagacctatgtgacacagcagctgatcagggccgccgagatcagggccagcgccaatctg gcagcaaccaagatgtccgagtgcgtgctgggccagtctaagagagtggacttttgtggcaagg gctatcacctgatgtccttccctcagtctgccccacacggcgtggtgtttctgcacgtgaccta -continued cgtgcccgcccaggagaagaacttcaccacagcccctgccatctgccacgatggcaaggcccac tttccaagggagggcgtgttcgtgtccaacggcacccactggtttgtgacacagcgcaatttct acgagccccagatcatcaccacagacaacaccttcgtgagcggcaactgtgacgtggtcatcgg catcgtgaacaataccgtgtatgatccactccagcccgagctggacagctttaaggaggagctg gataagtatttcaagaatcacacctcccctgacgtggatctgggcgacatcagcggcatcaatg cctccgtggtgaacatccagaaggagatcgaccgcctgaacgaggtggctaagaatctgaacga gagcctgatcgacctccaggagctgggcaagtatgagcagtacatcaagtggccctggtacatc tggctgggcttcatcgccggcctgatcgccatcgtgatggtgaccatcatgctgtgctgtatgA

AATTAAAGCACACCAAGAAAAGACAGATTTATACAGACATAGAGATGAACCGACTTGGAAAGTA

A

Amino Acid Sequence of Mutant VSV Matrix (M) Protein (M51R) (SEQ ID NO: 7)
MSSLKKILGLKGKGKKSKKLGIAPPPYEEDTSMEYAPSAPIDKSYFGVDERDTHDPNQLRYEKS

FFTVKMTVRSNRPFRTYSDVAAAVSHWDHMYIGMAGKRPFYKILAFLGSSNLKATPAVLADQGQ

PEYHAHCEGRAYLPHRMGKTPPMLNVPEHFRRPFNIGLYKGTIELTMTIYDDESLEAAPMIWDH

FNSSKFSDFREKALMFGLIVEEEASGAWVLDSVRHSKWASLASSF

Nucleotide Sequence of Mutant VSV Matrix (M) Protein (M51R) (SEQ ID NO: 8)
ATGAGTTCCTTAAAGAAGATTCTCGGTCTGAAGGGGAAAGGTAAGAAATCTAAGAAATTAGGGA

TCGCACCACCCCCTTATGAAGAGGACACTAGCATGGAGTATGCTCCGAGCGCTCCAATTGACAA

ATCCTATTTTGGAGTTGACGAGCGAGACACCTATGATCCGAATCAATTAAGATATGAGAAATTC

TTCTTTACAGTGAAAATGACGGTTAGATCTAATCGTCCGTTCAGAACATACTCAGATGTGGCAG

CCGCTGTATCCCATTGGGATCACATGTACATCGGAATGGCAGGGAAACGTCCCTTCTACAAAAT

CTTGGCTTTTTTGGGTTCTTCTAATCTAAAGGCCACTCCAGCGGTATTGGCAGATCAAGGTCAA

CCAGAGTATCACGCTCACTGCGAAGGCAGGGCTTATTTGCCACATAGGATGGGGAAGACCCCTC

CCATGCTCAATGTACCAGAGCACTTCAGAAGACCATTCAATATAGGTCTTTACAAGGGAACGAT

TGAGCTCACAATGACCATCTACGATGATGAGTCACTGGAAGCAGCTCCTATGATCTGGGATCAT

TTCAATTCTTCCAAATTTTCTGATTTCAGAGAGAAGGCCTTAATGTTTGGCCTGATTGTCGAGA

AAAAGGCATCTGGAGCGTGGGTCCTGGACTCTATCGGCCACTTCAAATGA

Amino Acid Sequence of the Wild-Type VSV Matrix (M) Protein (SEQ ID NO: 9)
MSSLKKILGLKGKGKKSKKLGIAPPPYEEDTSMEYAPSAPIDKSYFGVDEMDTHDPNQLRYEKS

FFTVKMTVRSNRPFRTYSDVAAAVSHWDHMYIGMAGKRPFYKILAFLGSSNLKATPAVLADQGQ

PEYHAHCEGRAYLPHRMGKTPPMLNVPEHFRRPFNIGLYKGTIELTMTIYDDESLEAAPMIWDH

FNSSKFSDFREKALMFGLIVEEEASGAWVLDSVRHSKWASLASSF

Nucleotide Sequence of the Wild-Type VSV Matrix (M) Protein (SEQ ID NO: 10)
ATGAGTTCCTTAAAGAAGATTCTCGGTCTGAAGGGGAAAGGTAAGAAATCTAAGAAATTAGGGA

TCGCACCACCCCCTTATGAAGAGGACACTAGCATGGAGTATGCTCCGAGCGCTCCAATTGACAA

ATCCTATTTTGGAGTTGACGAGATGGACACCTATGATCCGAATCAATTAAGATATGAGAAATTC

TTCTTTACAGTGAAAATGACGGTTAGATCTAATCGTCCGTTCAGAACATACTCAGATGTGGCAG

CCGCTGTATCCCATTGGGATCACATGTACATCGGAATGGCAGGGAAACGTCCCTTCTACAAAAT

CTTGGCTTTTTTGGGTTCTTCTAATCTAAAGGCCACTCCAGCGGTATTGGCAGATCAAGGTCAA

CCAGAGTATCACGCTCACTGCGAAGGCAGGGCTTATTTGCCACATAGGATGGGGAAGACCCCTC

CCATGCTCAATGTACCAGAGCACTTCAGAAGACCATTCAATATAGGTCTTTACAAGGGAACGAT

TGAGCTCACAATGACCATCTACGATGATGAGTCACTGGAAGCAGCTCCTATGATCTGGGATCAT

-continued

TTCAATTCTTCCAAATTTTCTGATTTCAGAGAGAAGGCCTTAATGTTTGGCCTGATTGTCGAGA

AAAAGGCATCTGGAGCGTGGGTCCTGGACTCTATCGGCCACTTCAAATGA wild-type VSV Kozak sequence (SEQ ID NO: 11)
CACTATG optimized Kozak sequence (SEQ ID NO: 12)
CACCATG Amino Acid Sequence of SARS-CoV-1 Spike (S) protein (SEQ ID NO: 13; UniProtKB/Swiss-Prot: P59594.1)
MFIFLLFLTLTSGSDLDRCTTFDDVQAPNYTQHTSSMRGVYYPDEIFRSDTLYLTQDLFLPFYS

NVTGFHTINHTFGNPVIPFKDGIYFAATEKSNVVRGWVFGSTMNNKSQSVIIINNSTNVVIRAC

NFELCDNPFFAVSKPMGTQTHTMIFDNAFNCTFEYISDAFSLDVSEKSGNFKHLREFVFKNKDG

FLYVYKGYQPIDVVRDLPSGFNTLKPIFKLPLGINITNFRAILTAFSPAQDIWGTSAAAYFVGY

LKPTTFMLKYDENGTITDAVDCSQNPLAELKCSVKSFEIDKGIYQTSNFRVVPSGDVVRFPNIT

NLCPFGEVFNATKFPSVYAWERKKISNCVADYSVLYNSTFFSTFKCYGVSATKLNDLCFSNVYA

DSFVVKGDDVRQIAPGQTGVIADYNYKLPDDFMGCVLAWNTRNIDATSTGNYNYKYRYLRHGKL

RPFERDISNVPFSPDGKPCTPPALNCYWPLNDYGFYTTTGIGYQPYRVVVLSFELLNAPATVCG

PKLSTDLIKNQCVNFNFNGLTGTGVLTPSSKRFQPFQQFGRDVSDFTDSVRDPKTSEILDISPC

SFGGVSVITPGTNASSEVAVLYQDVNCTDVSTAIHADQLTPAWRIYSTGNNVNFSISITTEVMP

VSMAKTSVDCNMYICGDSTECANLLLQYGSFCTQLNRALSGIAAEQDRNTREVFAQVKQMYKTP

TLKYFGGFNFSQILPDPLKPTKRSFIEDLLFNKVTLADAGFMKQYGECLGDINARDLICAQKFN

GLTVLPPLLTDDMIAAYTAALVSGTATAGWTFGAGAALQIPFAMQMAYRFNGIGVTQNVLYENQ

KQIANQFNKAISQIQESLTTTSTALGKLQDVVNQNAQALNTLVKQLSSNFGAISSVLNDILSRL

DKVEAEVQIDRLITGRLQSLQTYVTQQLIRAAEIRASANLAATKMSECVLGQSKRVDFCGKGYH

LMSFPQAAPHGVVFLHVTYVPSQERNFTTAPAICHEGKAYFPREGVFVFNGTSWFITQRNFFSP

QIITTDNTFVSGNCDVVIGIINNTVYDPLQPELDSFKEELDKYFKNHTSPDVDLGDISGINASV

VNIQKEIDRLNEVAKNLNESLIDLQELGKYEQYIKWPWYVWLGFIAGLIAIVMVTILLCCMTSC

CSCLKGACSCGSCCKFDEDDSEPVLKGVKLHYT

| SARS-CoV-1 subunits/domains | Residues SARS-CoV-1 (SEQ ID NO: 13) | Residues SARS-CoV-2 (SEQ ID NO: 1) | % identity |
|---|---|---|---|
| Full protein | 1-1255 | | 75.9 |
| Signal peptide | 1-13 | | 53.9 |
| Extracellular | 14-1195 | | |
| Transmembrane | 1196-1216 | | |
| Cytoplasmic | 1217-1255 | | 97.4 |
| S1 | 14-667 | 14-684 | 63.6 |
| S2 | 668-1255 | | 90 |
| S2' | 798-1255 | | 93 |
| Cleavage site | 667-668 | | 100 |
| Cleavage site | 797-798 | | 100 |
| Receptor-binding domain (RBD) | 306-527 | 319-541 | 73.1 |
| Fusion peptide | 770-788 | | 83.3 |

CLUSTAL O(1.2.4) multiple sequence alignment of spike (S) glycoprotein sequences from SARS-CoV-1 (SEQ ID NO: 13) and SARS-CoV-2 (SEQ ID NO: 1)

```
SARS1     MFIFLLFLTLTSGSDLDRCTTFDDVQAPNYTQHTSSMRGVYYPDEIFRSDT-        60
          LYLTQDLFL

SARS2     MFVFLVLLPLVSSQCVNLTT--RTQLPPAY--TNSFTRGVYYPDKVFRSSVLH-      56
          STQDLFL
          **:**::* *.*.. ::  *        * *   .*  *******::***,,*: ******

SARS1     PFYSNVTGFHTIN-------HTFGNPVIPFKDGIYFAATEKSNVVRGWVFG-       113
          STMNNKSQS
```

-continued

```
SARS2   PFFSNVTWFHAIHVSGTNGTKRFDNPVLPFNDGVYFASTEKSNIIRGWIFGTTLD-     116
        SKTQS
        **:**** **:*:       : *.***:**:**:***:*****::***:**:*::.*:**

SARS1   VIIINNSTNVVIRACNFELCDNPFFAVSKPMGT----QTHTMIFDNAFNCTFEYISDAFS 169

SARS2   LLIVNNATNVVIKVCEFQFCNDPFLGVYYHKNNKSWMESEFRVYSSANNCTFEYVSQPFL 176
        ::*:**:*****:.*:*::*::**:.*    ..    ::.  ::..* ******:*: *

SARS1   LDVSEKSGNFKHLREFVFKNKDGFLYVYKGYQPIDVVRDLPSGFNTLKPIFKLPLGINIT 229

SARS2   MDLEGKQGNFKNLREFVFKNIDGYFKIYSKHTPINLVRDLPQGFSALEPLVDLPIGINIT 236
        :*:. *.****:******** **:: :*. : **::*****.**.:*:*:..**:*****

SARS1   NFRAILTAFS------PAQDIWGTSAAAYFVGYLKPTTFMLKYDENGTITDAVDCSQNPL 283

SARS2   RFQTLLALHRSYLTPGDSSSGWTAGAAAYYVGYLQPRTFLLKYNENGTITDAVDCALDPL 296
        .*:::*: .        :.. * :.****:****:* **:***:***********: :**

SARS1   AELKCSVKSFEIDKGIYQTSNFRVVPSGDVVRFPNITNLCPFGEVFNATKFPSVYAWERK 343

SARS2   SETKCTLKSFTVEKGIYQTSNFRVQPTESIVRFPNITNLCPFGEVFNATRFASVYAWNRK 356
        :* **::*** ::*********** *: .:*******************:* *****:**

SARS1   KISNCVADYSVLYNSTFFSTFKCYGVSATKLNDLCFSNVYADSFVVKGDDVRQIAPGQTG 403

SARS2   RISNCVADYSVLYNSASFSTFKCYGVSPTKLNDLCFTNVYADSFVIRGDEVRQIAPGQTG 416
        :**************: ********** ********:********::**:**********

SARS1   VIADYNYKLPDDFMGCVLAWNTRNIDATSTGNYNYKYRYLRHGKLRPFERDISNVPFSPD 463

SARS2   KIADYNYKLPDDFTGCVIAWNSNNLDSKVGGNYNYLYRLFRKSNLKPFERDISTEIYQAG 476
         ************ ***:***:.*:*:.  ***** ** :*:..*:*******.  :. .

SARS1   GKPCTP-PALNCYWPLNDYGFYTTTGIGYQPYRVVVLSFELLNAPATVCGPKLSTDLIKN 522

SARS2   STPCNGVEGFNCYFPLQSYGFQPTNGVGYQPYRVVVLSFELLHAPATVCGPKKSTNLVKN 536
        ..**.   .:***:**:.***  *.*:***************:********* **:*:**

SARS1   QCVNFNFNGLTGTGVLTPSSKRFQPFQQFGRDVSDFTDSVRDPKTSEILDISPCSFGGVS 582

SARS2   KCVNFNFNGLTGTGVLTESNKKFLPFQQFGRDIADTTDAVRDPQTLEILDITPCSFGGVS 596

SARS1   VITPGTNASSEVAVLYQDVNCTDVSTAIHADQLTPAWRIYSTGNNV-------------- 628

SARS2   VITPGTNTSNQVAVLYQDVNCTEVPVAIHADQLTPTWRVYSTGSNVFQTRAGCLIGAEHV 656
        *******:*.:***********:* .*********:**:****.**

SARS1   ------------------------------------------------------------ 628

SARS2   NNSYECDIPIGAGICASYQTQTNSPRRARSVASQSIIAYTMSLGAENSVAYSNNSIAIPT 716

SARS1   NFSISITTEVMPVSMAKTSVDCNMYICGDSTECANLLLQYGSFCTQLNRALSGIAAEQDR 688

SARS2   NFTISVTTEILPVSMTKTSVDCTMYICGDSTECSNLLLQYGSFCTQLNRALTGIAVEQDK 776
        **:**:***::****:******.**********:*****************:***.***:

SARS1   NTREVFAQVKQMYKTPTLKYFGGFNFSQILPDPLKPTKRSFIEDLLFNKVTLADAGFMKQ 748

SARS2   NTQEVFAQVKQIYKTPPIKDFGGFNFSQILPDPSKPSKRSFIEDLLFNKVTLADAGFIKQ 836
        **:********:**** :* ************* **:********************:**

SARS1   YGECLGDINARDLICAQKFNGLTVLPPLLTDDMIAAYTAALVSGTATAGWTFGAGAALQI 808

SARS2   YGDCLGDIAARDLICAQKFNGLTVLPPLLTDEMIAQYTSALLAGTITSGWTFGAGAALQI 896
        **:***** **********************:*** **:**::** *:************

SARS1   PFAMQMAYRFNGIGVTQNVLYENQKQIANQFNKAISQIQESLTTTSTALGKLQDVVNQNA 868

SARS2   PFAMQMAYRFNGIGVTQNVLYENQKLIANQFNSAIGKIQDSLSSTASALGKLQDVVNQNA 956
        ************************* ******.**.:**:**::*::*************

SARS1   QALNTLVKQLSSNFGAISSVLNDILSRLDKVEAEVQIDRLITGRLQSLQTYVTQQLIRAA 928

SARS2   QALNTLVKQLSSNFGAISSVLNDILSRLDKVEAEVQIDRLITGRLQSLQTYVTQQLIRAA1016
        ************************************************************

SARS1   EIRASANLAATKMSECVLGQSKRVDFCGKGYHLMSFPQAAPHGVVFLHVTYVPSQERNFT 988
```

-continued

| | | |
|---|---|---|
| SARS2 | EIRASANLAATKMSECVLGQSKRVDFCGKGYHLMSFPQSAPHGVVFLHVTYVPAQEKNFT | 1076 |
| | ************************************:*************:**:*** | |
| SARS1 | TAPAICHEGKAYFPREGVFVFNGTSWFITQRNFFSPQIITTDNTFVSGNCDVVIGIINNT | 1048 |
| SARS2 | TAPAICHDGKAHFPREGVFVSNGTHWFVTQRNFYEPQIITTDNTFVSGNCDVVIGIVNNT | 1136 |
| | *******:***:******** *** **:*****:.********************:*** | |
| SARS1 | VYDPLQPELDSFKEELDKYFKNHTSPDVDLGDISGINASVVNIQKEIDRLNEVAKNLNES | 1108 |
| SARS2 | VYDPLQPELDSFKEELDKYFKNHTSPDVDLGDISGINASVVNIQKEIDRLNEVAKNLNES | 1196 |
| | ************************************************************ | |
| SARS1 | LIDLQELGKYEQYIKWPWYVWLGFIAGLIAIVMVTILLCCMTSCCSCLKGACSCGSCCKF | 1168 |
| SARS2 | LIDLQELGKYEQYIKWPWYIWLGFIAGLIAIVMVTIMLCCMTSCCSCLKGCCSCGSCCKF | 1256 |
| | *******************:***************:************.********* | |
| SARS1 | DEDDSEPVLKGVKLHYT | 1185 |
| SARS2 | DEDDSEPVLKGVKLHYT | 1273 |
| | ***************** | |

Rluc8 155-156DSP1-7 luciferase-GFP fusion protein (SEQ ID NO: 14; *Renilla luciferase* fragment aa 1-155 is underlined; linker is not highlighted; fragment aa 1-156 of engineered GFP is shown in bold)

MASKVYDPEQRKRMITGPQWWARCKQMNVLDSFINYYDSEKHAENAVIFLHGNATSSYLWRHVV

PHIEPVARCIIPDLIGMGKSGKSGNGSYRLLDHYKYLTAWFELLNLPKKIIFVGHDWGAALAFH

YAYEHQDRIKAIVHMESVVDVIESWDESGGGGMSKGEELFTGVVPILVELDGDVNGHKFSVRGE

GEGDATIGKLTLKFICTTGKLPVPWPTLVTTLTYGVQCFSRYPDHMKRHDFFKSAMPEGYVQER

TISFKDDGKYKTRAVVKFEGDTLVNRIELKGTDFKEDGNILGHKLEYNFNSHNVYITADK

Nucleotide Sequence of Rluc8155-156DSP1-7 construct (SEQ ID NO: 15; coding ORF nt 1068-2018)

agatcttcaatattggccattagccatattattcattggttatatagcataaatcaatat tggctattggccattgcatacgttgtatctatatcataatatgtacatttatattggctc atgtccaatatgaccgccatgttggcattgattattgactagttattaatagtaatcaat tacggggtcattagttcatagcccatatatggagttccgcgttacataacttacggtaaa tggcccgcctggctgaccgcccaacgacccccgcccattgacgtcaataatgacgtatgt tcccatagtaacgccaatagggactttccattgacgtcaatgggtggagtatttacggta aactgcccacttggcagtacatcaagtgtatcatatgccaagtccgccccctattgacgt caatgacggtaaatggcccgcctggcattatgcccagtacatgaccttacgggactttcc tacttggcagtacatctacgtattagtcatcgctattaccatggtgatgcggttttggca gtacaccaatgggcgtggatagcggtttgactcacggggatttccaagtctccacccccat tgacgtcaatgggagtttgttttggcaccaaaatcaacgggactttccaaaatgtcgtaa taaccccgccccgttgacgcaaatgggcggtaggcgtgtacggtgggaggtctatataag cagagctcgtttagtgaaccgtcagatcactagaagctttattgcggtagtttatcacag ttaaattgctaacgcagtcagtgcttctgacacaacagtctcgaacttaagctgcagaag ttggtcgtgaggcactgggcaggtaagtatcaaggttacaagacaggtttaaggagacca atagaaactgggcttgtcgagacagagaagactcttgcgtttctgataggcacctattgg tcttactgacatccactttgcctttctctccacaggtgtccactcccagttcaattacag ctcttaaggctagagtacttaatacgactcactataggctagccaccatggcttccaagg tgtacgaccccgagcaacgcaaacgcatgatcactgggcctcagtggtgggctcgctgca agcaaatgaacgtgctggactccttcatcaactactatgattccgagaagcacgccgaga acgccgtgatttttctgcatggtaacgctacctccagctacctgtggaggcacgtcgtgc -continued ctcacatcgagcccgtggctagatgcatcatccctgatctgatcggaatgggtaagtccg gcaagagcgggaatggctcatatcgcctcctggatcactacaagtacctcaccgcttggt tcgagctgctgaaccttccaaagaaaatcatctttgtgggccacgactggggggctgctc tggcctttcactacgcctacgagcaccaagacaggatcaaggccatcgtccatatggaga gtgtcgtggacgtgatcgagtcctgggacgagtccggaggaggcggaatgagcaagggcg aggagctgttcaccggcgtggtgcccatcctggtggagctggacggcgacgtgaacggcc acaagttcagcgtgagaggcgagggcgagggcgacgccaccatcggcaagctgaccctga agttcatctgcaccaccggcaagctgcccgtgccctggcccaccctggtgaccaccctga cctacggcgtgcagtgcttcagcagataccccgaccacatgaagagacacgacttcttca agagcgccatgcccgagggctacgtgcaggagagaaccatcagcttcaaggacgacggca agtacaagaccagagccgtggtgaagttcgagggcgacaccctggtgaacagaatcgagc tgaagggcaccgacttcaaggaggacggcaacatcctgggccacaagctggagtacaact tcaacagccacaacgtgtacatcaccgccgacaagtgatctagagcggccgcttcgagca gacatgataagatacattgatgagtttggacaaaccacaactagaatgcagtgaaaaaaa tgctttatttgtgaaatttgtgatgctattgctttatttgtaaccattataagctgcaat aaacaagttaacaacaacaattgcattcattttatgtttcaggttcagggggaggtgtgg gaggttttttaaagcaagtaaaacctctacaaatgtggtaaaatcgataaggatccaggt ggcacttttcggggaaatgtgcgcggaacccctatttgtttatttttctaaatacattca aatatgtatccgctcatgagacaataaccctgataaatgcttcaataatattgaaaaagg aagagtatgagtattcaacatttccgtgtcgcccttattcccttttttgcggcattttgc cttcctgtttttgctcacccagaaacgctggtgaaagtaaaagatgctgaagatcagttg ggtgcacgagtgggttacatcgaactggatctcaacagcggtaagatccttgagagtttt cgccccgaagaacgttttccaatgatgagcacttttaaagttctgctatgtggcgcggta ttatcccgtattgacgccgggcaagagcaactcggtcgccgcatacactattctcagaat gacttggttgagtactcaccagtcacagaaaagcatcttacggatggcatgacagtaaga gaattatgcagtgctgccataaccatgagtgataacactgcggccaacttacttctgaca acgatcggaggaccgaaggagctaaccgcttttttgcacaacatgggggatcatgtaact cgccttgatcgttgggaaccggagctgaatgaagccataccaaacgacgagcgtgacacc acgatgcctgtagcaatggcaacaacgttgcgcaaactattaactggcgaactacttact ctagcttcccggcaacaattaatagactggatggaggcggataaagttgcaggaccactt ctgcgctcggcccttccggctggctggtttattgctgataaatctggagccggtgagcgt gggtctcgcggtatcattgcagcactggggccagatggtaagccctcccgtatcgtagtt atctacacgacggggagtcaggcaactatggatgaacgaaatagacagatcgctgagata ggtgcctcactgattaagcattggtaactgtcagaccaagtttactcatatatactttag attgatttaaaacttcatttttaatttaaaaggatctaggtgaagatcctttttgataat ctcatgaccaaaatcccttaacgtgagttttcgttccactgagcgtcagaccccgtagaa aagatcaaaggatcttcttgagatcctttttttctgcgcgtaatctgctgcttgcaaaca aaaaaaccaccgctaccagcggtggtttgtttgccggatcaagagctaccaactcttttt ccgaaggtaactggcttcagcagagcgcagataccaaatactgttcttctagtgtagccg tagttaggccaccacttcaagaactctgtagcaccgcctacatacctcgctctgctaatc ctgttaccagtggctgctgccagtggcgataagtcgtgtcttaccgggttggactcaaga cgatagttaccggataaggcgcagcggtcgggctgaacggggggttcgtgcacacagccc agcttggagcgaacgacctacaccgaactgagatacctacagcgtgagctatgagaaagc gccacgcttcccgaagggagaaaggcggacaggtatccggtaagcggcagggtcggaaca ggagagcgcacgagggagcttccagggggaaacgcctggtatctttatagtcctgtcggg tttcgccacctctgacttgagcgtcgatttttgtgatgctcgtcaggggggcggagccta tggaaaaacgccagcaacgcggcctttttacggttcctggccttttgctggccttttgct cacatggctcgac Rluc8 155-156DSP8-11 luciferase-GFP fusion protein (SEQ ID NO: 16; *Renilla luciferase* fragment aa 156-311 is underlined; linker is not highlighted; fragment aa 157-231 of engineered GFP is shown in bold)

MQKNGIKANFTVRHNVEDGSVQLADHYQQNTPIGDGPVLLPDNHYLSTQTVLSKDPNEKRDHMV

LHEYVNAAGITGGGGSWPDIEEDIALIKSEEGEKMVLENNFFVETVLPSKIMRKLEPEEFAAYL

EPFKEKGEVRRPTLSWPREIPLVKGGKPDVVQIVRNYNAYLRASDDLPKLFIESDPGFFSNAIV

EGAKKFPNTEFVKVKGLHFLQEDAPDEMGKYIKSFVERVLKNEQ

Nucleotide Sequence of Rluc8155-156DSP8-11 construct (SEQ ID NO: 17; coding ORF nt 1068-1778)

agatcttcaatattggccattagccatattattcattggttatatagcataaatcaatat tggctattggccattgcatacgttgtatctatatcataatatgtacatttatattggctc atgtccaatatgaccgccatgttggcattgattattgactagttattaatagtaatcaat tacggggtcattagttcatagcccatatatggagttccgcgttacataacttacggtaaa tggcccgcctggctgaccgcccaacgacccccgcccattgacgtcaataatgacgtatgt tcccatagtaacgccaatagggactttccattgacgtcaatgggtggagtatttacggta aactgcccacttggcagtacatcaagtgtatcatatgccaagtccgccccctattgacgt caatgacggtaaatggcccgcctggcattatgcccagtacatgaccttacgggactttcc tacttggcagtacatctacgtattagtcatcgctattaccatggtgatgcggttttggca gtacaccaatgggcgtggatagcggtttgactcacggggatttccaagtctccaccccat tgacgtcaatgggagtttgttttggcaccaaaatcaacgggactttccaaaatgtcgtaa taaccccgccccgttgacgcaaatgggcggtaggcgtgtacggtgggaggtctatataag cagagctcgtttagtgaaccgtcagatcactagaagctttattgcggtagtttatcacag ttaaattgctaacgcagtcagtgcttctgacacaacagtctcgaacttaagctgcagaag ttggtcgtgaggcactgggcaggtaagtatcaaggttacaagacaggtttaaggagacca atagaaactgggcttgtcgagacagagaagactcttgcgtttctgataggcacctattgg tcttactgacatccactttgcctttctctccacaggtgtccactcccagttcaattacag ctcttaaggctagagtacttaatacgactcactataggctagccaccatgcagaagaacg gcatcaaggccaacttcaccgtgagacacaacgtggaggacggcagcgtgcagctggccg accactaccagcagaacacccccatcggcgacggccccgtgctgctgcccgacaaccact acctgagcacccagaccgtgctgagcaaggaccccaacgagaagagagaccacatggtgc tgcacgagtacgtgaacgccgccggcatcaccggcggtggcggatcctggcctgacatcg aggaggatatcgccctgatcaagagcgaagagggcgagaaaatggtgcttgagaataact tcttcgtcgagaccgtgctcccaagcaagatcatgcggaaactggagcctgaggagttcg -continued ctgcctacctggagccattcaaggagaagggcgaggttagacggcctaccctctcctggc ctcgcgagatccctctcgttaagggaggcaagcccgacgtcgtccagattgtccgcaact acaacgcctaccttcgggccagcgacgatctgcctaagctgttcatcgagtccgaccctg ggttcttttccaacgctattgtcgagggagctaagaagttccctaacaccgagttcgtga aggtgaagggcctccacttcctccaggaggacgctccagatgaaatgggtaagtacatca agagcttcgtggagcgcgtgctgaagaacgagcagtaattctagagcggccgcttcgagc agacatgataagatacattgatgagtttggacaaaccacaactagaatgcagtgaaaaaa atgctttatttgtgaaatttgtgatgctattgctttatttgtaaccattataagctgcaa taaacaagttaacaacaacaattgcattcattttatgtttcaggttcagggggaggtgtg ggaggttttttaaagcaagtaaaacctctacaaatgtggtaaaatcgataaggatccagg tggcacttttcggggaaatgtgcgcggaacccctatttgtttatttttctaaatacattc aaatatgtatccgctcatgagacaataaccctgataaatgcttcaataatattgaaaaag gaagagtatgagtattcaacatttccgtgtcgcccttattcccttttttgcggcattttg ccttcctgtttttgctcacccagaaacgctggtgaaagtaaaagatgctgaagatcagtt gggtgcacgagtgggttacatcgaactggatctcaacagcggtaagatccttgagagttt tcgccccgaagaacgttttccaatgatgagcacttttaaagttctgctatgtggcgcggt attatcccgtattgacgccgggcaagagcaactcggtcgccgcatacactattctcagaa tgacttggttgagtactcaccagtcacagaaaagcatcttacggatggcatgacagtaag agaattatgcagtgctgccataaccatgagtgataacactgcggccaacttacttctgac aacgatcggaggaccgaaggagctaaccgcttttttgcacaacatgggggatcatgtaac tcgccttgatcgttgggaaccggagctgaatgaagccataccaaacgacgagcgtgacac cacgatgcctgtagcaatggcaacaacgttgcgcaaactattaactggcgaactacttac tctagcttcccggcaacaattaatagactggatggaggcggataaagttgcaggaccact tctgcgctcggcccttccggctggctggtttattgctgataaatctggagccggtgagcg tgggtctcgcggtatcattgcagcactggggccagatggtaagccctcccgtatcgtagt tatctacacgacggggagtcaggcaactatggatgaacgaaatagacagatcgctgagat aggtgcctcactgattaagcattggtaactgtcagaccaagtttactcatatatacttta gattgatttaaaacttcatttttaatttaaaaggatctaggtgaagatcctttttgataa tctcatgaccaaaatcccttaacgtgagttttcgttccactgagcgtcagaccccgtaga aaagatcaaaggatcttcttgagatcctttttttctgcgcgtaatctgctgcttgcaaac aaaaaaaccaccgctaccagcggtggtttgtttgccggatcaagagctaccaactctttt tccgaaggtaactggcttcagcagagcgcagataccaaatactgttcttctagtgtagcc gtagttaggccaccacttcaagaactctgtagcaccgcctacatacctcgctctgctaat cctgttaccagtggctgctgccagtggcgataagtcgtgtcttaccgggttggactcaag acgatagttaccggataaggcgcagcggtcgggctgaacggggggttcgtgcacacagcc cagcttggagcgaacgacctacaccgaactgagatacctacagcgtgagctatgagaaag cgccacgcttcccgaagggagaaaggcggacaggtatccggtaagcggcagggtcggaac aggagagcgcacgagggagcttccagggggaaacgcctggtatctttatagtcctgtcgg -continued gtttcgccacctctgacttgagcgtcgatttttgtgatgctcgtcaggggggcggagcct atggaaaaacgccagcaacgcggcctttttacggttcctggccttttgctggccttttgc tcacatggctcgac Engineered GFP (SEP ID NO: 18)
MSKGEELFTGVVPILVELDGDVNGHKFSVRGEGEGDATIGKLTLKFICTTGKLPVPWPTLVTTL

TYGVQCFSRYPDHMKRHDFFKSAMPEGYVQERTISFKDDGKYKTRAVVKFEGDTLVNRIELKGT

DFKEDGNILGHKLEYNFNSHNVYITADKMQKNGIKANFTVRHNVEDGSVQLADHYQQNTPIGDG

PVLLPDNHYLSTQTVLSKDPNEKRDHMVLHEYVNAAGIT

RLuc8 (SEQ ID NO: 19)
MASKVYDPEQRKRMITGPQWWARCKQMNVLDSFINYYDSEKHAENAVIFLHGNATSSYLWRHVV

PHIEPVARCIIPDLIGMGKSGKSGNGSYRLLDHYKYLTAWFELLNLPKKIIFVGHDWGAALAFH

YAYEHQDRIKAIVHMESVVDVIESWDEWPDIEEDIALIKSEEGEKMVLENNFFVETVLPSKIMR

KLEPEEFAAYLEPFKEKGEVRRPTLSWPREIPLVKGGKPDVVQIVRNYNAYLRASDDLPKLFIE

SDPGFFSNAIVEGAKKFPNTEFVKVKGLHFLQEDAPDEMGKYIKSFVERVLKNEQ 19 amino acids of SARS-CoV-2 S glycoprotein cytoplasmic tail deleted in variant 2
(SEQ ID NO: 20)
KFDEDDSEPVLKGVKLHYT VSV G glycoprotein cytoplasmic tail sequence used in variant 3 (SEQ ID NO: 21)
KLKHTKKRQIYTDIEMNRLGK Sequences of mAb10914 antibody:

| Component Part | Sequence | SEQ ID NO |
|---|---|---|
| | Amino Acid Sequences | |
| HCVR | EVQLVESGGGLVQPGGSLRLSCAASGLIVSRNYMIWVRQAPGKGLEWVSV IYSGGSTFYADSVKGRFTISRHNSKNTLYLQMNSLRAEDTAVYYCARDLG TGGMDVWGQGTTVTVSS | 22 |
| HCDR1 | GLIVSRNY | 24 |
| HCDR2 | IYSGGST | 26 |
| HCDR3 | ARDLGTGGMDV | 28 |
| LCVR | DIQLTQSPSFLSASVGDRVTITCWASQGISSYLAWYQQKPGKAPKLLIYA ASTLQSGVPSRFSGSGSGTEFTLTISSLQPEDFATYYCQQLNSYPLTFGG GTKVEIK | 30 |
| LCDR1 | QGISSY | 32 |
| LCDR2 | AAS | 34 |
| LCDR3 | QQLNSYPLT | 36 |
| HC | EVQLVESGGGLVQPGGSLRLSCAASGLIVSRNYMIWVRQAPGKGLEWVSV IYSGGSTFYADSVKGRFTISRHNSKNTLYLQMNSLRAEDTAVYYCARDLG TGGMDVWGQGTTVTVSSASTKGPSVFPLAPSSKSTSGGTAALGCLVKDYF PEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPGK | 38 |
| LC | DIQLTQSPSFLSASVGDRVTITCWASQGISSYLAWYQQKPGKAPKLLIYA ASTLQSGVPSRFSGSGSGTEFTLTISSLQPEDFATYYCQQLNSYPLTFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 40 |

-continued

| Nucleotide Sequences | | |
|---|---|---|
| HCVR | gaggtgcagctggtggagtctggaggaggcttggtccagcctggggggtc cctgagactctcctgtgcagcctctgggttaatagtcagtcgcaactaca tgatctgggtccgccaggctccagggaaggggctggagtgggtctcagtt atttatagcggtggtagcacattctacgcagactccgtgaagggccgatt caccatctccagacacaattccaagaacacgctgtatcttcaaatgaaca gcctgagggctgaggacacggccgtatattactgtgcgagagatctgggt acaggaggtatggacgtctggggccaagggaccacggtcaccgtctcctc a | 23 |
| HCDR1 | gggttaatagtcagtcgcaactac | 25 |
| HCDR2 | atttatagcggtggtagcaca | 27 |
| HCDR3 | gcgagagatctgggtacaggaggtatggacgtc | 29 |
| LCVR | gacatccagttgacccagtctccatccttcctgtctgcatctgtaggaga cagagtcaccatcacttgctgggccagtcagggcattagcagttatttag cctggtatcagcaaaaaccagggaaagcccctaagctcctgatctatgct gcatccactttgcaaagtggggtcccatcaaggttcagcggcagtggatc tgggacagaattcactctcacaatcagcagcctgcagcctgaagattttg caacttattactgtcaacagcttaatagttaccctctcactttcggcgga gggaccaaggtggagatcaaa | 31 |
| LCDR1 | cagggcattagcagttat | 33 |
| LCDR2 | gctgcatcc | 35 |
| LCDR3 | caacagcttaatagttaccctctcact | 37 |
| HC | gaggtgcagctggtggagtctggaggaggcttggtccagcctggggggtc cctgagactctcctgtgcagcctctgggttaatagtcagtcgcaactaca tgatctgggtccgccaggctccagggaaggggctggagtgggtctcagtt atttatagcggtggtagcacattctacgcagactccgtgaagggccgatt caccatctccagacacaattccaagaacacgctgtatcttcaaatgaaca gcctgagggctgaggacacggccgtatattactgtgcgagagatctgggt acaggaggtatggacgtctggggccaagggaccacggtcaccgtctcctc agcctccaccaagggcccatcggtcttccccctggcaccctcctccaaga gcacctctgggggcacagcggccctgggctgcctggtcaaggactacttc cccgaaccggtgacggtgtcgtggaactcaggcgccctgaccagcggcgt gcacaccttcccggctgtcctacagtcctcaggactctactccctcagca gcgtggtgaccgtgccctccagcagcttgggcacccagacctacatctgc aacgtgaatcacaagcccagcaacaccaaggtggacaagaaagttgagcc caaatcttgtgacaaaactcacacatgcccaccgtgcccagcacctgaac tcctggggggaccgtcagtcttcctcttccccccaaaacccaaggacacc ctcatgatctcccggacccctgaggtcacatgcgtggtggtggacgtgag ccacgaagaccctgaggtcaagttcaactggtacgtggacggcgtggagg tgcataatgccaagacaaagccgcgggaggagcagtacaacagcacgtac cgtgtggtcagcgtcctcaccgtcctgcaccaggactggctgaatggcaa ggagtacaagtgcaaggtctccaacaaagccctcccagcccccatcgaga aaaccatctccaaagccaaagggcagccccgagaaccacaggtgtacacc ctgcccccatcccgggatgagctgaccaagaaccaggtcagcctgacctg cctggtcaaaggcttctatcccagcgacatcgccgtggagtgggagagca atgggcagccggagaacaactacaagaccacgcctcccgtgctggactcc gacggctccttcttcctctacagcaagctcaccgtggacaagagcaggtg gcagcaggggaacgtcttctcatgctccgtgatgcatgaggctctgcaca accactacacgcagaagtccctctccctgtctccgggtaaatga | 39 |
| LC | gacatccagttgacccagtctccatccttcctgtctgcatctgtaggaga cagagtcaccatcacttgctgggccagtcagggcattagcagttatttag cctggtatcagcaaaaaccagggaaagcccctaagctcctgatctatgct gcatccactttgcaaagtggggtcccatcaaggttcagcggcagtggatc tgggacagaattcactctcacaatcagcagcctgcagcctgaagattttg caacttattactgtcaacagcttaatagttaccctctcactttcggcgga gggaccaaggtggagatcaaacgaactgtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgttag | 41 |

-continued

Sequences of mAb10922 antibody:

| Component Part | Sequence | SEQ ID NO |
|---|---|---|
| **Amino Acid Sequences** | | |
| HCVR | EVQLVESGGGLVQPGGSLRLSCAASGFTFSIYEMNWVRQAPGKGLEWVSY ITSSGTTIYYADSVKGRFTISRDNAKNSLYLQMNSLRAEDTAVYYCASSS SSGYYFDYWGQGTLVTVSS | 45 |
| HCDR1 | GFTFSIYE | 46 |
| HCDR2 | ITSSGTTI | 47 |
| HCDR3 | ASSSSSGYYFDY | 48 |
| LCVR | DIVMTQSPDSLAVSLGERATINCKSSQSVLYSSNNKNYLAWYQQKPGQPP NLLIYWASTRESGVPDRFSGSGSGTDFTLTISSLQAEDVAVYYCQQYYST PPTFGQGTKLEIK | 49 |
| LCDR1 | QSVLYSSNNKNY | 50 |
| LCDR2 | WAS | 51 |
| LCDR3 | QQYYSTPPT | 52 |
| HC | EVQLVESGGGLVQPGGSLRLSCAASGFTFSIYEMNWVRQAPGKGLEWVSY ITSSGTTIYYADSVKGRFTISRDNAKNSLYLQMNSLRAEDTAVYYCASSS SSGYYFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 53 |
| LC | DIVMTQSPDSLAVSLGERATINCKSSQSVLYSSNNKNYLAWYQQKPGQPP NLLIYWASTRESGVPDRFSGSGSGTDFTLTISSLQAEDVAVYYCQQYYST PPTFGQGTKLEIKRTVAAPSVFIFPPSDEQLKSGTASVVCLLNNFYPREA KVQWKVDNALQSGNSQESVTEQDSKDSTYSLSSTLTLSKADYEKHKVYAC EVTHQGLSSPVTKSFNRGEC | 54 |
| **Nucleotide Sequences** | | |
| HCVR | gaggtgcagctggtggagtctgggggaggcttggtacagcctggagggtc cctgagactctcctgtgcagcctctggattcaccttcagtatttatgaaa tgaactgggtccgccaggctccagggaaggggctggagtgggtttcatac attactagtagtggtactaccatatactacgcagactctgtgaagggccg attcaccatctccagagacaacgccaagaactcactgtatctgcaaatga acagcctgagagccgaggacacggctgtttattactgtgcgagtagcagc tcgtccgggtactactttgactactggggccagggaaccctggtcaccgt ctcctca | 55 |
| HCDR1 | ggattcaccttcagtatttatgaa | 56 |
| HCDR2 | attactagtagtggtactaccata | 57 |
| HCDR3 | gcgagtagcagctcgtccgggtactactttgactac | 58 |
| LCVR | gacatcgtgatgacccagtctccagactccctggctgtgtctctgggcga gagggccaccatcaactgcaagtccagccagagtgttttatacagctcca acaataagaactacttagcttggtaccagcagaaaccaggacagcctcct aatctgctcatttactgggcatctacccgggaatccggggtccctgaccg attcagtggcagcgggtctgggacagatttcactctcaccatcagcagcc tgcaggctgaagatgtggcagtttattactgtcagcaatattatagtact cctcccacttttggccaggggaccaagctggagatcaaa | 59 |
| LCDR1 | cagagtgttttatacagctccaacaataagaactac | 60 |
| LCDR2 | tgggcatct | 61 |
| LCDR3 | cagcaatattatagtactcctcccact | 62 |
| HC | gaggtgcagctggtggagtctgggggaggcttggtacagcctggagggtc cctgagactctcctgtgcagcctctggattcaccttcagtatttatgaaa tgaactgggtccgccaggctccagggaaggggctggagtgggtttcatac attactagtagtggtactaccatatactacgcagactctgtgaagggccg attcaccatctccagagacaacgccaagaactcactgtatctgcaaatga acagcctgagagccgaggacacggctgtttattactgtgcgagtagcagc | 63 |

-continued

| | | |
|---|---|---|
| | tcgtccgggtactactttgactactggggccagggaaccctggtcaccgt<br>ctcctcagcctccaccaagggcccatcggtcttccccctggcaccctcct<br>ccaagagcacctctgggggcacagcggccctgggctgcctggtcaaggac<br>tacttccccgaaccggtgacggtgtcgtggaactcaggcgccctgaccag<br>cggcgtgcacaccttcccggctgtcctacagtcctcaggactctactccc<br>tcagcagcgtggtgaccgtgccctccagcagcttgggcacccagacctac<br>atctgcaacgtgaatcacaagcccagcaacaccaaggtggacaagaaagt<br>tgagcccaaatcttgtgacaaaactcacacatgcccaccgtgcccagcac<br>ctgaactcctggggggaccgtcagtcttcctcttccccccaaaacccaag<br>gacaccctcatgatctcccggacccctgaggtcacatgcgtggtggtgga<br>cgtgagccacgaagaccctgaggtcaagttcaactggtacgtggacggcg<br>tggaggtgcataatgccaagacaaagccgcgggaggagcagtacaacagc<br>acgtaccgtgtggtcagcgtcctcaccgtcctgcaccaggactggctgaa<br>tggcaaggagtacaagtgcaaggtctccaacaaagccctcccagcccccca<br>tcgagaaaaccatctccaaagccaaagggcagccccgagaaccacaggtg<br>tacaccctgcccccatcccgggatgagctgaccaagaaccaggtcagcct<br>gacctgcctggtcaaaggcttctatcccagcgacatcgccgtggagtggg<br>agagcaatgggcagccggagaacaactacaagaccacgcctcccgtgctg<br>gactccgacggctccttcttcctctacagcaagctcaccgtggacaagag<br>caggtggcagcaggggaacgtcttctcatgctccgtgatgcatgaggctc<br>tgcacaaccactacacgcagaagtccctctccctgtctccgggtaaatga | |
| LC | gacatcgtgatgacccagtctccagactccctggctgtgtctctgggcga<br>gagggccaccatcaactgcaagtccagccagagtgttttatacagctcca<br>acaataagaactacttagcttggtaccagcagaaaccaggacagcctcct<br>aatctgctcatttactgggcatctacccgggaatccggggtccctgaccg<br>attcagtggcagcgggtctgggacagatttcactctcaccatcagcagcc<br>tgcaggctgaagatgtggcagtttattactgtcagcaatattatagtact<br>cctcccactttttggccaggggaccaagctggagatcaaacgaactgtggc<br>tgcaccatctgtcttcatcttcccgccatctgatgagcagttgaaatctg<br>gaactgcctctgttgtgtgcctgctgaataacttctatcccagagaggcc<br>aaagtacagtggaaggtggataacgccctccaatcgggtaactcccagga<br>gagtgtcacagagcaggacagcaaggacagcacctacagcctcagcagca<br>ccctgacgctgagcaaagcagactacgagaaacacaaagtctacgcctgc<br>gaagtcacccatcagggcctgagctcgcccgtcacaaagagcttcaacag<br>gggagagtgttag | 64 |

Amino Acid Sequence of SARS-CoV-2 Δ19CT CPE Lytic Variant (SEQ ID NO: 42; CPE Variant)

MFVFLVLLPLVSSQCVNLTTRTQLPPAYTNSFTRGVYYPDKVFRSSVLHSTQDLFLPFFSNVTW

FHAIHVSGTNGTKRFDNPVLPFNDGVYFASTEKSNIIRGWIFGTTLDSKTQSLLIVNNATNVVI

KVCEFQFCNDPFLGVYYHKNNKSWMESEFRVYSSANNCTFEYVSQPFLMDLEGKQGNFKNLREF

VFKNIDGYFKIYSKHTPINLVRDLPQGFSALEPLVDLPIGINITRFQTLLALHRRYLTPGDSSS

GWTAGAAAYYVGYLQPRTFLLKYNENGTITDAVDCALDPLSETKCTLKSFTVEKGIYQTSNFRV

QPTESIVRFPNITNLCPFGEVFNATRFASVYAWNRKRISNCVADYSVLYNSASFSTFKCYGVSP

TKLNDLCFTNVYADSFVIRGDEVRQIAPGQTGKIADYNYKLPDDFTGCVIAWNSNNLDSKVGGN

YNYLYRLFRKSNLKPFERDISTEIYQAGSTPCNGVEGFNCYFPLQSYGFQPTNGVGYQPYRVVV

LSFELLHAPATVCGPKKSTNLVKNKCVNFNFNGLTGTGVLTESNKKFLPFQQFGRDIADTTDAV

RDPQTLEILDITPCSFGGVSVITPGTNTSNQVAVLYQNVNCTEVPVAIHADQLTPTWRVYSTGS

NVFQTRAGCLIGAEHVNNSYECDIPIGAGIGASYQTQTNSPRRAQSVASQSIIAYTMSLGAENS

VAYSNNSIAIPTNFTISVTTEILPVSMTKTSVDCTMYICGDSTECSNLLLQYGSFCTQLNRALT

GIAVEQDKNTQEVFAQVKQIYKTPPIKDFGGFNFSQILPDPSKPSKRSFIEDLLFNKVTLADAG

FIKQYGDCLGDIAARDLICAQKFNGLTVLPPLLTDEMIAQYTSALLAGTITSGWTFGAGAALQI

PFAMQMAYRFNGIGVTQNVLYENQKLIANQFNSAIGKIQDSLSSTASALGKLQDVVNQNAQALN

TLVKQLSSNFGAISSVLNDILSRLDKVEAEVQIDRLITGRLQSLQTYVTQQLIRAAEIRASANL

AATKMSECVLGQSKRVDFCGKGYHLMSFPQSAPHGVVFLHVTYVPAQEKNFTTAPAICHDGKAH

FPREGVFVSNGTHWFVTQRNFYEPQIITTDNTFVSGNCDWIGIVNNTVYDPLQPELDSFKEEL

DKYFKNHTSPDVDLGDISGINASVVNIQKEIDRLNEVAKNLNESLIDLQELGKYEQYIKWPWYI

WLGFIAGLIAIVMVTIMLCCMTSCCSCLKGCCSCGSCC

-continued

Codon Optimized Polynucleotide Sequence of SARS-CoV-2 Δ19CT CPE Lytic Variant
(SEQ ID NO: 43; CPE Variant)

atgttcgtcttcctggtcctgctgcctctggtctcctcacagtgcgtcaatctgacaactcgga ctcagctgccacctgcttatactaatagcttcaccagaggcgtgtactatcctgacaaggtgtt tagaagctccgtgctgcactctacacaggatctgtttctgccattctttagcaacgtgacctgg ttccacgccatccacgtgagcggcaccaatggcacaaagcggttcgacaatcccgtgctgcctt ttaacgatggcgtgtacttcgcctctaccgagaagagcaacattatcagaggctggatctttgg caccacactggactccaagacacagtctctgctgatcgtgaacaatgccaccaacgtggtcatc aaggtgtgcgagttccagttttgtaatgatcccttcctgggcgtgtactatcacaagaacaata agagctggatggagtccgagtttagagtgtattctagcgccaacaactgcacatttgagtacgt gagccagcctttcctgatggacctggagggcaagcagggcaatttcaagaacctgagggagttc gtgtttaagaatatcgacggctacttcaaaatctactctaagcacacccccatcaacctggtgc gcgacctgcctcagggcttcagcgccctggagcccctggtggatctgcctatcggcatcaacat cacccggtttcagacactgetggccctgcacagaagatacetgacacccggcgactcctctagc ggatggaccgccggcgctgccgcctactatgtgggctacctccagccccggaccttcctgctga agtacaacgagaatggcaccatcacagacgcagtggattgcgccctggacccccctgagcgagac aaagtgtacactgaagtcctttaccgtggagaagggcatctatcagacatccaatttcagggtg cagccaaccgagtctatcgtgcgctttcctaatatcacaaacctgtgcccatttggcgaggtgt tcaacgcaacccgcttcgccagcgtgtacgcctggaataggaagcggatcagcaactgcgtggc cgactatagcgtgctgtacaactccgcctctttcagcacctttaagtgctatggcgtgtccccc acaaagctgaatgacctgtgctttaccaacgtctacgccgattctttcgtgatcaggggcgacg aggtgcgccagatcgcccccggccagacaggcaagatcgcagactacaattataagctgccaga cgatttcaccggctgcgtgatcgcctggaacagcaacaatctggattccaaagtgggcggcaac tacaattatctgtaccggctgtttagaaagagcaatctgaagcccttcgagagggacatctcta cagaaatctaccaggccggcagcaccccttgcaatggcgtggagggctttaactgttatttccc actccagtcctacggcttccagcccacaaacggcgtgggctatcagccttaccgcgtggtggtg ctgagctttgagctgctgcacgccccagcaacagtgtgcggccccaagaagtccaccaatctgg tgaagaacaagtgcgtgaacttcaacttcaacggcctgaccggcacaggcgtgctgaccgagtc caacaagaagttcctgccatttcagcagttcggcagggacatcgcagataccacagacgccgtg cgcgacccacagaccctggagatcctggacatcacaccctgctctttcggcggcgtgagcgtga tcacacccggcaccaatacaagcaaccaggtggccgtgctgtatcagaacgtgaattgtaccga ggtgcccgtggctatccacgccgatcagctgaccccaacatggcgggtgtacagcaccggctcc aacgtcttccagacaagagccggatgcctgatcggagcagagcacgtgaacaattcctatgagt gcgacatcccaatcggcgccggcatctgtgcctcttaccagacccagacaaactctcccagaag agcccagagcgtggcctcccagtctatcatcgcctataccatgtccctgggcgccgagaacagc gtggcctactctaacaatagcatcgccatcccaaccaacttcacaatctctgtgaccacagaga tcctgcccgtgtccatgaccaagacatctgtggactgcacaatgtatatctgtggcgattctac cgagtgcagcaacctgctgctccagtacggcagcttttgtacccagctgaatagagccctgaca ggcatcgccgtggagcaggataagaacacacaggaggtgttcgcccaggtgaagcaaatctaca agacccccccctatcaaggactttggcggcttcaatttttcccagatcctgcctgatccatccaa gccttctaagcggagctttatcgaggacctgctgttcaacaaggtgaccctggccgatgccggc -continued ttcatcaagcagtatggcgattgcctgggcgacatcgcagccagggacctgatctgcgcccaga agtttaatggcctgaccgtgctgccacccctgctgacagatgagatgatcgcacagtacacaag cgccctgctggccggcaccatcacatccggatggaccttcggcgcaggagccgccctccagatc ccctttgccatgcagatggcctataggttcaacggcatcggcgtgacccagaatgtgctgtacg agaaccagaagctgatcgccaatcagtttaactccgccatcggcaagatccaggacagcctgtc ctctacagccagcgccctgggcaagctccaggatgtggtgaatcagaacgcccaggccctgaat accctggtgaagcagctgagcagcaacttcggcgccatctctagcgtgctgaatgacatcctga gccggctggacaaggtggaggcagaggtgcagatcgaccggctgatcaccggccggctccagag cctccagacctatgtgacacagcagctgatcagggccgccgagatcagggccagcgccaatctg gcagcaaccaagatgtccgagtgcgtgctgggccagtctaagagagtggacttttgtggcaagg gctatcacctgatgtccttccctcagtctgccccacacggcgtggtgtttctgcacgtgaccta cgtgcccgcccaggagaagaacttcaccacagcccctgccatctgccacgatggcaaggcccac tttccaagggagggcgtgttcgtgtccaacggcacccactggtttgtgacacagcgcaatttct acgagccccagatcatcaccacagacaacaccttcgtgagcggcaactgtgacgtggtcatcgg catcgtgaacaataccgtgtatgatccactccagcccgagctggacagctttaaggaggagctg gataagtatttcaagaatcacacctcccctgacgtggatctgggcgacatcagcggcatcaatg cctccgtggtgaacatccagaaggagatcgaccgcctgaacgaggtggctaagaatctgaacga gagcctgatcgacctccaggagctgggcaagtatgagcagtacatcaagtggccctggtacatc tggctgggcttcatcgccggcctgatcgccatcgtgatggtgaccatcatgctgtgctgtatga catcctgctgttcttgcctgaagggctgctgtagctgtggctcctgctgttaa Amino Acid Sequence of SARS-CoV-2 Δ19CT Variant(SEQ ID NO: 44; Variant)
MFVFLVLLPLVSSQCVNLTTRTQLPPAYTNSFTRGVYYPDKVFRSSVLHSTQDLFLPFFSNVTW

FHAISGTNGTKRFDNPVLPFNDGVYFASTEKSNIIRGWIFGTTLDSKTQSLLIVNNATNVVIKV

CEFQFCNDPFLGVYYHKNNKSWMESEFRVYSSANNCTFEYVSQPFLMDLEGKQGNFKNLREFVF

KNIDGYFKIYSKHTPINLVRDLPQGFSALEPLVDLPIGINITRFQTLLALHRSYLTPGDSSSGW

TAGAAAYYVGYLQPRTFLLKYNENGTITDAVDCALDPLSETKCTLKSFTVEKGIYQTSNFRVQP

TESIVRFPNITNLCPFGEVFNATRFASVYAWNRKRISNCVADYSVLYNSASFSTFKCYGVSPTK

LNDLCFTNVYADSFVIRGDEVRQIAPGQTGKIADYNYKLPDDFTGCVIAWNSNNLDSKVGGNYN

YLYRLFRKSNLKPFERDISTEIYQAGSTPCNGVKGFNCYFPLQSYGFQPTYGVGYQPYRVVVLS

FELLHAPATVCGPKKSTNLVKNKCVNFNFNGLTGTGVLTESNKKFLPFQQFGRDIADTTDAVRD

PQTLEILDITPCSFGGVSVITPGTNTSNQVAVLYQGVNCTEVPVAIHADQLTPTWRVYSTGSNV

FQTRAGCLIGAEHVNNSYECDIPIGAGIGASYQTQTNSPRRARSVASQSIIAYTMSLGAENSVA

YSNNSIAIPTNFTISVTTEILPVSMTKTSVDCTMYICGDSTECSNLLLQYGSFCTQLNRALTGI

AVEQDKNTQEVFAQVKQIYKTPPIKDFGGFNFSQILPDPSKPSKRSFIEDLLFNKVTLADAGFI

KQYGDCLGDIAARDLICAQKFNGLTVLPPLLTDEMIAQYTSALLAGTITSGWTFGAGAALQIPF

AMQMAYRFNGIGVTQNVLYENQKLIANQFNSAIGKIQDSLSSTASALGKLQDVVNQNAQALNTL

VKQLSSNFGAISSVLNDILSRLDKVEAEVQIDRLITGRLQSLQTYVTQQLIRAAEIRASANLAA

TKMSECVLGQSKRVDFCGKGYHLMSFPQSAPHGVVFLHVTYVPAQEKNFTTAPAICHDGKAHFP

REGVFVSNGTHWFVTQRNFYEPQIITTDNTFVSGNCDVVIGIVNNTVYDPLQPELDSFKEELDK

-continued

YFKNHTSPDVDLGDISGINASVVNIQKEIDRLNEVAKNLNESLIDLQELGKYEQYIKWPWYIWL

GFIAGLIAIVMVTIMLCCMTSCCSCLKGCCSCGSCC

The claimed subject matter is not to be limited in scope by the specific embodiments described herein. Indeed, various modifications of the claimed subject matter in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A replication competent recombinant rhabdovirus particle, wherein (i) the rhabdovirus glycoprotein (G) is replaced by a Severe Acute Respiratory Syndrome coronavirus 2 (SARS-CoV-2) spike (S) glycoprotein or a fragment of the SARS-CoV-2 S glycoprotein comprising the receptor binding domain thereof, and wherein (ii) the rhabdovirus particle comprises a nucleic acid molecule comprising a nucleic acid sequence encoding a reporter protein, wherein the nucleic acid sequence encoding the reporter protein is inserted between a nucleic acid sequence encoding the SARS-CoV-2 S glycoprotein or said fragment of the SARS-CoV-2 S glycoprotein, and a nucleic acid sequence encoding rhabdovirus large (L) protein.

2. The replication competent recombinant rhabdovirus particle of claim 1, wherein the reporter protein is a luciferase or a fluorescent protein.

3. The replication competent recombinant rhabdovirus particle of claim 1, wherein the recombinant rhabdovirus particle is a recombinant vesiculovirus particle.

4. The replication competent recombinant rhabdovirus particle of claim 1, wherein the recombinant rhabdovirus particle is a recombinant vesicular stomatitis virus (VSV) particle.

5. The replication competent recombinant rhabdovirus particle of claim 1, wherein:

(i) the SARS-CoV-2 S glycoprotein is a full-length SARS-CoV-2 S glycoprotein; or (ii) the fragment is a SARS-CoV-2 S glycoprotein lacking the 19 C-terminal amino acids as specified in relation to the amino acid sequence of the SARS-CoV-2 full-length S glycoprotein of SEQ ID NO: 1; or (iii) the SARS-CoV-2 S glycoprotein comprises a mutation one or more amino acid insertions, deletions, and/or substitutions listed in Tables 8 and 9, wherein the positions of said insertions, deletions, and/or substitutions are specified in relation as compared to the amino acid sequence of the SARS-CoV-2 full-length S glycoprotein of SEQ ID NO: 1.

6. The replication competent recombinant rhabdovirus particle of claim 1, wherein the recombinant rhabdovirus particle comprises a mutant rhabdovirus matrix (M) protein.

7. The replication competent recombinant rhabdovirus particle of claim 1, wherein the recombinant rhabdovirus particle is a recombinant VSV particle comprising the mutant VSV M protein which comprises a mutation at methionine 51.

8. The replication competent recombinant rhabdovirus particle of claim 7, wherein the recombinant rhabdovirus particle is a recombinant VSV particle comprising the mutant VSV M protein which comprises a mutation at methionine 51 from methionine (M) to arginine (R).

9. A method for determining the presence of a SARS-Cov-2 neutralizing antibody in a sample, the method comprising:

a) contacting the sample with a replication competent recombinant rhabdovirus particle according to claim 1;

b) after step (a), contacting the replication competent recombinant rhabdovirus particle with the target cell;

c) measuring a reporter signal in the cell after step (b); and d) comparing the reporter signal measured in step (c) with a control.

10. The method of claim 9, wherein the target cell is a Vero cell, or Vero-E6 cell.

11. The method of claim 9, further comprising adding a reporter protein substrate for obtaining the reporter signal.

12. The method of claim 11, wherein the reporter protein comprises a luciferase and the reporter protein substrate comprises Luciferin or EnduRen luciferase substrate.

13. The method of claim 9, wherein the sample is serum or plasma.

14. The method of claim 9, wherein the sample is heat-inactivated.

15. The method of claim 9, wherein the method further comprises diluting the sample by a factor of about 1:10 to about 1:320.

16. The method of claim 9, wherein the control is the reporter signal obtained with a control sample not comprising coronavirus neutralizing antibodies, and the method comprises concluding that the tested sample comprises the SARS-CoV-2 neutralizing antibodies when the reporter signal obtained in step (c) is reduced as compared to the control.

17. The method of claim 16, wherein the method comprises determining the concentration of SARS-CoV-2 neutralizing antibodies in the tested sample by comparing the reporter signal to a calibration curve determined from a serial dilution of the control sample comprising a SARS-CoV-2 neutralizing antibody, or a molecule that blocks interaction of the SARS-CoV-2 S glycoprotein with a protein with which the coronavirus S glycoprotein interacts on the target cell, or any combination thereof.

18. The method of claim 9, wherein the reporter signal is measured between about 24 to 30 hours after step (b).

19. The method of claim 9, wherein in step (a) the sample is contacted with the recombinant rhabdovirus particle for about 30 minutes at room temperature.

20. The method of claim 9, wherein the method is conducted in a high throughput format.

21. A polynucleotide encoding the replication competent recombinant rhabdovirus particle according to claim 1, wherein the polynucleotide comprises a nucleic acid sequence encoding a rhabdovirus nucleoprotein (N), a nucleic acid sequence encoding a rhabdovirus phosphoprotein (P), the nucleic acid sequence encoding the rhabdovirus L protein, the nucleic acid sequence encoding the SARS-CoV-2 S glycoprotein or said fragment of the SARS-CoV-2 S glycoprotein, and the nucleic acid sequence encoding the reporter protein inserted as specified in claim 1.

22. A kit for determining the presence of a SARS-Cov-2 neutralizing antibody in a sample comprising:

a) a replication competent recombinant rhabdovirus particle according to claim 1, or a polynucleotide encoding the replication competent recombinant rhabdovirus particle according to claim 1, wherein the polynucleotide comprises a nucleic acid sequence encoding a rhabdovirus nucleoprotein (N), a nucleic acid sequence encoding a rhabdovirus phosphoprotein (P), the nucleic acid sequence encoding the rhabdovirus L protein, the nucleic acid sequence encoding the SARS-CoV-2 S glycoprotein or said fragment of the SARS-CoV-2 S glycoprotein, and the nucleic acid sequence encoding the reporter protein inserted as specified in claim 1; and b) a target cell.

23. The kit of claim 22, further comprising c) a control sample not comprising coronavirus neutralizing antibodies; and/or d) a control sample comprising a SARS-CoV-2 neutralizing antibody, or a molecule that blocks interaction of the SARS-CoV-2 S glycoprotein with a protein with which the SARS-Cov-2 S glycoprotein interacts on the target cell, or any combination thereof; and/or e) a substrate for the reporter protein; and/or f) instructions for use.

24. The replication competent recombinant rhabdovirus particle of claim 5, wherein the mutation is selected from the group consisting of N501Y, 69-70 deletion, P681H, Y144 deletion, A570D, T716I, S982A, D1118H, K417N, E484K, D614G, A701V, L18F, D80A, D215G, 242-244 deletion, R246I, K417T, T20N, P26S, D138Y, R190S, H655Y, T1027I, S131, W152C, L452R, Q677H, A22V, S477N, N439K, H69 deletion, V70 deletion, Y453F, 1692V, and M1229I, wherein the position of said mutation is specified in relation to the amino acid sequence of the SARS-CoV-2 full-length S glycoprotein of SEQ ID NO: 1.

* * * * *

SEQUENCE LISTING

<160> NUMBER OF SEQ ID NOS: 75

<210> SEQ ID NO 1
<211> LENGTH: 1273
<212> TYPE: PRT
<213> ORGANISM: Severe acute respiratory syndrome coronavirus 2

<400> SEQUENCE: 1

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

```
Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
```

```
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095
```

Gly Thr His Trp Phe Val Thr Gln Arg Asn Phe Tyr Glu Pro Gln
1100 1105 1110

Ile Ile Thr Thr Asp Asn Thr Phe Val Ser Gly Asn Cys Asp Val
1115 1120 1125

Val Ile Gly Ile Val Asn Asn Thr Val Tyr Asp Pro Leu Gln Pro
1130 1135 1140

Glu Leu Asp Ser Phe Lys Glu Glu Leu Asp Lys Tyr Phe Lys Asn
1145 1150 1155

His Thr Ser Pro Asp Val Asp Leu Gly Asp Ile Ser Gly Ile Asn
1160 1165 1170

Ala Ser Val Val Asn Ile Gln Lys Glu Ile Asp Arg Leu Asn Glu
1175 1180 1185

Val Ala Lys Asn Leu Asn Glu Ser Leu Ile Asp Leu Gln Glu Leu
1190 1195 1200

Gly Lys Tyr Glu Gln Tyr Ile Lys Trp Pro Trp Tyr Ile Trp Leu
1205 1210 1215

Gly Phe Ile Ala Gly Leu Ile Ala Ile Val Met Val Thr Ile Met
1220 1225 1230

Leu Cys Cys Met Thr Ser Cys Cys Ser Cys Leu Lys Gly Cys Cys
1235 1240 1245

Ser Cys Gly Ser Cys Cys Lys Phe Asp Glu Asp Asp Ser Glu Pro
1250 1255 1260

Val Leu Lys Gly Val Lys Leu His Tyr Thr
1265 1270

<210> SEQ ID NO 2
<211> LENGTH: 3822
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 2
atgttcgtct tcctggtcct gctgcctctg gtctcctcac agtgcgtcaa tctgacaact 60
cggactcagc tgccacctgc ttatactaat agcttcacca gaggcgtgta ctatcctgac 120
aaggtgttta gaagctccgt gctgcactct acacaggatc tgtttctgcc attctttagc 180
aacgtgacct ggttccacgc catccacgtg agcggcacca atggcacaaa gcggttcgac 240
aatcccgtgc tgccttttaa cgatggcgtg tacttcgcct ctaccgagaa gagcaacatc 300
atcagaggct ggatctttgg caccacactg gactccaaga cacagtctct gctgatcgtg 360
aacaatgcca ccaacgtggt catcaaggtg tgcgagttcc agttttgtaa tgatcccttc 420
ctgggcgtgt actatcacaa gaacaataag agctggatgg agtccgagtt tagagtgtat 480
tctagcgcca acaactgcac atttgagtac gtgagccagc ctttcctgat ggacctggag 540
ggcaagcagg gcaatttcaa gaacctgagg gagttcgtgt ttaagaatat cgacggctac 600
ttcaaaatct actctaagca cacccccatc aacctggtgc gcgacctgcc tcagggcttc 660
agcgccctgg agcccctggt ggatctgcct atcggcatca acatcacccg gtttcagaca 720
ctgctggccc tgcacagaag ctacctgaca cccggcgact cctctagcgg atggaccgcc 780
ggcgctgccg cctactatgt gggctacctc cagccccgga ccttcctgct gaagtacaac 840
gagaatggca ccatcacaga cgcagtggat tgcgccctgg accccctgag cgagacaaag 900

-continued tgtacactga agtcctttac cgtggagaag ggcatctatc agacatccaa tttcagggtg 960
cagccaaccg agtctatcgt gcgctttcct aatatcacaa acctgtgccc atttggcgag 1020
gtgttcaacg caacccgctt cgccagcgtg tacgcctgga ataggaagcg gatcagcaac 1080
tgcgtggccg actatagcgt gctgtacaac tccgcctctt tcagcacctt taagtgctat 1140
ggcgtgtccc ccacaaagct gaatgacctg tgctttacca acgtctacgc cgattctttc 1200
gtgatcaggg gcgacgaggt gcgccagatc gccccccggcc agacaggcaa gatcgcagac 1260
tacaattata agctgccaga cgatttcacc ggctgcgtga tcgcctggaa cagcaacaat 1320
ctggattcca aagtgggcgg caactacaat tatctgtacc ggctgtttag aaagagcaat 1380
ctgaagccct tcgagaggga catctctaca gaaatctacc aggccggcag caccccttgc 1440
aatggcgtgg agggctttaa ctgttatttc ccactccagt cctacggctt ccagcccaca 1500
aacggcgtgg gctatcagcc ttaccgcgtg gtggtgctga gctttgagct gctgcacgcc 1560
ccagcaacag tgtgcggccc caagaagtcc accaatctgg tgaagaacaa gtgcgtgaac 1620
ttcaacttca acggcctgac cggcacaggc gtgctgaccg agtccaacaa gaagttcctg 1680
ccatttcagc agttcggcag ggacatcgca gataccacag acgccgtgcg cgacccacag 1740
accctggaga tcctggacat cacaccctgc tctttcggcg gcgtgagcgt gatcacaccc 1800
ggcaccaata caagcaacca ggtggccgtg ctgtatcagg acgtgaattg taccgaggtg 1860
cccgtggcta tccacgccga tcagctgacc ccaacatggc gggtgtacag caccggctcc 1920
aacgtcttcc agacaagagc cggatgcctg atcggagcag agcacgtgaa caattcctat 1980
gagtgcgaca tcccaatcgg cgccggcatc tgtgcctctt accagaccca gacaaactct 2040
cccagaagag cccggagcgt ggcctcccag tctatcatcg cctataccat gtccctgggc 2100
gccgagaaca gcgtggccta ctctaacaat agcatcgcca tcccaaccaa cttcacaatc 2160
tctgtgacca cagagatcct gcccgtgtcc atgaccaaga catctgtgga ctgcacaatg 2220
tatatctgtg gcgattctac cgagtgcagc aacctgctgc tccagtacgg cagcttttgt 2280
acccagctga atagagccct gacaggcatc gccgtggagc aggataagaa cacacaggag 2340
gtgttcgccc aggtgaagca aatctacaag accccccccta tcaaggactt tggcggcttc 2400
aatttttccc agatcctgcc tgatccatcc aagccttcta agcggagctt tatcgaggac 2460
ctgctgttca acaaggtgac cctggccgat gccggcttca tcaagcagta tggcgattgc 2520
ctgggcgaca tcgcagccag ggacctgatc tgcgcccaga agtttaatgg cctgaccgtg 2580
ctgccacccc tgctgacaga tgagatgatc gcacagtaca caagcgccct gctggccggc 2640
accatcacat ccggatggac cttcggcgca ggagccgccc tccagatccc ctttgccatg 2700
cagatggcct ataggttcaa cggcatcggc gtgacccaga atgtgctgta cgagaaccag 2760
aagctgatcg ccaatcagtt taactccgcc atcggcaaga tccaggacag cctgtcctct 2820
acagccagcg ccctgggcaa gctccaggat gtggtgaatc agaacgccca ggccctgaat 2880
accctggtga agcagctgag cagcaacttc ggcgccatct ctagcgtgct gaatgacatc 2940
ctgagccggc tggacaaggt ggaggcagag gtgcagatcg accggctgat caccggccgg 3000
ctccagagcc tccagaccta tgtgacacag cagctgatca gggccgccga gatcagggcc 3060
agcgccaatc tggcagcaac caagatgtcc gagtgcgtgc tgggccagtc taagagagtg 3120
gacttttgtg gcaagggcta tcacctgatg tccttccctc agtctgcccc acacggcgtg 3180
gtgtttctgc acgtgaccta cgtgcccgcc caggagaaga acttcaccac agcccctgcc 3240
atctgccacg atggcaaggc ccactttcca agggagggcg tgttcgtgtc caacggcacc 3300

```
cactggtttg tgacacagcg caatttctac gagccccaga tcatcaccac agacaacacc   3360

ttcgtgagcg gcaactgtga cgtggtcatc ggcatcgtga acaataccgt gtatgatcca   3420

ctccagcccg agctggacag ctttaaggag gagctggata agtatttcaa gaatcacacc   3480

tcccctgacg tggatctggg cgacatcagc ggcatcaatg cctccgtggt gaacatccag   3540

aaggagatcg accgcctgaa cgaggtggct aagaatctga acgagagcct gatcgacctc   3600

caggagctgg gcaagtatga gcagtacatc aagtggccct ggtacatctg gctgggcttc   3660

atcgccggcc tgatcgccat cgtgatggtg accatcatgc tgtgctgtat gacatcctgc   3720

tgttcttgcc tgaagggctg ctgtagctgt ggctcctgct gtaagtttga cgaggatgac   3780

tctgaacctg tgctgaaggg cgtgaagctg cattacacct aa                      3822
```

<210> SEQ ID NO 3
<211> LENGTH: 1254
<212> TYPE: PRT
<213> ORGANISM: Severe acute respiratory syndrome coronavirus 2

<400> SEQUENCE: 3

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
```

-continued

```
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700
```

-continued

```
Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110
```

-continued

```
Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys
    1250
```

<210> SEQ ID NO 4
<211> LENGTH: 3765
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4

```
atgttcgtct tcctggtcct gctgcctctg gtctcctcac agtgcgtcaa tctgacaact     60

cggactcagc tgccacctgc ttatactaat agcttcacca gaggcgtgta ctatcctgac    120

aaggtgttta gaagctccgt gctgcactct acacaggatc tgtttctgcc attctttagc    180

aacgtgacct ggttccacgc catccacgtg agcggcacca atggcacaaa gcggttcgac    240

aatcccgtgc tgccttttaa cgatggcgtg tacttcgcct ctaccgagaa gagcaacatc    300

atcagaggct ggatctttgg caccacactg gactccaaga cacagtctct gctgatcgtg    360

aacaatgcca ccaacgtggt catcaaggtg tgcgagttcc agttttgtaa tgatcccttc    420

ctgggcgtgt actatcacaa gaacaataag agctggatgg agtccgagtt tagagtgtat    480

tctagcgcca acaactgcac atttgagtac gtgagccagc ctttcctgat ggacctggag    540

ggcaagcagg gcaatttcaa gaacctgagg gagttcgtgt ttaagaatat cgacggctac    600

ttcaaaatct actctaagca cacccccatc aacctggtgc gcgacctgcc tcagggcttc    660

agcgccctgg agcccctggt ggatctgcct atcggcatca acatcacccg gtttcagaca    720

ctgctggccc tgcacagaag ctacctgaca cccggcgact cctctagcgg atggaccgcc    780

ggcgctgccg cctactatgt gggctacctc cagccccgga ccttcctgct gaagtacaac    840

gagaatggca ccatcacaga cgcagtggat tgcgccctgg acccccctgag cgagacaaag    900

tgtacactga agtcctttac cgtggagaag ggcatctatc agacatccaa tttcagggtg    960

cagccaaccg agtctatcgt gcgctttcct aatatcacaa acctgtgccc atttggcgag   1020

gtgttcaacg caacccgctt cgccagcgtg tacgcctgga ataggaagcg gatcagcaac   1080

tgcgtggccg actatagcgt gctgtacaac tccgcctctt tcagcacctt taagtgctat   1140
```

-continued ggcgtgtccc ccacaaagct gaatgacctg tgctttacca acgtctacgc cgattctttc 1200
gtgatcaggg gcgacgaggt gcgccagatc gcccccggcc agacaggcaa gatcgcagac 1260
tacaattata agctgccaga cgatttcacc ggctgcgtga tcgcctggaa cagcaacaat 1320
ctggattcca aagtgggcgg caactacaat tatctgtacc ggctgtttag aaagagcaat 1380
ctgaagccct tcgagaggga catctctaca gaaatctacc aggccggcag cacccccttgc 1440
aatggcgtgg agggctttaa ctgttatttc ccactccagt cctacggctt ccagcccaca 1500
aacggcgtgg gctatcagcc ttaccgcgtg gtggtgctga gctttgagct gctgcacgcc 1560
ccagcaacag tgtgcggccc caagaagtcc accaatctgg tgaagaacaa gtgcgtgaac 1620
ttcaacttca acggcctgac cggcacaggc gtgctgaccg agtccaacaa gaagttcctg 1680
ccatttcagc agttcggcag ggacatcgca gataccacag acgccgtgcg cgacccacag 1740
accctggaga tcctggacat cacaccctgc tctttcggcg gcgtgagcgt gatcacaccc 1800
ggcaccaata caagcaacca ggtggccgtg ctgtatcagg acgtgaattg taccgaggtg 1860
cccgtggcta tccacgccga tcagctgacc ccaacatggc gggtgtacag caccggctcc 1920
aacgtcttcc agacaagagc cggatgcctg atcggagcag agcacgtgaa caattcctat 1980
gagtgcgaca tcccaatcgg cgccggcatc tgtgcctctt accagaccca gacaaactct 2040
cccagaagag cccggagcgt ggcctcccag tctatcatcg cctataccat gtccctgggc 2100
gccgagaaca gcgtggccta ctctaacaat agcatcgcca tcccaaccaa cttcacaatc 2160
tctgtgacca cagagatcct gcccgtgtcc atgaccaaga catctgtgga ctgcacaatg 2220
tatatctgtg gcgattctac cgagtgcagc aacctgctgc tccagtacgg cagcttttgt 2280
acccagctga atagagccct gacaggcatc gccgtggagc aggataagaa cacacaggag 2340
gtgttcgccc aggtgaagca aatctacaag acccccccta tcaaggactt tggcggcttc 2400
aatttttccc agatcctgcc tgatccatcc aagccttcta agcggagctt tatcgaggac 2460
ctgctgttca acaaggtgac cctggccgat gccggcttca tcaagcagta tggcgattgc 2520
ctgggcgaca tcgcagccag ggacctgatc tgcgcccaga agtttaatgg cctgaccgtg 2580
ctgccacccc tgctgacaga tgagatgatc gcacagtaca caagcgccct gctggccggc 2640
accatcacat ccggatggac cttcggcgca ggagccgccc tccagatccc ctttgccatg 2700
cagatggcct ataggttcaa cggcatcggc gtgacccaga atgtgctgta cgagaaccag 2760
aagctgatcg ccaatcagtt taactccgcc atcggcaaga tccaggacag cctgtcctct 2820
acagccagcg ccctgggcaa gctccaggat gtggtgaatc agaacgccca ggccctgaat 2880
accctggtga agcagctgag cagcaacttc ggcgccatct ctagcgtgct gaatgacatc 2940
ctgagccggc tggacaaggt ggaggcagag gtgcagatcg accggctgat caccggccgg 3000
ctccagagcc tccagaccta tgtgacacag cagctgatca gggccgccga gatcagggcc 3060
agcgccaatc tggcagcaac caagatgtcc gagtgcgtgc tgggccagtc taagagagtg 3120
gacttttgtg gcaagggcta tcacctgatg tccttccctc agtctgcccc acacggcgtg 3180
gtgtttctgc acgtgaccta cgtgcccgcc caggagaaga acttcaccac agcccctgcc 3240
atctgccacg atggcaaggc ccactttcca agggagggcg tgttcgtgtc caacggcacc 3300
cactggtttg tgacacagcg caatttctac gagccccaga tcatcaccac agacaacacc 3360
ttcgtgagcg gcaactgtga cgtggtcatc ggcatcgtga acaataccgt gtatgatcca 3420
ctccagcccg agctggacag ctttaaggag gagctggata agtatttcaa gaatcacacc 3480

```
tcccctgacg tggatctggg cgacatcagc ggcatcaatg cctccgtggt gaacatccag   3540

aaggagatcg accgcctgaa cgaggtggct aagaatctga acgagagcct gatcgacctc   3600

caggagctgg gcaagtatga gcagtacatc aagtggccct ggtacatctg gctgggcttc   3660

atcgccggcc tgatcgccat cgtgatggtg accatcatgc tgtgctgtat gacatcctgc   3720

tgttcttgcc tgaagggctg ctgtagctgt ggctcctgct gttaa                   3765


<210> SEQ ID NO 5
<211> LENGTH: 1258
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300
```

-continued

```
Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
```

```
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                1020

Leu Ala  Ala Thr Lys Met Ser  Glu Cys Val Leu Gly  Gln Ser Lys
    1025                 1030                1035

Arg Val  Asp Phe Cys Gly Lys  Gly Tyr His Leu Met  Ser Phe Pro
    1040                 1045                1050

Gln Ser  Ala Pro His Gly Val  Val Phe Leu His Val  Thr Tyr Val
    1055                 1060                1065

Pro Ala  Gln Glu Lys Asn Phe  Thr Thr Ala Pro Ala  Ile Cys His
    1070                 1075                1080

Asp Gly  Lys Ala His Phe Pro  Arg Glu Gly Val Phe  Val Ser Asn
    1085                 1090                1095

Gly Thr  His Trp Phe Val Thr  Gln Arg Asn Phe Tyr  Glu Pro Gln
    1100                 1105                1110

Ile Ile  Thr Thr Asp Asn Thr  Phe Val Ser Gly Asn  Cys Asp Val
    1115                 1120                1125

Val Ile  Gly Ile Val Asn Asn  Thr Val Tyr Asp Pro  Leu Gln Pro
    1130                 1135                1140
```

```
Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Lys Leu Lys  His Thr Lys Lys Arg  Gln Ile Tyr
    1235                 1240                 1245

Thr Asp  Ile Glu Met Asn Arg  Leu Gly Lys
    1250                 1255
```

<210> SEQ ID NO 6
<211> LENGTH: 3777
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

```
atgttcgtct tcctggtcct gctgcctctg gtctcctcac agtgcgtcaa tctgacaact     60

cggactcagc tgccacctgc ttatactaat agcttcacca gaggcgtgta ctatcctgac    120

aaggtgttta gaagctccgt gctgcactct acacaggatc tgtttctgcc attctttagc    180

aacgtgacct ggttccacgc catccacgtg agcggcacca atggcacaaa gcggttcgac    240

aatcccgtgc tgccttttaa cgatggcgtg tacttcgcct ctaccgagaa gagcaacatc    300

atcagaggct ggatctttgg caccacactg gactccaaga cacagtctct gctgatcgtg    360

aacaatgcca ccaacgtggt catcaaggtg tgcgagttcc agttttgtaa tgatcccttc    420

ctgggcgtgt actatcacaa gaacaataag agctggatgg agtccgagtt tagagtgtat    480

tctagcgcca acaactgcac atttgagtac gtgagccagc ctttcctgat ggacctggag    540

ggcaagcagg gcaatttcaa gaacctgagg gagttcgtgt ttaagaatat cgacggctac    600

ttcaaaatct actctaagca caccccccatc aacctggtgc gcgacctgcc tcagggcttc    660

agcgccctgg agcccctggt ggatctgcct atcggcatca acatcacccg gtttcagaca    720

ctgctggccc tgcacagaag ctacctgaca cccggcgact cctctagcgg atggaccgcc    780

ggcgctgccg cctactatgt gggctacctc cagccccgga ccttcctgct gaagtacaac    840

gagaatggca ccatcacaga cgcagtggat tgcgccctgg accccctgag cgagacaaag    900

tgtacactga agtcctttac cgtggagaag ggcatctatc agacatccaa tttcagggtg    960

cagccaaccg agtctatcgt gcgctttcct aatatcacaa acctgtgccc atttggcgag   1020

gtgttcaacg caacccgctt cgccagcgtg tacgcctgga ataggaagcg gatcagcaac   1080

tgcgtggccg actatagcgt gctgtacaac tccgcctctt tcagcacctt taagtgctat   1140

ggcgtgtccc ccacaaagct gaatgacctg tgctttacca acgtctacgc cgattctttc   1200

gtgatcaggg gcgacgaggt gcgccagatc gcccccggcc agacaggcaa gatcgcagac   1260
```

-continued tacaattata agctgccaga cgatttcacc ggctgcgtga tcgcctggaa cagcaacaat 1320
ctggattcca aagtgggcgg caactacaat tatctgtacc ggctgtttag aaagagcaat 1380
ctgaagccct tcgagaggga catctctaca gaaatctacc aggccggcag caccccttgc 1440
aatggcgtgg agggctttaa ctgttatttc ccactccagt cctacggctt ccagcccaca 1500
aacggcgtgg gctatcagcc ttaccgcgtg gtggtgctga gctttgagct gctgcacgcc 1560
ccagcaacag tgtgcggccc caagaagtcc accaatctgg tgaagaacaa gtgcgtgaac 1620
ttcaacttca acggcctgac cggcacaggc gtgctgaccg agtccaacaa gaagttcctg 1680
ccatttcagc agttcggcag ggacatcgca gataccacag acgccgtgcg cgacccacag 1740
accctggaga tcctggacat cacaccctgc tctttcggcg gcgtgagcgt gatcacaccc 1800
ggcaccaata caagcaacca ggtggccgtg ctgtatcagg acgtgaattg taccgaggtg 1860
cccgtggcta tccacgccga tcagctgacc ccaacatggc gggtgtacag caccggctcc 1920
aacgtcttcc agacaagagc cggatgcctg atcggagcag agcacgtgaa caattcctat 1980
gagtgcgaca tcccaatcgg cgccggcatc tgtgcctctt accagaccca gacaaactct 2040
cccagaagag cccggagcgt ggcctcccag tctatcatcg cctataccat gtccctgggc 2100
gccgagaaca gcgtggccta ctctaacaat agcatcgcca tcccaaccaa cttcacaatc 2160
tctgtgacca cagagatcct gcccgtgtcc atgaccaaga catctgtgga ctgcacaatg 2220
tatatctgtg gcgattctac cgagtgcagc aacctgctgc tccagtacgg cagcttttgt 2280
acccagctga atagagccct gacaggcatc gccgtggagc aggataagaa cacacaggag 2340
gtgttcgccc aggtgaagca aatctacaag accccccccta tcaaggactt tggcggcttc 2400
aatttttccc agatcctgcc tgatccatcc aagccttcta agcggagctt tatcgaggac 2460
ctgctgttca acaaggtgac cctggccgat gccggcttca tcaagcagta tggcgattgc 2520
ctgggcgaca tcgcagccag ggacctgatc tgcgcccaga agtttaatgg cctgaccgtg 2580
ctgccacccc tgctgacaga tgagatgatc gcacagtaca caagcgccct gctggccggc 2640
accatcacat ccggatggac cttcggcgca ggagccgccc tccagatccc ctttgccatg 2700
cagatggcct ataggttcaa cggcatcggc gtgacccaga atgtgctgta cgagaaccag 2760
aagctgatcg ccaatcagtt taactccgcc atcggcaaga tccaggacag cctgtcctct 2820
acagccagcg ccctgggcaa gctccaggat gtggtgaatc agaacgccca ggccctgaat 2880
accctggtga agcagctgag cagcaacttc ggcgccatct ctagcgtgct gaatgacatc 2940
ctgagccggc tggacaaggt ggaggcagag gtgcagatcg accggctgat caccggccgg 3000
ctccagagcc tccagaccta tgtgacacag cagctgatca gggccgccga gatcagggcc 3060
agcgccaatc tggcagcaac caagatgtcc gagtgcgtgc tgggccagtc taagagagtg 3120
gacttttgtg gcaagggcta tcacctgatg tccttccctc agtctgcccc acacggcgtg 3180
gtgtttctgc acgtgaccta cgtgcccgcc caggagaaga acttcaccac agcccctgcc 3240
atctgccacg atggcaaggc ccactttcca agggagggcg tgttcgtgtc caacggcacc 3300
cactggtttg tgacacagcg caatttctac gagccccaga tcatcaccac agacaacacc 3360
ttcgtgagcg gcaactgtga cgtggtcatc ggcatcgtga acaataccgt gtatgatcca 3420
ctccagcccg agctggacag ctttaaggag gagctggata agtatttcaa gaatcacacc 3480
tcccctgacg tggatctggg cgacatcagc ggcatcaatg cctccgtggt gaacatccag 3540
aaggagatcg accgcctgaa cgaggtggct aagaatctga acgagagcct gatcgacctc 3600
caggagctgg gcaagtatga gcagtacatc aagtggccct ggtacatctg gctgggcttc 3660
atcgccggcc tgatcgccat cgtgatggtg accatcatgc tgtgctgtat gaaattaaag 3720
cacaccaaga aaagacagat ttatacagac atagagatga accgacttgg aaagtaa 3777

<210> SEQ ID NO 7
<211> LENGTH: 237
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

Met Ser Ser Leu Lys Lys Ile Leu Gly Leu Lys Gly Lys Gly Lys Lys
1 5 10 15

Ser Lys Lys Leu Gly Ile Ala Pro Pro Pro Tyr Glu Glu Asp Thr Ser
20 25 30

Met Glu Tyr Ala Pro Ser Ala Pro Ile Asp Lys Ser Tyr Phe Gly Val
35 40 45

Asp Glu Arg Asp Thr His Asp Pro Asn Gln Leu Arg Tyr Glu Lys Ser
50 55 60

Phe Phe Thr Val Lys Met Thr Val Arg Ser Asn Arg Pro Phe Arg Thr
65 70 75 80

Tyr Ser Asp Val Ala Ala Ala Val Ser His Trp Asp His Met Tyr Ile
85 90 95

Gly Met Ala Gly Lys Arg Pro Phe Tyr Lys Ile Leu Ala Phe Leu Gly
100 105 110

Ser Ser Asn Leu Lys Ala Thr Pro Ala Val Leu Ala Asp Gln Gly Gln
115 120 125

Pro Glu Tyr His Ala His Cys Glu Gly Arg Ala Tyr Leu Pro His Arg
130 135 140

Met Gly Lys Thr Pro Pro Met Leu Asn Val Pro Glu His Phe Arg Arg
145 150 155 160

Pro Phe Asn Ile Gly Leu Tyr Lys Gly Thr Ile Glu Leu Thr Met Thr
165 170 175

Ile Tyr Asp Asp Glu Ser Leu Glu Ala Ala Pro Met Ile Trp Asp His
180 185 190

Phe Asn Ser Ser Lys Phe Ser Asp Phe Arg Glu Lys Ala Leu Met Phe
195 200 205

Gly Leu Ile Val Glu Glu Glu Ala Ser Gly Ala Trp Val Leu Asp Ser
210 215 220

Val Arg His Ser Lys Trp Ala Ser Leu Ala Ser Ser Phe
225 230 235

<210> SEQ ID NO 8
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8
atgagttcct taaagaagat tctcggtctg aaggggaaag gtaagaaatc taagaaatta 60
gggatcgcac caccccctta tgaagaggac actagcatgg agtatgctcc gagcgctcca 120
attgacaaat cctattttgg agttgacgag cgagacacct atgatccgaa tcaattaaga 180

-continued

```
tatgagaaat tcttctttac agtgaaaatg acggttagat ctaatcgtcc gttcagaaca    240

tactcagatg tggcagccgc tgtatcccat tgggatcaca tgtacatcgg aatggcaggg    300

aaacgtccct tctacaaaat cttggctttt ttgggttctt ctaatctaaa ggccactcca    360

gcggtattgg cagatcaagg tcaaccagag tatcacgctc actgcgaagg cagggcttat    420

ttgccacata ggatggggaa gacccctccc atgctcaatg taccagagca cttcagaaga    480

ccattcaata taggtcttta caagggaacg attgagctca caatgaccat ctacgatgat    540

gagtcactgg aagcagctcc tatgatctgg gatcatttca attcttccaa attttctgat    600

ttcagagaga aggccttaat gtttggcctg attgtcgaga aaaaggcatc tggagcgtgg    660

gtcctggact ctatcggcca cttcaaatga                                     690


<210> SEQ ID NO 9
<211> LENGTH: 237
<212> TYPE: PRT
<213> ORGANISM: Vesicular stomatitis virus

<400> SEQUENCE: 9

Met Ser Ser Leu Lys Lys Ile Leu Gly Leu Lys Gly Lys Gly Lys Lys
1               5                   10                  15

Ser Lys Lys Leu Gly Ile Ala Pro Pro Pro Tyr Glu Glu Asp Thr Ser
            20                  25                  30

Met Glu Tyr Ala Pro Ser Ala Pro Ile Asp Lys Ser Tyr Phe Gly Val
        35                  40                  45

Asp Glu Met Asp Thr His Asp Pro Asn Gln Leu Arg Tyr Glu Lys Ser
    50                  55                  60

Phe Phe Thr Val Lys Met Thr Val Arg Ser Asn Arg Pro Phe Arg Thr
65                  70                  75                  80

Tyr Ser Asp Val Ala Ala Ala Val Ser His Trp Asp His Met Tyr Ile
                85                  90                  95

Gly Met Ala Gly Lys Arg Pro Phe Tyr Lys Ile Leu Ala Phe Leu Gly
            100                 105                 110

Ser Ser Asn Leu Lys Ala Thr Pro Ala Val Leu Ala Asp Gln Gly Gln
        115                 120                 125

Pro Glu Tyr His Ala His Cys Glu Gly Arg Ala Tyr Leu Pro His Arg
    130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Ile Glu Leu Thr Met Thr
                165                 170                 175

Ile Tyr Asp Asp Glu Ser Leu Glu Ala Ala Pro Met Ile Trp Asp His
            180                 185                 190

Phe Asn Ser Ser Lys Phe Ser Asp Phe Arg Glu Lys Ala Leu Met Phe
        195                 200                 205

Gly Leu Ile Val Glu Glu Glu Ala Ser Gly Ala Trp Val Leu Asp Ser
    210                 215                 220

Val Arg His Ser Lys Trp Ala Ser Leu Ala Ser Ser Phe
225                 230                 235


<210> SEQ ID NO 10
<211> LENGTH: 690
<212> TYPE: DNA
<213> ORGANISM: Vesicular stomatitis virus

<400> SEQUENCE: 10
```

```
atgagttcct taaagaagat tctcggtctg aaggggaaag gtaagaaatc taagaaatta     60

gggatcgcac cacccctta tgaagaggac actagcatgg agtatgctcc gagcgctcca    120

attgacaaat cctattttgg agttgacgag atggacacct atgatccgaa tcaattaaga    180

tatgagaaat tcttctttac agtgaaaatg acggttagat ctaatcgtcc gttcagaaca    240

tactcagatg tggcagccgc tgtatcccat tgggatcaca tgtacatcgg aatggcaggg    300

aaacgtccct tctacaaaat cttggctttt ttgggttctt ctaatctaaa ggccactcca    360

gcggtattgg cagatcaagg tcaaccagag tatcacgctc actgcgaagg cagggcttat    420

ttgccacata ggatggggaa gacccctccc atgctcaatg taccagagca cttcagaaga    480

ccattcaata taggtcttta caagggaacg attgagctca caatgaccat ctacgatgat    540

gagtcactgg aagcagctcc tatgatctgg gatcatttca attcttccaa attttctgat    600

ttcagagaga aggccttaat gtttggcctg attgtcgaga aaaaggcatc tggagcgtgg    660

gtcctggact ctatcggcca cttcaaatga                                     690
```

```
<210> SEQ ID NO 11
<211> LENGTH: 7
<212> TYPE: DNA
<213> ORGANISM: Vesicular stomatitis virus

<400> SEQUENCE: 11

cactatg                                                                7


<210> SEQ ID NO 12
<211> LENGTH: 7
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12

caccatg                                                                7


<210> SEQ ID NO 13
<211> LENGTH: 1185
<212> TYPE: PRT
<213> ORGANISM: Severe acute respiratory syndrome coronavirus

<400> SEQUENCE: 13

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
```

-continued

```
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540
```

-continued

Phe Gln Pro Phe Gln Gln Phe Gly Arg Asp Val Ser Asp Phe Thr Asp
545 550 555 560

Ser Val Arg Asp Pro Lys Thr Ser Glu Ile Leu Asp Ile Ser Pro Cys
565 570 575

Ser Phe Gly Gly Val Ser Val Ile Thr Pro Gly Thr Asn Ala Ser Ser
580 585 590

Glu Val Ala Val Leu Tyr Gln Asp Val Asn Cys Thr Asp Val Ser Thr
595 600 605

Ala Ile His Ala Asp Gln Leu Thr Pro Ala Trp Arg Ile Tyr Ser Thr
610 615 620

Gly Asn Asn Val Asn Phe Ser Ile Ser Ile Thr Thr Glu Val Met Pro
625 630 635 640

Val Ser Met Ala Lys Thr Ser Val Asp Cys Asn Met Tyr Ile Cys Gly
645 650 655

Asp Ser Thr Glu Cys Ala Asn Leu Leu Leu Gln Tyr Gly Ser Phe Cys
660 665 670

Thr Gln Leu Asn Arg Ala Leu Ser Gly Ile Ala Ala Glu Gln Asp Arg
675 680 685

Asn Thr Arg Glu Val Phe Ala Gln Val Lys Gln Met Tyr Lys Thr Pro
690 695 700

Thr Leu Lys Tyr Phe Gly Gly Phe Asn Phe Ser Gln Ile Leu Pro Asp
705 710 715 720

Pro Leu Lys Pro Thr Lys Arg Ser Phe Ile Glu Asp Leu Leu Phe Asn
725 730 735

Lys Val Thr Leu Ala Asp Ala Gly Phe Met Lys Gln Tyr Gly Glu Cys
740 745 750

Leu Gly Asp Ile Asn Ala Arg Asp Leu Ile Cys Ala Gln Lys Phe Asn
755 760 765

Gly Leu Thr Val Leu Pro Pro Leu Leu Thr Asp Asp Met Ile Ala Ala
770 775 780

Tyr Thr Ala Ala Leu Val Ser Gly Thr Ala Thr Ala Gly Trp Thr Phe
785 790 795 800

Gly Ala Gly Ala Ala Leu Gln Ile Pro Phe Ala Met Gln Met Ala Tyr
805 810 815

Arg Phe Asn Gly Ile Gly Val Thr Gln Asn Val Leu Tyr Glu Asn Gln
820 825 830

Lys Gln Ile Ala Asn Gln Phe Asn Lys Ala Ile Ser Gln Ile Gln Glu
835 840 845

Ser Leu Thr Thr Thr Ser Thr Ala Leu Gly Lys Leu Gln Asp Val Val
850 855 860

Asn Gln Asn Ala Gln Ala Leu Asn Thr Leu Val Lys Gln Leu Ser Ser
865 870 875 880

Asn Phe Gly Ala Ile Ser Ser Val Leu Asn Asp Ile Leu Ser Arg Leu
885 890 895

Asp Lys Val Glu Ala Glu Val Gln Ile Asp Arg Leu Ile Thr Gly Arg
900 905 910

Leu Gln Ser Leu Gln Thr Tyr Val Thr Gln Gln Leu Ile Arg Ala Ala
915 920 925

Glu Ile Arg Ala Ser Ala Asn Leu Ala Ala Thr Lys Met Ser Glu Cys
930 935 940

Val Leu Gly Gln Ser Lys Arg Val Asp Phe Cys Gly Lys Gly Tyr His
945 950 955 960

-continued

```
Leu Met Ser Phe Pro Gln Ala Ala Pro His Gly Val Val Phe Leu His
                965                 970                 975

Val Thr Tyr Val Pro Ser Gln Glu Arg Asn Phe Thr Thr Ala Pro Ala
            980                 985                 990

Ile Cys His Glu Gly Lys Ala Tyr  Phe Pro Arg Glu Gly  Val Phe Val
        995                 1000                 1005

Phe Asn  Gly Thr Ser Trp Phe  Ile Thr Gln Arg Asn  Phe Phe Ser
    1010                 1015                 1020

Pro Gln  Ile Ile Thr Thr Asp  Asn Thr Phe Val Ser  Gly Asn Cys
    1025                 1030                 1035

Asp Val  Val Ile Gly Ile Ile  Asn Asn Thr Val Tyr  Asp Pro Leu
    1040                 1045                 1050

Gln Pro  Glu Leu Asp Ser Phe  Lys Glu Glu Leu Asp  Lys Tyr Phe
    1055                 1060                 1065

Lys Asn  His Thr Ser Pro Asp  Val Asp Leu Gly Asp  Ile Ser Gly
    1070                 1075                 1080

Ile Asn  Ala Ser Val Val Asn  Ile Gln Lys Glu Ile  Asp Arg Leu
    1085                 1090                 1095

Asn Glu  Val Ala Lys Asn Leu  Asn Glu Ser Leu Ile  Asp Leu Gln
    1100                 1105                 1110

Glu Leu  Gly Lys Tyr Glu Gln  Tyr Ile Lys Trp Pro  Trp Tyr Val
    1115                 1120                 1125

Trp Leu  Gly Phe Ile Ala Gly  Leu Ile Ala Ile Val  Met Val Thr
    1130                 1135                 1140

Ile Leu  Leu Cys Cys Met Thr  Ser Cys Cys Ser Cys  Leu Lys Gly
    1145                 1150                 1155

Ala Cys  Ser Cys Gly Ser Cys  Cys Lys Phe Asp Glu  Asp Asp Ser
    1160                 1165                 1170

Glu Pro  Val Leu Lys Gly Val  Lys Leu His Tyr Thr
    1175                 1180                 1185


<210> SEQ ID NO 14
<211> LENGTH: 316
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
```

-continued

```
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Ser Gly Gly Gly Gly
145                 150                 155                 160

Met Ser Lys Gly Glu Glu Leu Phe Thr Gly Val Val Pro Ile Leu Val
                165                 170                 175

Glu Leu Asp Gly Asp Val Asn Gly His Lys Phe Ser Val Arg Gly Glu
            180                 185                 190

Gly Glu Gly Asp Ala Thr Ile Gly Lys Leu Thr Leu Lys Phe Ile Cys
        195                 200                 205

Thr Thr Gly Lys Leu Pro Val Pro Trp Pro Thr Leu Val Thr Thr Leu
    210                 215                 220

Thr Tyr Gly Val Gln Cys Phe Ser Arg Tyr Pro Asp His Met Lys Arg
225                 230                 235                 240

His Asp Phe Phe Lys Ser Ala Met Pro Glu Gly Tyr Val Gln Glu Arg
                245                 250                 255

Thr Ile Ser Phe Lys Asp Asp Gly Lys Tyr Lys Thr Arg Ala Val Val
            260                 265                 270

Lys Phe Glu Gly Asp Thr Leu Val Asn Arg Ile Glu Leu Lys Gly Thr
        275                 280                 285

Asp Phe Lys Glu Asp Gly Asn Ile Leu Gly His Lys Leu Glu Tyr Asn
    290                 295                 300

Phe Asn Ser His Asn Val Tyr Ile Thr Ala Asp Lys
305                 310                 315


<210> SEQ ID NO 15
<211> LENGTH: 4093
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15

agatcttcaa tattggccat tagccatatt attcattggt tatatagcat aaatcaatat     60

tggctattgg ccattgcata cgttgtatct atatcataat atgtacattt atattggctc    120

atgtccaata tgaccgccat gttggcattg attattgact agttattaat agtaatcaat    180

tacggggtca ttagttcata gcccatatat ggagttccgc gttacataac ttacggtaaa    240

tggcccgcct ggctgaccgc ccaacgaccc ccgcccattg acgtcaataa tgacgtatgt    300

tcccatagta acgccaatag ggactttcca ttgacgtcaa tgggtggagt atttacggta    360

aactgcccac ttggcagtac atcaagtgta tcatatgcca agtccgcccc ctattgacgt    420

caatgacggt aaatggcccg cctggcatta tgcccagtac atgaccttac gggactttcc    480

tacttggcag tacatctacg tattagtcat cgctattacc atggtgatgc ggttttggca    540

gtacaccaat gggcgtggat agcggtttga ctcacgggga tttccaagtc tccaccccat    600

tgacgtcaat gggagtttgt tttggcacca aaatcaacgg gactttccaa aatgtcgtaa    660

taaccccgcc ccgttgacgc aaatgggcgg taggcgtgta cggtgggagg tctatataag    720

cagagctcgt ttagtgaacc gtcagatcac tagaagcttt attgcggtag tttatcacag    780

ttaaattgct aacgcagtca gtgcttctga cacaacagtc tcgaacttaa gctgcagaag    840

ttggtcgtga ggcactgggc aggtaagtat caaggttaca agacaggttt aaggagacca    900
```

-continued

```
atagaaactg ggcttgtcga gacagagaag actcttgcgt ttctgatagg cacctattgg    960
tcttactgac atccactttg cctttctctc cacaggtgtc cactcccagt tcaattacag   1020
ctcttaaggc tagagtactt aatacgactc actataggct agccaccatg gcttccaagg   1080
tgtacgaccc cgagcaacgc aaacgcatga tcactgggcc tcagtggtgg gctcgctgca   1140
agcaaatgaa cgtgctggac tccttcatca actactatga ttccgagaag cacgccgaga   1200
acgccgtgat ttttctgcat ggtaacgcta cctccagcta cctgtggagg cacgtcgtgc   1260
ctcacatcga gcccgtggct agatgcatca tccctgatct gatcggaatg ggtaagtccg   1320
gcaagagcgg gaatggctca tatcgcctcc tggatcacta caagtacctc accgcttggt   1380
tcgagctgct gaaccttcca aagaaaatca tctttgtggg ccacgactgg ggggctgctc   1440
tggcctttca ctacgcctac gagcaccaag acaggatcaa ggccatcgtc catatggaga   1500
gtgtcgtgga cgtgatcgag tcctgggacg agtccggagg aggcggaatg agcaagggcg   1560
aggagctgtt caccggcgtg gtgcccatcc tggtggagct ggacggcgac gtgaacggcc   1620
acaagttcag cgtgagaggc gagggcgagg gcgacgccac catcggcaag ctgaccctga   1680
agttcatctg caccaccggc aagctgcccg tgccctggcc caccctggtg accaccctga   1740
cctacggcgt gcagtgcttc agcagatacc ccgaccacat gaagagacac gacttcttca   1800
agagcgccat gcccgagggc tacgtgcagg agagaaccat cagcttcaag gacgacggca   1860
agtacaagac cagagccgtg gtgaagttcg agggcgacac cctggtgaac agaatcgagc   1920
tgaagggcac cgacttcaag gaggacggca acatcctggg ccacaagctg gagtacaact   1980
tcaacagcca caacgtgtac atcaccgccg acaagtgatc tagagcggcc gcttcgagca   2040
gacatgataa gatacattga tgagtttgga caaaccacaa ctagaatgca gtgaaaaaaa   2100
tgctttattt gtgaaatttg tgatgctatt gctttatttg taaccattat aagctgcaat   2160
aaacaagtta acaacaacaa ttgcattcat tttatgtttc aggttcaggg ggaggtgtgg   2220
gaggtttttt aaagcaagta aaacctctac aaatgtggta aaatcgataa ggatccaggt   2280
ggcacttttc ggggaaatgt gcgcggaacc cctatttgtt tatttttcta aatacattca   2340
aatatgtatc cgctcatgag acaataaccc tgataaatgc ttcaataata ttgaaaaagg   2400
aagagtatga gtattcaaca tttccgtgtc gcccttattc ccttttttgc ggcattttgc   2460
cttcctgttt ttgctcaccc agaaacgctg gtgaaagtaa aagatgctga agatcagttg   2520
ggtgcacgag tgggttacat cgaactggat ctcaacagcg gtaagatcct tgagagtttt   2580
cgccccgaag aacgttttcc aatgatgagc acttttaaag ttctgctatg tggcgcggta   2640
ttatcccgta ttgacgccgg gcaagagcaa ctcggtcgcc gcatacacta ttctcagaat   2700
gacttggttg agtactcacc agtcacagaa aagcatctta cggatggcat gacagtaaga   2760
gaattatgca gtgctgccat aaccatgagt gataacactg cggccaactt acttctgaca   2820
acgatcggag gaccgaagga gctaaccgct tttttgcaca acatggggga tcatgtaact   2880
cgccttgatc gttgggaacc ggagctgaat gaagccatac caaacgacga gcgtgacacc   2940
acgatgcctg tagcaatggc aacaacgttg cgcaaactat taactggcga actacttact   3000
ctagcttccc ggcaacaatt aatagactgg atggaggcgg ataaagttgc aggaccactt   3060
ctgcgctcgg cccttccggc tggctggttt attgctgata aatctggagc cggtgagcgt   3120
gggtctcgcg gtatcattgc agcactgggg ccagatggta agccctcccg tatcgtagtt   3180
atctacacga cggggagtca ggcaactatg gatgaacgaa atagacagat cgctgagata   3240
```

```
ggtgcctcac tgattaagca ttggtaactg tcagaccaag tttactcata tatactttag   3300

attgatttaa aacttcattt ttaatttaaa aggatctagg tgaagatcct ttttgataat   3360

ctcatgacca aaatccctta acgtgagttt tcgttccact gagcgtcaga ccccgtagaa   3420

aagatcaaag gatcttcttg agatcctttt tttctgcgcg taatctgctg cttgcaaaca   3480

aaaaaaccac cgctaccagc ggtggtttgt ttgccggatc aagagctacc aactcttttt   3540

ccgaaggtaa ctggcttcag cagagcgcag ataccaaata ctgttcttct agtgtagccg   3600

tagttaggcc accacttcaa gaactctgta gcaccgccta catacctcgc tctgctaatc   3660

ctgttaccag tggctgctgc cagtggcgat aagtcgtgtc ttaccgggtt ggactcaaga   3720

cgatagttac cggataaggc gcagcggtcg ggctgaacgg ggggttcgtg cacacagccc   3780

agcttggagc gaacgaccta caccgaactg agatacctac agcgtgagct atgagaaagc   3840

gccacgcttc ccgaagggag aaaggcggac aggtatccgg taagcggcag ggtcggaaca   3900

ggagagcgca cgagggagct tccaggggga aacgcctggt atctttatag tcctgtcggg   3960

tttcgccacc tctgacttga gcgtcgattt ttgtgatgct cgtcaggggg gcggagccta   4020

tggaaaaacg ccagcaacgc ggccttttta cggttcctgg ccttttgctg gccttttgct   4080

cacatggctc gac                                                      4093
```

```
<210> SEQ ID NO 16
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Gln Lys Asn Gly Ile Lys Ala Asn Phe Thr Val Arg His Asn Val
1               5                   10                  15

Glu Asp Gly Ser Val Gln Leu Ala Asp His Tyr Gln Gln Asn Thr Pro
            20                  25                  30

Ile Gly Asp Gly Pro Val Leu Leu Pro Asp Asn His Tyr Leu Ser Thr
        35                  40                  45

Gln Thr Val Leu Ser Lys Asp Pro Asn Glu Lys Arg Asp His Met Val
    50                  55                  60

Leu His Glu Tyr Val Asn Ala Ala Gly Ile Thr Gly Gly Gly Gly Ser
65                  70                  75                  80

Trp Pro Asp Ile Glu Glu Asp Ile Ala Leu Ile Lys Ser Glu Glu Gly
                85                  90                  95

Glu Lys Met Val Leu Glu Asn Asn Phe Phe Val Glu Thr Val Leu Pro
            100                 105                 110

Ser Lys Ile Met Arg Lys Leu Glu Pro Glu Glu Phe Ala Ala Tyr Leu
        115                 120                 125

Glu Pro Phe Lys Glu Lys Gly Glu Val Arg Arg Pro Thr Leu Ser Trp
    130                 135                 140

Pro Arg Glu Ile Pro Leu Val Lys Gly Gly Lys Pro Asp Val Val Gln
145                 150                 155                 160

Ile Val Arg Asn Tyr Asn Ala Tyr Leu Arg Ala Ser Asp Asp Leu Pro
                165                 170                 175

Lys Leu Phe Ile Glu Ser Asp Pro Gly Phe Phe Ser Asn Ala Ile Val
            180                 185                 190

Glu Gly Ala Lys Lys Phe Pro Asn Thr Glu Phe Val Lys Val Lys Gly
```

```
        195                 200                 205

Leu His Phe Leu Gln Glu Asp Ala Pro Asp Glu Met Gly Lys Tyr Ile
    210                 215                 220

Lys Ser Phe Val Glu Arg Val Leu Lys Asn Glu Gln
225                 230                 235


<210> SEQ ID NO 17
<211> LENGTH: 3854
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

agatcttcaa tattggccat tagccatatt attcattggt tatatagcat aaatcaatat     60

tggctattgg ccattgcata cgttgtatct atatcataat atgtacattt atattggctc    120

atgtccaata tgaccgccat gttggcattg attattgact agttattaat agtaatcaat    180

tacggggtca ttagttcata gcccatatat ggagttccgc gttacataac ttacggtaaa    240

tggcccgcct ggctgaccgc ccaacgaccc ccgcccattg acgtcaataa tgacgtatgt    300

tcccatagta acgccaatag ggactttcca ttgacgtcaa tgggtggagt atttacggta    360

aactgcccac ttggcagtac atcaagtgta tcatatgcca agtccgcccc ctattgacgt    420

caatgacggt aaatggcccg cctggcatta tgcccagtac atgaccttac gggactttcc    480

tacttggcag tacatctacg tattagtcat cgctattacc atggtgatgc ggttttggca    540

gtacaccaat gggcgtggat agcggtttga ctcacgggga tttccaagtc tccaccccat    600

tgacgtcaat gggagtttgt tttggcacca aaatcaacgg gactttccaa aatgtcgtaa    660

taaccccgcc ccgttgacgc aaatgggcgg taggcgtgta cggtgggagg tctatataag    720

cagagctcgt ttagtgaacc gtcagatcac tagaagcttt attgcggtag tttatcacag    780

ttaaattgct aacgcagtca gtgcttctga cacaacagtc tcgaacttaa gctgcagaag    840

ttggtcgtga ggcactgggc aggtaagtat caaggttaca agacaggttt aaggagacca    900

atagaaactg ggcttgtcga gacagagaag actcttgcgt ttctgatagg cacctattgg    960

tcttactgac atccactttg cctttctctc cacaggtgtc cactcccagt tcaattacag   1020

ctcttaaggc tagagtactt aatacgactc actataggct agccaccatg cagaagaacg   1080

gcatcaaggc caacttcacc gtgagacaca acgtggagga cggcagcgtg cagctggccg   1140

accactacca gcagaacacc cccatcggcg acggccccgt gctgctgccc gacaaccact   1200

acctgagcac ccagaccgtg ctgagcaagg accccaacga gaagagagac cacatggtgc   1260

tgcacgagta cgtgaacgcc gccggcatca ccggcggtgg cggatcctgg cctgacatcg   1320

aggaggatat cgccctgatc aagagcgaag agggcgagaa aatggtgctt gagaataact   1380

tcttcgtcga gaccgtgctc ccaagcaaga tcatgcggaa actggagcct gaggagttcg   1440

ctgcctacct ggagccattc aaggagaagg gcgaggttag acggcctacc ctctcctggc   1500

ctcgcgagat ccctctcgtt aagggaggca agcccgacgt cgtccagatt gtccgcaact   1560

acaacgccta ccttcgggcc agcgacgatc tgcctaagct gttcatcgag tccgaccctg   1620

ggttcttttc caacgctatt gtcgagggag ctaagaagtt ccctaacacc gagttcgtga   1680

aggtgaaggg cctccacttc ctccaggagg acgctccaga tgaaatgggt aagtacatca   1740

agagcttcgt ggagcgcgtg ctgaagaacg agcagtaatt ctagagcggc cgcttcgagc   1800
```

agacatgata agatacattg atgagtttgg acaaaccaca actagaatgc agtgaaaaaa 1860
atgctttatt tgtgaaattt gtgatgctat tgctttattt gtaaccatta taagctgcaa 1920
taaacaagtt aacaacaaca attgcattca ttttatgttt caggttcagg gggaggtgtg 1980
ggaggttttt taaagcaagt aaaacctcta caaatgtggt aaaatcgata aggatccagg 2040
tggcactttt cggggaaatg tgcgcggaac ccctatttgt ttatttttct aaatacattc 2100
aaatatgtat ccgctcatga gacaataacc ctgataaatg cttcaataat attgaaaaag 2160
gaagagtatg agtattcaac atttccgtgt cgcccttatt cccttttttg cggcattttg 2220
ccttcctgtt tttgctcacc cagaaacgct ggtgaaagta aaagatgctg aagatcagtt 2280
gggtgcacga gtgggttaca tcgaactgga tctcaacagc ggtaagatcc ttgagagttt 2340
tcgccccgaa gaacgttttc caatgatgag cacttttaaa gttctgctat gtggcgcggt 2400
attatcccgt attgacgccg ggcaagagca actcggtcgc cgcatacact attctcagaa 2460
tgacttggtt gagtactcac cagtcacaga aaagcatctt acggatggca tgacagtaag 2520
agaattatgc agtgctgcca taaccatgag tgataacact gcggccaact tacttctgac 2580
aacgatcgga ggaccgaagg agctaaccgc ttttttgcac aacatggggg atcatgtaac 2640
tcgccttgat cgttgggaac cggagctgaa tgaagccata ccaaacgacg agcgtgacac 2700
cacgatgcct gtagcaatgg caacaacgtt gcgcaaacta ttaactggcg aactacttac 2760
tctagcttcc cggcaacaat taatagactg gatggaggcg gataaagttg caggaccact 2820
tctgcgctcg gcccttccgg ctggctggtt tattgctgat aaatctggag ccggtgagcg 2880
tgggtctcgc ggtatcattg cagcactggg gccagatggt aagccctccc gtatcgtagt 2940
tatctacacg acggggagtc aggcaactat ggatgaacga aatagacaga tcgctgagat 3000
aggtgcctca ctgattaagc attggtaact gtcagaccaa gtttactcat atatacttta 3060
gattgattta aaacttcatt tttaatttaa aaggatctag gtgaagatcc tttttgataa 3120
tctcatgacc aaaatccctt aacgtgagtt ttcgttccac tgagcgtcag accccgtaga 3180
aaagatcaaa ggatcttctt gagatccttt ttttctgcgc gtaatctgct gcttgcaaac 3240
aaaaaaacca ccgctaccag cggtggtttg tttgccggat caagagctac caactctttt 3300
tccgaaggta actggcttca gcagagcgca gataccaaat actgttcttc tagtgtagcc 3360
gtagttaggc caccacttca agaactctgt agcaccgcct acatacctcg ctctgctaat 3420
cctgttacca gtggctgctg ccagtggcga taagtcgtgt cttaccgggt tggactcaag 3480
acgatagtta ccggataagg cgcagcggtc gggctgaacg gggggttcgt gcacacagcc 3540
cagcttggag cgaacgacct acaccgaact gagataccta cagcgtgagc tatgagaaag 3600
cgccacgctt cccgaaggga gaaaggcgga caggtatccg gtaagcggca gggtcggaac 3660
aggagagcgc acgagggagc ttccaggggg aaacgcctgg tatctttata gtcctgtcgg 3720
gtttcgccac ctctgacttg agcgtcgatt tttgtgatgc tcgtcagggg ggcggagcct 3780
atggaaaaac gccagcaacg cggccttttt acggttcctg gccttttgct ggccttttgc 3840
tcacatggct cgac 3854

<210> SEQ ID NO 18
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 18

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Met Gln Lys Asn
145                 150                 155                 160

Gly Ile Lys Ala Asn Phe Thr Val Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Thr Val Leu
        195                 200                 205

Ser Lys Asp Pro Asn Glu Lys Arg Asp His Met Val Leu His Glu Tyr
    210                 215                 220

Val Asn Ala Ala Gly Ile Thr
225                 230
```

<210> SEQ ID NO 19
<211> LENGTH: 311
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 19

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95
```

-continued

His Tyr Lys Tyr Leu Thr Ala Trp Phe Glu Leu Leu Asn Leu Pro Lys
100 105 110

Lys Ile Ile Phe Val Gly His Asp Trp Gly Ala Ala Leu Ala Phe His
115 120 125

Tyr Ala Tyr Glu His Gln Asp Arg Ile Lys Ala Ile Val His Met Glu
130 135 140

Ser Val Val Asp Val Ile Glu Ser Trp Asp Glu Trp Pro Asp Ile Glu
145 150 155 160

Glu Asp Ile Ala Leu Ile Lys Ser Glu Glu Gly Glu Lys Met Val Leu
165 170 175

Glu Asn Asn Phe Phe Val Glu Thr Val Leu Pro Ser Lys Ile Met Arg
180 185 190

Lys Leu Glu Pro Glu Glu Phe Ala Ala Tyr Leu Glu Pro Phe Lys Glu
195 200 205

Lys Gly Glu Val Arg Arg Pro Thr Leu Ser Trp Pro Arg Glu Ile Pro
210 215 220

Leu Val Lys Gly Gly Lys Pro Asp Val Val Gln Ile Val Arg Asn Tyr
225 230 235 240

Asn Ala Tyr Leu Arg Ala Ser Asp Asp Leu Pro Lys Leu Phe Ile Glu
245 250 255

Ser Asp Pro Gly Phe Phe Ser Asn Ala Ile Val Glu Gly Ala Lys Lys
260 265 270

Phe Pro Asn Thr Glu Phe Val Lys Val Lys Gly Leu His Phe Leu Gln
275 280 285

Glu Asp Ala Pro Asp Glu Met Gly Lys Tyr Ile Lys Ser Phe Val Glu
290 295 300

Arg Val Leu Lys Asn Glu Gln
305 310

<210> SEQ ID NO 20
<211> LENGTH: 19
<212> TYPE: PRT
<213> ORGANISM: Severe acute respiratory syndrome coronavirus 2

<400> SEQUENCE: 20

Lys Phe Asp Glu Asp Asp Ser Glu Pro Val Leu Lys Gly Val Lys Leu
1 5 10 15

His Tyr Thr

<210> SEQ ID NO 21
<211> LENGTH: 21
<212> TYPE: PRT
<213> ORGANISM: Vesicular stomatitis virus

<400> SEQUENCE: 21

Lys Leu Lys His Thr Lys Lys Arg Gln Ile Tyr Thr Asp Ile Glu Met
1 5 10 15

Asn Arg Leu Gly Lys
20

<210> SEQ ID NO 22
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Val Ser Arg Asn
            20                  25                  30

Tyr Met Ile Trp Val Arg Gln Ala Pro Gly Lys Gly Leu Glu Trp Val
        35                  40                  45

Ser Val Ile Tyr Ser Gly Gly Ser Thr Phe Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Leu Gly Thr Gly Gly Met Asp Val Trp Gly Gln Gly Thr Thr
            100                 105                 110

Val Thr Val Ser Ser
        115
```

<210> SEQ ID NO 23
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
gaggtgcagc tggtggagtc tggaggaggc ttggtccagc ctgggggtc cctgagactc      60

tcctgtgcag cctctgggtt aatagtcagt cgcaactaca tgatctgggt ccgccaggct    120

ccagggaagg ggctggagtg ggtctcagtt atttatagcg gtggtagcac attctacgca    180

gactccgtga agggccgatt caccatctcc agacacaatt ccaagaacac gctgtatctt    240

caaatgaaca gcctgagggc tgaggacacg gccgtatatt actgtgcgag agatctgggt    300

acaggaggta tggacgtctg gggccaaggg accacggtca ccgtctcctc a             351
```

<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 24

```
Gly Leu Ile Val Ser Arg Asn Tyr
1               5
```

<210> SEQ ID NO 25
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 25

```
gggttaatag tcagtcgcaa ctac                                            24
```

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 26

Ile Tyr Ser Gly Gly Ser Thr
1 5

<210> SEQ ID NO 27
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 27
atttatagcg gtggtagcac a 21

<210> SEQ ID NO 28
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 28

Ala Arg Asp Leu Gly Thr Gly Gly Met Asp Val
1 5 10

<210> SEQ ID NO 29
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 29
gcgagagatc tgggtacagg aggtatggac gtc 33

<210> SEQ ID NO 30
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

Asp Ile Gln Leu Thr Gln Ser Pro Ser Phe Leu Ser Ala Ser Val Gly
1 5 10 15

Asp Arg Val Thr Ile Thr Cys Trp Ala Ser Gln Gly Ile Ser Ser Tyr
20 25 30

Leu Ala Trp Tyr Gln Gln Lys Pro Gly Lys Ala Pro Lys Leu Leu Ile
35 40 45

-continued

```
Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105


<210> SEQ ID NO 31
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31

gacatccagt tgacccagtc tccatccttc ctgtctgcat ctgtaggaga cagagtcacc     60

atcacttgct gggccagtca gggcattagc agttatttag cctggtatca gcaaaaacca    120

gggaaagccc ctaagctcct gatctatgct gcatccactt tgcaaagtgg ggtcccatca    180

aggttcagcg gcagtggatc tgggacagaa ttcactctca caatcagcag cctgcagcct    240

gaagattttg caacttatta ctgtcaacag cttaatagtt accctctcac tttcggcgga    300

gggaccaagg tggagatcaa a                                              321


<210> SEQ ID NO 32
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gln Gly Ile Ser Ser Tyr
1               5


<210> SEQ ID NO 33
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33

cagggcatta gcagttat                                                   18


<210> SEQ ID NO 34
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Ala Ser
1
```

<210> SEQ ID NO 35
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 35 gctgcatcc 9

<210> SEQ ID NO 36
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 36

Gln Gln Leu Asn Ser Tyr Pro Leu Thr
1 5

<210> SEQ ID NO 37
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 37
caacagctta atagttaccc tctcact 27

<210> SEQ ID NO 38
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

Glu Val Gln Leu Val Glu Ser Gly Gly Gly Leu Val Gln Pro Gly Gly
1 5 10 15

Ser Leu Arg Leu Ser Cys Ala Ala Ser Gly Leu Ile Val Ser Arg Asn
20 25 30

Tyr Met Ile Trp Val Arg Gln Ala Pro Gly Lys Gly Leu Glu Trp Val
35 40 45

Ser Val Ile Tyr Ser Gly Gly Ser Thr Phe Tyr Ala Asp Ser Val Lys
50 55 60

Gly Arg Phe Thr Ile Ser Arg His Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Leu Gly Thr Gly Gly Met Asp Val Trp Gly Gln Gly Thr Thr
100 105 110

Val Thr Val Ser Ser Ala Ser Thr Lys Gly Pro Ser Val Phe Pro Leu
115 120 125

```
Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 39
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 39

```
gaggtgcagc tggtggagtc tggaggaggc ttggtccagc ctggggggtc cctgagactc      60

tcctgtgcag cctctgggtt aatagtcagt cgcaactaca tgatctgggt ccgccaggct     120

ccagggaagg ggctggagtg ggtctcagtt atttatagcg gtggtagcac attctacgca     180
```

-continued

```
gactccgtga agggccgatt caccatctcc agacacaatt ccaagaacac gctgtatctt    240

caaatgaaca gcctgagggc tgaggacacg gccgtatatt actgtgcgag agatctgggt    300

acaggaggta tggacgtctg ggccaaggg accacggtca ccgtctcctc agcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggatga gctgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagtcc   1320

ctctccctgt ctccgggtaa atga                                           1344
```

<210> SEQ ID NO 40
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 40

```
Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

-continued

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 41
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 41

```
gacatccagt tgacccagtc tccatccttc ctgtctgcat ctgtaggaga cagagtcacc     60

atcacttgct gggccagtca gggcattagc agttatttag cctggtatca gcaaaaacca    120

gggaaagccc ctaagctcct gatctatgct gcatccactt tgcaaagtgg ggtcccatca    180

aggttcagcg gcagtggatc tgggacagaa ttcactctca caatcagcag cctgcagcct    240

gaagattttg caacttatta ctgtcaacag cttaatagtt accctctcac tttcggcgga    300

gggaccaagg tggagatcaa acgaactgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 42
<211> LENGTH: 1254
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95
```

```
Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Arg Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
```

```
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asn Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Gln Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940
```

Leu Gly Lys Leu Gln Asp Val Val Asn Gln Asn Ala Gln Ala Leu Asn
945 950 955 960

Thr Leu Val Lys Gln Leu Ser Ser Asn Phe Gly Ala Ile Ser Ser Val
965 970 975

Leu Asn Asp Ile Leu Ser Arg Leu Asp Lys Val Glu Ala Glu Val Gln
980 985 990

Ile Asp Arg Leu Ile Thr Gly Arg Leu Gln Ser Leu Gln Thr Tyr Val
995 1000 1005

Thr Gln Gln Leu Ile Arg Ala Ala Glu Ile Arg Ala Ser Ala Asn
1010 1015 1020

Leu Ala Ala Thr Lys Met Ser Glu Cys Val Leu Gly Gln Ser Lys
1025 1030 1035

Arg Val Asp Phe Cys Gly Lys Gly Tyr His Leu Met Ser Phe Pro
1040 1045 1050

Gln Ser Ala Pro His Gly Val Val Phe Leu His Val Thr Tyr Val
1055 1060 1065

Pro Ala Gln Glu Lys Asn Phe Thr Thr Ala Pro Ala Ile Cys His
1070 1075 1080

Asp Gly Lys Ala His Phe Pro Arg Glu Gly Val Phe Val Ser Asn
1085 1090 1095

Gly Thr His Trp Phe Val Thr Gln Arg Asn Phe Tyr Glu Pro Gln
1100 1105 1110

Ile Ile Thr Thr Asp Asn Thr Phe Val Ser Gly Asn Cys Asp Val
1115 1120 1125

Val Ile Gly Ile Val Asn Asn Thr Val Tyr Asp Pro Leu Gln Pro
1130 1135 1140

Glu Leu Asp Ser Phe Lys Glu Glu Leu Asp Lys Tyr Phe Lys Asn
1145 1150 1155

His Thr Ser Pro Asp Val Asp Leu Gly Asp Ile Ser Gly Ile Asn
1160 1165 1170

Ala Ser Val Val Asn Ile Gln Lys Glu Ile Asp Arg Leu Asn Glu
1175 1180 1185

Val Ala Lys Asn Leu Asn Glu Ser Leu Ile Asp Leu Gln Glu Leu
1190 1195 1200

Gly Lys Tyr Glu Gln Tyr Ile Lys Trp Pro Trp Tyr Ile Trp Leu
1205 1210 1215

Gly Phe Ile Ala Gly Leu Ile Ala Ile Val Met Val Thr Ile Met
1220 1225 1230

Leu Cys Cys Met Thr Ser Cys Cys Ser Cys Leu Lys Gly Cys Cys
1235 1240 1245

Ser Cys Gly Ser Cys Cys
1250

<210> SEQ ID NO 43
<211> LENGTH: 3765
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43
atgttcgtct tcctggtcct gctgcctctg gtctcctcac agtgcgtcaa tctgacaact 60
cggactcagc tgccacctgc ttatactaat agcttcacca gaggcgtgta ctatcctgac 120
aaggtgttta gaagctccgt gctgcactct acacaggatc tgtttctgcc attctttagc 180
aacgtgacct ggttccacgc catccacgtg agcggcacca atggcacaaa gcggttcgac 240
aatcccgtgc tgccttttaa cgatggcgtg tacttcgcct ctaccgagaa gagcaacatt 300
atcagaggct ggatctttgg caccacactg gactccaaga cacagtctct gctgatcgtg 360
aacaatgcca ccaacgtggt catcaaggtg tgcgagttcc agttttgtaa tgatcccttc 420
ctgggcgtgt actatcacaa gaacaataag agctggatgg agtccgagtt tagagtgtat 480
tctagcgcca acaactgcac atttgagtac gtgagccagc ctttcctgat ggacctggag 540
ggcaagcagg gcaatttcaa gaacctgagg gagttcgtgt ttaagaatat cgacggctac 600
ttcaaaatct actctaagca cacccccatc aacctggtgc gcgacctgcc tcagggcttc 660
agcgccctgg agcccctggt ggatctgcct atcggcatca acatcacccg gtttcagaca 720
ctgctggccc tgcacagaag atacctgaca cccggcgact cctctagcgg atggaccgcc 780
ggcgctgccg cctactatgt gggctacctc cagccccgga ccttcctgct gaagtacaac 840
gagaatggca ccatcacaga cgcagtggat tgcgccctgg acccccctgag cgagacaaag 900
tgtacactga agtcctttac cgtggagaag ggcatctatc agacatccaa tttcagggtg 960
cagccaaccg agtctatcgt gcgctttcct aatatcacaa acctgtgccc atttggcgag 1020
gtgttcaacg caacccgctt cgccagcgtg tacgcctgga ataggaagcg gatcagcaac 1080
tgcgtggccg actatagcgt gctgtacaac tccgcctctt tcagcacctt taagtgctat 1140
ggcgtgtccc ccacaaagct gaatgacctg tgctttacca acgtctacgc cgattctttc 1200
gtgatcaggg gcgacgaggt gcgccagatc gcccccggcc agacaggcaa gatcgcagac 1260
tacaattata agctgccaga cgatttcacc ggctgcgtga tcgcctggaa cagcaacaat 1320
ctggattcca aagtgggcgg caactacaat tatctgtacc ggctgtttag aaagagcaat 1380
ctgaagccct tcgagaggga catctctaca gaaatctacc aggccggcag caccccttgc 1440
aatggcgtgg agggctttaa ctgttatttc ccactccagt cctacggctt ccagcccaca 1500
aacggcgtgg gctatcagcc ttaccgcgtg gtggtgctga gctttgagct gctgcacgcc 1560
ccagcaacag tgtgcggccc caagaagtcc accaatctgg tgaagaacaa gtgcgtgaac 1620
ttcaacttca acggcctgac cggcacaggc gtgctgaccg agtccaacaa gaagttcctg 1680
ccatttcagc agttcggcag ggacatcgca gataccacag acgccgtgcg cgacccacag 1740
accctggaga tcctggacat cacaccctgc tctttcggcg gcgtgagcgt gatcacaccc 1800
ggcaccaata caagcaacca ggtggccgtg ctgtatcaga acgtgaattg taccgaggtg 1860
cccgtggcta tccacgccga tcagctgacc ccaacatggc gggtgtacag caccggctcc 1920
aacgtcttcc agacaagagc cggatgcctg atcggagcag agcacgtgaa caattcctat 1980
gagtgcgaca tcccaatcgg cgccggcatc tgtgcctctt accagaccca gacaaactct 2040
cccagaagag cccagagcgt ggcctcccag tctatcatcg cctataccat gtccctgggc 2100
gccgagaaca gcgtggccta ctctaacaat agcatcgcca tcccaaccaa cttcacaatc 2160
tctgtgacca cagagatcct gcccgtgtcc atgaccaaga catctgtgga ctgcacaatg 2220
tatatctgtg gcgattctac cgagtgcagc aacctgctgc tccagtacgg cagcttttgt 2280
acccagctga atagagccct gacaggcatc gccgtggagc aggataagaa cacacaggag 2340
gtgttcgccc aggtgaagca aatctacaag acccccccta tcaaggactt tggcggcttc 2400
aatttttccc agatcctgcc tgatccatcc aagccttcta agcggagctt tatcgaggac 2460

```
ctgctgttca acaaggtgac cctggccgat gccggcttca tcaagcagta tggcgattgc   2520

ctgggcgaca tcgcagccag ggacctgatc tgcgcccaga agtttaatgg cctgaccgtg   2580

ctgccacccc tgctgacaga tgagatgatc gcacagtaca caagcgccct gctggccggc   2640

accatcacat ccggatggac cttcggcgca ggagccgccc tccagatccc ctttgccatg   2700

cagatggcct ataggttcaa cggcatcggc gtgacccaga atgtgctgta cgagaaccag   2760

aagctgatcg ccaatcagtt taactccgcc atcggcaaga tccaggacag cctgtcctct   2820

acagccagcg ccctgggcaa gctccaggat gtggtgaatc agaacgccca ggccctgaat   2880

accctggtga agcagctgag cagcaacttc ggcgccatct ctagcgtgct gaatgacatc   2940

ctgagccggc tggacaaggt ggaggcagag gtgcagatcg accggctgat caccggccgg   3000

ctccagagcc tccagaccta tgtgacacag cagctgatca gggccgccga gatcagggcc   3060

agcgccaatc tggcagcaac caagatgtcc gagtgcgtgc tgggccagtc taagagagtg   3120

gacttttgtg gcaagggcta tcacctgatg tccttccctc agtctgcccc acacggcgtg   3180

gtgtttctgc acgtgaccta cgtgcccgcc caggagaaga acttcaccac agcccctgcc   3240

atctgccacg atggcaaggc ccactttcca agggagggcg tgttcgtgtc caacggcacc   3300

cactggtttg tgacacagcg caatttctac gagccccaga tcatcaccac agacaacacc   3360

ttcgtgagcg gcaactgtga cgtggtcatc ggcatcgtga acaataccgt gtatgatcca   3420

ctccagcccg agctggacag ctttaaggag gagctggata agtatttcaa gaatcacacc   3480

tcccctgacg tggatctggg cgacatcagc ggcatcaatg cctccgtggt gaacatccag   3540

aaggagatcg accgcctgaa cgaggtggct aagaatctga acgagagcct gatcgacctc   3600

caggagctgg gcaagtatga gcagtacatc aagtggccct ggtacatctg gctgggcttc   3660

atcgccggcc tgatcgccat cgtgatggtg accatcatgc tgtgctgtat gacatcctgc   3720

tgttcttgcc tgaagggctg ctgtagctgt ggctcctgct gttaa                  3765
```

```
<210> SEQ ID NO 44
<211> LENGTH: 1252
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile Ser Gly Thr Asn Gly Thr Lys Arg Phe Asp Asn Pro
65                  70                  75                  80

Val Leu Pro Phe Asn Asp Gly Val Tyr Phe Ala Ser Thr Glu Lys Ser
                85                  90                  95

Asn Ile Ile Arg Gly Trp Ile Phe Gly Thr Thr Leu Asp Ser Lys Thr
            100                 105                 110

Gln Ser Leu Leu Ile Val Asn Asn Ala Thr Asn Val Val Ile Lys Val
        115                 120                 125
```

```
Cys Glu Phe Gln Phe Cys Asn Asp Pro Phe Leu Gly Val Tyr Tyr His
    130                 135                 140

Lys Asn Asn Lys Ser Trp Met Glu Ser Glu Phe Arg Val Tyr Ser Ser
145                 150                 155                 160

Ala Asn Asn Cys Thr Phe Glu Tyr Val Ser Gln Pro Phe Leu Met Asp
                165                 170                 175

Leu Glu Gly Lys Gln Gly Asn Phe Lys Asn Leu Arg Glu Phe Val Phe
            180                 185                 190

Lys Asn Ile Asp Gly Tyr Phe Lys Ile Tyr Ser Lys His Thr Pro Ile
        195                 200                 205

Asn Leu Val Arg Asp Leu Pro Gln Gly Phe Ser Ala Leu Glu Pro Leu
    210                 215                 220

Val Asp Leu Pro Ile Gly Ile Asn Ile Thr Arg Phe Gln Thr Leu Leu
225                 230                 235                 240

Ala Leu His Arg Ser Tyr Leu Thr Pro Gly Asp Ser Ser Ser Gly Trp
                245                 250                 255

Thr Ala Gly Ala Ala Ala Tyr Tyr Val Gly Tyr Leu Gln Pro Arg Thr
            260                 265                 270

Phe Leu Leu Lys Tyr Asn Glu Asn Gly Thr Ile Thr Asp Ala Val Asp
        275                 280                 285

Cys Ala Leu Asp Pro Leu Ser Glu Thr Lys Cys Thr Leu Lys Ser Phe
    290                 295                 300

Thr Val Glu Lys Gly Ile Tyr Gln Thr Ser Asn Phe Arg Val Gln Pro
305                 310                 315                 320

Thr Glu Ser Ile Val Arg Phe Pro Asn Ile Thr Asn Leu Cys Pro Phe
                325                 330                 335

Gly Glu Val Phe Asn Ala Thr Arg Phe Ala Ser Val Tyr Ala Trp Asn
            340                 345                 350

Arg Lys Arg Ile Ser Asn Cys Val Ala Asp Tyr Ser Val Leu Tyr Asn
        355                 360                 365

Ser Ala Ser Phe Ser Thr Phe Lys Cys Tyr Gly Val Ser Pro Thr Lys
    370                 375                 380

Leu Asn Asp Leu Cys Phe Thr Asn Val Tyr Ala Asp Ser Phe Val Ile
385                 390                 395                 400

Arg Gly Asp Glu Val Arg Gln Ile Ala Pro Gly Gln Thr Gly Lys Ile
                405                 410                 415

Ala Asp Tyr Asn Tyr Lys Leu Pro Asp Asp Phe Thr Gly Cys Val Ile
            420                 425                 430

Ala Trp Asn Ser Asn Asn Leu Asp Ser Lys Val Gly Gly Asn Tyr Asn
        435                 440                 445

Tyr Leu Tyr Arg Leu Phe Arg Lys Ser Asn Leu Lys Pro Phe Glu Arg
    450                 455                 460

Asp Ile Ser Thr Glu Ile Tyr Gln Ala Gly Ser Thr Pro Cys Asn Gly
465                 470                 475                 480

Val Lys Gly Phe Asn Cys Tyr Phe Pro Leu Gln Ser Tyr Gly Phe Gln
                485                 490                 495

Pro Thr Tyr Gly Val Gly Tyr Gln Pro Tyr Arg Val Val Val Leu Ser
            500                 505                 510

Phe Glu Leu Leu His Ala Pro Ala Thr Val Cys Gly Pro Lys Lys Ser
        515                 520                 525

Thr Asn Leu Val Lys Asn Lys Cys Val Asn Phe Asn Phe Asn Gly Leu
    530                 535                 540
```

-continued

```
Thr Gly Thr Gly Val Leu Thr Glu Ser Asn Lys Lys Phe Leu Pro Phe
545                 550                 555                 560

Gln Gln Phe Gly Arg Asp Ile Ala Asp Thr Thr Asp Ala Val Arg Asp
                565                 570                 575

Pro Gln Thr Leu Glu Ile Leu Asp Ile Thr Pro Cys Ser Phe Gly Gly
            580                 585                 590

Val Ser Val Ile Thr Pro Gly Thr Asn Thr Ser Asn Gln Val Ala Val
        595                 600                 605

Leu Tyr Gln Gly Val Asn Cys Thr Glu Val Pro Val Ala Ile His Ala
    610                 615                 620

Asp Gln Leu Thr Pro Thr Trp Arg Val Tyr Ser Thr Gly Ser Asn Val
625                 630                 635                 640

Phe Gln Thr Arg Ala Gly Cys Leu Ile Gly Ala Glu His Val Asn Asn
                645                 650                 655

Ser Tyr Glu Cys Asp Ile Pro Ile Gly Ala Gly Ile Cys Ala Ser Tyr
            660                 665                 670

Gln Thr Gln Thr Asn Ser Pro Arg Arg Ala Arg Ser Val Ala Ser Gln
        675                 680                 685

Ser Ile Ile Ala Tyr Thr Met Ser Leu Gly Ala Glu Asn Ser Val Ala
    690                 695                 700

Tyr Ser Asn Asn Ser Ile Ala Ile Pro Thr Asn Phe Thr Ile Ser Val
705                 710                 715                 720

Thr Thr Glu Ile Leu Pro Val Ser Met Thr Lys Thr Ser Val Asp Cys
                725                 730                 735

Thr Met Tyr Ile Cys Gly Asp Ser Thr Glu Cys Ser Asn Leu Leu Leu
            740                 745                 750

Gln Tyr Gly Ser Phe Cys Thr Gln Leu Asn Arg Ala Leu Thr Gly Ile
        755                 760                 765

Ala Val Glu Gln Asp Lys Asn Thr Gln Glu Val Phe Ala Gln Val Lys
    770                 775                 780

Gln Ile Tyr Lys Thr Pro Pro Ile Lys Asp Phe Gly Gly Phe Asn Phe
785                 790                 795                 800

Ser Gln Ile Leu Pro Asp Pro Ser Lys Pro Ser Lys Arg Ser Phe Ile
                805                 810                 815

Glu Asp Leu Leu Phe Asn Lys Val Thr Leu Ala Asp Ala Gly Phe Ile
            820                 825                 830

Lys Gln Tyr Gly Asp Cys Leu Gly Asp Ile Ala Ala Arg Asp Leu Ile
        835                 840                 845

Cys Ala Gln Lys Phe Asn Gly Leu Thr Val Leu Pro Pro Leu Leu Thr
    850                 855                 860

Asp Glu Met Ile Ala Gln Tyr Thr Ser Ala Leu Leu Ala Gly Thr Ile
865                 870                 875                 880

Thr Ser Gly Trp Thr Phe Gly Ala Gly Ala Ala Leu Gln Ile Pro Phe
                885                 890                 895

Ala Met Gln Met Ala Tyr Arg Phe Asn Gly Ile Gly Val Thr Gln Asn
            900                 905                 910

Val Leu Tyr Glu Asn Gln Lys Leu Ile Ala Asn Gln Phe Asn Ser Ala
        915                 920                 925

Ile Gly Lys Ile Gln Asp Ser Leu Ser Ser Thr Ala Ser Ala Leu Gly
    930                 935                 940

Lys Leu Gln Asp Val Val Asn Gln Asn Ala Gln Ala Leu Asn Thr Leu
945                 950                 955                 960

Val Lys Gln Leu Ser Ser Asn Phe Gly Ala Ile Ser Ser Val Leu Asn
```

965 970 975

Asp Ile Leu Ser Arg Leu Asp Lys Val Glu Ala Glu Val Gln Ile Asp
980 985 990

Arg Leu Ile Thr Gly Arg Leu Gln Ser Leu Gln Thr Tyr Val Thr Gln
995 1000 1005

Gln Leu Ile Arg Ala Ala Glu Ile Arg Ala Ser Ala Asn Leu Ala
1010 1015 1020

Ala Thr Lys Met Ser Glu Cys Val Leu Gly Gln Ser Lys Arg Val
1025 1030 1035

Asp Phe Cys Gly Lys Gly Tyr His Leu Met Ser Phe Pro Gln Ser
1040 1045 1050

Ala Pro His Gly Val Val Phe Leu His Val Thr Tyr Val Pro Ala
1055 1060 1065

Gln Glu Lys Asn Phe Thr Thr Ala Pro Ala Ile Cys His Asp Gly
1070 1075 1080

Lys Ala His Phe Pro Arg Glu Gly Val Phe Val Ser Asn Gly Thr
1085 1090 1095

His Trp Phe Val Thr Gln Arg Asn Phe Tyr Glu Pro Gln Ile Ile
1100 1105 1110

Thr Thr Asp Asn Thr Phe Val Ser Gly Asn Cys Asp Val Val Ile
1115 1120 1125

Gly Ile Val Asn Asn Thr Val Tyr Asp Pro Leu Gln Pro Glu Leu
1130 1135 1140

Asp Ser Phe Lys Glu Glu Leu Asp Lys Tyr Phe Lys Asn His Thr
1145 1150 1155

Ser Pro Asp Val Asp Leu Gly Asp Ile Ser Gly Ile Asn Ala Ser
1160 1165 1170

Val Val Asn Ile Gln Lys Glu Ile Asp Arg Leu Asn Glu Val Ala
1175 1180 1185

Lys Asn Leu Asn Glu Ser Leu Ile Asp Leu Gln Glu Leu Gly Lys
1190 1195 1200

Tyr Glu Gln Tyr Ile Lys Trp Pro Trp Tyr Ile Trp Leu Gly Phe
1205 1210 1215

Ile Ala Gly Leu Ile Ala Ile Val Met Val Thr Ile Met Leu Cys
1220 1225 1230

Cys Met Thr Ser Cys Cys Ser Cys Leu Lys Gly Cys Cys Ser Cys
1235 1240 1245

Gly Ser Cys Cys
1250

<210> SEQ ID NO 45
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ile Tyr
20 25 30

Glu Met Asn Trp Val Arg Gln Ala Pro Gly Lys Gly Leu Glu Trp Val
35 40 45

Ser Tyr Ile Thr Ser Ser Gly Thr Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Ser Ser Ser Ser Gly Tyr Tyr Phe Asp Tyr Trp Gly Gln Gly
            100                 105                 110

Thr Leu Val Thr Val Ser Ser
        115

<210> SEQ ID NO 46
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 46

Gly Phe Thr Phe Ser Ile Tyr Glu
1               5

<210> SEQ ID NO 47
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 47

Ile Thr Ser Ser Gly Thr Thr Ile
1               5

<210> SEQ ID NO 48
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 48

Ala Ser Ser Ser Ser Ser Gly Tyr Tyr Phe Asp Tyr
1               5                   10

<210> SEQ ID NO 49
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
35 40 45

Pro Pro Asn Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro Pro Thr Phe Gly Gln Gly Thr Lys Leu Glu Ile
100 105 110

Lys

<210> SEQ ID NO 50
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 50

Gln Ser Val Leu Tyr Ser Ser Asn Asn Lys Asn Tyr
1 5 10

<210> SEQ ID NO 51
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 51

Trp Ala Ser
1

<210> SEQ ID NO 52
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 52

Gln Gln Tyr Tyr Ser Thr Pro Pro Thr
1 5

<210> SEQ ID NO 53
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ile Tyr
20 25 30

```
Glu Met Asn Trp Val Arg Gln Ala Pro Gly Lys Gly Leu Glu Trp Val
        35                  40                  45

Ser Tyr Ile Thr Ser Ser Gly Thr Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Ser Ser Ser Ser Gly Tyr Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

Lys

<210> SEQ ID NO 54
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 55
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55

```
gaggtgcagc tggtggagtc tgggggaggc ttggtacagc ctggagggtc cctgagactc     60

tcctgtgcag cctctggatt caccttcagt atttatgaaa tgaactgggt ccgccaggct    120

ccagggaagg ggctggagtg ggtttcatac attactagta gtggtactac catatactac    180

gcagactctg tgaagggccg attcaccatc tccagagaca acgccaagaa ctcactgtat    240

ctgcaaatga acagcctgag agccgaggac acggctgttt attactgtgc gagtagcagc    300

tcgtccgggt actactttga ctactggggc cagggaaccc tggtcaccgt ctcctca       357
```

<210> SEQ ID NO 56
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 56
ggattcacct tcagtattta tgaa 24

<210> SEQ ID NO 57
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 57
attactagta gtggtactac cata 24

<210> SEQ ID NO 58
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 58
gcgagtagca gctcgtccgg gtactacttt gactac 36

<210> SEQ ID NO 59
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 59
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg acagcctcct aatctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatagtact 300
cctcccactt ttggccaggg gaccaagctg gagatcaaa 339

<210> SEQ ID NO 60
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 60

-continued cagagtgttt tatacagctc caacaataag aactac 36

<210> SEQ ID NO 61
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 61 tgggcatct 9

<210> SEQ ID NO 62
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 62
cagcaatatt atagtactcc tcccact 27

<210> SEQ ID NO 63
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 63
gaggtgcagc tggtggagtc tgggggaggc ttggtacagc ctggagggtc cctgagactc 60
tcctgtgcag cctctggatt caccttcagt atttatgaaa tgaactgggt ccgccaggct 120
ccagggaagg ggctggagtg ggtttcatac attactagta gtggtactac catatactac 180
gcagactctg tgaagggccg attcaccatc tccagagaca acgccaagaa ctcactgtat 240
ctgcaaatga acagcctgag agccgaggac acggctgttt attactgtgc gagtagcagc 300
tcgtccgggt actactttga ctactggggc cagggaaccc tggtcaccgt ctcctcagcc 360
tccaccaagg gcccatcggt cttccccctg gcaccctcct ccaagagcac ctctgggggc 420
acagcggccc tgggctgcct ggtcaaggac tacttccccg aaccggtgac ggtgtcgtgg 480
aactcaggcg ccctgaccag cggcgtgcac accttcccgg ctgtcctaca gtcctcagga 540
ctctactccc tcagcagcgt ggtgaccgtg ccctccagca gcttgggcac ccagacctac 600
atctgcaacg tgaatcacaa gcccagcaac accaaggtgg acaagaaagt tgagcccaaa 660
tcttgtgaca aaactcacac atgcccaccg tgcccagcac ctgaactcct ggggggaccg 720
tcagtcttcc tcttcccccc aaaacccaag gacaccctca tgatctcccg gacccctgag 780
gtcacatgcg tggtggtgga cgtgagccac gaagaccctg aggtcaagtt caactggtac 840
gtggacggcg tggaggtgca taatgccaag acaaagccgc gggaggagca gtacaacagc 900
acgtaccgtg tggtcagcgt cctcaccgtc ctgcaccagg actggctgaa tggcaaggag 960
tacaagtgca aggtctccaa caaagccctc ccagccccca tcgagaaaac catctccaaa 1020
gccaaagggc agccccgaga accacaggtg tacaccctgc ccccatcccg ggatgagctg 1080
accaagaacc aggtcagcct gacctgcctg gtcaaaggct tctatcccag cgacatcgcc 1140
gtggagtggg agagcaatgg gcagccggag aacaactaca agaccacgcc tcccgtgctg 1200
gactccgacg gctccttctt cctctacagc aagctcaccg tggacaagag caggtggcag 1260
caggggaacg tcttctcatg ctccgtgatg catgaggctc tgcacaacca ctacacgcag 1320
aagtccctct ccctgtctcc gggtaaatga 1350

<210> SEQ ID NO 64
<211> LENGTH: 663
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 64
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg acagcctcct aatctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatagtact 300
cctcccactt ttggccaggg gaccaagctg gagatcaaac gaactgtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660
tag 663

<210> SEQ ID NO 65
<211> LENGTH: 11
<212> TYPE: PRT
<213> ORGANISM: Severe acute respiratory syndrome coronavirus 2

<400> SEQUENCE: 65

Gln Thr Asn Ser Pro Arg Arg Ala Arg Ser Val
1 5 10

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 66

Gln Thr Ile Leu Arg Ser Val
1 5

<210> SEQ ID NO 67
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 67

Gln Thr Asn Ser Pro Gly Ser Ala Ser Ser Val
1 5 10

<210> SEQ ID NO 68
<211> LENGTH: 4
<212> TYPE: PRT
<213> ORGANISM: Vesicular stomatitis virus

<400> SEQUENCE: 68

Pro Pro Pro Tyr
1

<210> SEQ ID NO 69
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 69

Ala Pro Pro Tyr
1

<210> SEQ ID NO 70
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 70

Ala Ala Pro Tyr
1

<210> SEQ ID NO 71
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 71

Pro Pro Ala Tyr
1

<210> SEQ ID NO 72
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 72

Ala Pro Pro Ala
1

-continued

```
<210> SEQ ID NO 73
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Ala Ala Pro Ala
1


<210> SEQ ID NO 74
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Pro Pro Pro Ala
1


<210> SEQ ID NO 75
<211> LENGTH: 4
<212> TYPE: PRT
<213> ORGANISM: Vesicular stomatitis virus

<400> SEQUENCE: 75

Pro Ser Ala Pro
1
```